United States Patent
Siddiqui-Jain et al.

(10) Patent No.: US 12,077,554 B2
(45) Date of Patent: *Sep. 3, 2024

(54) CDK9 INHIBITORS AND POLYMORPHS THEREOF FOR USE AS AGENTS FOR TREATMENT OF CANCER

(71) Applicant: Sumitomo Pharma Oncology, Inc., Marlborough, MA (US)

(72) Inventors: Adam Siddiqui-Jain, South Jordan, UT (US); Paul Flynn, Citrus Heights, CA (US); Yuji Fujiwara, Draper, UT (US); Shuji Masumoto, Toyonaka (JP); Hiroaki Tanaka, Toyonaka (JP); Hirotaka Kurebayashi, Minoh (JP); Takahiko Hashizuka, Matsubara (JP); Yuka Arikawa, Minoh (JP)

(73) Assignee: Sumitomo Pharma Oncology, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/054,435

(22) Filed: Nov. 10, 2022

(65) Prior Publication Data

US 2023/0250116 A1 Aug. 10, 2023

Related U.S. Application Data

(63) Continuation of application No. 17/225,836, filed on Apr. 8, 2021, now Pat. No. 11,530,231, which is a continuation of application No. 16/703,773, filed on Dec. 4, 2019, now Pat. No. 11,034,710.

(60) Provisional application No. 62/775,303, filed on Dec. 4, 2018.

(51) Int. Cl.
*A61P 35/00* (2006.01)
*A61K 9/00* (2006.01)
*C07F 9/6558* (2006.01)

(52) U.S. Cl.
CPC ........ *C07F 9/65586* (2013.01); *A61K 9/0053* (2013.01); *A61P 35/00* (2018.01); *C07B 2200/13* (2013.01)

(58) Field of Classification Search
CPC .... C07F 9/65586; A61P 35/00; A61K 9/0053; C07B 2200/13
See application file for complete search history.

(56) References Cited

U.S. PATENT DOCUMENTS

| | | |
|---|---|---|
| 4,132,710 A | 1/1979 | Gauthier et al. |
| 4,146,629 A | 3/1979 | Kubela et al. |
| 4,522,811 A | 6/1985 | Eppstein et al. |
| 4,676,980 A | 6/1987 | Segal et al. |
| 4,816,567 A | 3/1989 | Cabilly et al. |
| 4,900,727 A | 2/1990 | Kattige et al. |
| 4,946,778 A | 8/1990 | Ladner et al. |
| 4,971,909 A | 11/1990 | Kaneoya et al. |
| 5,225,539 A | 7/1993 | Winter |
| 5,284,856 A | 2/1994 | Naik et al. |
| 5,310,763 A | 5/1994 | Campion et al. |
| 5,545,806 A | 8/1996 | Lonberg et al. |
| 5,545,807 A | 8/1996 | Surani et al. |
| 5,569,825 A | 10/1996 | Lonberg et al. |
| 5,587,458 A | 12/1996 | King et al. |
| 5,625,126 A | 4/1997 | Lonberg et al. |
| 5,633,425 A | 5/1997 | Lonberg et al. |
| 5,661,016 A | 8/1997 | Lonberg et al. |

(Continued)

FOREIGN PATENT DOCUMENTS

| | | |
|---|---|---|
| CN | 1583776 A | 2/2005 |
| EP | 0 137 193 A2 | 4/1985 |

(Continued)

OTHER PUBLICATIONS

"Alvocidib Biomarker-driven Phase 2 AML Study," Sumitomo Dainippon Pharma Oncology, ClinicalTrials.gov identifier: NTC0252001 1, URL:https://www.clinicaltrials.gov/ct2/show/NCT0252001 1, Accessed: Dec. 31, 2020, (8 pages).

(Continued)

*Primary Examiner* — Timothy R Rozof
(74) *Attorney, Agent, or Firm* — Hamilton, Brook, Smith & Reynolds, P.C.

(57) ABSTRACT

A crystalline form and/or polymorph of a compound having the following structure (I), including tautomeric and zwitterionic forms thereof, are provided:

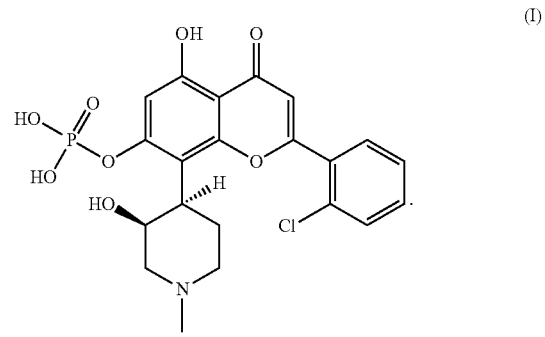

(I)

Methods associated with preparation and use of the polymorphs, and pharmaceutical compositions comprising the same are also provided. Also provided are methods for preparing a compound having formula (I), or a salt, tautomer or zwitterionic form thereof.

20 Claims, 46 Drawing Sheets

(56) References Cited

U.S. PATENT DOCUMENTS

| | | |
|---|---|---|
| 5,674,980 A | 10/1997 | Frankel et al. |
| 5,747,498 A | 5/1998 | Schnur et al. |
| 5,792,783 A | 8/1998 | Tang et al. |
| 5,804,604 A | 9/1998 | Frankel et al. |
| 5,834,504 A | 11/1998 | Tang et al. |
| 5,849,733 A | 12/1998 | Kim |
| 5,861,510 A | 1/1999 | Piscopio et al. |
| 5,863,949 A | 1/1999 | Robinson et al. |
| 5,877,305 A | 3/1999 | Huston et al. |
| 5,883,113 A | 3/1999 | Tang et al. |
| 5,886,020 A | 3/1999 | Tang et al. |
| 5,908,934 A | 6/1999 | Kim |
| 5,916,771 A | 6/1999 | Hori et al. |
| 5,932,595 A | 8/1999 | Bender et al. |
| 5,939,598 A | 8/1999 | Kucherlapati et al. |
| 5,965,703 A | 10/1999 | Horne et al. |
| 6,077,864 A | 6/2000 | Burgess et al. |
| 6,087,366 A | 7/2000 | Park et al. |
| 6,087,392 A | 7/2000 | Reiter |
| 6,090,852 A | 7/2000 | Dack et al. |
| 6,110,964 A | 8/2000 | Robinson |
| 6,136,981 A | 10/2000 | Brion et al. |
| 6,147,061 A | 11/2000 | Reiter |
| 6,153,609 A | 11/2000 | Robinson et al. |
| 6,177,401 B1 | 1/2001 | Ullrich et al. |
| 6,207,669 B1 | 3/2001 | Cockerill et al. |
| 6,214,872 B1 | 4/2001 | Robinson |
| 6,225,473 B1 | 5/2001 | Breipohl et al. |
| 6,258,540 B1 | 7/2001 | Lo et al. |
| 6,284,764 B1 | 9/2001 | Kath et al. |
| 6,291,455 B1 | 9/2001 | Thomas et al. |
| 6,294,532 B1 | 9/2001 | Thomas et al. |
| 6,303,636 B1 | 10/2001 | Robinson, Jr. et al. |
| 6,362,336 B1 | 3/2002 | Lohmann et al. |
| 6,399,633 B1 | 6/2002 | Dumont et al. |
| 6,406,912 B1 | 6/2002 | Holla |
| 6,437,136 B2 | 8/2002 | Breipohl et al. |
| 6,492,383 B1 | 12/2002 | Munchhof et al. |
| 6,495,568 B1 | 12/2002 | Dack et al. |
| 6,511,993 B1 | 1/2003 | Dack et al. |
| 6,576,647 B2 | 6/2003 | Bafus et al. |
| 6,596,726 B1 | 7/2003 | Bridges et al. |
| 6,599,890 B1 | 7/2003 | McClure et al. |
| 6,723,726 B1 | 4/2004 | Cockerill et al. |
| 6,821,990 B2 | 11/2004 | Kesseler |
| 6,828,320 B2 | 12/2004 | Cockerill et al. |
| 6,849,631 B2 | 2/2005 | Carini |
| 7,064,193 B1 | 6/2006 | Cory et al. |
| 7,119,090 B2 | 10/2006 | Tang et al. |
| 7,332,582 B2 | 2/2008 | Hardy et al. |
| 7,417,055 B2 | 8/2008 | Cannizzaro et al. |
| 7,452,901 B2 | 11/2008 | Booiamra et al. |
| 7,488,802 B2 | 2/2009 | Collins et al. |
| 7,572,924 B2 | 8/2009 | Tang et al. |
| 7,695,715 B2 | 4/2010 | Hardy et al. |
| 7,714,005 B2 | 5/2010 | Chen et al. |
| 7,790,902 B2 | 9/2010 | Larson et al. |
| 7,816,398 B2 | 10/2010 | Swindell et al. |
| 7,829,662 B2 | 11/2010 | Korsmeyer et al. |
| 7,868,133 B2 | 1/2011 | Korsmeyer et al. |
| 7,884,127 B2 | 2/2011 | Lal et al. |
| 7,943,743 B2 | 5/2011 | Korman et al. |
| 8,008,449 B2 | 8/2011 | Korman et al. |
| 8,168,179 B2 | 5/2012 | Honjo et al. |
| 8,168,755 B2 | 5/2012 | Cardone et al. |
| 8,217,149 B2 | 7/2012 | Irving et al. |
| 8,221,966 B2 | 7/2012 | Letai |
| 8,304,449 B2 | 11/2012 | Lal et al. |
| 8,354,509 B2 | 1/2013 | Carven et al. |
| 8,372,819 B2 | 2/2013 | Jones et al. |
| 8,460,927 B2 | 6/2013 | Chen |
| 8,552,154 B2 | 10/2013 | Freeman et al. |
| 8,552,156 B2 | 10/2013 | Takayanagi et al. |
| 8,686,119 B2 | 4/2014 | Rotem-Yehudar et al. |
| 8,735,553 B1 | 5/2014 | Li et al. |
| 8,758,752 B2 | 6/2014 | Govindan et al. |
| 8,779,108 B2 | 7/2014 | Queva et al. |
| 8,822,526 B2 | 9/2014 | Rathos et al. |
| 8,841,418 B2 | 9/2014 | Karsunky et al. |
| 8,907,053 B2 | 12/2014 | Sasikumar et al. |
| 8,927,697 B2 | 1/2015 | Davis et al. |
| 8,975,239 B2 | 3/2015 | Green et al. |
| 8,993,731 B2 | 3/2015 | Tyson |
| 9,102,727 B2 | 8/2015 | Freeman et al. |
| 9,138,485 B2 | 9/2015 | Govindan et al. |
| 9,163,087 B2 | 10/2015 | Kuchroo et al. |
| 9,175,082 B2 | 11/2015 | Zhou et al. |
| 9,199,973 B2 | 12/2015 | Carter et al. |
| 9,205,148 B2 | 12/2015 | Langermann et al. |
| 9,241,941 B2 | 1/2016 | Wendel et al. |
| 9,244,059 B2 | 1/2016 | Triebel et al. |
| 9,340,524 B2 | 5/2016 | Chen et al. |
| 9,360,473 B2 | 6/2016 | Cardone |
| 9,493,454 B2 | 11/2016 | Zeng et al. |
| 9,505,839 B2 | 11/2016 | Lonberg et al. |
| 9,540,674 B2 | 1/2017 | Letai |
| 9,605,070 B2 | 3/2017 | Sabatos-Peyton et al. |
| 9,683,048 B2 | 6/2017 | Freeman et al. |
| 9,758,539 B2 | 9/2017 | Siddiqui-Jain et al. |
| 9,856,303 B2 | 1/2018 | Korsmeyer et al. |
| 9,901,574 B2 | 2/2018 | Warner et al. |
| 9,902,759 B2 | 2/2018 | Korsmeyer et al. |
| 9,925,192 B2 | 3/2018 | Strack et al. |
| 9,988,452 B2 | 6/2018 | Freeman et al. |
| 10,132,797 B2 | 11/2018 | Bearss et al. |
| 10,259,835 B2 | 4/2019 | Siddiqui-Jain et al. |
| 10,267,787 B2 | 4/2019 | Bearss et al. |
| 10,357,488 B2 | 7/2019 | Warner et al. |
| 10,422,788 B2 | 9/2019 | Bearss et al. |
| 10,562,925 B2 | 2/2020 | Siddiqui-Jain et al. |
| 10,568,887 B2 | 2/2020 | Bearss et al. |
| 10,624,880 B2 | 4/2020 | Warner et al. |
| 10,682,356 B2 | 6/2020 | Bearss et al. |
| 10,793,915 B2 | 10/2020 | Dettman et al. |
| 10,835,537 B2 | 11/2020 | Bearss et al. |
| 11,034,710 B2 * | 6/2021 | Siddiqui-Jain ........ A61P 35/00 |
| 11,279,694 B2 | 3/2022 | Siddiqui-Jain et al. |
| 11,497,756 B2 | 11/2022 | Bearss et al. |
| 11,530,231 B2 * | 12/2022 | Siddiqui-Jain ....... A61K 9/2054 |
| 11,793,802 B2 | 10/2023 | Bearss et al. |
| 2001/0021704 A1 | 9/2001 | Ghyczy et al. |
| 2002/0016293 A1 | 2/2002 | Ratain et al. |
| 2002/0115613 A1 | 8/2002 | Kumar |
| 2002/0177609 A1 | 11/2002 | Swindell et al. |
| 2003/0065023 A1 | 4/2003 | Swindell et al. |
| 2003/0073661 A1 | 4/2003 | Matsuyama et al. |
| 2003/0119816 A1 | 6/2003 | Haesslein et al. |
| 2004/0106647 A1 | 6/2004 | Schneider et al. |
| 2004/0171809 A1 | 9/2004 | Korsmeyer et al. |
| 2004/0235783 A1 | 11/2004 | Ghyczy et al. |
| 2005/0026959 A1 | 2/2005 | Kesseler |
| 2005/0153991 A1 | 7/2005 | Gianella-Borradori et al. |
| 2007/0093490 A1 | 4/2007 | Prien et al. |
| 2008/0027105 A1 | 1/2008 | Suarez et al. |
| 2008/0108657 A1 | 5/2008 | Kessler |
| 2009/0030005 A1 | 1/2009 | Kamb et al. |
| 2009/0142337 A1 | 6/2009 | Squires |
| 2010/0143350 A1 | 6/2010 | Green et al. |
| 2010/0286057 A1 | 11/2010 | Walensky et al. |
| 2011/0008371 A1 | 1/2011 | Michelson |
| 2011/0251240 A1 | 10/2011 | Suarez et al. |
| 2012/0225851 A1 | 9/2012 | Cardone et al. |
| 2013/0079424 A1 | 3/2013 | Gerber et al. |
| 2013/0122492 A1 | 5/2013 | Khosravi et al. |
| 2013/0210024 A1 | 8/2013 | Yu et al. |
| 2014/0140956 A1 | 5/2014 | Fairfax et al. |
| 2014/0286861 A1 | 9/2014 | Govindan et al. |
| 2014/0303167 A1 | 10/2014 | Choidas et al. |
| 2015/0051249 A1 | 2/2015 | Walensky |
| 2015/0150869 A1 | 6/2015 | Cardone et al. |
| 2015/0259420 A1 | 9/2015 | Triebel et al. |
| 2015/0301053 A1 | 10/2015 | Pierceall et al. |
| 2015/0352097 A1 | 12/2015 | Cardone et al. |
| 2015/0362479 A1 | 12/2015 | Letai et al. |

(56) References Cited

U.S. PATENT DOCUMENTS

| | | |
|---|---|---|
| 2016/0178612 A1 | 6/2016 | Cardone |
| 2016/0231314 A1 | 8/2016 | Ryan et al. |
| 2016/0235779 A1 | 8/2016 | Marcus |
| 2016/0258933 A1 | 9/2016 | Letai |
| 2016/0273020 A1 | 9/2016 | Pierceall et al. |
| 2016/0279106 A1 | 9/2016 | Ueda et al. |
| 2017/0184567 A1 | 6/2017 | Letai |
| 2017/0260268 A1 | 9/2017 | Beatty et al. |
| 2018/0280407 A1 | 10/2018 | Warner et al. |
| 2019/0314357 A1 | 10/2019 | Bearss et al. |
| 2020/0048228 A1 | 2/2020 | Siddiqui-Jain et al. |
| 2020/0131210 A1 | 4/2020 | Siddiqui-Jain et al. |
| 2020/0200737 A1 | 6/2020 | Bearss et al. |
| 2020/0255462 A1 | 8/2020 | Siddiqui-Jain et al. |
| 2020/0276174 A1 | 9/2020 | Bearss et al. |
| 2020/0281949 A1 | 9/2020 | Warner et al. |
| 2020/0316084 A1 | 10/2020 | Warner et al. |
| 2021/0052568 A1 | 2/2021 | Warner et al. |
| 2021/0261585 A1 | 8/2021 | Siddiqui-Jain et al. |
| 2021/0277037 A1 | 9/2021 | Siddiqui-Jain |
| 2021/0379402 A1 | 12/2021 | Smith et al. |
| 2022/0125776 A1 | 4/2022 | Bearss et al. |
| 2022/0339172 A1 | 10/2022 | Warner et al. |

FOREIGN PATENT DOCUMENTS

| | | |
|---|---|---|
| EP | 0 253 739 B1 | 10/1989 |
| EP | 0 253 738 B1 | 1/1990 |
| EP | 0 507 278 A2 | 10/1992 |
| EP | 0 241 003 B1 | 10/1993 |
| EP | 0 321 918 B1 | 3/1994 |
| EP | 0 606 046 A1 | 7/1994 |
| EP | 0 366 061 B1 | 1/1996 |
| EP | 0 474 129 B1 | 12/1996 |
| EP | 0 780 386 A1 | 6/1997 |
| EP | 0 818 442 A2 | 1/1998 |
| EP | 0 931 788 A2 | 7/1999 |
| EP | 1 004 578 A2 | 5/2000 |
| EP | 0 979 824 B1 | 10/2004 |
| FR | 2 338 043 A1 | 8/1977 |
| GB | 9912961.1 | 6/1999 |
| IN | CHENP-2007-03645 A | 8/2007 |
| JP | 2003-519698 | 6/2003 |
| JP | 2004-529125 A | 9/2004 |
| JP | 2007-291111 A | 11/2007 |
| JP | 2008-513494 A | 5/2008 |
| JP | 2009-507820 A | 2/2009 |
| JP | 2011-511803 A | 4/2011 |
| JP | 2013-533213 A | 8/2013 |
| RU | 2 438 664 C2 | 1/2012 |
| RU | 2 474 582 C2 | 2/2013 |
| RU | 2 552 642 C2 | 6/2015 |
| WO | WO 1990/005719 A1 | 5/1990 |
| WO | WO 1991/000360 A1 | 1/1991 |
| WO | WO 1992/009589 A1 | 11/1992 |
| WO | WO 1992/020373 A1 | 11/1992 |
| WO | WO 1993/008829 A1 | 5/1993 |
| WO | WO 1994/002602 A1 | 2/1994 |
| WO | WO 1994/011026 A2 | 5/1994 |
| WO | WO 1995/019970 A1 | 7/1995 |
| WO | WO 1995/021613 A1 | 8/1995 |
| WO | WO 1996/015263 A1 | 5/1996 |
| WO | WO 1996/027011 A1 | 9/1996 |
| WO | WO 1996/027583 A1 | 9/1996 |
| WO | WO 1996/033172 A1 | 10/1996 |
| WO | WO 1996/033735 A1 | 10/1996 |
| WO | WO 1996/034096 A1 | 10/1996 |
| WO | WO 1997/005265 A1 | 2/1997 |
| WO | WO 1997/013760 A1 | 4/1997 |
| WO | WO 1997/016447 A1 | 5/1997 |
| WO | WO 1997/022596 A1 | 6/1997 |
| WO | WO 1997/030174 A1 | 8/1997 |
| WO | WO 1997/032856 A1 | 9/1997 |
| WO | WO 1997/042949 A1 | 11/1997 |
| WO | WO 1998/002434 A1 | 1/1998 |
| WO | WO 1998/002437 A1 | 1/1998 |
| WO | WO 1998/002438 A1 | 1/1998 |
| WO | WO 1998/003516 A1 | 1/1998 |
| WO | WO 1998/007697 A1 | 2/1998 |
| WO | WO 1998/013344 A1 | 4/1998 |
| WO | WO 1998/014451 A1 | 4/1998 |
| WO | WO 1998/030566 A1 | 7/1998 |
| WO | WO 1998/033768 A1 | 8/1998 |
| WO | WO 1998/033798 A2 | 8/1998 |
| WO | WO 1998/034915 A1 | 8/1998 |
| WO | WO 1998/034918 A1 | 8/1998 |
| WO | WO 1998/050356 A1 | 11/1998 |
| WO | WO 1998/054093 A1 | 12/1998 |
| WO | WO 1999/007675 A1 | 2/1999 |
| WO | WO 1999/010349 A1 | 3/1999 |
| WO | WO 1999/016755 A1 | 4/1999 |
| WO | WO 1999/016787 A1 | 4/1999 |
| WO | WO 1999/024440 A1 | 5/1999 |
| WO | WO 1999/029667 A1 | 6/1999 |
| WO | WO 1999/035132 A1 | 7/1999 |
| WO | WO 1999/035146 A1 | 7/1999 |
| WO | WO 1999/052889 A1 | 10/1999 |
| WO | WO 1999/052910 A1 | 10/1999 |
| WO | WO 1999/053049 A1 | 10/1999 |
| WO | WO 1999/061422 A1 | 12/1999 |
| WO | WO 1999/062890 A1 | 12/1999 |
| WO | WO 2000/006134 A2 | 2/2000 |
| WO | WO 2000/012071 A2 | 3/2000 |
| WO | WO 2000/044362 A2 | 8/2000 |
| WO | WO 2000/059526 A1 | 10/2000 |
| WO | WO 2001/012661 A2 | 2/2001 |
| WO | WO 2001/060814 A2 | 8/2001 |
| WO | WO 2002/020568 A2 | 3/2002 |
| WO | WO 2003/028001 A1 | 4/2003 |
| WO | WO 2003/040168 A2 | 5/2003 |
| WO | WO 2004/022580 A2 | 3/2004 |
| WO | WO 2004/058804 A1 | 7/2004 |
| WO | WO 2005/017107 A2 | 2/2005 |
| WO | WO 2005/044839 A2 | 5/2005 |
| WO | WO 2006/099667 A1 | 9/2006 |
| WO | WO 2006/101846 A1 | 9/2006 |
| WO | WO 2006/121168 A1 | 11/2006 |
| WO | WO 2007/123791 A2 | 11/2007 |
| WO | WO 2008/021484 A2 | 2/2008 |
| WO | WO 2008/106635 A1 | 9/2008 |
| WO | WO 2008/132601 A1 | 11/2008 |
| WO | WO 2009/044273 A2 | 4/2009 |
| WO | WO 2010/019570 A2 | 2/2010 |
| WO | WO 2010/027827 A2 | 3/2010 |
| WO | WO 2010/030727 A1 | 3/2010 |
| WO | WO 2010/093742 A1 | 8/2010 |
| WO | WO 2010/147961 A1 | 12/2010 |
| WO | WO 2011/054553 A1 | 5/2011 |
| WO | WO 2011/066342 A2 | 6/2011 |
| WO | WO 2011/088137 A2 | 7/2011 |
| WO | WO 2011/143660 A2 | 11/2011 |
| WO | WO 2011/153374 A1 | 12/2011 |
| WO | WO 2012/075383 A2 | 6/2012 |
| WO | WO 2012/122370 A2 | 9/2012 |
| WO | WO 2012/145493 A1 | 10/2012 |
| WO | WO 2013/079174 A1 | 6/2013 |
| WO | WO 2013/082660 A1 | 6/2013 |
| WO | WO 2013/138702 A2 | 9/2013 |
| WO | WO 2013/170176 A2 | 11/2013 |
| WO | WO 2013/182519 A1 | 12/2013 |
| WO | WO 2013/188355 A1 | 12/2013 |
| WO | WO 2013/188978 A1 | 12/2013 |
| WO | WO 2014/022758 A1 | 2/2014 |
| WO | WO 2014/047342 A1 | 3/2014 |
| WO | WO 2014/055897 A2 | 4/2014 |
| WO | WO 2014/059028 A1 | 4/2014 |
| WO | WO 2014/066848 A1 | 5/2014 |
| WO | WO 2014/100079 A1 | 6/2014 |
| WO | WO 2014/140180 A1 | 9/2014 |
| WO | WO 2014/179664 A2 | 11/2014 |
| WO | WO 2014/194302 A2 | 12/2014 |
| WO | WO 2014/209804 A1 | 12/2014 |
| WO | WO 2013/170176 A3 | 1/2015 |
| WO | WO 2015/010094 A1 | 1/2015 |

(56) References Cited

FOREIGN PATENT DOCUMENTS

| | | |
|---|---|---|
| WO | WO 2015/017788 A1 | 2/2015 |
| WO | WO 2015/042249 A1 | 3/2015 |
| WO | WO 2015/047510 A1 | 4/2015 |
| WO | WO 2015/061668 A1 | 4/2015 |
| WO | WO 2015/066305 A1 | 5/2015 |
| WO | WO 2015/070020 A2 | 5/2015 |
| WO | WO 2015/081158 A1 | 6/2015 |
| WO | WO 2015/085847 A1 | 6/2015 |
| WO | WO 2015/109124 A2 | 7/2015 |
| WO | WO 2015/112800 A1 | 7/2015 |
| WO | WO 2015/112805 A1 | 7/2015 |
| WO | WO 2015/116539 A1 | 8/2015 |
| WO | WO 2015/130585 A1 | 9/2015 |
| WO | WO 2015/161247 A1 | 10/2015 |
| WO | WO 2015/181342 A1 | 12/2015 |
| WO | WO 2015/195163 A1 | 12/2015 |
| WO | WO 2015/200119 A1 | 12/2015 |
| WO | WO 2016/000619 A1 | 1/2016 |
| WO | WO 2016/028672 A1 | 2/2016 |
| WO | WO 2016/061144 A1 | 4/2016 |
| WO | WO 2016/071448 A1 | 5/2016 |
| WO | WO 2016/073913 A1 | 5/2016 |
| WO | WO 2016/092419 A1 | 6/2016 |
| WO | WO 2016/111947 A2 | 7/2016 |
| WO | WO 2016/115105 A1 | 7/2016 |
| WO | WO 2016/144803 A2 | 9/2016 |
| WO | WO 2016/149613 A2 | 9/2016 |
| WO | WO 2016/154380 A1 | 9/2016 |
| WO | WO 2016/161270 A1 | 10/2016 |
| WO | WO 2016/172214 A1 | 10/2016 |
| WO | WO 2016/176288 A1 | 11/2016 |
| WO | WO 2016/176299 A1 | 11/2016 |
| WO | WO 2016/187316 A1 | 11/2016 |
| WO | WO 2017/024073 A1 | 2/2017 |
| WO | WO 2017/075349 A1 | 5/2017 |
| WO | WO 2017/187316 A1 | 11/2017 |
| WO | WO 2018/013918 A1 | 1/2018 |
| WO | WO 2018/094275 A1 | 5/2018 |
| WO | WO 2018/119000 A1 | 6/2018 |
| WO | WO 2019/055579 A1 | 3/2019 |
| WO | WO 2019/200243 A1 | 10/2019 |
| WO | WO 2019/246421 A1 | 12/2019 |
| WO | WO 2020/077300 A1 | 4/2020 |
| WO | WO 2020/092615 A1 | 5/2020 |
| WO | WO 2020/117988 A1 | 6/2020 |
| WO | WO 2020/118252 A1 | 6/2020 |
| WO | WO2020/191326 A1 | 9/2020 |
| WO | WO 2021/007316 | 1/2021 |
| WO | WO 2021/007314 | 2/2021 |
| WO | WO 2021/113688 A1 | 6/2021 |

OTHER PUBLICATIONS

Alvocidib, definition of alvocidib, NCI Dictionary of Cancer Terms-National Cancer Institute, retrieved from URL: https://www.cancer.gov/publications/dictionaries/cancer-terms/def/alvocidib on Jan. 7, 2021, 1 page.
"Common Terminology Criteria for Adverse Events, Version 5.0" National Cancer Institute, National Institutes of Health, U.S. Department of Health and Human Services, Published: Nov. 27, 2017, URL=https://ctep.cancer.gov/protocoldevelopment/electronic _applications/docs/CTCAE _ v5 Quick Reference 8.5x1 1.pdf, Accessed: Dec. 31, 2020, (147 pages).
Adams, et al., "The Bcl-2 Protein Family: Arbiters of Cell Survival," Science, 281(5381):1322-1326 (1998).
Adlard, et al., "Prediction of the response of colorectal cancer to systemic therapy," The Lancet Oncology, 3:75-82 (2002).
Aït-Ikhlef, et al., "The motoneuron degeneration in the wobbler mouse is independent of the overexpression of a Bcl2 transgene in neurons," Neurosci Lett, 199: 163-166 (1995).
Akgul, C., "Mcl-1 is a Potential Therapeutic Target in Multiple Types of Cancer", Cell. Mol. Life Sci., 66:1326-1336 (2009).
Almarzooqi, et al., "Comparison of Peripheral Blood versus Bone Marrow Blasts Immunophenotype in Pediatric Acute Leukemias," Ibnosina Journal of Medicine and Biomedical Sciences, pp. 195-204, 2011 (10 pages).
Altschul, et al., "Gapped BLAST and PSI-BLAST: a new generation of protein database search programs," Nucleic Acids Res., 25:3389-3402 (1997).
Al-Mawali, "Leukemic Stem Cells Shows the Way for Novel Target of Acute Myeloid Leukemia Therapy," J. Stem Cell Res. Ther., 3(4):1-8 (2013).
Araki et al., "Allogeneic Hematopoietic Cell Transplantation for Acute Myeloid Leukemia: Time to Move Toward a Minimal Residual Disease-Based Definition of Complete Remission?" J Clin Oncol, 34(4):329-336 (2016).
Arguello et al., "Flavopiridol induces apoptosis of normal lymphoid cells, causes immunosuppression, and has potent antitumor activity in vivo against human leukemia and lymphoma xenografts," Blood, 91(7):2482-2490 (1998).
Attal, M., et al., "Lenalidomide Maintenance after Stem-Cell Transplantation for Multiple Myeloma," The New England Journal of Medicine, 366:1782-1791 (2012).
Awan, F. T., et al., "A Phase I Clinical Trial of Flavopiridol Consolidation in Chronic Lymphocytic Leukemia Patients Following Chemoimmunotherapy", Ann Hematol, 95:1137-1143 (2016).
Bae et al., "Underphosphorylated BAD interacts with diverse antiapoptotic Bcl-2 family proteins to regulate apoptosis," Apoptosis, 6:319-330 (2001).
Barretina et al., "The Cancer Cell Line Encyclopedia enables predictive modelling of anticancer drug sensitivity," Nature, 483(7391):603-607, 2012; Erratum in: Nature, 492(7428):290 (2012).
Bearss, "NOXA Priming—Predictive Biomarker For Patients With Acute Myeloid Leukemia To Improve Treatment Outcomes," 2016, retrieved from https: // openforum .hbs. org/challenge/ precision -medicine/ submit-ideas/noxa-priming-predic . . . , (7 pages).
Bearss, "Targeting MCL1 dependent cancers by CDK9 inhibition," Abstract for Keynote Address, 9th International Conference on Leukemia and Hematologic Oncology, Oct. 5-6, 2017 London, UK, J Hematol Thrombo Dis 5(5 Suppl), 2017. (1 page).
Beauchamp, et al., "Amino Acid Ester Prodrugs of Acyclovir", Antiviral Chemistry and Chemotherapy, 3(3):157-164 (1992).
Beesley, A.H. et al., "Comparative drug screening in NUT midline carcinoma," British Journal of Cancer, vol. 110; 1189-1198 (2014).
Belikov, "Pharmaceutical chemistry," High School, 1:43-47, Moscow, 1993 (English translation attached) (14 pages).
Belmar, J. and Fesik, S.W., "Small Molecule Mcl-1 Inhibitors for the Treatment of Cancer", Pharmacol Ther., 145:76-84 (2015).
Benyon, B., "FDA Grants Venclexta an Accelerated Approval for AML Treatment", Nov. 21, 2018, 2 pages, URL: https://www.curetoday.com/articles/fda-grants-venclexta-an-accelerated-approval-for-aml-treatment.
Berge, et al., "Pharmaceutical Salts," Journal of Pharmaceutical Sciences, 66(1):1-19 (1977).
Besbes et al. "First MCL-1-selective BH3 mimetics as potential therapeutics for targeted treatment of cancer," Cell Death and Disease, 6(7) (2015). (2 pages).
Bible et al., "Cytotoxic Synergy Between Flavopiridol (NSC 649890, L86-8275) and Various Antineoplastic Agents: The Importance of Sequence of Administration," Cancer Research, 57:3375-3380 (1997).
Billard, C., "BH3 Mimetics: Status of the Field and New Developments", Mol Cancer Ther, 12(9):1671-1700 (2013).
Blachly et al., "Emerging Drug Profile: Cyclin-Dependent Kinase Inhibitors," Leuk Lymphoma, 54:2133-2143 (2013). (22 pages).
Blum, et al., "Phase I clinical and pharmacokinetic study of a novel schedule of flavopiridol in relapsed or refractory acute leukemias," Haematologica, 95(7): 1098-1105 (2010).
Bodet et al., "BH3-only protein Bik is involved in both apoptosis induction and sensitivity to oxidative stress in multiple myeloma," Br. J Cancer, 103: 1808-1814 (2010).
Boffo et al., "CDK9 Inhibitors in Acute Myeloid Leukemia," Journal of Experimental & Clinical Cancer Research, 37(36):1-10 (2018).

(56) References Cited

OTHER PUBLICATIONS

Bogenberger et al., "BCL-2 family proteins as 5-Azacytidine-sensitizing targets and determinants of response in myeloid malignancies," Leukemia, 28(8): 1657-1665 (2014).
Bogenberger, et al., "Combined venetoclax and alvocidib in acute myeloid leukemia," Oncotarget, 8(63): 107206-107222 (2017).
Bose, et al., "Mcl-1 as a therapeutic target in acute myelogenous leukemia (AML)," Leukemia Research Reports, 2: 12-14 (2013).
Bouillet, et al., "Proapoptotic Bcl-2 Relative Bim Required for Certain Apoptotic Responses, Leukocyte Homeostasis, and to Preclude Autoimmunity," Science, 286:1735-1738 (1999).
Boyd, et al., "Bik, a novel death-inducing protein shares a distinct sequence motif with Bcl-2 family proteins and interacts with viral and cellular survival-promoting proteins," Oncogene, 11(9):1921-1928 (1995).
Brady, et al., "Reflections on a peptide," Nature 368:692-693 (1994).
Bradbury, et al., "Optimisation of a series of bivalent triazolopyridazine based bromodomain and extraterminal inhibitors: the discovery of (3R)-4-[2-[4-[1-(3-methoxy-[1,2,4]triazolo[4,3-b]pyridazin-6-yl)-4-piperidyl]phenoxy]ethyl]-1,3-dimethyl-piperazin-2-one (AZD5153)," Journal of Medicinal Chemistry 59(17):7801-7817, 2016. [journal accepted manuscript].
Braun et al., "Preclinical Study Of The Bromodomain Inhibitor OTX015 In Acute Myeloid (AML) and Lymphoid (ALL) Leukemias," Blood, 122:4218 (2013). (5 pages) (Abstract Only).
Brennan et al., "Preparation of Bispecific Antibodies by Chemical Recombination of Monoclonal Immunoglobulin G1 Fragments," Science, 229:81 (1985) 4 pages.
Brüsselbach, et al., "Cell cycle-independent induction of apoptosis by the anti-tumor drug Flavopiridol in endothelial cells," Int. J. Cancer, 77(1): 146-152 (1998).
Brooks et al., "CVT-313, a specific and potent inhibitor of CDK2 that prevents neointimal proliferation," J Biol. Chem., 272(46):29207-29211 (1997).
Brunelle et al., "MCL-1-dependent leukemia cells are more sensitive to chemotherapy than BCL-2-dependent counterparts," J Cell. Biol., 187(3):429-442 (2009).
Brunetto, et al., "First-in-human, Pharmacokinetic and Pharmacodynamic Phase I Study of Resminostat, an Oral Histone Deacetylase Inhibitor, in Patients with Advanced Solid Tumors," Clinical Cancer Research, 20:5494-5504 (2013).
Buccisano, et al., "Prognostic and therapeutic implications of minimal residual disease detection in acute myeloid leukemia," Blood, 119(2):332-341 (2012).
Buggy, et al., "CRA-024781: a novel synthetic inhibitor of histone deacetylase enzymes with antitumor activity in vitro and in vivo," Mal Cancer Ther, 5:1309-1317 (2006).
Buijs, et al., "A novel CBFA2 single-nucleotide Mutation in Familial Platelet Disorder with Propensity to Develop Myeloid Malignancies," Blood 98(9):2856-2858 (2001).
Bundgard, H., in Design of Prodrugs, Bungard, H. ed., (NY:Elsevier),pp. 7-9 and 21-24, (1985).
Buron, et al., "Use of human cancer cell lines mitochondria to explore the mechanisms of BH3 peptides and ABT-73 7-induced mitochondrial membrane permeabilization," PLoS One, Mar. 2010, 5(3): e9924.
Burrer et al., "Selective Peptide Inhibitors of Antiapoptotic Cellular and Viral Bcl-2 Proteins Lead to Cytochrome C Release During Latent Kaposi's Sarcoma-Associated Herpesvirus Infection," Virus Res. 211:86-88, 2016. (Author's manuscript).
Byrd, et al., "Pretreatment cytogenetic abnormalities are predictive of induction success, cumulative incidence of relapse, and overall survival in adult patients with de novo acute myeloid leukemia: results from Cancer and Leukemia Group B (CALGB 8461)" Blood, 100(13):4325-4336 (2002).
Byrd, et al., "Chronic Lymphocytic Leukemia," American Society of Hematology Education Program Book, pp. 163-183 (2004).
Byrd, et al., "Flavopiridol Administered as a Pharmacologically-Derived Schedule Demonstrates Marked Clinical Activity in Refractory, Genetically High Risk, Chronic Lymphocytic Leukemia (CLL)," Blood, 104:341 (2004). (2 pages).
Byrd, et al., "Flavopiridol administered using a pharmacologically derived schedule is associated with marked clinical efficacy in refractory, genetically high-risk chronic lymphocytic leukemia," Blood, 109:399-404 (2007).
Byrd, et al., "Flavopiridol Induces Apoptosis in Chronic Lymphocytic Leukemia Cells Via Activation of Caspase-3 Without Evidence of bcl-2 Modulation or Dependence on Functional p53," Blood, 92:3804-3816 (1998).
Byrd, et al., "Sequential Phase II Studies of Flavopiridol by 72-Hour Continuous Infusion and 1-Hour Intravenous Bolus for the Treatment of Relapsed B-Cell Chronic Lymphocytic Leukemia: Results from CALGB Study 19805," Blood, 104:348 (2004) (2 pages).
Byrd, et al., "Treatment of Relapsed Chronic Lymphocytic Leukemia by 72-Hour Continuous Infusion or I-Hour Bolus Infusion of Flavopiridol: Results from Cancer and Leukemia Group B Study 19805," Clin Cancer Res, 11:4176-4181 (2005).
Byrn, S et al., "Pharmaceutical Solids: A Strategic Approach to Regulatory Considerations," Pharmaceutical Research, vol. 12; No. 7; 10 pages (1995).
Calin, et al., "A MicroRNA Signature Associated with Prognosis and Progression in Chronic Lymphocytic Leukemia," N. Engl. J. Med., 353: 1793-1801 (2005).
Cannon, "Chapter Nineteen: Analog Design," Burger's Medicinal Chemistry and Drug Discovery, Fifth Edition, vol. 1: Principles and Practice, Wiley-Interscience, pp. 783-802, 784 (1995).
Carlson, et al., "Flavopiridol Induces G, Arrest with Inhibition of Cyclin-dependent Kinase (CDK) 2 and CDK4 in Human Breast Carcinoma Cells," Cancer Research, 56:2973-2978 (1996).
Caron, et al., "Engineered Humanized Dimeric Forms of IgG are More Effective Antibodies," J Exp Med, 176:1191-1195 (1992).
Cartron, et al., "The first a Helix of Bax Plays a Necessary Role in Its Ligand-Induced Activation by the BH3-Only Proteins Bid and PUMA," Mal. Cell. 16:807-818, 2004. by the BH3-Only Proteins Bid and PUMA, Mal. Cell., 16:807-818 (2004).
CAS Registry No. 146426-40-6—Flavopiridol (1993).
CAS Registry No. 951209-71-5, "IRX 2" Entered STN Oct. 23, 2007, 1 page.
Certo, et al., "Mitochondria Primed by Death Signals Determine Cellular Addiction to Antiapoptotic BCL-2 Family Members," Cancer Cell, 9:351-365 (2006).
Chan, et al., "Belinostat and panobinostat (HDACI): in vitro and in vivo studies in thyroid cancer," J Cancer Res Clin Oncol, 139:1507-1514 (2013).
Chang, et al., "Adenovirus-mediated over-expression of the cyclin/cyclin-dependent kinase inhibitor, p21 inhibits vascular smooth muscle cell proliferation and neointima formation in the rat carotid artery model of balloon angioplasty," J Clin. Invest., 96:2260-2268 (1995).
Chao, et al., "Flavopiridol Inactivates P-TEFb and Blocks Most RNA Polymerase II Transcription in Vivo," The Journal of Biological Chemistry, 276:31793-31799 (2001).
Chao, et al., "Flavopiridol Inhibits P-TEFb and Blocks HIV-1 Replication," The Journal of Biological Chemistry, 275:28345-28348 (2000).
Chen, et al., "Androgen Receptor Serine 81 Phosphorylation Mediates Chromatin Binding and Transcriptional Activation," Journal of Biological Chemistry, 287(11):8571-8583 (2012).
Chen, et al., "Caspase cleavage of BIMEL triggers a positive feedback amplification of apoptotic signaling," Proc. Natl. Acad. Sci. USA, 101(5):1235-1240 (2004).
Chen, C., et al., "Lenalidomide in Multiple Myeloma—a Practice Guideline", Curr Oncol, 20(2):e136-e149 (2013).
Chen et al., "Differential Targeting of Prosurvival Bcl-2 Proteins by Their BH3-Only Ligands Allows Complementary Apoptotic Function," Molecular Cell, 17:393-403 (2005).
Chen, et al., "Downregulation of cyclin-dependent kinase 2 activity and cyclin A promoter activity in vascular smooth muscle cells by p27(KIP1), an inhibitor of neointima formation in the rat carotid artery," J Clin. Invest., 99:2334-2341 (1997).

(56) References Cited

OTHER PUBLICATIONS

Chen, et al., "Mcl-1 Down-regulation Potentiates ABT-737 Lethality by Cooperatively Inducing Bak Activation and Bax Translocation," Cancer Res 67(2):782-791 (2007).
Chen, et al., "Mechanism of action of SNS-032, a novel cyclin-dependent kinase inhibitor in chronic lymphocytic leukemia," Blood, 113:4637-4645 (2009).
Chen, et al., "Transcription inhibition by flavopiridol: mechanism of chronic lymphocytic leukemia cell death," Blood, 106:2513-2519 (2005).
Cheng, et al., "Bax-independent inhibition of apoptosis by Bel-XL," Nature, 379:554-556 (1996).
Cheng, et al., "BCL-2, BCL-XL Sequester BH3 Domain-Only Molecules Preventing BAX- and BAK-Mediated Mitochondrial Apoptosis," Mal. Cell, 8(3):705-711 (2001).
Cheronis, "Semimicro Experimental Organic Chemistry," deGratt, pp. 67-69 (1958).
Cheson, et al., "National Cancer Institute-Sponsored Working Group Guidelines for Chronic Lymphocytic Leukemia: Revised Guidelines for Diagnosis and Treatment," Blood, 87:4990-4997 (1996).
Chipuk, et al., "Direct Activation of Bax by p53 Mediates Mitochondrial Membrane Permeabilization and Apoptosis," Science, 303: 1010-1014 (2004).
Chittenden, et al., "A Conserved Domain in Bak, Distinct from BH1 and BH2, Mediates Cell Death and Protein Binding Functions," The EMBO Journal, 14(22):5589-5596 (1995).
Chittenden, et al., "Induction of apoptosis by the Bcl-2 homologue Bak," Nature, 374(6524):733-736 (1995).
Chonghaile, et al., "Mimicking the BH3 domain to kill cancer cells," Oncogene, 27:S149-S157 (2009).
Chonghaile, et al., "Mitochondrial Apoptotic Priming Measured by BH3 Profiling Regulates Clinical Response to Chemotherapy in Myeloma and Acute Lymphoblastic Leukemia and Explains Therapeutic Index," Abstract 1442, 53rd ASH Annual Meeting and Exposition, Dec. 10-13, 2011, American Society of Hematology, 6 pages.
Chonghaile, et al., "Pretreatment mitochondrial priming correlates with clinical response to cytotoxic chemotherapy," Science, 334(6059):1129-1133 (2011).
Chonghaile, et al., "Pretreatment mitochondrial priming correlates with clinical response to cytotoxic chemotherapy," Science, 334(6059):1129-1133 (2011). Supporting Online Material, 36 pages.
Chou, et al., "Quantitative Analysis of Dose-Effect Relationships: The Combined Effects of Multiple Drugs or Enzyme Inhibitors," Advances in Enzyme Regulation, 22:27-55 (1984).
Christian, B. A., et al., "Flavopiridol in Chronic Lymphocytic Leukemia: A Concise Review," Clinical Lymphoma & Myeloma, 9(Suppl 3):S179-S185 (2009).
Choudhary, et al., "MCL-1 and BCL-xL-dependent resistance to the BCL-2 inhibitor ABT-199 can be overcome by preventing P13K/AKT/mTOR activation in lymphoid malignancies," Cell Death and Disease, 6:e1593 (2015). (12 pages).
Caira, M.R., "Crystalline Polymorphism of Organic Compounds," Topics in Current Chemistry, vol. 198; Springer Verlag; 46 pages (1998).
Clinical Study, "Alvocidib, followed by cytarabine + mitoxantrone, makes impact in AML", Inpharma Wkly, 1606: 8 (2007). (Abstract).
Clowes, et al., "Significance of quiescent smooth muscle migration in the injured rat carotid artery," Circ. Res., 56(1):139-145 (1985).
Clowes A W, et al., "Kinetics of cellular proliferation after arterial injury", Lab. Invest, 49:327-333 (1998).
Common Terminology Criteria for Adverse Events (CTCAE) Version 5.0 Publichsed: Nov. 7, 2017 U.S. Department of Health and Human Services, National Institutes of Health, National Cancer Institute, URL=https://ctep.cancer.gov/protocoldevelopment/electronic_applications/docs/CTCAE_v5_Quick Reference Accessed: Dec. 31, 2020, 147 pages.
Cole, et al., "The EBV-Hybridoma technique and its application to human lung cancer," Monoclonal Antibodies and Cancer Therapy, :77-96 (1985).

Conaway, et al., "The Mediator Complex and Transcription Elongation," Biochim Biophys Acta, 1829:69-75 (2013). (16 pages).
Corbett, et al., "Evaluation of Single Agents and Combinations of Chemotherapeutic Agents in Mouse Colon Carcinomas," Cancer, 40:2660-2680 (1977).
Corbett, et al., "Response to Transplantable Tumors of Mice to Antracenedione Derivatives Alone and in Combination with Clinically Useful Agents", Cancer Treatment Reports 66:1187-1200 (1982).
Cory, et al., "The Bcl2 Family: Regulators of the Cellular Life-Or-Death Switch," Nat. Rev. Cancer, 2(9):647-656 (2002).
Cosulich, et al., "Regulation of apoptosis by BH3 domains in a cell-free system," Curr. Biol, 7(12):913-920 (1997).
Cote, et al., "Generation of human monoclonal antibiotics reactive with cellular antigens," Proc. Natl. Acad. Sci. USA 80:2026-2030, 1983.
Czabotar, et al., "Bax Activation by Bim?," Cell Death and Differentiation, 16: 1187-1191 (2009).
Czabotar et al., "Structural insights into the degradation of Mcl-1 induced by BH3 domains," PNAS, 104:6217-6222 (2007).
Czech, et al., "Antitumoral activity of flavone L 86-8275 ," International Journal of Oncology, 6: 31-36 (1995).
Daigle, et al., "Potent Inhibition of DOTIL as Treatment of MLL-fusion Leukemia," Blood, 122:1017-1025 (2013).
Danial, et al., "Cell Death: Critical Control Points," Cell, 116:205-219 (2004).
Davids, et al., "BH3 profiling demonstrates that restoration of apoptotic priming contributes to increased sensitivity to PBK inhibition in stroma-exposed chronic lymphocytic leukemia cells," Blood, 118(21): Nov. 18, 2011, Abstract.
Davids, et al., "Targeting the B-Cell Lymphoma/Leukemia 2 Family in Cancer," Journal of Clinical Oncology, 30(25):3127-3135 (2012).
Dawson, et al. "Inhibition of BET recruitment to chromatin as an effective treatment for MLL-fusion leukaemia" Nature, 478:529-533 (2011).
De Azevedo, Jr. et al., "Structural basis for specificity and potency of a flavanoid inhibitor of human CDK2, a cell cycle kinase," Proc. Natl. Acad. Sci. USA, 93:2735-2740 (1996).
De Azevedo, Jr., et al., "Structural basis for inhibition of cyclin-dependent kinase 9 by flavopiridol," Biochemical and Biophysical Research Communications, 293:566-571 (2002).
De Young M. B, and Dichek D. A., "Gene therapy for restenosis", Circ. Res., 82:306-313 (1998).
Debrincat, et al., "BCL-2 is dispensable for thrombopoiesis and platelet survival," Cell Death & Disease, 6:el 721 (2015). (8 pages).
DeGrado, "Design of peptides and proteins," Adv. Protein Chem, 39:51-124 (1988).
De Haas et al., "Initial Diagnostic Work-Up of Acute Leukemia: ASCO Clinical Practice Guideline Endorsement of the College of American Pathologists and American Society of Hematology Guideline," J Clin Oncol 37(3):239-253, 2018.
Dehm, et al., "Alternatively spliced androgen receptor variants," Endocrine-Related Cancer, 18(5):R183-R196 (2011).
Deng, et al., "BH3 Profiling Identifies Three Distinct Classes of Apoptotic Blocks to Predict Response to ABT-737 and Conventional Chemotherapeutic Agents," Cancer Cell, 12: 171-185 (2007).
Derenne, et al., "Antisense strategy shows that Mcl-1 rather than Bcl-2 or Bel-XL is an essential survival protein of human myeloma cells," Blood, 100: 194-199 (2002).
Desagher, et al., "Bid-induced Conformational Change of Bax Is Responsible for Mitochondrial Cytochrome c Release during Apoptosis," J Cell Biol, 144(5):891-901 (1999).
Dettman, et al., "Abstract 3400: Mitochondrial profiling in AML patients treated with an Alvocidib containing regimen reveals MCL1 dependency in responder bone marrow," Cancer Res, 75:3400 (2015). (2 pages).
Di Lisa, et al., "Mitochondrial Function and Cell Injury in Single Cardiac Myocytes Exposed to Anoxia and Reoxygenation," Transplantation Proceedings, 27(5):2829-2830 (1995).
Di Lisa, et al., "Mitochondrial membrane potential in single living adult rat cardiac myocytes exposed to anoxia or metabolic inhibition," J Physiol, 486(1): 1-13 (1995).
Diamandis, et al., Immunoassay, Academic Press, Inc., NY (1996).

(56) References Cited

OTHER PUBLICATIONS

Dillman, et al., "A comparative study of two different doses of cytarabine for acute myeloid leukemia: a phase III trial of Cancer and Leukemia Group B," Blood, 78(10):2520-2526 (1991).
Dimopoulos et al., "Multiple Myeloma: EAH-ESMO Clinical Practice Guidelines for Diagnosis, Treatment and Follow-Up," Annals of Oncology, 32(3):309-322 (2021).
Dinardo, C.D., et al., "Venetoclax Combined with Decitabine or Azacitidine in Treatment-Naïve, Elderly Patients With Acute Myeloid Leukemia", Blood, 133:7-17 (2019).
Dinardo, C.D. and Cortes, J.E., "New Treatment for Acute Myelogenous Leukemia", Expert Opin. Pharmacother, 16(1):95-106 (2015).
Dinnen, et al., "Redirecting Apoptosis to Aponecrosis Induces Selective Cytotoxicity to Pancreatic Cancer Cells through Increased ROS, Decline in ATP Levels, and VDAC," Molecular Cancer Therapeutics 12:2792-2803, 2013.
Dittmann, et al., "The Commonly Used PB-Kinase Probe LY294002 Is an Inhibitor of BET Bromodomains," ACS Chem. Biol., 9(2):495-502 (2014).
Döhner, et al., "Genomic Aberrations and Survival in Chronic Lymphocytic Leukemia," N Engl. J Med., 343: 1910-1916 (2000).
Döhner, H., et al., "Acute Myeloid Leukemia", The New England Journal of Medicine, 373(12), 1136-1152 (2015).
Döhner et al., "Diagnosis and Management of AML in Adults: 2017 ELN Recommendations From an International Expert Panel," Blood 129(4):424-447, 2017.
Drees, et al., "Flavopiridol (L86-8275): Selective antitumor activity in vitro and activity in vivo for prostate carcinoma cells," Clin. Cancer Res., 3:273-279 (1997).
Egle, et al., "Bim is a suppressor of Myc-induced mouse B cell leukemia," Proc. Natl. Acad. Sci USA, 101(16):6164-6169 (2004).
Eichhorst et al., "Chronic Lymphocytic Leukaemia: ESMO Clinical Practice Guidelines for diagnosis, treatment and follow up," Annals of Oncology, 32(1):23-33 (2020).
Ellerby, et al., "Anti-cancer activity of targeted pro-apoptotic peptides," Nat. Med., 5(9): 1032-1038 (1999).
Elliott, et al., "Intercellular Trafficking and Protein Delivery by a Herpesvirus Structural Protein," Cell, 88:223-233 (1997).
Elston, et al., "Pathological prognostic factors in breast cancer. I. The value of histological grade in breast cancer: experience from a large study with long-term follow-up," Histopathology, 19:403-410 (1991).
Ember, et al., "Acetyl-lysine Binding Site of Bromodomain-Containing Protein 4 (BRD4) Interacts with Diverse Kinase Inhibitors," ACS Chemical Biology, 9: 1160-1171 (2014).
Eskes, et al., "Bid Induces the Oligomerization and Insertion of Bax into the Outer Mitochondrial Membrane," Mal. Cell. Biol., 20(3):929-935 (2000).
Evans, "Clathrate Compouns" in An Introduction to Crystal Chemistry, (London:Cambridge University Press), pp. 393-397 (1964).
Falkenberg, et al., "Histone deacetylases and their inhibitors in cancer, neurological diseases and immune disorders," Nature Reviews Drug Discovery, 13:673-691 (2014).
Fanidi, et al., "Cooperative interaction between c-myc and bcl-2 proto-oncogenes," Nature, 359:554-556 (1992).
Fenaux et al., "Myelodysplastic syndromes: ESMO Clinical Practice Guidelines for diagnosis, treatment and follow-up," Annals of Oncology, 25(Supplement 3):iii57-iii69 (2014).
Fernandez, et al., "Anthracycline Dose Intensification in Acute Myeloid Leukemia," New England Journal of Medicine, 361(13):1249-1259 (2009).
Ferrara, et al., "Consensus-based definition of unfitness to intensive and nonintensive chemotherapy in acute myeloid leukemia: a project of SIE, SIES and GITMO group on a new tool for therapy decision making," Leukemia, 27:997-999 (2013).
Férriz, et al., "Prodrug design of phenolic drugs," Current Pharmaceutical Design, 16(18): 2033-2052 (2010).
Filippakopoulos, et al., "Targeting bromodomains: epigenetic readers of lysine acetylation," Nature Reviews Drug. Discovery, 13:337-356, (2014).
Filippakopoulos, et al., "Selective inhibition of BET bromodomains," Nature, 468: 1067-1073 (2010).
Fish, et al., "Identification of a Chemical Probe for Bromo and Extra C-Terminal Bromodomain Inhibition through Optimization of a Fragment-Derived Hit," J Med. Chem., 55:9831-9837 (2012).
Fiskum, et al., "Apoptosis-Related Activities Measured with Isolated Mitochondria and Digitonin-Permeabilized Cells," Methods in Enzymology, 322:222-234 (2000).
Fiskus, et al., "Highly Active Combination of BRD4 Antagonist and Histone Deacetylase Inhibitor against Human Acute Myelogenous Leukemia Cells," Molecular Cancer Therapeutics, 13: 1142-1154 (2014).
Flinn, et al., "Flavopiridol Administered as a 24-Hour Continuous Infusion in Chronic Lymphocytic Leukemia lacks Clinical Activity," Leukemia Res, 29: 1253-1257 (2005).
Foight, et al., "Designed BH3 Peptides with High Affinity and Specificity for Targeting Mcl-1 in Cells," ACS Chem. Biol., 9: 1962-1968 (2014).
Forostyan, T.V., et al., "Abstract C081: Targeting CDK9 and MCL1 in Castration-Sensitive and Resistant Prostate Cancer Models", as present at AACR-NCI-EORTC International Conference on Molecular Targets and Cancer Therapeutiics, Oct.26-30, 2019, Boston , MA, Molecular Cancer Therapeutic, 18(12): Supplement, 4 pages (2019).
Frankel, et al., "Activity of synthetic peptides from the Tat protein of human immunodeficiency virus type 1," Proc. Natl. Acad. Sci. USA, 86:7397-7401 (1989).
Freeman et al., "Measurable Residual Disease at Induction Redefines Partial Response in Acute Myeloid Leukemia and Stratifies Outcomes in Patients at Standard Risk Without NPM1 Mutations," J Clin Oncol, 36(15):1486-1497 (2018).
Freeman et al., "Prognostic Relevance of Treatment Response Measured by Flow Cytometric Residual Disease Detection in Older Patients with Acute Myeloid Leukemia," J Clin Oncol, 31(32):4123-4131 (2013).
Friedman, et al., "Precision medicine for cancer with next-generation functional diagnostics," Nat Rev Cancer, 15(12):747-756 (2015).
Fuchs, et al., "Pathway for Polyarginine Entry into Mammalian Cells," Biochemistry, 43(9):2438-2444 (2004).
Fukui, et al., "The Analysis of the Effect of JQ 1 and Flavopiridol on Chondrocytes under Inflammatory Stimuli," ORS 2014 Annual Meeting (4 pages).
Futaki, et al., "Arginine-rich Peptides: An Abundant Source of Membrane-Permeable Peptides Having Potential as Carriers for Intracellular Protein Delivery," J Biol. Chem, 276(8):5836-5840 (2001).
Gambella et al., "Minimal Residual Disease by Flow Cytometry and Allelic-Specific Oligonucleotide Real-Time Quantitative Polymerase Chain Reaction in Patients With Myeloma Receiving Lenalidomide Maintenance: A Pooled Analysis," Cancer, 125:750-760 (2019).
Gao et al., "Multiple Myeloma Cancer Stem Cells," Oncotarget, 7(23):35466-35477 (2016).
Geng, et al., "Apoptosis of vascular smooth muscle cells induced by in vitro stimulation with interferon-γ, tumor necrosis factor-α, and interleukin-Iβ," Arterioscier. Thromb. Biol, 16: 19-27 (1996).
George, B., et al., "A Phase I, First-In-Human, Open-Label, Dose-Escalation, Safety, Pharmacokinetic, and Pharmacodynamic Study of Oral TP-1287 Administered Daily to Patients with Advanced Solid Tumors", Journal of Clinical Oncology, 38(15) Abstract 3611-3 pages (2020).
George B, et al., "A Phase I, First-in-human, Open-label, Dose escalation, Safety, Pharmacokinetic, and Pharmacodynamic Study of Oral TP-1287 Administered Daily to Patients with Advanced Solid Tumors," American Society of Clinical Oncology—56th Annual Meeting. 2020, poster, 1 page.
Gerber, et al., "Association of acute myeloid leukemia's most immature phenotype with risk groups and outcomes," Haematologica, 101(5):607-616 (2016). (18 pages).
Gerber, et al., "A clinically relevant population of leukemic CD34+ CD38-cells in acute myeloid leukemia," Blood, 1 19(15):3671-3577 (2012).

(56) References Cited

OTHER PUBLICATIONS

Geserick, et al., "The Ratio of Mcl-1 and Noxa Determines ABT737 Resistance in Squamous Cell Carcinoma of the Skin," Cell Death and Disease, 5:e1412, 14 pages (2014).
Ghyczy, et al., "Electrophilic Methyl Groups Present in the Diet Ameliorate Pathological States Induced by Reductive and Oxidative Stress: A Hypothesis," British Journal of Nutrition, 85(4):409-414 (2001).
Giles, et al., "A Phase I Study of Intravenous LBH589, a Novel Cinnamic Hydroxamic Acid Analogue Histone Deacetylase Inhibitor in Patients with Refractory Hematologic Malignancies," Clin Cancer Res, 12:4628-4635 (2006).
Glossary of medical education terms, Institute of International Medical Education, URL: http://www.iime.org/glossart.htm, accessed Mar. 2013.
Gojo, et al., "The Cyclin-dependent Kinase Inhibitor Flavopiridol Induces Apoptosis in Multiple Myeloma Cells through Transcriptional Repression and Down-Regulation of Mcl-1," Clinical Cancer Research, 8:3527-3538 (2002).
Goldsmith, et al., "BH3 peptidomimetics potently activate apoptosis and demonstrate single agent efficacy in neuroblastoma," Oncogene, 25:4525-4533 (2006).
Gomez, L. et al., "Sequential combination of flavopiridol and docetaxel reduces the levels of X-linked inhibitor of apoptosis and AKT proteins and stimulates apoptosis in human LNCaP prostate cancer cells," Molecular Cancer, vol. 5; No. 5; 1216-1226 (2006).
Gordon, V. et al., "CDK9 Regulated AR Promoter Selectivity and Cell Growth through Serine 81 Phosphorylation," Molecular Endocrinology, vol. 24; 2267-2280 (2010).
Gores, et al., "Selectively targeting Mcl-1 for the treatment of acute myelogenous leukemia and solid tumors," Genes & Development, 26:305-311 (2012).
Göttlicher, et al., "Valproic acid defines a novel class of HDAC inhibitors inducing differentiation of transformed cells," The EMBO Journal, 20: 6969-6978 (2001).
Green, et al., "A matter of life and death," Cancer Cell, 1: 19-30 (2002).
Green, et al., "The Pathophysiology of Mitochondrial Cell Death," Science, 305:626-629, (2004).
Green, "Life, Death, BH3 Profiles, and the Salmon Mousse," Cancer Cell, 12:97-99 (2007).
Griffiths, et al., "Cell Damage-induced Conformational Changes of the Pro-Apoptotic Protein Bak In Vivo Precede the Onset of Apoptosis," J Cell. B+G186iol. 144(5):903-914, (1999).
Gross, et al., "Enforced dimerization of BAX results in its translocation, mitochondrial dysfunction and apoptosis," EMBO J, 17(14):3878-3885 (1998).
Gruber, et al., "Efficient Tumor Cell Lysis Mediated by a Bispecific Single Chain Antibody Expressed in *Escherichia coli*," J Immunol, 152:5368-5374 (1994).
Guha, "Cyclin-dependent kinase inhibitors move into Phase III," Nature Reviews Drug Discovery, 11;892-894 (2012).
Gul, et al., "Apoptotic blocks and chemotherapy resistance: strategies to identify Bcl-2 protein signatures," Briefings in Functional Genomics and Proteomics, 7(1):27-34 (2008).
Hamid, et al., "Safety and Tumor Responses with Lambrolizumab (Anti-PD-I) in Melanoma," the New England Journal of Medicine, 369(2):134-144 (2013).
Hanahan, et al., "Heritable formation of pancreatic β-cell tumours in transgenic mice expressing recombinant insulin/simian virus 40 oncogenes," Nature, 315: 115-122 (1985).
Hanahan, et al., "The Hallmarks of Cancer," Cell I 00:57-70 (2000).
Hans, et al., "β-Carbolines induce apoptosis in cultured cerebellar granule neurons via the mitochondrial pathway," Neuropharmacology, 48: 105-117 (2005).
Harada, et al., "Survival factor-induced extracellular signal-regulated kinase phosphorylates BIM, inhibiting its association with BAX and proapoptotic activity," Proc. Natl. Acad. Sci. USA, 101(43):15313-15317 (2004).

Harada, et al., "Discovery of potent and orally bioavailable 17β-hydroxysteroid dehydrogenase type 3 inhibitors," Bioorganic & Medicinal Chemistry, 20:3242-3254 (2012).
Harkevich, "Pharmacology," Medicine, Third Edition: 51-55, Moscow, 1987 (English translation attached) (10 pages).
Haws, et al., "El 204: Alvocidib Synergizes with Venetoclax in Preclinical Models of Multiple Myeloma," Hematologica, 102(Suppl. 2):495 (2017).
Haws, et al., "E881: By an MCL-1-Dependent Mechanism, Alvocidib Potentiates the Activity of Cytarabine and Mitoxantrone when Administered in a Time Sequential Regimen in AML," Hematologica, 102(Suppl. 2):362 (2017).
Hemann, et al., "Evasion of the p53 tumour surveillance network by tumour-derived MYC mutants," Nature, 436:807-811 (2005).
Hemann, et al., "Suppression of tumorigenesis by the p53 target PUMA," Proc. Natl. Acad. Sci. USA, 101(25):9333-9338 (2004).
"Hematologic Malignancies: Regulatory Considerations for Use of Minimal Residual Disease in Development of Drug and Biological Products for Treatment, Guidance For Industry," U.S. Department of Health and Human Services, Food and Drug Administration, Oncology Center of Excellence (OCE), Center for Drug Evaluation and Research (CDER), Center for Biologics Evaluation and Research (CBER), Jan. 2020, available from https://www.fda.gov/media/134605/download. 21 pages.
Hengartner, et al., "C. elegans Cell Survival Gene ced-9 Encodes a functional Homolog of the Mammalian Proto-Oncogene bcl-2," Cell, 76:665-676 (1994).
Heuser et al., "Acute Myeloid Leukaemia in Adult Patients: ESMO Clinical Practice Guidelines for diagnosis, treatment and follow-up," Annals of Oncology, 31(6):697-712 (2020).
Hewings, et al., "Optimization of 3,5-Dimethylisoxazole Derivatives as Potent Bromodomain Ligands" J Med. Chem., 56:3217-3227 (2013).
Higuchi, T. and Stella, V., "Pro-drugs as Novel Delivery Systems," A.C.S. Symposium Series 14; ACS meeting, Atlantic City, NJ, 118 pages (1975).
Hilfiker, R. et al., "Relevance of Solid-State Properties for Pharmaceutical Products," Polymorphism: In the Pharmaceutical Industry, Wiley-VCH; Chapter 1; 19 pages (2006).
Hillengass et al., "Minimal Residual Disease in Multiple Myeloma: Use of Magnetic Resonance Imaging," Seminars in Hematology, 55(1):19-21 (2018) (Abstract Only).
Hirst, et al., "Application of Non-Parametric Regression to Quantitative Structure-Activity Relationships," Bioorganic & Medicinal Chemistry, 10: 1037-1041 (2002).
Hnisz, et al., "Super-Enhancers in the Control of Cell Identity and Disease," Cell, 155:934-947 (2013).
Holinger, et al., "Bak BH3 Peptides Antagonize Bcl-XL Function and Induce Apoptosis through Cytochrome c-independent Activation of Caspases," J Biol. Chem., 274(19):13298-13304 (1999).
Hoelzer et al., "Acute Lymphoblastic Leukaemia in adult patients: ESMO Clinical Practice Guidelines for diagnosis, treatment, and follow-up" Annals of Oncology 27(Supplement 5):v69-v82, 2016.
Hollenbach et al., "A Comparison of Azacitidine and Decitabine Activities in Acute Myeloid Leukemia Cell Lines," PLoS ONE, 5(2):e9001, 2010.
Holliger et al., "Diabodies: Small bivalent and bispecific antibody fragments," Proc. Natl. Acad. Sci. USA, 90:6444-6448 (1993).
Hoogenboom, et al., "By-passing Immunisation. Human Antibodies from Synthetic Repertoires of Germline VH Gene Segments rearranged in Vitro," J Mal. Biol., 227:381-388 (1992).
Hopp, et al., "Prediction of protein antigenic determinants from amino acid sequences," Proc. Natl. Acad. Sci. USA, 78:3824-3828 (1981).
Hoppel, et al., "The action of digitonin on rat liver mitochondria. The effects on enzyme content," Biochem J, 107(3):367-375 (1968).
Hourigan, et al., "Development of therapeutic agents for elderly patients with acute myelogenous leukemia," Curr Opin Investig Drugs, 11(6): 669-677 (2010).
Hourigan, C.S. and Karp, J.E., "Minimal Residual Disease in Acute Myeloid Leukaemia", Nature, 10:460-471 (2013).

(56) References Cited

OTHER PUBLICATIONS

Hsu, et al., "Nonionic Detergents Induce Dimerization among Members of the Bcl-2 Family," J Biol. Chem, 272(21): 13829-13834 (1997).
Huang, et al., "BH3-Only Proteins—Essential Initiators of Apoptotic Cell Death," Cell 103:839-842 (2000).
Huber, et al., "Profile of venetoclax and its potential in the context of treatment of relapsed or refractory chronic lymphocytic leukemia," Onco. Targets Ther., 10:645-656 (2017).
Hunter, T., "Braking the cycle," Cell, 75:839-841 (1993).
Hunter, T., "Protein kinases and phosphatases: The yin and yang of protein phosphorylation and signaling," Cell, 80:225-236 (1995).
Huse, et al., "Generation of a large Combinatorial Library of the Immunoglobulin Repertoire in Phage Lambda," Science, 246:1275-1281 (1989).
Innocenti, et al., "Flavopiridol Metabolism in Cancer Patients Is Associated with the Occurrence of Diarrhea," Clinical Cancer Research, 6:3400-3405 (2000).
Inohara, et al., "harakiri, a novel regulator of cell death, encodes a protein that activates apoptosis and interacts selectively with survival-promoting proteins Bcl-2 and Bel-XL," EMBO J, 16(7):1686-1694 (1997).
Ishizawa, et al., "Mitochondrial Profiling of Acute Myeloid Leukemia in the Assessment of Response to Apoptosis Modulating Drugs," PLoS One 10:e0138377 (2015) (16 pages).
Itzykson, et al., "Predicting the outcome of patients with higher-risk myelodysplastic syndrome treated with hypomethylating agents," Leukemia & Lymphoma, 53(5):760-762 (2012).
Ivey et al., "Assessment of Minimal Residual Disease in Standard-Risk AML," The New England Journal of Medicine, 374(5):422-433 (2016).
Jackson, et al., "Heat shock induces the release of fibroblast growth factor 1 from NIH 3T3 cells," Proc. Natl. Acad. Sci. USA, 89:10691-10695 (1992).
Jameson, et al., "A rationally designed CD4 analogue inhibits experimental allergic encephalomyelitis," Nature, 368:744-746 (1994).
Ji, et al., "A Pharmacokinetic/Pharmacodynamic Model of Tumor Lysis Syndrome in Chronic Lymphocytic Leukemia Patients Treated with Flavopiridol," Clinical Cancer Research, 19(5):1269-1280 (2013).
Jones, et al., "Replacing the complementarity-determining regions in a human antibody with those from a mouse," Nature, 321:522-525 (1986).
Jongen-Lavrencic et al., "Molecular Minimal Residual Disease in Acute Myeloid Leukemia," The New England Journal of Medicine, 378(13):1189-1199 (2018).
Jonkers, et al., "Oncogene addiction: Sometimes a temporary slavery," Cancer Cell, 6:535-538 (2004).
Jornada, D.H., et al., "The Prodrug Approach: A Successful Tool for Improving Drug Solubility", Molecules, 21,42, 31 pages (2016).
Kantarjian, et al., "Decitabine Improves Patient Outcomes in Myelodysplastic Syndromes," Cancer, 106(8):1794-1803 (2006).
Karp, et al., "Phase I and pharmacokinetic study of flavopiridol followed by 1-β-D-arabinofuranosylcytosine and mitoxantrone in relapsed and refractory adult acute leukemias," Clin. Cancer Res., 11(23): 8403-8412 (2005).
Karp, et al., "Phase I and pharmacokinetic study of bolus-infusion flavopiridol followed by cytosine arabinoside and mitoxantrone for acute leukemias," Blood 1 17(12):3302-3310 (2011).
Karp, et al., "Randomized phase II study of two schedules of flavopiridol given as timed sequential therapy with cytosine arabinoside and mitoxantrone for adults with newly diagnosed, poor-risk acute myelogenous leukemia," Haematologica, 97(11): 1736-1742 (2012).
Karp, et al., "Sequential flavopiridol, cytosine arabinoside, and mitoxantrone: a phase II trial in adults with poor-risk acute myelogenous leukemia," Clin. Cancer Res., 13(15 Pt. 1):4467-4473 (2007).
Karp, et al., "Timed Sequential Therapy of Acute Leukemia with Flavopiridol: In Vitro Model for a Phase I Clinical Trial," Clin. Cancer Res., 9:307-315 (2003).

Kasper, et al., "Targeting MCL-1 sensitizes FLT3-ITD-positive leukemias to cytotoxic therapies," Blood Cancer J, 2(10 pages) (2012).
Kaur, et al., "Growth Inhibition with Reversible Cell Cycle Arrest of Carcinome Cells by Falvone L86-8275,", JNCI, 22(84):1736-1740 (1992).
Kearney, et al., "Histopathology of in-stent restenosis in patients with peripheral artery disease," Circulation, 95: 1998-2002 (1997).
Keating, et al., "Results of First Salvage Therapy for Patients Refractory to a Fludarabine Regimen in Chronic Lymphocytic Leukemia," Leuk. Lymph., 43:1755-1762 (2002).
Keating, et al., "Therapeutic role of alemtuzumab (Campath-1H) in patients who have failed fludarabine: results of a large international study," Blood, 99:3554-3561 (2002).
Kelekar, et al., "Bad is a BH3 Domain-Containing Protein that Forms an Inactivating Dimer with Bcl-xL," Mal. Cell. Biol., 17(12):7040-7046 (1997).
Kelekar, et al., "Bcl-2-family proteins: the role of the BH3 domain in apoptosis," Trends in Cell Biol, 8:324-330 (1998).
Kelland, L.R., "Flavopiridol, The First Cyclin-Dependent Kinase Inhibitor to Enter the Clinic: Current Status", Expert Opinion on Investigational Drugs, 9(12):2903-2911 (2000).
Kern et al., "Determination of Relapse Risk Based on Assessment of Minimal Residual Disease during Complete Remission by Multiparameter Flow Cytometry in Unselected Patients with Acute Myeloid Leukemia," Blood, 104(10):3078-3085 (2004).
KG-la, ATCCÂ® CCC-246.1â"¢ATCC Product Sheet, 3 pages, May 31, 2013.
Kim, et al., "Abstract 3728: Targeting MCL-1 expression, through the inhibition of CDK9 and super enhancer driven transcription, offers multiple opportunities for rational drug combinations," Cancer Research, 76(14 Suppl.):3728 (2016).
Kim, et al., "Alvocidib Synergizes with Cytarabine and Daunorubicin (7+3) in Preclinical Models of Acute Myeloid Leukemia," EHA Leaning Center, May 18, 2017, retrieved from https://learningcenter.ehaweb.org/eha/2017 /22nd/I 80678 (3 pages).
Kim, et al., "The CDK9 Inhibitor, Alvocidib, Potentiates the Non-Clinical Activity of Azacytidine or Decitabine in an MCL-1-Dependent Fashion, Supporting Clinical Exploration of a Decitabine and Alvocidib Combination," Blood, 132(Suppl. 1):4355 (2018) (6 pages).
Kim, et al., "TP-1287, an oral prodrug of the cyclin-dependent kinase-9 inhibitor alvocidib", EHA Learning Center, Jun. 9, 2016, retrieved from https://library.ehaweb.org/eha/2016/21st/132440/clifford.whatcott.tp-1287.an.oral.prodrug.of.the.103cyclin-dependent.kinase-9 .html (2 pages).
Kim, W., et al., "Alvocidib Potentiates the Activity of Azacytidine in an MCL-1-Dependent Fashion", Blood, 126(23):Abstract 1343, 3 pages (2015).
Kim et al., "Alvocidib Potentiates the Activity of Cytarabine and Mitoxantrone through the Targeting of MCL-1 When Administered in a Time Sequential Regimen in AML," Blood 126(23), 3799, 2015. (Abstract Only).
Kim et al., "Alvocidib Potentiates the Activity of Cytarabine and Mitoxantrone through the Targeting of MCL-1 When Administered in a Time Sequential Regimen in AML," Blood 126(23), 3799, 2015.
Kim, W. et al., "Abstract 5133: TP-1287, an oral prodrug of the cyclin-dependent kinase-9 inhibitor alvocidib," Cancer Res, vol. 77; 13 Suppl; 2 pages; 5133 (2017).
Kimura, et al. "Antiproliferative and Antitumor Effects of Azacitidine Against Human Myelodysplastic Syndrome Cell Line SKM-1", Anticancer Research, 32:795-798 (2012).
Kitada, et al., "Protein kinase inhibitors flavopiridol and 7-hydroxystaurosporine down-regulate antiapoptosis proteins in B-cell chronic lymphocytic leukemia," Blood 96:393-397 (2000).
Klaeger, et al., "The target landscape of clinical kinase drugs," Science, 358: 1148-1164 (2017).
Knutson, et al., "Synergistic Anti-Tumor Activity of EZH2 Inhibitors and Glucocorticoid Receptor Agonists in Models of Germinal Center Non-Hodgkin Lymphomas," PLoS One, 9(12):el 11840 (2014).

(56) References Cited

OTHER PUBLICATIONS

Köhler, et al., "Continuous cultures of fused cells secreting antibody of predefined specificity," Nature, 256:495-497 (1975).
König, et al., "The Novel Cyclin-Dependent Kinase Inhibitor Flavopiridol Downregulates Bcl-2 and Induces Growth Arrest and Apoptosis in Chronic B-Cell Leukemia Lines," Blood, 90:4307-4312 (1997).
Konopleva, et al., "BCL-2 Inhibition in AML: An Unexpected Bonus?" Blood, 132(10):1007-1012 (2018).
Korsmeyer, et al., "Pro-apoptotic cascade activates BID, which oligomerizes BAK or BAX into pores that result in the release of cytochrome c," Cell Death Differ, 7(12):1166-1173 (2000).
Kozbor, et al., "The production of monoclonal antibodies from human lymphocytes," Immunol Today, 4:72-79 (1983).
Kryštof, et al., "Cyclin-Dependent Kinase Inhibitors as Anticancer Drugs," Current Drug Targets, 11:291-302 (2010).
Kumar, S., et al., "International Myeloma Working Group Consensus Criteria for Response and Minimal Residual Disease Assessment in Multiple Myeloma," Lancet Oncology, 17:e328-e346 (2016).
Kuwana, et al., "BH3 Domains of BH3-Only Proteins Differentially Regulate Bax-Mediated Mitochondrial Membrane Permeabilization Both Directly and Indirectly," Mal. Cell., 17:525-535 (2005).
Kuwana, et al., "Bid, Bax, and Lipids Cooperate to Form Supramolecular Openings in the Outer Mitochondrial Membrane," Cell, 111:331-342 (2002).
Kyte, et al., "A Simple Method for displaying the Hydropathic Character of a protein," J Mal. Biol., 157:105-132 (1982).
La Vieira, et al., "Cell permeable BH3-peptides overcome the cytoprotective effect of Bcl-2 and Bcl-XL," Oncogene, 21:1963-1977 (2002).
Labi, et al., "Targeting the Bcl-2-regulated apoptosis pathway by BH3 mimetics: a breakthrough in anticancer therapy?" Cell Death and Differentiation, 15:977-987 (2008).
Landgren et al., "MRD Testing in Multiple Myeloma: The Main Future Driver for Modern Tailored Treatment," Seminars in Hematology 55(1):44-50, 2018. (Abstract Only).
Landgren, "MRD Testing in Multiple Myeloma: From a Surrogate Marker of Clinical Outcomes to an Every-Day Clinical Tool," Seminars in Hematology 55(1):1-3, 2018. (Abstract Only).
Lazarus, et al., "High-Dose Cytosine Arabinoside and Daunorubicin as Primary Therapy in Elderly Patients With Acute Myelogenous Leukemia," Cancer, 63:1055-1059 (1989).
Lee DJ et al., "Zella 101: Phase 1 Study of Alvocidib Followed by 7+3 Induction in Newly Diagnosed AML Patients," European Hematology Association—24th Congress, Jun. 13-16, 2019.
Lee, D., et al., "Abstract PF285: Zella 101: Phase I Study of Alvocidib Followed by 7+3 Induction in Newly Diagnosed AML Patients" as present during the 24th Annual Congress of the European Hematology Association 2019, HemaSphere, 3:S1: 94 (2019).
Lemke, et al., "Immunobiology of the TAM Receptors," Nature Reviews Immunology, 8:327-336 (2008).
Leo, et al., "Characterization of the Antiapoptotic Bcl-2 Family Member Myeloid Cell Leukemia-I (Mcl-1) and the Stimulation of Its Message by Gonadotropins in the Rat Ovary," Endocrinol, 140:5469-5477 (1999).
Letai, et al., "Antiapoptotic BCL-2 is required for maintenance of a model leukemia," Cancer Cell, 6:241-249 (2004).
Letai, et al., "Distinct BH3 domains either sensitize or activate mitochondrial apoptosis, serving as prototype cancer therapeutics," Cancer Cell, 2:183-192 (2002).
Letai, "Perturbing cancer cell mitochondria to learn how to kill cancer with BH3 profiling," Broad Institute, Seminar Series on Cell Circuits and Epigenomics (Jul. 28, 2014) Presentation (47 pages).
Letai, "The BCL-2 network: Mechanistic insights and therapeutic potential," Drug Disc. Today: Disease Mechanisms, 2(2):145-151 (2005).
Letai, "BH3 domains as BCL-2 inhibitors: prototype cancer therapeutics," Expert Opin. Biol. Ther., 3:293-304 (2003).

Li, et al., "Cleavage of BID by Caspase 8 Mediates the Mitochondrial Damage in the Fas Pathway of Apoptosis," Cell, 94(4):491-501 (1998).
Li, et al., "Endonuclease G is an apoptotic DNase when released from mitochondria," Nature, 412:95-99 (2001).
Li, et al., "tsg101: A Novel tumor susceptibility gene isolated by controlled Homozygous functional knockout of Allelic Loci in Mammalian Cells," Cell, 85:319-329 (1996).
Lin, et al., "Targeting MCL-1/BCL-XL Forestalls the Acquisition of Resistance to ABT-199 in Acute Myeloid Leukemia," Scientific Reports, 6(1):1-10 (2016).
Lin, et al., "Flavopiridol given as a 30-min intravenous (IV) bolus followed by 4-hr continuous IV infusion (CIVI) results in clinical activity and tumor lysis in refractory chronic lymphocytic leukemia (CLL)," Journal of Clinical Oncology, 2004 ASCO Annual Meeting Proceedings, (Post-Meeting, Edition) 22(14S):6564 (2004) (1 page).
Lin, et al., "Seventy-Two Hour Continuous Infusion Flavopiridol in Relapsed and Refractory Mantle Cell Lymphoma," Leukemia & Lymphoma, 43:793-797 (2002).
Lin, T.S., et al., "Phase II Study of Flavopiridol in Relapsed Chronic Lymphocytic Leukemia Demonstrating High Response Rates in Genetically High-Risk Disease", Journal of Clinical Oncology, 27(35):6012-6018 (2009).
Lin, C.Y., et al., "Transcriptional Amplification in Tumor Cells with Elevated c-Myc", Cell, 151:56-67 (2012).
Lindsley, R.C., et al., "Acute Myeloid Leukemia Ontogeny is Defined by Distinct Somatic Mutations", Blood, 125(9):1367-1376 (2015).
Linenberger, et al., "Biochemistry Students' Ideas About Shape and Charge in Enzyme-Substrate Interactions," Biochemistry and Molecular Biology Education, 42(3):203-212 (2014).
Litzow, M.R., et al., "A Randomized Trial of Three Novel Regimens for Recurrent Acute Myeloid Leukemia Demonstrates the Continuing Challenge of Treating this Difficult Disease", Am. J. of Hematol, 94(1):111-117 (Jan. 2019).
Liu, et al., "Bax conformational change is a crucial step for PUMA-mediated apoptosis in human leukemia," BioChem. Biophys. Res. Commun., 310(3):956-962 (2003).
Liu, et al., "BH3-based Fusion Artificial Peptide Induces Apoptosis and Targets Human Colon Cancer," Molecular Therapy, 17:1509-1516 (2009).
Liu, et al., "CDKI-71, a novel CDK9 inhibitor, is preferentially cytotoxic to cancer cells compared to flavopiridol," Int. J Cancer, 130:1216-1226 (2012).
Lonberg, et al., "Antigen-specific human antibodies from mice comprising four distinct genetic modifications," Nature, 368:856-859 (1994).
Londoño, et al., "A reliable method for quantification of splice variants using RT-qPCR," BMC Mol. Biol., 17(8):1-12 (2016).
Long, et al., "Optimization and validation of mitochondria-based functional assay as a useful tool to identify BH3-like molecules selectively targeting anti-apoptotic Bcl-2 proteins," BMC Biotechnol, 13:45 (2013) (10 pages).
Lovén, et al., "Selective Inhibition of Tumor Oncogenes by Disruption of Super-Enhancers," Cell, 153:320-334 (2013) (27 pages).
Lozanski, et al., "Alemtuzumab is an effective therapy for chronic lymphocytic leukemia with p53 mutations and deletions," Blood, 103:3278-3281 (2004).
Lu, et al., "Compensatory Induction of MYC Expression by Sustained CDK9 Inhibition via a BRD4-dependent Mechanism," eLife, 2015 (26 pages).
Luo, et al., "Bid, a Bcl2 interacting protein, mediates cytochrome c release from mitochondria in response to activation of cell surface death receptors," Cell, 94(4):481-490 (1998).
Lutter, et al., "The pro-apoptotic Bcl-2 family member tBid localizes to mitochondrial contact sites," BMC Cell Biology, 2:22 (2001) (9 pages).
Malcovati et al., "Diagnosis and Treatment of Primary Myelodysplastic Syndromes in Adults: Recommendations From the European LeukemiaNet," Blood, 122(17):2943-2964 (2013).
Malumbres, "Cyclin-dependent kinases," Genome Biol., 15(122):1-10 (2014).

(56) References Cited

OTHER PUBLICATIONS

Mann, et al., "Cell cycle inhibition preserves endothelial function in genetically engineered rabbit vein grafts," J Clin. Invest., 99(6):1295-1301 (1997).
Marani, et al., "Identification of Novel Isoforms of the BH3 Domain Protein Bim which Directly Activate Bax to Trim1:er Apoptosis," Mal. Cell. Biol., 22(11):3577-3589 (2002).
Marks, et al., "By-passing Immunization. Human Antibodies from v-gene libraries displayed on phage," J Mal. Biol., 222:581-597 (1991).
Marks, et al., "By-passing Immunization: building high affinity human antibodies by chain shuffling," Bio/Technology, 10:779-783 (1992).
Martin, "Opening the Cellular Poison Cabinet," Science 330:1330-1331 (2010).
Mason, et al., "The Hypogonadal mouse: reproductive functions restored by gene therapy," Science, 234:1372-1378, 1986.
Matsumura, Y., et al., "1959-CDK9 Inhibition Combined with Hypomethylating Agents Target MCL-1 Dependency in MDS and AML", AACR Annual Meeting 2021—Virtual-Poster to be presented during Session PO.MCB06.01-Cell Cycle on Apr. 10, 2021, downloaded from AACR website, URL: https://www.abstractsonline.com/pp8/#!/9325/presentation/3238 on Mar. 30, 2021 (2 pages).
Matsumura Y et al., "CDK9 Inhibition Combined with Hypomethylating Agents Target MCL-1 Dependency in MDS and AML," American Association for Cancer Research—112th Annual Meeting, Poster, 2021.
Matsumura Y, et al., "Pharmacodynamic biomarker strategies for CDK9 inhibition," American Association for Cancer Research—111th Annual Meeting. 2020.
Matsumura, Y., et al., "Abstract 5813: Pharmacodynamic Biomarker Strategies for CDK9 Inhibition" as presented Annual Meeting of the American Association for Cancer Research 2020; Apr. 27-28 and Jun. 22-24, 2020 in Philadelphia, PA, Cancer Res., 80(Supplement 16):4 pages.
Matsushita, et al., "A high-efficiency protein transduction system demonstrating the role of PKA in long-lasting long-term potentiation," J Neuroscience, 21:6000-6007 (2001).
Matsuzaki, "Why and how are peptide-lipid interactions utilized for self-defense?" Biochem. Soc. Transactions, 29:598-601 (2001).
Mayer, "Induction of apoptosis by flavopiridol unrelated to cell cycle arrest in germ cell tumour derived cell lines," Invest New Drugs 23(3):205-211, 2005.
McDonnell, et al., "bcl-2-Immunoglobulin Transgenic Mice Demonstrate Extended B Cell Survival and Follicular Lymphoproliferation," Cell, 57:79-88 (1989).
Means, et al., "Modifications to change properties," in Chemical Modification of Protein, Chapter 3, pp. 35-54, Holden-Day (1971).
Mian, S.A., et al., "Splicesome Mutations Exhibit Specific Associations with Epigenetic Modifiers and Proto-Oncogenes Mutated in Myelodysplastic Syndrome", Haematologica, 98(7):1058-1066 (2013).
Mikhael, et al., "Treatment of Multiple Myeloma: ASCO and CCO Joint Clinical Practice Guideline," J Clin Oncol, 37(14):1228-1264 (2019).
Miller, et al., "Therapeutic Strategies to Enhance the Anticancer Efficacy of Histone Deacetylase Inhibitors," J Bio med. Biotechnol. 2011:17 pages, 2011.
Milstein, et al., "Hybrid hybridomas and their use in immunohistochemistry," Nature, 305:537-539 (1983).
Mintz G.S., "In-stent restenosis: the Washington Hospital Center experience", Am. J. Cardiol., 81:7E-13E (1998).
Mintz G.S., "Arterial remodeling after coronary angioplasty: a serial intravascular ultrasound study", Circulation,; 94:35-43 (1996).
Mirguet, O., et al., "Discovery of Epigenetic Regulator I-BET762: Lease Optimization to Afford a Clinical Candidate Inhibitor of the BET Bromodomains", Journal of Medicinal Chemistry, 56:7501-7515 (2013).
Molassiotis, et al., "Use of complementary and alternative medicine in cancer patients: A European survey," Annals of Oncology, 16:655-663 (2005).

Montero, et al., "Drug-induced death signaling strategy rapidly predicts cancer response to chemotherapy," Cell, 160(5):977-989 (2015).
Montesinos, et al., "Tumor lysis syndrome in patients with acute myeloid leukemia: identification of risk factors and development of a predictive model," Haematologica, 93(1):67-74 (2008).
Moore et al., "BH3 profiling—measuring integrated function of the mitochondrial apoptotic pathway to predict cell fate decisions," Cancer Lett, 332:202-205 (2013).
Moore, et al., "Chronic lymphocytic leukemia requires BCL2 to sequester prodeath BIM, explaining sensitivity to BCL2 antagonist ABT-737," J Clin. Invest., 117(1):112-121 (2007).
Morishita, et al., "A gene therapy strategy using a transcription factor decoy of the E2F binding site inhibits smooth muscle proliferation in vivo," Proc. Natl. Acad. Sci. USA, 92:5855-5859 (1995).
Morita, Y., et al., "Phase 1 Study of Alvocidib (DSP-2033) in Combination with Cytarabine/Mitoxantrone (ACM) or Cytarabine/Daunorubicin (A+7+3) in Japanese Patients (pts) with Acute Myeloid Leukemia (AML)", Blood, 136(Supplement 1):4 pages (2020).
Morita, Y. et al., "Phase 1 Study of Alvocidib (DSP-2033) in Combination with Cytarabine/Mitoxantrone (ACM) or Cytarabine/Daunorubicin (A+7+3) in Japanese Patients (Pts) with Acute Myeloid Leukemia (AML)," American Society of Hematology—62nd Annual Meeting. 2020.
Moros, et al., "Synergistic antitumor activity of lenalidomide with the BET bromodomain inhibitor CPI203 in bortezomib-resistant mantle cell lymphoma," Leukemia, 28(10):2049-2059 (2014).
Morrison, et al., "Success in specification," Nature, 368:812-813 (1994).
Motwani, M., et al., "Docetaxel and Navelbine Induced Apoptosis is Enhanced by Flavopiridol (Flavo) in Breast Cancer Cells and is Sequence Dependent", Proceedings of the American Association for Cancer Research, 41, p. 143, Abstract #912 (2000).
Motwani, et al., "Sequential Dependent Enhancement of Caspase Activation and Apoptosis by Flavopiridol on Paclitaxel-Treated Human Gastric and Breast Cancer Cells," Clinical Cancer Research, 5(7):1876-1883 (1999).
Muchmore, et al., "X-ray and NMR Structure of Human Bcl-xL, an Inhibitor of Programmed Cell Death," Nature, 381:335-341 (1996).
Munson, et al., "Ligand: A Versatile Computerized Approach for Characterization of Ligand Binding Systems," Analytical Biochemistry, 107:220-239 (1980).
Murthi, et al., "Structure-Activity Relationship Studies of Flavopiridol Analogues," Bioorganic & Medicinal Chemistry Letters, 10:1037-1041 (2000).
Nagai, et al., "Studies on Psychotropic Agents. VI. Synthesis of 1'-Methylspiro[6-fluoroindan-1, 3'-pvrrolidine]-3-one and Related Compounds," Chem. Pharm. Bull., 28(5):1387-1393 (1980).
Naik, et al., "An Antiinflammatory Cum Immunomodulatory Piperidinylbenzopyranone From Dysoxylum Binectariferum: Isolation, Structure and Total Synthesis," Tetrahedron, 44:2081-2086 (1988).
Nakanishi, T. and Tamai, I., "Solute Carrier Transporters as Targets for Drug Delivery and Pharmacological Intervention for Chemotherapy," J. Pharm Sci, vol. 100; 3731-3750 (2011).
Nakano, et al., "PUMA, a Novel Proapoptotic Gene, Is Induced By p53," Molecular Cell, 7:683-694 (2001).
Narita, et al., "Bax interacts with the permeability transition pore to induce permeability transition and cytochrome c release in isolated mitochondria," Proc. Natl. Acad. Sci. USA, 95:14681-14686 (1998).
National Comprehensive Cancer Network® clinical practice guidelines for Acute Myeloid Leukemia version 2.2014 (2014).
Nathwani, S. et al., "Novel microtubule-targeting agents, pyrrolo-1,5-benzoxazepines, induce cell cycle arrest and apoptosis in prostate cancer cells," Oncology Reports, vol. 24; 1499-1507 (2010).
Neuberger, et al., "Generating high-avidity human Mabs in mice," Nature Biotechnology, 14:826 (1996).
Nguyen, et al., "Azacitidine and decitabine have different mechanisms of action in non-small cell lung cancer cell lines," Lung Cancer: Targets and Therapy, 1:119-140 (2010).
NICE guidelines, "Myeloma: Diagnosis and Management," National Institute for Health and Care Excellence: 1-27 (2016).

(56) References Cited

OTHER PUBLICATIONS

Noel, et al., "Abstract C244: Development of the BET bromodomain inhibitor OTX015," Molecular Cancer Therapeutics, 12(11): Supplement (2013).
O'Brien, et al., "Phase I to II Multicenter Study of Oblimersen Sodium, a Bcl-2 Antisense Oligonucleotide, in Patients With Advanced Chronic Lymphocytic Leukemia," J Clin. Oncol., 23(30):7697-7702 (2005).
O'Brien, et al., "Proliferation in primary and restenotic coronary atherectomy tissue: implications for antiproliferative therapy," Circ. Res., 73(2):223-231 (1993).
O'Connor, et al., "Bim: a novel member of the Bcl-2 family that promotes apoptosis," EMBO J, 17(2):384-395 (1998).
Oda, et al., "Noxa, a BH3-Only Member of the Bcl-2 Family and Candidate Mediator of p53- Induced Apoptosis," Science, 288: 1053-1058 (2000).
Odore, et al., "Abstract LB-231: A phase I pharmacokinetic study of OTX0 15 for the treatment of patients with hematologic malignancies," Cancer Research, 74(Supplement 19) (2014) (4 pages) (Abstract Only).
Oh, et al., "Conformational Changes in BID, a Pro-apoptotic BCL-2 Family Member, upon Membrane Binding," J Biol. Chem., 280(1):753-767 (2005).
Okamoto, et al., "Increased antitumor potential of the raloxifene prodrug, raloxifene diphosphate," Int. J Cancer, 122:2142-2147 (2008).
Oken, et al., "Toxicity and response criteria of the Eastern Cooperative Oncology Group," Am. J. Clin. Oncol., 5(6):649-655 (1982).
Oltersdorf, et al., "An inhibitor of Bcl-2 family proteins induces regression of solid tumours," Nature, 435:677-681 (2005).
Opferman, et al., "Development and maintenance of B and T lymphocytes requires antiapoptotic MCL-1," Nature 426:671-676, 2003.
Opferman, et al., "Obligate Role of Anti-Apoptotic MCL-1 in the Survival of Hematopoietic Stem Cells," Science, 307: 1101-1104 (2005).
Oppermann, et al., "High-content screening identifies kinase inhibitors that overcome venetoclax resistance in activated CLL cells," Blood, 128(7):934-947 (2016).
Oscier, et al., "Multivariate analysis of prognostic factors in CLL: clinical stage, IGVH gene mutational status, and loss or mutation of the p53 gene are independent prognostic factors," Blood, 100:1177-1184 (2002).
Otsuka, et al., "Effect of Polymorphic Forms of Bulk Powders on Pharmaceutical Properties of Carbamazepine Granules," Chem. Pharm. Bull., 47(6):852-856 (1999).
Pandit-Taskar, "Functional Imaging Methods for Assessment of Minimal Residual Disease in Multiple Myeloma: Current Status and Novel ImmunoPET Based Methods," Seminars in Hematology, 55(1):22-32 (2018).
Paoluzzi, et al., "The BH3-only mimetic ABT-737 synergizes the antineoplastic activity of proteasome inhibitors in lymphoid malignancies," Blood, 112:2906-2916 (2008).
Papaemmanuil et al., "Genomic Classification and Prognosis in Acute Myeloid Leukemia," The New England Journal of Medicine, 374(23):2209-2221 (2016).
Paquin, et al., "Design and synthesis of 4-[(s-triazin-2-ylamino)methyl]-N-(2-aminophenyl)-benzamides and their analogues as a novel class of histone deacetylase inhibitors," Bioorganic & Medicinal Chemistry Letters, 18:1067-1071 (2008).
Park, et al., "Inhibitors of cyclin-dependent kinases promote survival of post-mitotic neuronally differentiated PC12 cells and sympathetic neurons," J Biol. Chem., 271(14):8161-8169 (1996).
Parker, et al., "Early Induction of Apoptosis in Hematopoietic Cell Lines After Exposure to Flavopiridol," Blood, 91:458-465 (1998).
Parovichnikova, E., et al., "The MRD-Negativity Rate Measured By Flow Cytometry After the 1st and 2nd Induction Course Among CR AML Patients from Different Cytogenetic Subgroups Does Not Differ Though the Morphological CR Achievement Does", Blood, 132(Suppl.1):1495, 6 pages (2018).
Parry, et al., "Dinaciclib (SCH 727965), a Novel and Potent Cyclin-Dependent Kinase Inhibitor," Molecular Cell Therapy, 9:2344-2353 (2010).
Paruch, et al., "Discovery of Dinaciclib (SCH 727965): A Potent and Selective Inhibitor of Cyclin-Dependent Kinases," ACS Medicinal Chemistry Letters, 1:204-208 (2010).
Payne, et al., "Identification of the regulatory phosphorylation sites in pp42/mitogen-activated protein kinase (MAP kinase)," The EMBO Journal, 10(4):885-892 (1991).
Pepper, et al., "Flavopiridol circumvents Bcl-2 family mediated inhibition of apoptosis and drug resistance in B-cell chronic lymphocytic leukaemia," Br. J Haematol, 114(1):70-77 (2001).
Perkins, et al., "Frequency and Type of Serious Infections in Fludarabine-Refractory B-Cell Chronic Lymphocytic Leukemia and Small Lymphocytic Lymphoma," Cancer, 94:2033-2039 (2002).
Perrot et al., "Minimal Residual Disease Negativity Using Deep Sequencing is a Major Prognostic Factor in Multiple Myeloma," Blood, 132(23):2456-2464 (2018).
Phelps, et al., "Clinical response and pharmacokinetics from a phase I study of an active dosing schedule of flavopiridol in relapsed chronic lymphocytic leukemia," Blood, 1 13(12):2637-2645 (2009).
Phillips, et al., "Loss in MCL-1 function sensitizes non-Hodgkin's lymphoma cell lines to the BCL-2-selective inhibitor venetoclax (ABT-199)," Blood Cancer J, 5:e368 (2015) (8 pages).
Picaud, et al., "PFI-1, a Highly Selective Protein Interaction Inhibitor Targeting BET Bromodomains," Cancer Research, 73:3336-3346 (2013).
Picaud, et al., "RVX-208, an inhibitor of BET transcriptional regulators with selectivity for the second bromodomain," PNAS, 1 10(49):19754-19759 (2013).
Piekarz, et al., "Inhibitor of histone deacetylation, depsipeptide (FR901228), in the treatment of peripheral and cutaneous T-cell lymphoma: a case report," Blood, 98:2865-2868 (2001).
Pierceall, et al., "BH3 Profiling Discriminates Response to Cytarabine-Based Treatment of Acute Myelogenous Leukemia," Mal. Cancer. Ther., 12(12):2940-2949 (2013).
Pierceall, et al., "Mcl-1 Dependence Predicts Response to Vorinostat and Gemtuzumab Ozogamicin in Acute Myeloid Leukemia," Leuk Res, 38:564-568, 2014. (13 pages).
Pierceall, et al., "Mitochondrial Priming of Chronic Lymphocytic Leukemia Patients Associates Bcl-XL Dependence with Alvocidib Response," Leukemia, 28:2251-2254 (2014). (7 pages).
Pinckert, et al., "An albumin enhancer located 10 kb upstream functions along with its promoter to direct efficient, liver-specific expression in transgenic mice," Genes and Dev, 1:268-276 (1987).
Plumb, et al., "Pharmacodynamic Response and Inhibition of Growth of Human Tumor Xenografts by the Novel Histone Deacetylase Inhibitor PXD101," Molecular Cancer Therapeutics, 2:721-728 (2003).
Pode-Shakked, et al., "Developmental tumourigenesis: NCAM as a putative marker for the malignant renal stem/progenitor cell population," J Cell. Mal. Med., 13(8b):1792-1808 (2009).
Polster, et al., "BH3 Death Domain Peptide Induces Cell Type-selective Mitochondrial Outer Membrane Permeability," The Journal of Biological Chemistry, 276:37887-37894 (2001).
Presta, "Antibody engineering," Curr. Opin. Struct. Biol., 2:593-596 (1992).
Pritzker, "Cancer Biomarkers: Easier Said Than Done," Clinical Chemistry, 48:1147-1150 (2002).
Pugh, "Circulating Tumour DNA for Detecting Minimal Residual Disease in Multiple Myeloma," Seminars in Hematology, 55:38-40 (2018).
Putcha, et al., "Induction of BIM, a Proapoptotic BH3-Only BCL-2 Family Member, is Critical for Neuronal Apoptosis," Neuron 29(3):615-628 (2001).
Puthalakath, et al., "Bmf: A Proapoptotic BH3-Only Protein Regulated by Interaction with the Myosin V Actin Motor Complex, Activated by Anoikis," Science, 293: 1829-1832 (2001).
Puthalakath, et al., "Keeping killers on a tight leash: transcriptional and post-translational control of the pro-apoptotic activity of BH3-only proteins," Cell Death Differ., 9:505-512 (2002).

(56) References Cited

OTHER PUBLICATIONS

Puthalakath, et al., "The Proapoptotic Activity of the Bcl-2 Family Member Bim is Regulated by Interaction with the Dynein Motor Complex," Mal. Cell., 3:287-296 (1999).
Qi, et al., "Abstract 2016: A subset of small cell lung cancer (SCLC) cell lines is Mcl-I-dependent and responds to cyclin-dependent kinase (cdk)9 inhibition in vitro and in vivo", Cancer Research, 72:8 Suppl. 1, Abstract 2016 (2012) (4 pages).
Quinsay, et al. "Pro-Apoptotic Bnip3 Mediates Permeabilization of Mitochondria and Release of Cytochrome c Via a Novel Mechanism," Circulation, 118:Abstract 1783 (S388)—5 pages (2008).
Quinsay, et al., "Abstract 1783: Proapoptotic Bnip3 Mediates Permeabilization of Mitochondria and Release of Cytochrome c via a Novel Mechanism," Circulation, 118(18):Supply 2, S388 (2008).
Quinsay, et al., "Bnip3 Mediates Permeabilization of Mitochondria and Release of Cytochrome c Via a Novel Mechanism," J Mol Cell Cardiol, 48(6):1146-1156 (2010).
Raff, "Social controls on cell survival and cell death," Nature, 356:397-400 (1992).
Ramsey, H.E., et al., "A Novel MCL1 Inhibitor Combined with Venetoclax Rescues Venetoclax-Resistant Acute Myelogenous Leukemia", Cancer Discov, 8(12):1566-1581 (2018).
Rassenti, et al., "ZAP-70 Compared with Immunoglobulin Heavy-Chain Gene Mutation Status as a Predictor of Disease Progression in Chronic Lymphocytic Leukemia," N Engl. J Med., 351:893-901 (2004).
Ravandi, et al., "Evaluating measurable residual disease in acute myeloid leukemia," Blood Adv. 2(11):1356-1366 (2018) (23 pages).
Ray, et al., "BNIP3 Heterodimerizes with Bcl-2/Bcl-xL and Induces Cell Death Independent of a Bcl-2 Homology 3 (BH3) Domain at Both Mitochondrial and Nonmitochondrial Sites," J Biol. Chem. 275(2):1439-1448 (2000).
Raychaudhuri, "Low probability Bid-Bax reaction generates heterogeneity in apoptosis resistance of cancer and cancer stem cells," arXiv: 1108.2091 a-bio.MN] (2011).
Riechmann, et al., "Reshaping human antibodies for therapy," Nature, 332:323-327 (1988).
Ren, et al., "BID, BIM, and PUMA Are Essential for Activation of the BAX- and BAK-Dependent Cell Death Program," Science 330:1390-1393 (2010).
Rezaei, et al., "Leukemia Markers Expression of Peripheral Blood vs. Bone Marrow Blasts Using Flow Cytometry," Medical Science Monitor, 9(8):CR359-CR362 (2003).
Riabov, V., et al., "Preclinical Assessment of Alvocidib in Combination with 5-Azacytidine in High-Risk Myelodysplastic Syndromes", Blood, 138(Supplement 1):4649 (2021).
Richard, D.., et al., "Hydroxyquinoline-derived compounds and analoguing of selective Mcl-1 inhibitors using a functional biomarker" Bioorg Med Chem., 21(21):6642-9 (2013).
Richon, et al., "A Class of Hybrid Polar Inducers of Transformed Cell Differentiation Inhibits Histone Deacetylases," Proc. Natl. Acad. Sci. USA, 95:3003-3007 (1998).
Rollins-Raval, et al., "The value of immunohistochemistry for CD14, CD123, CD33, myeloperoxidase and CD68R in the diagnosis of acute and chronic myelomonocytic leukaemias," Histopathology, 60:933-942 (2012).
Rosenblatt, et al., "PD-I blockade by CT-011, anti PD-I antibody, enhances ex-vivo T cell responses to autologous dendritic/myeloma fusion vaccine," J. Immunother., 34(5):409-418 (2011).
Roshal, "Minimal Residual Disease Detection by Flow Cytometry in Multiple Myeloma: Why and How?" Seminars in Hematology 55(1):4-12, 2018.
Rothbard, et al., "Conjugation of arginine oligomers to cyclosporine A facilitates topical delivery and inhibition of inflammation," Nat. Med. ,6(11):1253-1257 (2000).
Rudek, et al., "Clinical Pharmacology of Flavopiridol Following a 72-Hour Continuous Infusion," Ann Pharmacother, 37:1369-1374 (2003).
Ruef, et al., "Induction of rat aortic smooth muscle cell growth by the lipid peroxidation product 4-hydroxy-2-nonenal," Circulation, 97:1071-1078 (1998).
Ruef, et al., "Induction of vascular endothelial growth factor in balloon-injured baboon arteries," Circ. Res. 81:24-33 (1997).
Ruef, et al., "Flavopiridol Inhibits Smooth Muscle Cell Proliferation In Vitro and Neointimal Formation In Vivo After Carotid Injury in the Rat," Circulation, 100(6):659-665 (1999).
Ryan, et al., "Heightened mitochondrial priming is the basis for apoptotic hypersensitivity of $CD4^+$ $CD8^+$ thymocytes," Proc. Natl. Acad. Sci USA, 107(29):12895-12900 (2010).
Ryan, et al., "BH3 Profiling in Whole Cells by Fluorimeter or FACS," Methods 61:156-164 (2013) (22 pages).
Saito, et al., "A synthetic inhibitor of histone deacetylase, MS-27-275, with marked in vivo antitumor activity against human tumors," Proc. Natl. Acad. Sci. USA, 96:4592-4597 (1999).
Salomon, C.J., et al., "Recent Developments in Chemical Deprotection of Ester Functional Groups", Tetrahedron, 49(18):3691-3748 (1993).
Samson, et al., "A 35 amino acid fragment of leptin inhibits feeding in the rat," Endocrinology, 137:5182-5185 (1996).
San Miguel, et al., "Early Immunophenotypical Evaluation of Minimal Residual Disease in Acute Myeloid Leukemia Identifies Different Patient Risk Groups and May Contribute to Postinduction Treatment Stratification," Blood, 98(6):1746-1751 (2001).
Sata, et al., "Fas ligand gene transfer to the vessel wall inhibits neointima formation and overrides the adenovirus-mediated T cell response," Proc. Natl. Acad. Sci. USA, 95:1213-1217 (1998).
Sattler, et al., "Structure of Bcl-xL-Bak Peptide Complex: Recognition Between Regulators of Apoptosis," Science, 275:983-986 (1997).
Sausville, et al., "Inhibition of CD Ks as a Therapeutic Modality," Ann NY Acad of Sci, 910:207-222 (2000).
Schimmer, et al., "The BH3 domain of BAD fused to the Antennapedia peptide induces apoptosis via its alpha helical structure and independent of Bcl-2," Cell Death and Differentiation, 8:725-733 (2001).
Schuurhuis, et al., "Minimal/measureable residual disease in AML: a consensus document from the European LeukemiaNet MRD Working Party," Blood ,131(12):1275-1291 (2018).
Schwartz, G.K., et al., "Phase I Trial of Sequential Paclitaxel and Cisplatin in Combination with the Cyclin Dependent Kinase Inhibitor Flavopiridol (Flavo) In Patients with Advances Solid Tumors", Clinical Cancer Research, 5, p. 3754s, Abstract #122 (1999).
Schwartz, et al., "Phase II Study of the Cyclin-Dependent Kinase Inhibitor Flavopiridol Administered to Patients With Advanced Gastric Carcinoma," J Clin. One., 19:1985-1992, (2001).
Schwartz, et al., "The intima: soil for atherosclerosis and restenosis," Circ. Res., 77:445-465 (1995).
Schwartz, G.K., et al., "Phase I Study of the Cyclin-Dependent Kinase Inhibitor flavopiridol in combination with Paclitaxel in Patients with Advanced Solid Tumors", Journal of Clinical Oncology, 20(8) (Apr. 15) 2002: pp. 2157-2170.
Score, "Search Results Details for U.S. Appl. No. 11/789,557 and Search Result Nov. 6, 2009_104627 _ . . . ," Nov. 24, 2009, URL=http://es/ScoreAccessWeb/Getitem.action? Appid= 11789557 &sewid=09323b6780cf45 la&ItemN . . . , (4 pages).
Seal, et al., "Identification of a novel series of BET family bromodomain inhibitors: binding mode and profile ofl-BET151 (GSK1210151A),"  Bioorg. Med. Chem. Lett , 22:2968-2972 (2012).
Sedlacek, et al., "Flavopiridol (L86 8275; NSC 649890), a new kinase inhibitor for tumor therapy," International Journal of Oncology, 9: 1143-1168 (1996).
Sen, et al., "Artemisinin triggers induction of cell-cycle arrest and apoptosis in *Leishmania donovani promastigotes*," J Med Microbiol, 56(Pt. 9): 1213-1218 (2007).
Senderowicz, et al., "Phase I Trial of Continuous Infusion Flavopiridol, A Novel Cyclin-Dependent Kinase Inhibitor, in Patients with Refractory Neoplasms," J Clin Oncol, 16:2986-2999 (1998).
Senderowicz, "Flavopiridol: the first cyclin-dependent kinase inhibitor in human clinical trials," Investigational New Drugs, 17:313-320 (1999).

(56) References Cited

OTHER PUBLICATIONS

Senderowicz, et al., "Preclinical and Clinical Development of Cyclin-Dependent Kinase Modulators," J Natl Cancer Inst, 92:376-387 (2000).
Shalaby, et al., "Development of humanized bi specific antibodies reactive with cytotoxic lymphocytes and tumor cells overexpressing the HER2 protooncogene," J Exp. Med., 175:217-225 (1992).
Shangary, et al., "Peptides derived from BH3 domains of Bcl-2 family members: a comparative analysis of inhibition of Bcl-2, Bel-XL and Bax oligomerization, induction of cytochrome c release, and activation of cell death," Biochemistry, 41: 9485-9495 (2002).
Shapiro, et al., "A Phase II Trial of the Cyclin-Dependent Kinase Inhibitor Flavopiridol in Patients with Previously Untreated Stage IV Non-Small Cell Lung Cancer," Clinical Cancer Research, 7:1590-1599 (2001).
Shibue et al., "Differential contribution of Puma and Noxa in dual regulation of p53-mediated apoptotic pathways," The EMBO Journal, 25:4952-4962 (2006).
Shimizu, et al., "Proapoptotic BH3-only Bcl-2 family members induce cytochrome c release, but not mitochondrial membrane potential loss, and do not directly modulate voltage-dependent anion channel activity," PNAS, 97:577-582 (2000).
Shopes, "A genetically engineered human IgG mutant with enhanced cytolytic activity," J Immunol, 148:2918-2922 (1992).
Sinicrope, et al., "Proapoptotic Bad and Bid Protein Expression Predict Survival in Stages II and III Colon Cancers," Clin. Cane. Res., 14(13):4128-4133 (2008).
Sinicrope, et al., "Prognostic Impact of Bim, Puma, and Noxa Expression in Human Colon Carcinomas," Clin. Cane. Res., 14(18):5810-5818 (2008).
Sirois, et al., "Antisense oligonucleotide inhibition of PDGFR-beta receptor subunit expression directs suppression of intimal thickening," Circulation, 95:669-676 (1997).
Smith, et al., "Abstract P047: Real-World Outcomes Among AML Patients Treated with Decitabine or Azacitidine," Haematologica 98(Suppl 1):19 (2013).
Smith, et al., "An alvocidib-containing regimen is highly effective in AML patients through a mechanism dependent on MCLI expression and function," Journal of Clinical Oncology, 33(15 Suppl.): Abstract No. 7062 (3 pages) (2015).
Smith, et al., "Enhancer biology and enhanceropathies," Nature Structural & Molecular Biology, 21:210-219 (2014).
Soltow, et al., "Overexpression of CuZnSOD or MnSOD protects satellite cells from doxorubicin-induced apoptosis," FASEB J 21:A449 (2007)—Abstract.
Sommakia, S., et al., "Alvocidib Synergizes with BRD4 Inhibitors to Improve Cytotoxity in an AML Cell Line" Poster P255 presented at AACR-NCI-EORTC Virtual International Conference on Molecular Targets and Cancer Therapeutics, Oct. 7-10, 2021.
Song, et al., "Application of Flavopiridol, Novel Small Molecule Cyclin-Dependent Kinase Inhibitor, in Tumor Therapy" National Medical Journal of China, 85(12): 862-864, 2005 (With English Translation) (10 Pages).
Song, et al., "Carbon Monoxide Promotes Fas/CD95-Induced Apoptosis in Jurkat Cells," J Biol Chem 279(43):44327-44334, 2004.
Song, et al., "Carbon Monoxide Promotes Fas/CD9-Induced Apoptosis in Jurkat Cells," The Journal of Biological Chemisry, 279(43):44327-44334 (2004)—Additions and Correction, The Journal of Biological Chemistry, 280(23):22555-22556 (2005).
Stephens, et al., "Cyclophosphamide, alvocidib (flavopiridol), and rituximab, a novel feasible chemoimmunotherapy regimen for patients with high-risk chronic lymphocytic leukemia", Leukemia Research, 37:1195-1199 (2013).
Stevenson, et al., "A chimeric antibody with dual Fe regions (bisFabFc) prepared by manipulations at IgG hinge," Anti-Cancer Drug Design, 3:219-230 (1989).
Stewart, et al., "The MCL-1 BH3 Helix is an Exclusive MCL-1 inhibitor and Apoptosis Sensitizer," Nat. Chem. Biol., 6(8):595-601 (2010).
Sturm, et al., "Mutation of p53 and consecutive selective drug resistance in B-CLL occurs as a consequence of prior DNA-damaging chemotherapy," Cell Death and Differentiation, 10:477-484 (2003).
Sugiyama, et al., "Activation of mitochondrial voltage-dependent anion channel by a pro-apoptotic BH3-onlv protein Bim," Oncogene, 21(32):4944-4956 (2002).
Suzuki, et al., "Possible Existence of Common Internalization Mechanisms among Arginine-rich Peptides," J. Biol Chem, 277:2437-2443 (2002).
Szabo, C., "Understanding What Causes Relapse in Patients with Acute Myeloid Leukemia", Sep. 8, 2015, 3 pages. URL:https://www.pharmacytimes.com/ajax/understanding-what-cause-relpase-in-ptients-with-acute-myeloid-leukemia.
Tahir, et al., "Potential mechanisms of resistance to venetoclax and strategies to circumvent it," BMC Cancer 17:399, 2017 (10 pages).
Tan, et al., "Phase I Clinical and Pharmacokinetic Study of Flavopiridol Administered as a Daily 1-Hour Infusion in Patients with Advanced Neoplasms," J Clin Oncol, 20:4074-4082 (2002).
Tan, et al., "The DNA methyltransferase inhibitor zebularine induces mitochondria-mediated apoptosis in gastric cancer cells in vitro and in vivo" Biochemical and Biophysical Research Communications, 430:250-255 (2013).
Tanaka et al., "Design and Characterization of Bivalent BET Inhibitors," Nat. Chem. Biol. 12(12):1089-1096, 2016.
Taussig, et al., "Anti-CD38 antibody-mediated clearance of human repopulating cells masks the heterogeneity of leukemia-initiating cells," Blood, 112(3):568-575 (2008).
Tefferi, A. and Vardiman, J.W., "Mechanics of Disease: Myelodysplastic Syndromes," The New England Journal of Medicine, vol. 361; 1872-1885 (2009).
Terradillos, et al., "Direct addition of BimL to mitochondria does not lead to cytochrome c release," FEES Lett, 522(1-3):29-34 (2002).
Terwijn et al., "High Prognostic Impact of Flow Cytometric Minimal Residual Disease Detection in Acute Myeloid Leukemia: Data From the HOVON/SAKK AML 42A Study," J Clin Oncol 31(31):3889-3897, 2013.
Theisen, et al., "Reversible inhibition of lysine specific demethylase 1 is a novel anti-tumor strategy for poorly differentiated endometrial carcinoma," BMC Cancer, 14:752 (2014) (12 pages).
Thomas, et al., "Phase I Clinical and Pharmacokinetic Trial of the Cyclin-Dependent Kinase Inhibitor Flavopiridol," Cancer Chemother Pharmacol, 50:465-472 (2002).
Thomas, et al., "Phase I Clinical and Pharmacokinetic Trial of Flavopiridol," Proc of Annual Meeting. of Amer Assoc, 38:Abstract 1496, 222 (1997).
Thomenius, et al., "Using BH3 Profiling As a Predictive Indicator for Myeloma Patient Response to Bortezomib," Blood, 118(21): Abstract No. 3952 (2011).
Thoren, "Mass Spectrometry Methods for Detecting Monoclonal Immunoglobulins in Multiple Myeloma Minimal Residual Disease," Seminars in Hematology, 55(1):41-43 (2018).
Thornton, et al., "Characterisation of TP53 abnormalities in chronic lymphocytic leukemia," The Hematology Journal, 5:47-54 (2004).
Thornton, et al., "High dose methylprednisolone can induce remissions in CLL patients with p53 abnormalities," Ann Hematol, 82:759-765 (2003).
Tibes, R. and Bogenberger, J.M., "Transcriptional Silencing of MCL-1 Through Cyclin-Dependent Kinase Inhibition in Acute Myeloid Leukemia", Frontiers in Oncoogy, 9:Article 1205, 13 pages (2019).
Tolero Pharmaceuticals, "Making Meaningful Medicines," presented at the Jefferies 2016 Heathcare Conference, New York, NY Jun. 7-10, 2016: 31 pages.
Toogood, et al., "Discovery of a Potent and Selective Inhibitor of Cyclin-Dependent Kinase 4/6," J Med. Chem., 48:2388-2406 (2005).
Touzeau, et al., "BH3-profiling identifies heterogeneous dependency on Bcl-2 family members in multiple myeloma and predicts sensitivity to BH3 mimetics," Leukemia, 30:761-764 (2016).
Traunecker, et al., "Bispecific single chain molecules (Janusins) target cytotoxic lymphocytes on HIV infected cells," EMBO J, 10:3655-3659 (1991).

(56) References Cited

OTHER PUBLICATIONS

Tsao, et al., "Concomitant inhibition of DNA methyltransferase and BCL-2 protein function synergistically induce mitochondrial apoptosis in acute myelogenous leukemia cells," Ann Hematol, 91(12):1861-1870 (2012).
Tutt, et al., "Trispecific F(ab')₃ derivatives that use cooperative signaling via the TCR/CD3 complex and CD2 to activate and redirect resting cytotoxic T cells," J Immunol, 147:60-69 (1991).
U.S. National Library of Medicine, "Alvocidib, Cytarabine, and Mitoxantrone in Treating Patients With Newly Diagnosed Acute Myeloid Leukemia" First Posted Nov. 21, 2008, Last Update Posted Aug. 7, 2018 URL=https://clinicaltrials.gov/ct2/show/NCT00795002, retrieved Jan. 28, 2020, 11 pages.
U.S. National Library of Medicine, "Flavopiridol in Treating Patients With Previously Treated Chronic Lymphocytic Leukemia or Lymphocytic Lymphoma," Apr. 9, 2003, URL=https://www.clinicaltrials.gov I ct2/show IN CT0005 8240?term-alvocidib &rank= 16, retrieved Dec. 11, 2018 (8 pages).
U.S. National Library of Medicine, "Flavopiridol in Treating Patients With Relapsed or Refractory Lymphoma or Multiple Myeloma," Jun. 3, 2005, URL=https://www .clinicaltrials.gov/ct2/show/record/NCT00 112723 ?term-alvocidib&rank=8, retrieved Dec. 11, 2018 (13 pages).
U.S. National Library of Medicine, "History of Changes for Study: NCT01949883 A Phase 1 Study Evaluating CP1-0610 in Patients With Progressive Lymphoma" ClinicalTrials.gov Identifier: NCT01949883, First Posted Sep. 13, 2013, Last Update Posted Sep. 26, 2013, retrieved from https://clinicaltrials.gov/ct2/history/NCT01949883?A=2&B=2&C=merged#StudyPageTop, 7 pages.
U.S. National Library of Medicine, "Ph I Study of Alvocidib and Cytarabine/Daunorubicin (7+3) in Patients With Newly Diagnosed Acute Myeloid Leukemia (AML)," ClinicalTrials.gov Identifier: NCT03298984, First Posted Oct. 2, 2017, Last Update Posted Mar. 14, 2019, retrieved from https://clinicaltrials.gov/ct2/show/study/NCT03298984 (9 pages).
Use of a novel small molecule cyclin inhibitor flavopiridol in tumor therapy, Natl Med J China, vol. 85, No. 12, pp. 862-864 (2005).
Valencia, et al., "A new reliable fluorescence in situ hybridization method for identifying multiple specific cytogenetic abnormalities in acute myeloid leukemia," Leukemia & Lymphoma, 51(4):680-685 (2010).
Vaquero, et al., "Extracellular matrix proteins protect pancreatic cancer cells from death via mitochondrial and nonmitochondrial pathways," Gastroenterology, 125(4):1188-1202 (2003).
Vaux, et al., "Bcl-2 gene promotes haemopoietic cell survival and cooperates with c-myc to immortalize pre-B cells," Nature, 335(6189):440-442 (1988).
Venkat, "Flavopiridol: A Drug that May Save Lives," 2004, retrieved from https ://web .archive .org/we b/2006061511221 7 /http://clltopics.org/Chemo/flavopiridol .htm, (7 pages).
Venkatesh, et al., "Mini-Review: Role of the development scientist in compound lead selection and optimization," Journal of Pharmaceutical Sciences, 89(2):145-154 (2000).
Venugopal, et al., "A Phase I Study of Quisinostat (JNJ-26481585), an Oral Hydroxamate Histone Deacetylase Inhibitor with Evidence of Target Modulation and Antitumor Activity, in Patients with Advanced Solid Tumors," Clinical Cancer Research, 19:4262-4272 (2013).
Verhoeyen, et al., "Reshaping Human Antibodies: Grafting an Antilysozyme Activity," Science, 239:1534-1536 (1988).
Ververis, et al., "Histone deacetylase inhibitors (HDACis): multitargeted anticancer agents," Biologics: Targets and Therapy, 7:47-60 (2013).
Villela, et al., "Acute Myeloid Leukaemia: Optimal Management and Recent Developments," Drugs, 71(12):1537-1550 (2011).
Vitetta, et al., "Redesigning Nature's Poisons to Create Anti-Tumor Reagents," Science, 238:1098-1104 (1987).
Vivès, et al., "A Truncated HIV-1 Tat Protein Basic Domain Rapidly Translocates through the Plasma Membrane and Accumulates in the Cell Nucleus," J Biol. Chem., 272(25):16010-16017 (1997).
Vo, et al., "Relative Mitochondrial Priming of Myeloblasts and Normal HSCs Determines Chemotherapeutic Success in AML," Cell, 151:344-355 (2012).
Vo, "Mitochondrial Priming Determines Chemotherapeutic Response in Acute Myeloid Leukemia," Dissertation, Harvard University, 119 pages (2012).
Vogelzang, N.J., et al., "Phase I, first-in-human, dose-expansion study of oral TP-1287, a cyclin-dependent kinase 9 (CDK9) inhibitor, in patients with advanced solid tumors (ASTs)", Poster presented at the annual meeting of the American Association for Cancer Research, New Orleans, Louisiana, Apr. 8-13, 2022.
Wagner, A.J., et al., "Phase 1, first-in-human, dose-expansion study of oral TP-1287, a cyclin-dependent kinase 9 (CDK9) inhibitor, in patients with sarcoma", Poster presented at the American Association for Cancer Research (AACR): Special Conference on Sarcomas | May 9-12, 2022; Montreal, Quebec, Canada.
Waldschmidt et al., "Comprehensive Characterization of Circulating and Bone Marrow-Derived Multiple Myeloma Cells at Minimal Residual Disease," Seminars in Hematology 55(1):33-37, 2018.
Wang, et al., "BID: A Novel BH3 Domain-Only Death Agonist," Genes & Development, 10(22):2859-2869 (1996).
Wang, et al., "Cell Permeable Bcl-2 binding peptides: A Chemical Approach to Apoptosis Induction in Tumor Cells," Cancer Res., 60: 1498-1502 (2000).
Wang et al., "Structure based discovery of an organic compound that binds Bcl-2 protein and induces apoptosis of tumor cells," PNAS, 97:7124-7129 (2000).
Wang et al., "Synthesis of pochoxime prodrugs as potent HSP90 inhibitors," Bioorganic & Medicinal Chemistry Letters, 19:3836-3840 (2009).
Wang, "The Expanding Role of Mitochondria in Apoptosis," Genes Dev, 15:2922-2933 (2001).
Wei, et al., "Proapoptotic BAX and Bak: A Requisite Gateway to Mitochondrial Dysfunction and Death," Science, 292(5517):727-730 (2001).
Wei, et al., "tBID, a membrane-targeted death ligand, oligomerizes BAK to release cytochrome c," Genes & Development, 14:2060-2071 (2000).
Wei, et al., "Temporally and spatially coordinated expression of cell cycle regulatory factors after angioplasty," Circ. Res., 80:418-426 (1997).
Weinstein, et al., "Addiction to Oncogenes—the Achilles Heal to Cancer," Science, 297:63-64 (2002).
Weniger, et al., "Treatment-Induced Oxidative Stress and Cellular Antioxidant Capacity Determine Response to Bortezomib in Mantle Cell Lymphoma," Clin. Cancer Res., 17(15):5101-5112 (2011).
Werner, et al., "Bcl-2 Family Member Bfl-1/A1 Sequesters Truncated Bid to Inhibit its Collaboration With Pro-Apoptotic Bak or Bax," J Biol. Chem, 277(25):22781-22788 (2002).
Westerhoff et al., "Magainins and the disruption of membrane-linked free-energy transduction," Proc. Natl. Acad. Sci USA, 86(17):6597-6601 (1989).
Whatcott, et al., "Alvocidib Potentiates the Activity of Venetoclax in Preclinical Models of Acute Myeloid Leukemia," Blood, 128(22): 1652 (2016).
Wilkinson, "Immunochemical techniques inspire development of new antibody purification methods," The Scientist, 14(8):25-28 (2000).
Willis, et al., "Apoptosis Initiated When BH3 Ligands Engage Multiple Bcl-2 Homologs, not Bax or Bak," Science, 315:856-859 (2007).
Willis, et al., "Proapoptotic Bak is sequestered by Mcl-1 and Bcl-xL, but not Bcl-2, until displaced by BH3-only proteins," Genes Dev., 19:1294-1305 (2005).
Wolff, et al., "Monoclonal antibody homodimers: Enhanced antitumor activity in Nude Mice," Cancer Research, 53:2560-2565 (1993).
Wolff, M.E., "9 Some Considerations for Prodrug Design" in Burger's Medicinal Chemistry and Drug Discovery, Fifth Edition, vol. 1: Principles and Practice, Wolff, Manfred ed. (NY: Wiley & Sons) pp. 975-977 (1997).
Wolter, et al., "Movement of Bax from the Cytosol to Mitochondria during Apoptosis," J Cell. Biol, 139(5):1281-1292 (1997).

(56) References Cited

OTHER PUBLICATIONS

Worland, et al., "Alteration of the Phosphorylation State of p34cdc2 Kinase by the Flavone L86-8275 in Breast Carcinoma Cells: Correlation with Decreased H1 Kinase Activity," Biochem. Pharmacol, 46:1831-1840 (1993).

Woyach, et al., "Targeted therapies in CLL: mechanisms of resistance and strategies for management," Blood, 126:471-477 (2015).

Wyatt, et al., "Identification of N-( 4-Piperidinyl)-4-(2,6-dichlorobenzoylamino )-1H-pyrazole-3-carboxamide (AT7519), a Novel Cyclin Dependent Kinase Inhibitor Using Fragment-Based X-Ray Crystallography and Structure Based Drug Design," J Med. Chem., 51:4986-4999 (2008).

Xiang et al., "Mc11 haploinsufficiency protects mice from Myc-induced Acute Myeloid Leukemia," J Clin Invest., 120(6):2109-2118, 2010.

Yamaguchi, et al., "Bcl-XL Protects BimEL-induced Bax Conformational Change and Cytochrome c Release Independent of Interacting with Bax or BimEL," J Biol. Chem, 277(44):41604-41612 (2002).

Yamauchi, "Incorporation of novel agents into the treatment for acute myeloid leukemia," Rinsho Ketsueki, 59(10): 1988-1996 (2018). (1 page) (English Abstract Only).

Yanagisawa, et al., "Translating leukemia stem cells into the clinical setting: Harmonizing the heterogeneity," Experimental Hematology, 44(12):1130-1137 (2016).

Yancey, D., et al., "BAD Dephosphorylation and Decreased Expression of MCL-1 Induce Rapid Apoptosis in Prostate Cancer Cells", PLOS One, 8(9):e74561, 11 pages (2013).

Yang, et al., "Calculation of Protein Conformation from Circular Dichroism," Methods Enzymol, 130:208-269 (1986).

Yang,et al. "A Novel Liposomal Formulation of Flavopiridol," International Journal of Phamaceutics, 365:170-174 (2009).

Yang,et al. "Bad, a Heterodimeric Partner for Bcl-xL and Bcl-2, Displaces Bax and Promotes Cell Death," Cell, 80:285-291 (1995).

Yang, et al., "Bone marrow stroma-mediated resistance to FLT3 inhibitors in FLT3-ITD AML is mediated by persistent activation of extracellular regulated kinase," British Journal of Haematology, 164:61-72 (2014).

Yasuda, et al., "BNIP3a: a Human Homolog of Mitochondrial Proapoptotic protein BNIP3," Cancer Res., 59:533-537 (1999).

Yeh, et al., "Up-regulation of CDK9 kinase activity and Mcl-1 stability contributes to the acquired resistance to cyclin-dependent kinase inhibitors in leukemia," Oncotarget, 6(5):2667-2679 (2014).

Yi, et al., "Inhibition of Bid-induced apoptosis by Bcl-2." J Biol. Chem., 278(19):16992-16999 (2003).

Yoshimoto, et al., "FLT3-ITD up-regulates MCL-1 to promote survival of stem cells in acute myeloid leukemia via FLT3-ITD-specific STAT5 activation," Blood, 114(24):5034-5043 (2009).

Yu, et al., "Catalytic Site Remodelling of the DOT1L Methyltransferase by Selective Inhibitors," Nat Commun, 3:1288 (2012).

Zalazar, F. et al., "Abstract 2340: CPS49 and Flavopiridol: A new selective drug combination for advanced prostate cancer," Cancer Res, vol. 72; Supplement 8; 2 pages (2012).

Zeidener, J.F. and Karp, J.E., "Clinical Activity of Alvocidib (Flavopiridol) in Acute Myeloid Leukemia", Leukemia Research, 39:1312-1318 (2015).

Zeidner, et al., "Randomized multicenter phase II study of flavopiridol (alvocidib), cytarabine, and mitoxantrone (FLAM) versus cytarabine/ daunorubicin (7+3) in newly diagnosed acute myeloid leukemia," Haematologica, 100(9):1172-1179 (2015).

Zeidner, et al., "Randomized Phase II Trial of Timed-Sequential Therapy (TST) with Flavopiridol (Alvocidib), Ara-C and Mitoxantrone (FLAM) Versus "7+3" for Adults Ages 70 Years and Under with Newly Diagnosed Acute Myeloid Leukemia (AML)," Blood, 120:21, Abstract 47 (5 pages) (2012).

Zeidner, J.F., et al., "Phase II Study Incorporating A Novel BH3-Profiling Biomarker Approach of Alvocidib Followed by Cytarabine and Mitoxantrone in Relapsed/Refractory Acute Myeloid Leukemia (AML)", Abstract PF243, 23rd European Hematology Association Congress, Stockholm Sweden Jun. 14-17, 2018-Jun. 15, 2018, EAH library, retrieved from https://library,ehaweb.org.eha.2018/stockholm/ 214729/joshua.f.zeidner.phase.ii.study.incorporating.a.nove.bh3-profileing.biomarker.html?f=topic=1574*media=3, 3 pages.

Zeidner, J.F., et al., "Zella201: A Biomarker-Guided Phase II Study of Alvocidib Followed by Cytarabine and Mitoxantrone in MCL-1 Dependent Relapsed/Refractory Acute Myeloid Leukemia (AML)", Blood, 132(Suppl 1):6 pages (2018).

Zeidner, J.F., et al., "Final Results of a Randomized Multicenter Phase II Study of Alvocidib, Cytarabine, and Mitoxantrone Versus Cytarabine and Daunorubicin (7+3) in Newly Diagnosed High-Risk Acute Myeloid Leukemia (AML)", Leukemia Research, 72:92-95 (2018).

Zeidner, J.F., et al., "Phase I Study of Alvocidib Followed by 7+3 (Cytarabine + Daunorubicin) in Newly Diagnosed Acute Myeloid Leukemia", Clin Cancer Res, 27:60-69 (2021).

Zeidner, J.F., et al., "Zella-101: Phase 1 Study of Alvocidib Followed by 7 + 3 Induction in Newly Diagnosed AML Patients," Poster as presented at European Hematology Association, 25th Congress held virtually Jun. 11-21, 2020, 1 page.

Zeidner, J.F., et al., "Zella 201: A Biomarker-Guided Phase II Study of Alvocidib Followed by Cytarabine and Mitoxantrone in MCL-1 Dependent Acute Myeloid Leukemia (AML): Results of Newly Diagnosed High-Risk Exploratory Arm", Blood, 136(Supplement 1):48-50 (2020).

Zeidner J et al., "Zella 201: A Biomarker-Guided Phase II Study of Alvocidib Followed by Cytarabine and Mitoxantrone in MCL-1 Dependent Acute Myeloid Leukemia (AML): Results of Newly Diagnosed High-Risk Exploratory Arm," American Society of Hematology—62nd Annual Meeting, 2020.

Zeidner, J.F., et al., "A Prospective Biomarker Analysis of Alvocidib Followed by Cytarabine and Mitoxantrone in MCL-1-dependent Relapsed/Refractory Acute Myeloid Leukemia", Blood Cancer Journal, 11(175):5 pages (2021).

Zeng, et al., "Targeting the leukemia microenvironment by CXCR4 inhibition overcomes resistance to kinase inhibitors and chemotherapy in AML," Blood, 113:6215-6224 (2009).

Zha, et al., "BH3 Domain of BAD is Required for Heterodimerization with Bcl-XL and Pro-apoptotic Activity," J Biol. Chem., 272(39):24101-24104 (1997).

Zha, et al., "Posttranslational N-Myristoylation of BID as a Molecular Switch for targeting Mitochondria and Apoptosis," Science, 290(5497): 1761-1765 (2000).

Zha, et al., "Serine Phosphorylation of Death Agonist BAD in Response to Survival Factor Results in Binding to 14-3-3 Not BCL-XL," Cell, 87:619-628 (1996).

Zhai, et al., "Clinical pharmacology and pharmacogenetics of flavopiridol 1-h i.v. infusion in patients with refractory neoplasms," Anti-Cancer Drugs 14: 125-135, 2003. Zhang et al., "Bcl-2 family proteins are essential for platelet survival," Cell Death Differ., 14(5):943-951 (2007).

Zhang, et al., "Bcl-2 Family Proteins are Essential for Platelet Survival", Cell Death Differ, 14(5):943-951 (2007).

Zhao, et al., "BCL2 Amplicon Loss and Transcriptional Remodeling Drives ABT-199 Resistance in B Cell Lymphoma Models", Cancer Cell, 35:752-766 (2019).

Zhao, et al., "The Making ofl-BET762, a BET Bromodomain Inhibitor Now in Clinical Development," Journal of Medicinal Chemistry, 56:7498-7500 (2013).

Zhou, et al., "Flavopiridol enhances ABT-199 sensitivity in unfavourable-risk multiple myeloma cells in vitro and in vivo," Br. J Cancer, 118(3):388-397 (2018).

Zhou, et al., "Novel mutant-selective EGFR kinase inhibitors against EGFR T790M," Nature, 462(7276):1070-1074 (2009).

Zhu, et al., "Development of venetoclax for therapy of lymphoid malignancies," Drug Des. Devel. Ther., 11:685-694 (2017).

Zong, et al., "BH3-only proteins that bind pro-survival Bcl-2 family members fail to induce apoptosis in the absence of Bax and Bak," Genes & Development, 15:1481-1486 (2001).

Decker, R.H. et al., "The cyclin-dependent kinase inhibitor flavopiridol induces apoptosis in human leukemia cells (U937) through the mitochondrial rather than the receptor-mediated pathway," Cell Death and Differentiation, vol. 8; 715-724 (2001).

(56) References Cited

OTHER PUBLICATIONS

Hirayama, N., yukikagobutsukcssho sakusci handobukku (handbook for preparation of organic compound crystals)—genri to nouhau—(principle and know-how), Maruzen Inc., Jul. 25, 2008, p. 57-84.

Karpinski, P.H., "Polymorphism of Active Pharmaceutical Ingredients," Chem. Eng. Technol., vol. 29; No. 2; 233-237 (2006).

Kawaguchi, Y. et al., "Drug and Crystal Polymorphism," Journal of Human Environmental Engineering, 310-317 (2002).

Leverson et al., "Potent and selective small-molecule MCL-1 inhibitors demonstrate on-target cancer cell killing activity as single agents and in combination with ABT-263 (navitoclax)", Cell Death and Disease, vol. 6, No. 1, Jan. 15, 2015, p. e1590.

"Shiniyakuhin no kikaku oyobi shakenhoho no settei nitsuite" (setting of the standard and test method for new pharmaceuticals), iyakushinpatsu No. 568, May 1, 2001.

Takata, N., API form screening and selection in drug discovery stage, Pharm Stage, vol. 6, No. 10, Jan. 15, 2007, p. 20-25.

Tenuta, A. et al., "Clinical trial risk in castration-resistant prostate cancer: immunotherapies show promise," BJU Int, vol. 113; E82-E89 (2014).

Tosi, P. et al., "Concensus conference on the management of tumor lysis syndrome," Haematologica, vol. 93; No. 12; 1877-1885 (2008).

Yamano, M., Approach to Crystal Polymorph in Process Research of New Drug, Journal of Synthetic Organic Chemistry, 2007.

\* cited by examiner

CDK9 INHIBITORS AND POLYMORPHS THEREOF FOR USE AS AGENTS FOR TREATMENT OF CANCER

RELATED APPLICATIONS

This application is a Continuation of U.S. application Ser. No. 17/225,836, filed Apr. 8, 2021, which is a Continuation of U.S. application Ser. No. 16/703,773, now U.S. Pat. No. 11,034,710, filed Dec. 4, 2019, which claims the benefit of U.S. Provisional Application No. 62/775,303, filed Dec. 4, 2018. The entire teachings of the above applications are incorporated herein by reference.

BACKGROUND

Alvocidib (flavopiridol) is a potent cyclin-dependent kinase (CDK) inhibitor with selectivity for CDKs 9, 1, 2, 4 and 7. 2-(2-Chlorophenyl)-5-hydroxy-8-((3S,4R)-3-hydroxy-1-methylpiperidin-4-yl)-4-oxo-4H-chromen-7-yl dihydrogen phosphate, disclosed in International Publication No. WO 2016/187316, is an orally bioavailable prodrug of alvocidib.

There is a need for crystalline forms and/or polymorphs of 2-(2-chlorophenyl)-5-hydroxy-8-((3S,4R)-3-hydroxy-1-methylpiperidin-4-yl)-4-oxo-4H-chromen-7-yl dihydrogen phosphate that are suitable for use in pharmaceutical compositions and methods for treating diseases associated with overexpression of a CDK. There is a further need for methods for preparing 2-(2-chlorophenyl)-5-hydroxy-8-((3S,4R)-3-hydroxy-1-methylpiperidin-4-yl)-4-oxo-4H-chromen-7-yl dihydrogen phosphate that enable the manufacture of 2-(2-chlorophenyl)-5-hydroxy-8-((3S,4R)-3-hydroxy-1-methylpiperidin-4-yl)-4-oxo-4H-chromen-7-yl dihydrogen phosphate for use in pharmaceutical compositions and methods for treating diseases associated with overexpression of a CDK.

BRIEF SUMMARY

Embodiments of the present invention are generally directed to CDK (e.g., CDK9) inhibitors and polymorphs thereof as well as pharmaceutical compositions comprising the same, for use as therapeutic or prophylactic agents, for example, for treatment of cancer (e.g., hematological cancer) and other conditions.

Some embodiments provide a crystalline form of a compound having the structure (I):

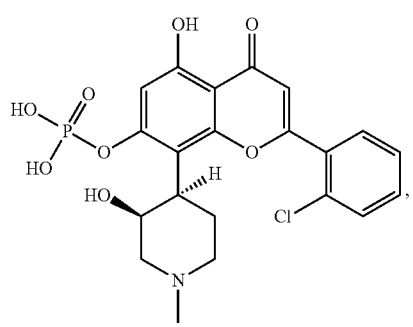

(I)

or a tautomer or zwitterionic form thereof.

More specifically, aspects of the present disclosure are directed to a polymorph of a compound having the structure (I), or a tautomer or zwitterionic form thereof. For example, in some embodiments the polymorph has an X-ray powder diffraction pattern comprising the following: D space (Å): 18.3±0.09, 8.1±0.06, 6.4±0.08, 5.9±0.06, 4.4±0.05 expressed in terms of "D" spacing.

Another embodiment affords a polymorph of a compound of structure (I) or a tautomer or zwitterionic form thereof, the polymorph being a crystalized form having a monoclinic space group $P2_1$ with lattice parameters of a=6.46(1) Å, b=9.07(2) Å, c=18.25(4) Å, β=95.457(2°), and a volume of 1066.11(4) Å$^3$.

One embodiment provides a crystalline form of a compound of structure (I), or a tautomer or zwitterionic form thereof, having an x-ray powder diffraction pattern substantially in accordance with that depicted in FIG. 1.

Yet another embodiment provides a polymorph of a compound of structure (I) or a tautomer or zwitterionic form thereof, wherein the polymorph is Form B as described herein.

Still another embodiment affords a polymorph of a compound of structure (I) or a tautomer or zwitterionic form thereof, wherein the polymorph is formed by a method comprising (a) contacting an amorphous compound of structure (I) with a lattice forming reagent; and (b) treating the product of step (a) with solvent having water content less than about 0.05% v/v and removing the solvent, thereby forming the polymorph.

One embodiment provides a polymorph of a compound of structure (I) or a tautomer or zwitterionic form thereof, wherein the polymorph has an initial purity of at least 99.5% and a subsequent purity of at least 99.5% after being stored from about 12 hours up to about 7 days at about 25° C.±2° C. at a relative humidity of 60%.

One embodiment provides a polymorph of a compound of structure (I) or a tautomer or zwitterionic form thereof having an endotherm peak value at about 256° C.-268° C. as determined by differential scanning calorimetry.

Pharmaceutical compositions comprising a compound having structure (I) (e.g., a polymorph or crystalline form of a compound having structure (I)), or a tautomer or zwitterionic form thereof, and a pharmaceutically acceptable carrier or excipient are also provided in various other embodiments. One embodiment provides a pharmaceutical composition comprising from about 0.5 weight percent to about 11.25 weight percent of a compound having the structure (I), or a tautomer or zwitterionic form thereof; and from about 85 weight percent to about 99.5 weight percent of a pharmaceutically acceptable carrier or excipient. One embodiment provides a pharmaceutical composition comprising about 0.6 weight percent of a compound having structure (I), or a tautomer or zwitterionic form thereof; about 97.4 weight percent of anhydrous lactose; about 1 weight percent colloidal silicon dioxide; and about 1 weight percent magnesium stearate. Another embodiment provides a pharmaceutical composition comprising about 11 weight percent of a compound having the structure (I), or a tautomer or zwitterionic form thereof; about 87 weight percent of anhydrous lactose; about 1 weight percent colloidal silicon dioxide; and about 1 weight percent magnesium stearate. Yet another embodiment provides a pharmaceutical composition comprising about 0.6 weight percent of a compound having structure (I), or a tautomer or zwitterionic form thereof; and from about 98 weight percent to about 99.5 weight percent of cornstarch. Another embodiment provides a pharmaceutical composition comprising about 11 weight percent of a compound of the structure (I), or a tautomer or zwitterionic form thereof; and about 88 weight percent of cornstarch.

Other embodiments provide methods including a method for treatment of a disease associated with overexpression of a cyclin-dependent kinase (CDK), such as cancer (e.g., a hematologic cancer), in a mammal in need thereof, for example, by administering to the mammal a therapeutically effective amount of a crystalline form or a polymorph of a compound having structure (I), or a tautomer or zwitterionic form thereof.

In other embodiments, the present disclosure provides a method for preparing a polymorph or crystalline form of the compound of structure (I). One embodiment provides a method for preparing crystalline Form B of a compound having structure (II):

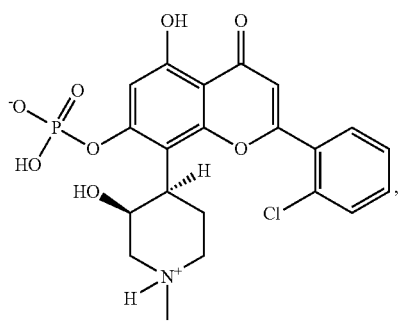

(II)

the method comprising contacting amorphous compound having the structure (I), or a tautomer or zwitterionic form thereof, with an acid in a solvent, thereby preparing the crystalline Form B of the compound having structure (II). Another embodiment provides a method for preparing crystalline Form B of the compound having structure (II), the method comprising contacting a compound having structure (V):

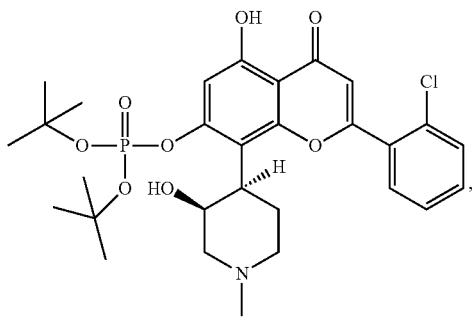

(V)

or a tautomer, salt or zwitterionic form thereof, with an acid in a solvent, thereby preparing the crystalline Form B of the compound having structure (II). Yet another embodiment provides a method for preparing crystalline Form B of a compound having structure (II), the method comprising contacting a compound having the following structure (IV):

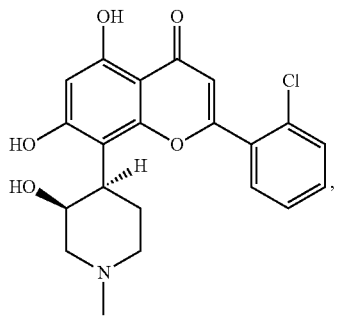

(IV)

or a tautomer or salt thereof, with di-tert-butylhalophosphonate (e.g., di-tert-butylchlorophosphonate, di-tert-butylbromophosphonate) in the presence of an amine base, thereby forming a compound having structure (V), or a tautomer or salt thereof; and contacting the compound having structure (V), or a tautomer or salt thereof, in an organic solvent, with an acid having a $pK_a$ value of greater than about 1 (e.g., an acid having at least one $pK_a$ value that is less than about 5 and a $pK_a$ value of greater than about 1), thereby preparing crystalline Form B of a compound having structure (II). Another embodiment is a method for preparing crystalline Form B of a compound having structure (II), the method comprising contacting a compound having structure (IV), or a tautomer or salt thereof, with di-tert-butylhalophosphonate (e.g., di-tert-butylchlorophosphonate, di-tert-butylbromophosphonate) in the presence of an amine base, thereby forming a compound having structure (V), or a tautomer or salt thereof; contacting the compound having structure (V), or a tautomer or salt thereof, with an acid having a $pK_a$ value of less than about 1, thereby forming a salt of a compound having structure (I); contacting the salt of a compound having structure (I) with a base, thereby forming amorphous compound having structure (I); and contacting the amorphous form of the compound having structure (I), in an organic solvent, with an acid having a $pK_a$ value of greater than about 1 (e.g., an acid having at least one $pK_a$ value that is less than about 5 and a $pK_a$ value of greater than about 1), thereby preparing crystalline Form B of the compound having structure (II).

The present disclosure also provides methods for preparing a compound having structure (I), or a salt, tautomer or zwitterionic form thereof. The method comprises contacting a compound having structure (IV), or a tautomer or salt thereof, with di-tert-butylhalophosphonate (e.g., di-tert-butylchlorophosphonate, di-tert-butylbromophosphonate) in the presence of an amine base, thereby forming a compound having structure (V), or a tautomer or salt thereof; and contacting the compound having structure (V), or a tautomer or salt thereof, with an acid, thereby preparing a compound having structure (I), or a salt, tautomer or zwitterionic form thereof.

These and other aspects of the disclosure will be apparent upon reference to the following detailed description.

BRIEF DESCRIPTION OF THE DRAWINGS

In the figures, identical reference numbers identify similar elements. The sizes and relative positions of elements in the figures are not necessarily drawn to scale and some of these elements are enlarged and positioned to improve figure legibility. Further, the particular shapes of the elements as drawn are not intended to convey any information regarding the actual shape of the particular elements, and have been solely selected for ease of recognition in the figures.

Figure 11A:
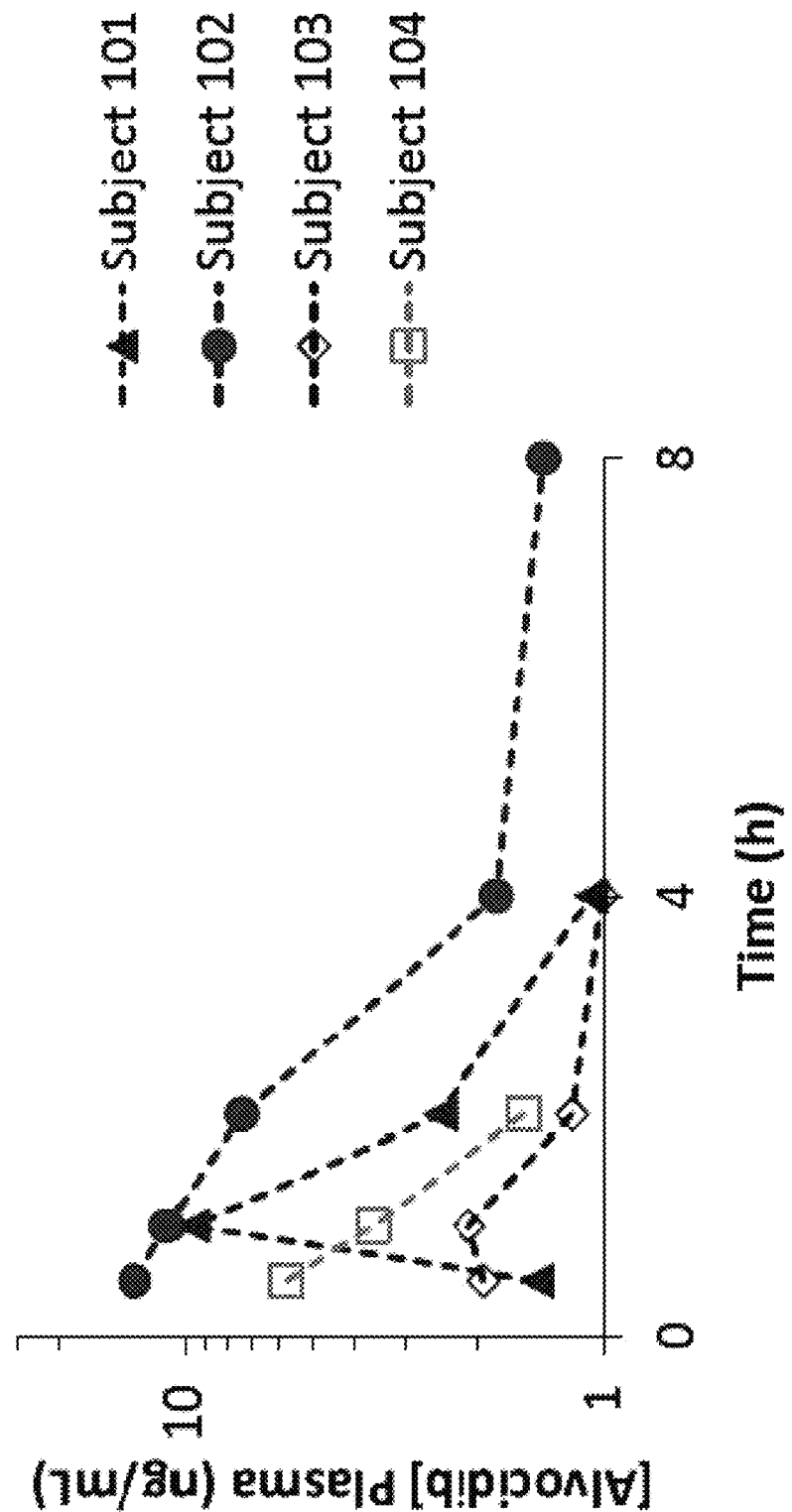
FIG. 11A is a graph of plasma alvocidib concentration (ng/mL) versus time, and shows the concentration of alvocidib in the plasma of patients in cohort 1 on day 1 following daily oral QD dosing with a 1-mg strength capsule containing Formulation No. 401-01.
Figure 11B:
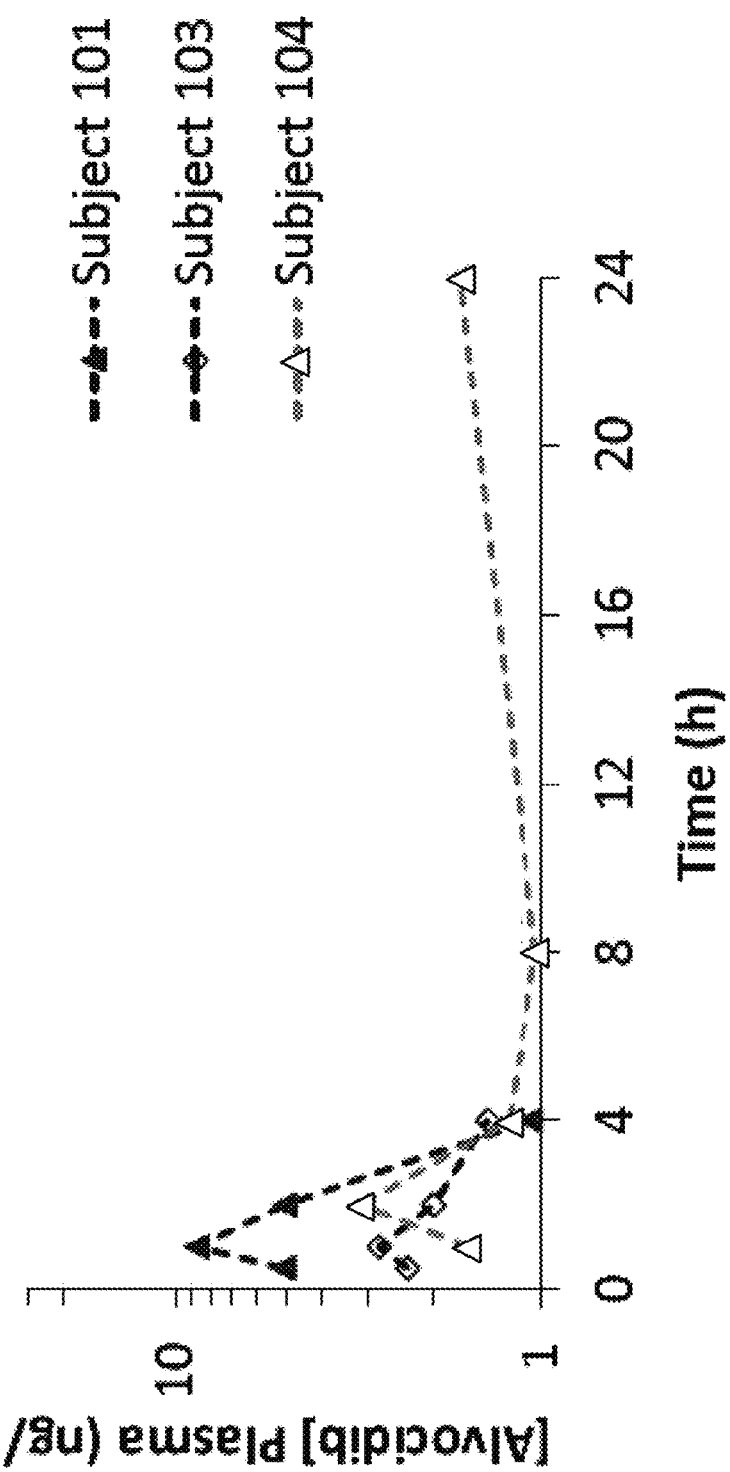
FIG. 11B is a graph of plasma alvocidib concentration (ng/mL) versus time, and shows the concentration of alvocidib in the plasma of patients in cohort 1 on day 14 following daily oral QD dosing with a 1-mg strength capsule containing Formulation No. 401-01.
Figure 11C:
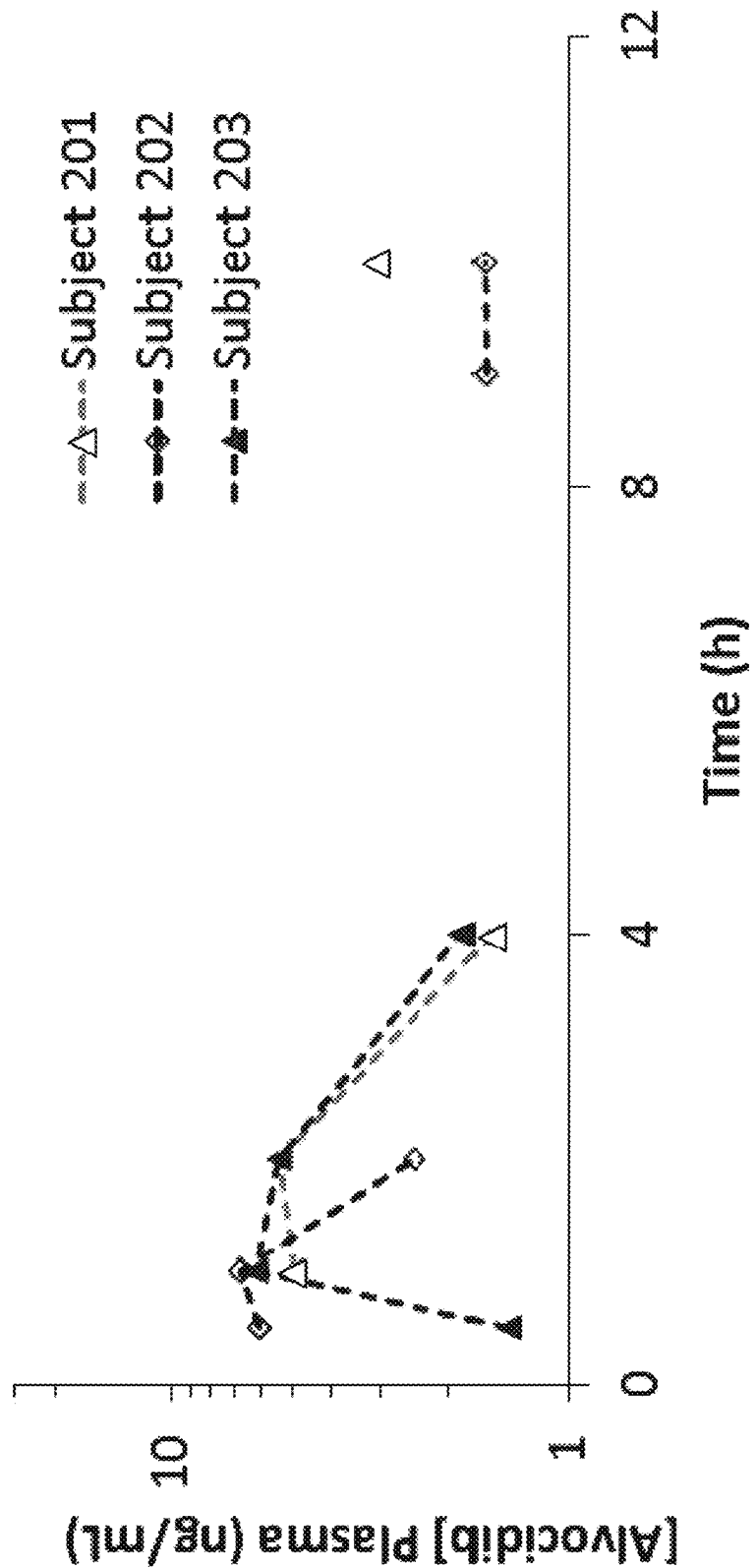

FIG. 11C is a graph of plasma alvocidib concentration (ng/mL) versus time, and shows the concentration of alvocidib in the plasma of patients in cohort 2 on day 1 following daily oral BID dosing with a 1-mg strength capsule containing Formulation No. 401-01.

Figure 11D:
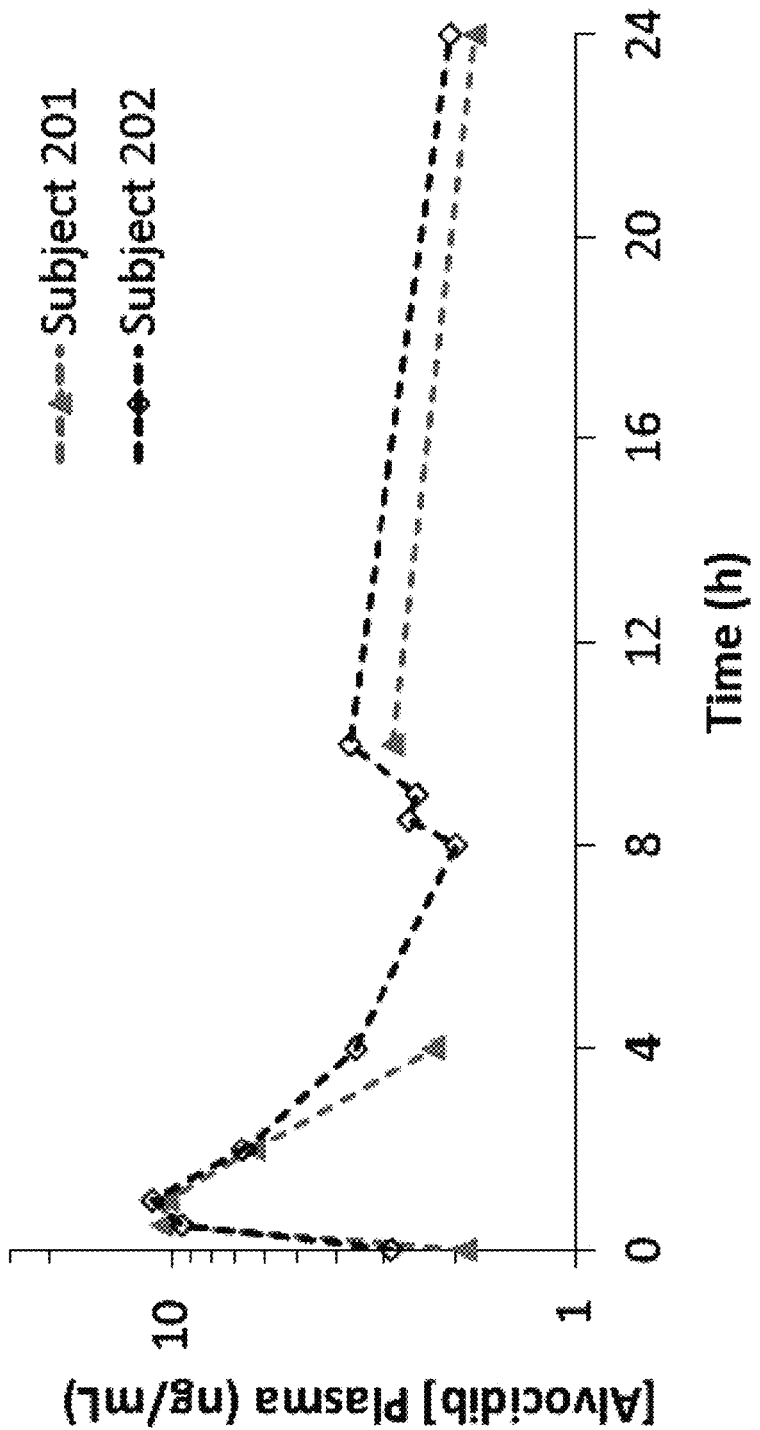

FIG. 11D is a graph of plasma alvocidib concentration (ng/mL) versus time, and shows the concentration of alvocidib in the plasma of patients in cohort 2 on day 14 following daily oral BID dosing with a 1-mg strength capsule containing Formulation No. 401-01.

Figure 11E:
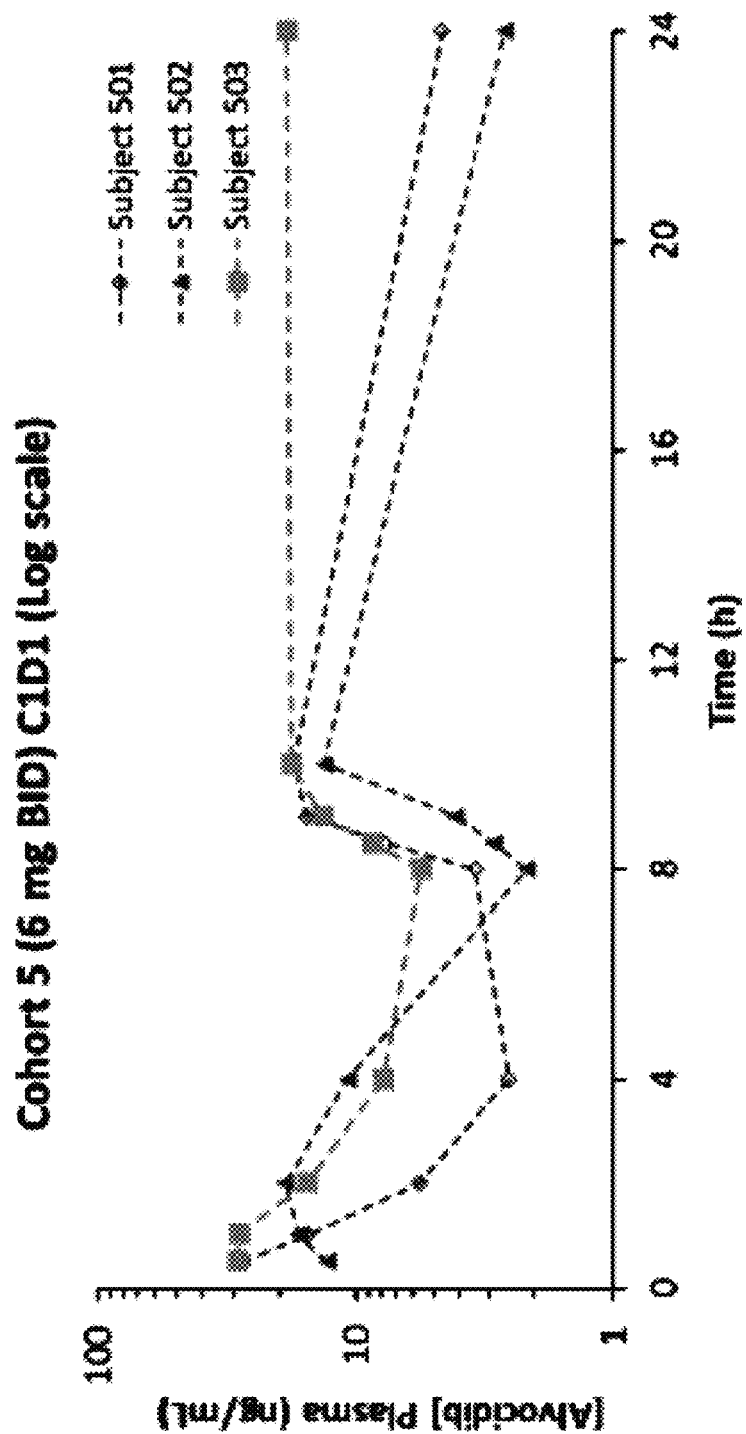

FIG. 11E is a graph of plasma alvocidib concentration (ng/mL) versus time, and shows the concentration of alvocidib in the plasma of patients in Cohort 5 on day 1 following daily oral BID dosing with 6 mg of Formulation No. 401-01.

Figure 11F:
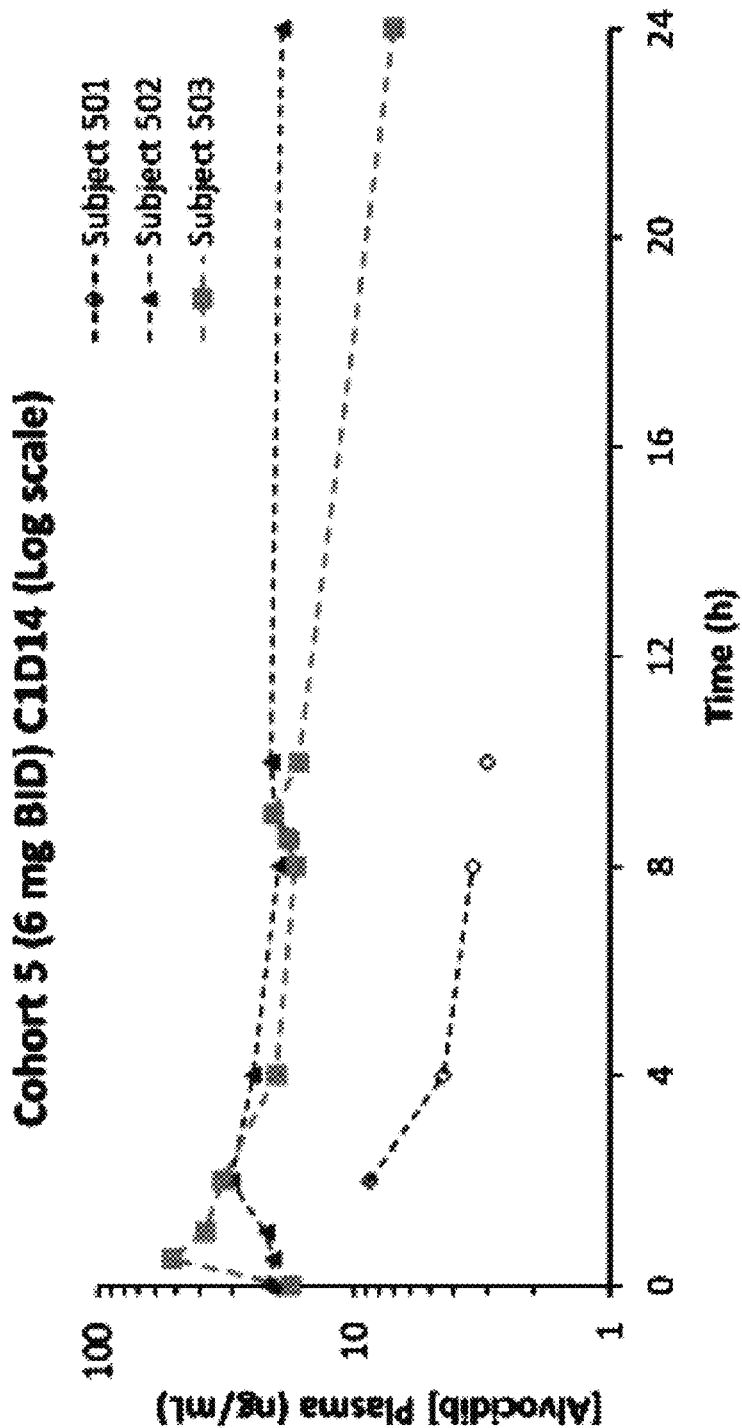

FIG. 11F is a graph of plasma alvocidib concentration (ng/mL) versus time, and shows the concentration of alvocidib in the plasma of patients in Cohort 5 on day 14 following daily oral BID dosing with 6 mg of Formulation No. 401-01.

Figure 11G:
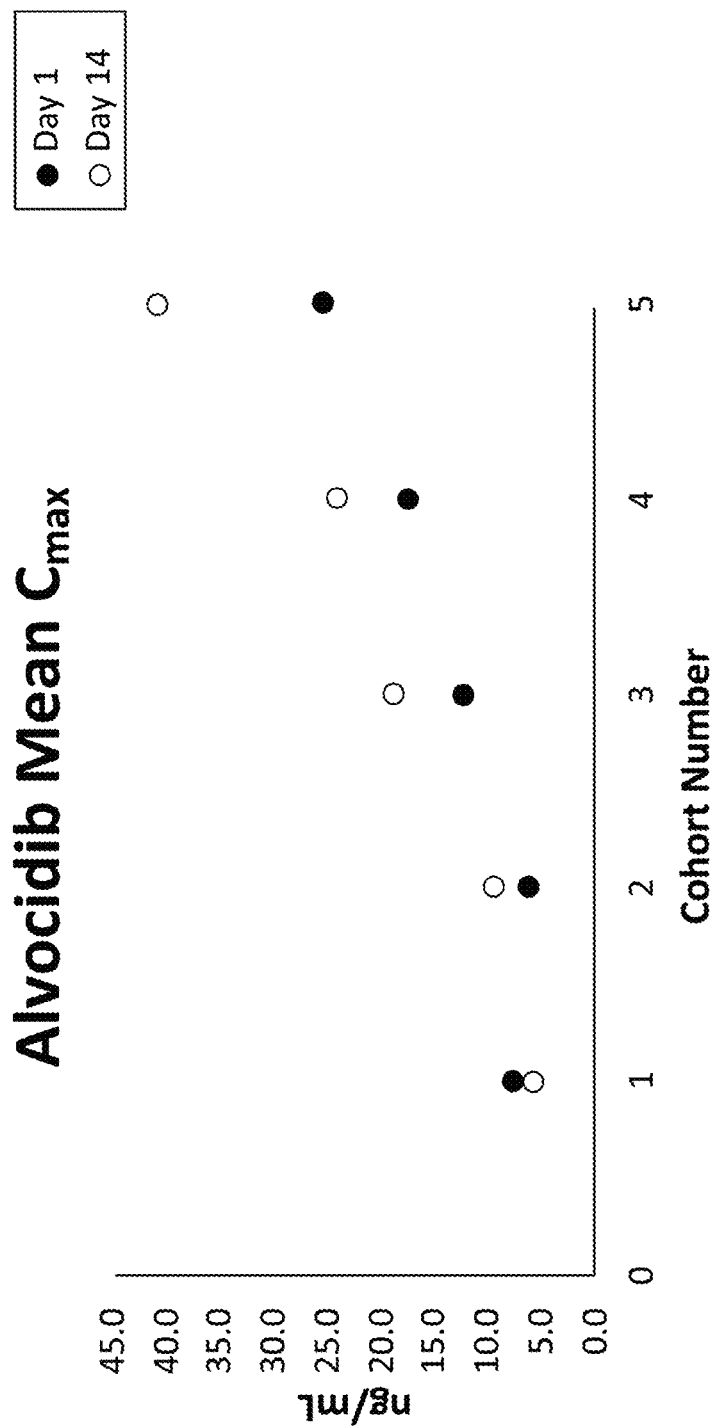

FIG. 11G is a graph of alvocidib (ng/mL) versus cohort, and shows the average $C_{max}$ of alvocidib on day 1 and day 14 following daily oral QD dosing with a 1-mg strength capsule containing Formulation No. 401-01.

Figure 11H:
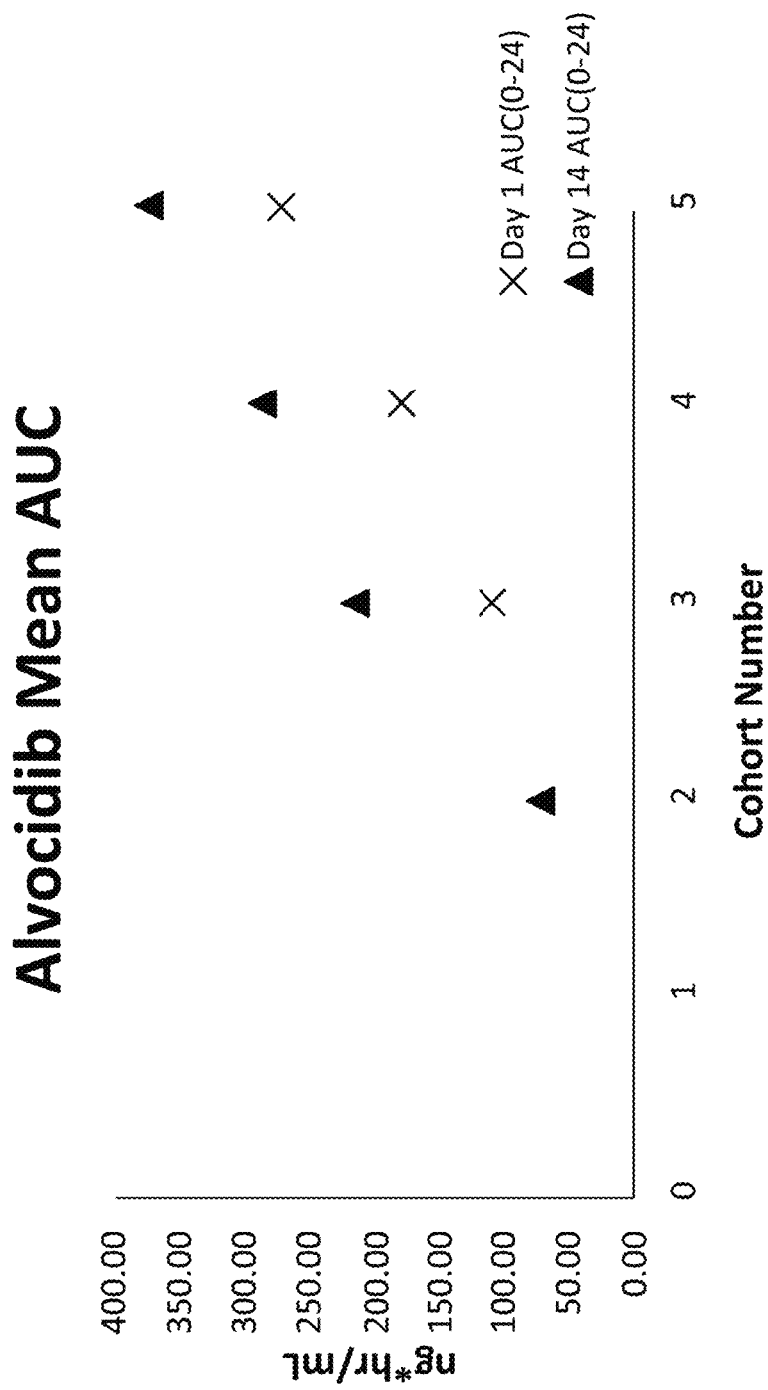

FIG. 11H is a graph of alvocidib (ng*hr/mL) versus cohort, and shows the area under the curve (AUC) of alvocidib on day 1 ($AUC_{0-8}$) and day 14 ($AUC_{0-8}$ and $AUC_{0-24}$) following daily oral BID dosing with a 1-mg strength capsule containing Formulation No. 401-01.

Figure 11I:
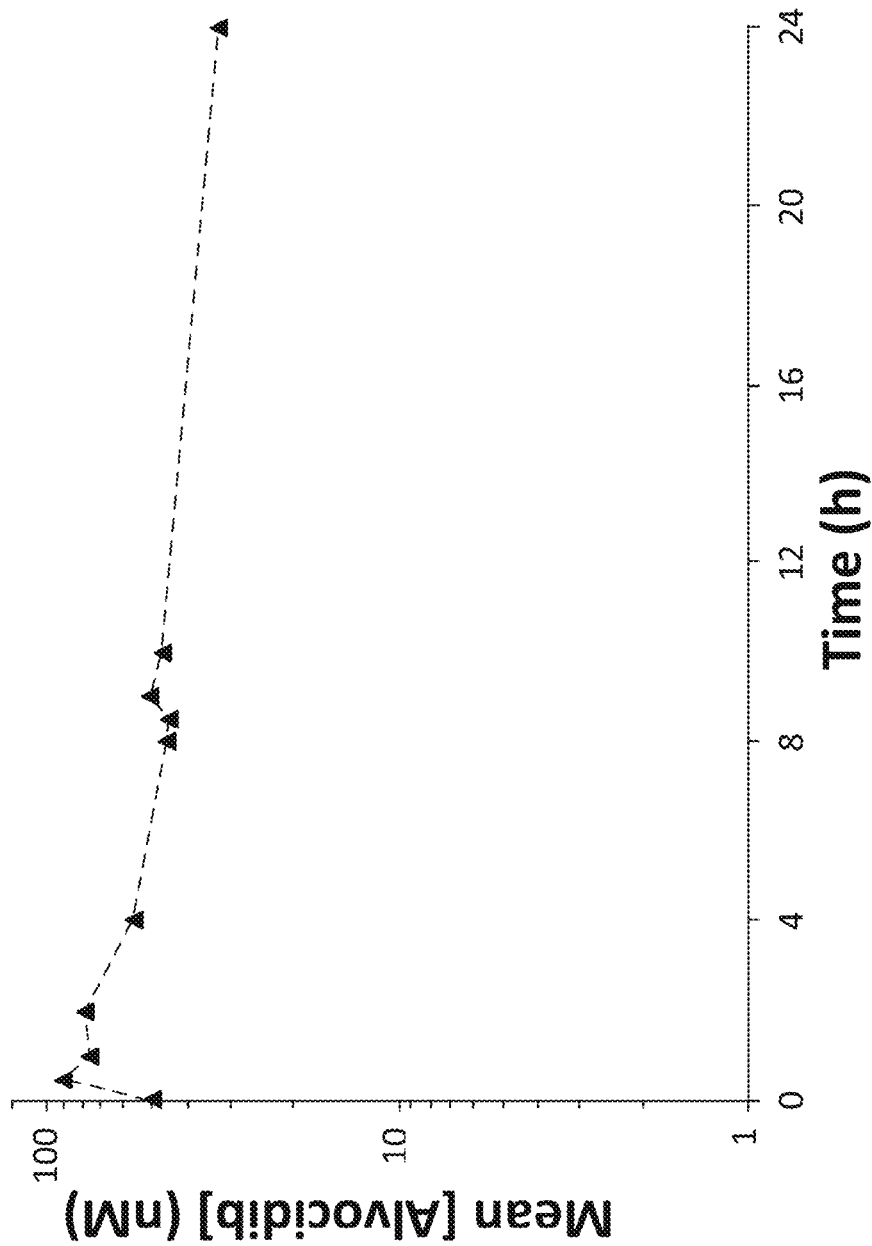

FIG. 11I is a graph of mean concentration of alvocidib (nM) versus time, and shows the mean concentration of alvocidib in plasma of Cohort 5 patients over a 24-hour period.

Figure 12:
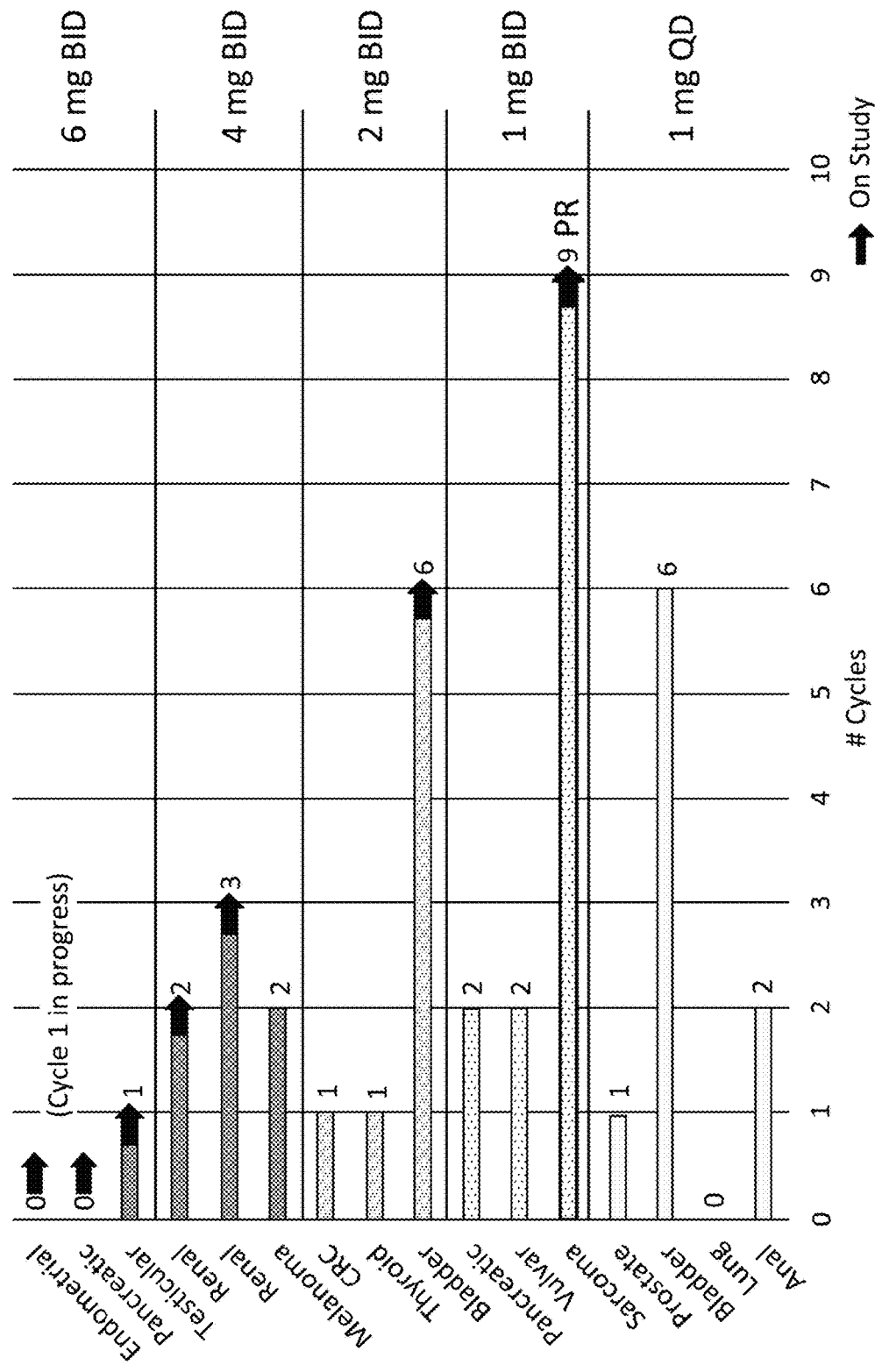

FIG. 12 is a graph, and shows the completed cycles on the study described in Example 15 through Cohort 5.

DETAILED DESCRIPTION

In the following description, certain specific details are set forth in order to provide a thorough understanding of various embodiments of the disclosure. However, one skilled in the art will understand that the disclosure may be practiced without these details.

Unless the context requires otherwise, throughout the present specification and claims, the word "comprise" and variations thereof, such as, "comprises" and "comprising" are to be construed in an open, inclusive sense (i.e., as "including, but not limited to").

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this invention belongs. As used in the specification and claims, the singular form "a," "an," and "the" include plural referents unless the context clearly dictates otherwise.

"Crystalline," as used herein, refers to a homogeneous solid formed by a repeating, three-dimensional pattern of atoms, ions or molecules having fixed distances between constituent parts. The unit cell is the simplest repeating unit in this pattern. Notwithstanding the homogenous nature of an ideal crystal, a perfect crystal rarely, if ever, exists. "Crystalline," as used herein, encompasses crystalline forms that include crystalline defects, for example, crystalline defects commonly formed by manipulating (e.g., preparing, purifying) the crystalline forms described herein. A person skilled in the art is capable of determining whether a sample of a compound is crystalline notwithstanding the presence of such defects.

"Polymorph," as used herein, refers to a crystalline form of a compound characterized by a distinct arrangement of its molecules in a crystal lattice. Polymorphs can be characterized by analytical methods such as x-ray powder diffraction (XRPD), differential scanning calorimetry (DSC) and thermogravimetric analysis.

The crystalline forms and/or polymorphs described herein can be substantially pure. As used herein, "substantially pure," used without further qualification, means the indicated compound has a purity greater than 90 weight percent, for example, greater than 90, 91, 92, 93, 94, 95, 96, 97, 98, or 99 weight percent, and also including a purity equal to about 100 weight percent, based on the weight of the compound. The remaining material comprises other form(s) of the compound, and/or reaction impurities and/or processing impurities arising from its preparation (e.g., alvocidib). Purity can be assessed using techniques known in the art, for example, using an HPLC assay described herein. "Substantially pure" can also be qualified as in "substantially pure of other physical forms of the compound having structure (I), or a tautomer or zwitterionic form thereof" or "substantially pure of alvocidib." When qualified thus, "substantially pure" means that the indicated compound contains less than 10%, preferably less than 5%, more preferably less than 3%, most preferably, less than 1% by weight of the indicated impurity (e.g., any other physical forms of an indicated crystalline form of a compound; alvocidib).

As used herein, the term "alvocidib" means 2-(2-chlorophenyl)-5,7-dihydroxy-8-[(3S,4R)-3-hydroxy-1-methylpiperidin-4-yl]chromen-4-one, or a salt (e.g., a pharmaceutically acceptable salt) thereof (e.g., 2-(2-chlorophenyl)-5,7-dihydroxy-8-[(3S,4R)-3-hydroxy-1-methylpiperidin-4-yl]chromen-4-one hydrochloride).

An XRPD pattern or DSC thermogram that is "substantially in accordance" with one or more figures herein showing an XRPD pattern or diffractogram or DSC thermogram, respectively, is one that would be considered by one skilled in the art to represent the same single crystalline form of the compound having structure (I), or a tautomer or zwitterionic form thereof, as the sample of the compound having structure (I), or a tautomer or zwitterionic form thereof, that provided the pattern or diffractogram or thermogram of one or more figures provided herein. Thus, an XRPD pattern or DSC thermogram that is substantially in accordance may be identical to that of one of the figures or, more likely, may be somewhat different from one or more of the figures. For example, an XRPD pattern that is somewhat different from one or more of the figures may not necessarily show each of the lines of the diffraction pattern presented herein and/or may show a slight change in appearance or intensity of the lines or a shift in the position of the lines. These differences typically result from differences in the conditions involved in obtaining the data or differences in the purity of the sample used to obtain the data. A person skilled in the art is capable of determining if a sample of a crystalline compound is of the same form as or a different form from a form disclosed herein by comparison of the XRPD pattern or DSC thermogram of the sample and the corresponding XRPD pattern or DSC thermogram disclosed herein.

The crystalline forms provided herein can also be identified on the basis of differential scanning calorimetry (DSC) and/or thermogravimetric analysis (TGA). DSC is a thermoanalytical technique in which the difference in the amount of heat required to increase the temperature of a sample is measured as a function of temperature. DSC can be used to detect physical transformations, such as phase transitions, of a sample. For example. DSC can be used to detect the temperature(s) at which a sample undergoes crystallization, melting or glass transition. It is to be understood that any temperature associated with DSC specified herein, with the exception of the DSC temperatures in the Figures or Examples, means the specified value ±5° C. or less. For example, when an embodiment or a claim specifies an endothermic peak at 264° C., this is to be understood to mean 264° C.±5° C. or less, that is a temperature of from 259° C. to 269° C. In preferred embodiments, a DSC is the specified value ±3° C. or less, in more preferred embodiments, ±2° C. or less.

"Lattice forming reagent" or "salt former" refers to a chemical substance that is used in combination with another compound to facilitate the formation of a crystalline or polymorphic solid. For example, in some embodiments, a lattice forming reagent facilitates the formation of polymorph Form B of the compound of structure (I). Lattice forming reagents include acids, bases, sugars, peptides, and the like. In some embodiments, the lattice forming reagent is an acid (e.g., an acid having at least one $pK_a$ value that is less than about 5, such as about 4). For example, a lattice forming reagent may be an organic acid (e.g., maleic acid, acetic acid, fumaric acid, tartaric acid). In some embodiments, the acid is a diprotic acid.

The term "effective amount" or "therapeutically effective amount" refers to that amount of a compound (e.g., polymorph Form B of a compound of structure (I)) described herein that is sufficient to effect the intended application including disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compound chosen, the dosing regimen to be followed, whether it is administered in combination with other compounds, timing of administration, the tissue to which it is administered, and the physical delivery system in which it is carried.

As used herein, "treatment" or "treating" refers to an approach for obtaining beneficial or desired results with respect to a disease, disorder or medical condition including a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "co-administration," "administered in combination with," and their grammatical equivalents, as used herein, encompass administration of two or more agents to a subject, such as an animal, including humans, to treat a disease, disorder or condition described herein. In some embodiments, administration of the two or more agents is such that both agents and/or their metabolites are present in the subject at the same time. Co-administration includes simultaneous administration in separate compositions, administration at different times in separate compositions, or administration in a composition in which the two or more agents are present.

An "anti-cancer agent," "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

"Subject" refers to an animal, such as a mammal, for example, a human. The methods described herein can be useful in both human therapeutics and veterinary applications. In some embodiments, the subject is a mammal, and in some embodiments, the subject is human.

"Mammal" includes humans and both domestic animals such as laboratory animals and household pets (e.g., cats, dogs, swine, cattle, sheep, goats, horses, rabbits), and non-domestic animals, such as wildlife and the like. In some embodiments, the mammal is a human.

"Radiation therapy" means exposing a subject, using routine methods and compositions known to the practitioner, to radiation emitters such as alpha-particle emitting radionuclides (e.g., actinium and thorium radionuclides), low linear energy transfer (LET) radiation emitters (i.e., beta emitters), conversion electron emitters (e.g., strontium-89 and samarium-153-EDTMP, or high-energy radiation, including without limitation x-rays, gamma rays, and neutrons.

The term "in vivo" refers to an event that takes place in a subject's body.

Embodiments of the invention disclosed herein are also meant to encompass crystallin forms and/or polymorphs of a compound of structure (I), or a tautomer or zwitterioninc form thereof, being isotopically-labelled by having one or more atoms replaced by an atom having a different atomic mass or mass number (i.e., an "isotopic form" of the crystalline forms and/or polymorphs of a compound of structure (I), or a tautomer or zwitterionic form thereof). Examples of isotopes that can be incorporated into the disclosed crystalline forms and/or polymorphs, or a tautomer or zwitterionic form thereof, include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabeled compounds could be useful to help determine or measure the effectiveness of the compounds, by characterizing, for example, the site or mode of action, or binding affinity to pharmacologically important site of action. Certain isotopically-labeled crystalline forms and/or polymorphs of compounds of structure (I), or a tautomer or zwitterionic form thereof, for example, those incorporating a radioactive isotope, are useful in drug and/or substrate tissue distribution studies. The radioactive isotopes tritium (i.e., $^3$H), and carbon-14 (i.e., $^{14}$C) are particularly useful for this purpose in view of their ease of incorporation and ready means of detection.

Substitution with heavier isotopes such as deuterium (i.e., $^2$H) may afford certain therapeutic advantages resulting from greater metabolic stability, for example, increased in vivo half-life or reduced dosage requirements, and hence are preferred in some circumstances.

Substitution with positron emitting isotopes, such as $^{11}$C, $^{18}$F, $^{15}$O and $^{13}$N, can be useful in positron emission topography (PET) studies for examining substrate receptor occupancy. Isotopically-labeled crystalline forms and/or polymorphs of compounds of structure (I), or a tautomer or zwitterionic form thereof, can generally be prepared by conventional techniques known to those skilled in the art or by processes analogous to those described in the Examples as set out below using an appropriate isotopically-labeled reagent in place of the non-labeled reagent previously employed.

It is understood that in the present description, combinations of substituents and/or variables of the depicted formulae are permissible only if such contributions result in stable compounds. "Stable compound" and "stable structure" are meant to indicate a compound that is sufficiently robust to survive isolation to a useful degree of purity from a reaction mixture, and formulation into an efficacious therapeutic agent.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

"Pharmaceutically acceptable carrier or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "tautomer" refers to a proton shift from one atom of a molecule to another atom of the same molecule. Embodiments thus include tautomers of the disclosed compounds, crystalline forms and polymorphs.

"Zwitterionic form" refers to a form of a compound, wherein at least one functional group has a positive electrical charge, at least one functional group has a negative electrical charge, and the net charge of the entire molecule is zero. For example, the phosphate group ($-PO_3H_2$) of a compound having structure (I) may exist in an anionic form (e.g., $-PO_3H^-$), and the nitrogen atom of a compound having structure (I) may exist in the protonated (cationic) form. The compound having structure (II) is a zwitterionic form of the compound having structure (I), for example. Embodiments include zwitterions of the disclosed compounds, crystalline forms and polymorphs.

The chemical naming protocol and structure diagrams used herein are a modified form of the I.U.P.A.C. nomenclature system, using the ACD/Name Version 9.07 software program and/or ChemDraw Ultra Version 11.0.1 software naming program (CambridgeSoft). For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

Crystalline and Polymorph Forms of Compounds of Structure (I)

It has been found that compounds having structure (I), or a tautomer or zwitterionic form thereof, can exist in various crystalline and/or polymorphic forms.

Accordingly, one embodiment provides a crystalline form of a compound having the following structure (I):

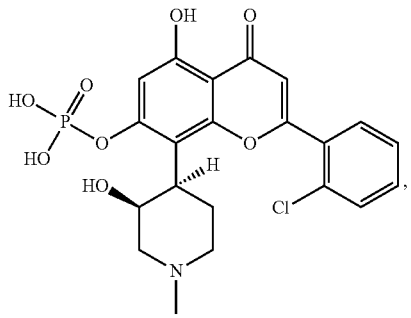

or a tautomer or zwitterionic form thereof. In some embodiments, the crystalline form comprises Form B. In some embodiments, the crystalline form consists essentially of Form B. In some embodiments, the crystalline form consists of Form B. In some embodiments, the crystalline form (e.g., Form B) is substantially pure (e.g., of other physical forms of the compound having structure (I), or a tautomer or zwitterionic form thereof; of impurities; of alvocidib). In some embodiments, the crystalline form is of a compound having structure (II).

Figure 8:
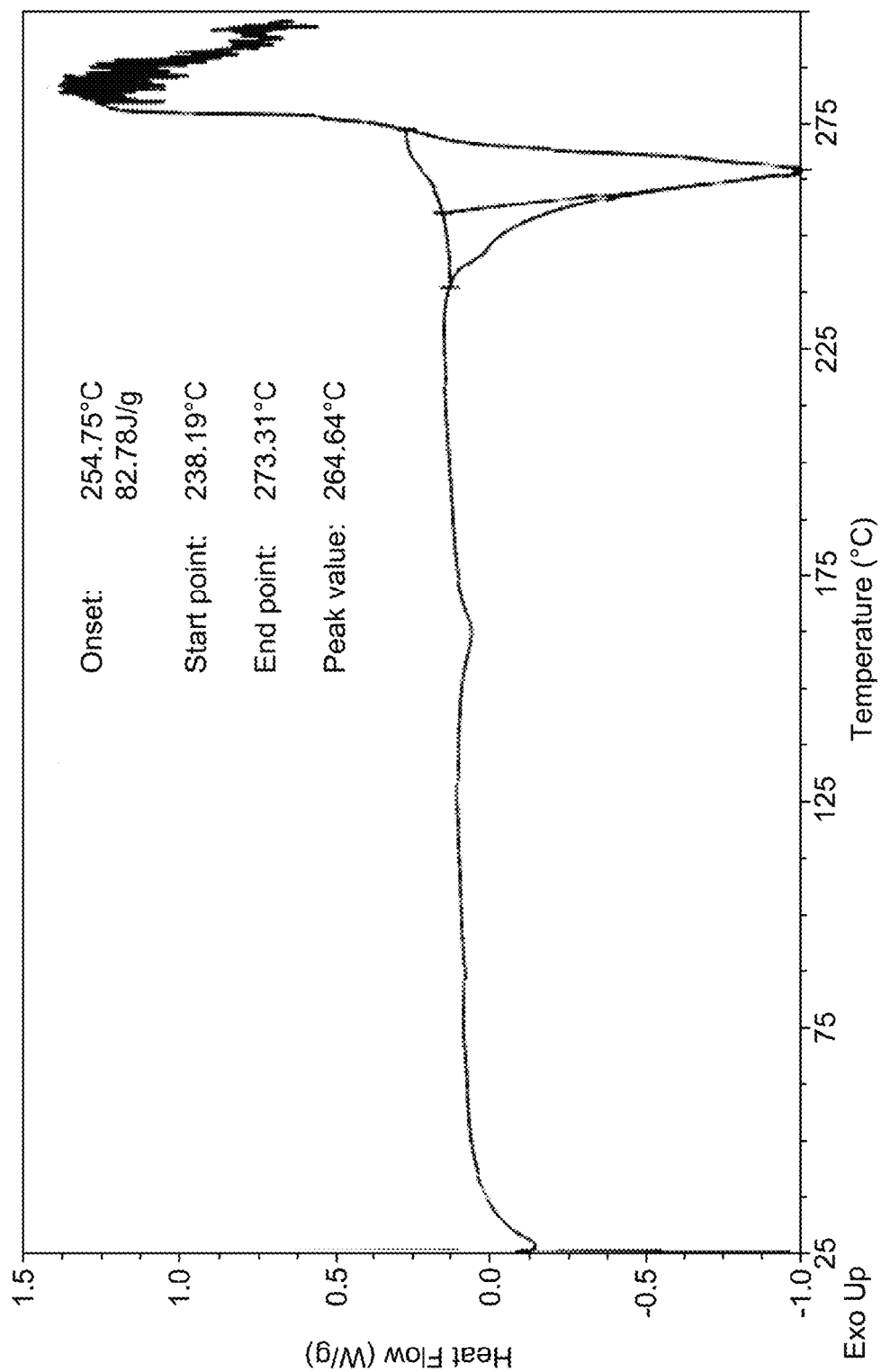
FIG. 8 shows the differential scanning calorimetry output of heat flow plotted as a function of temperature for polymorph form B.
Figure 9A:
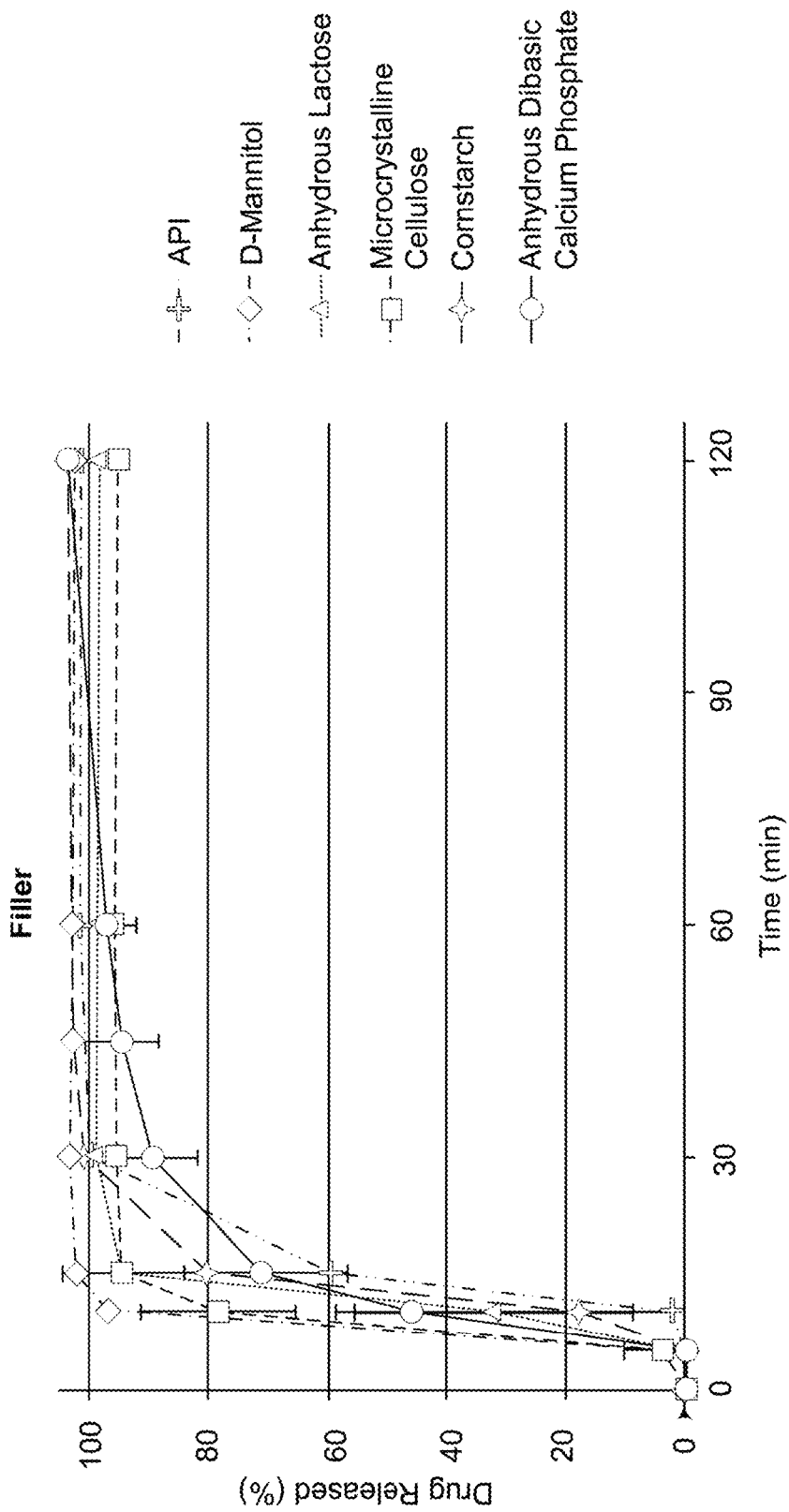
FIG. 9A is a graph of percentage of drug released versus time, and shows the amount of API released from various formulations of API and filler in the excipient compatibility study described in Example 13.
Figure 9B:
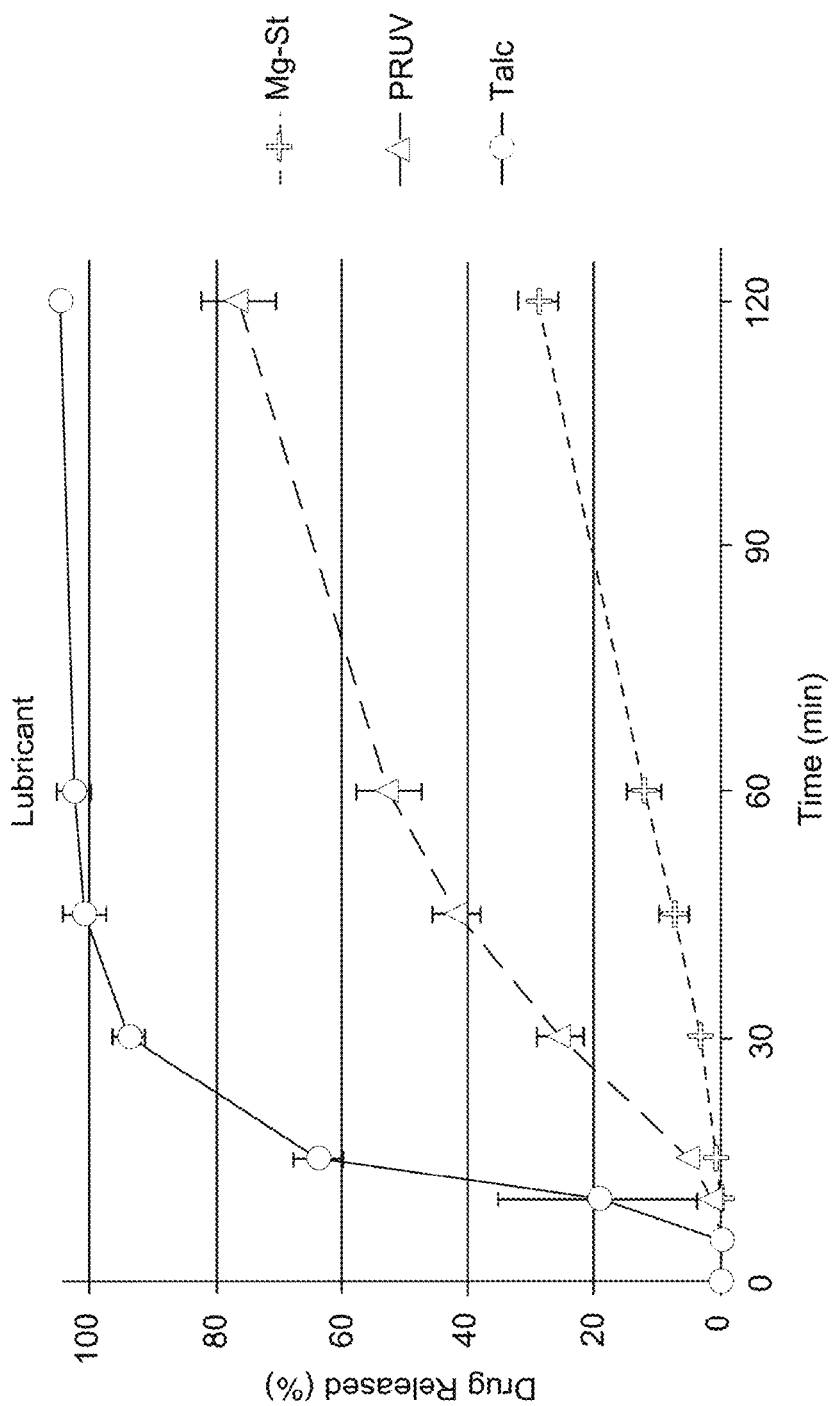
FIG. 9B is a graph of percentage of drug released versus time, and shows the amount of API released from various formulations of API and lubricant in the excipient compatibility study described in Example 13.
Figure 9C:
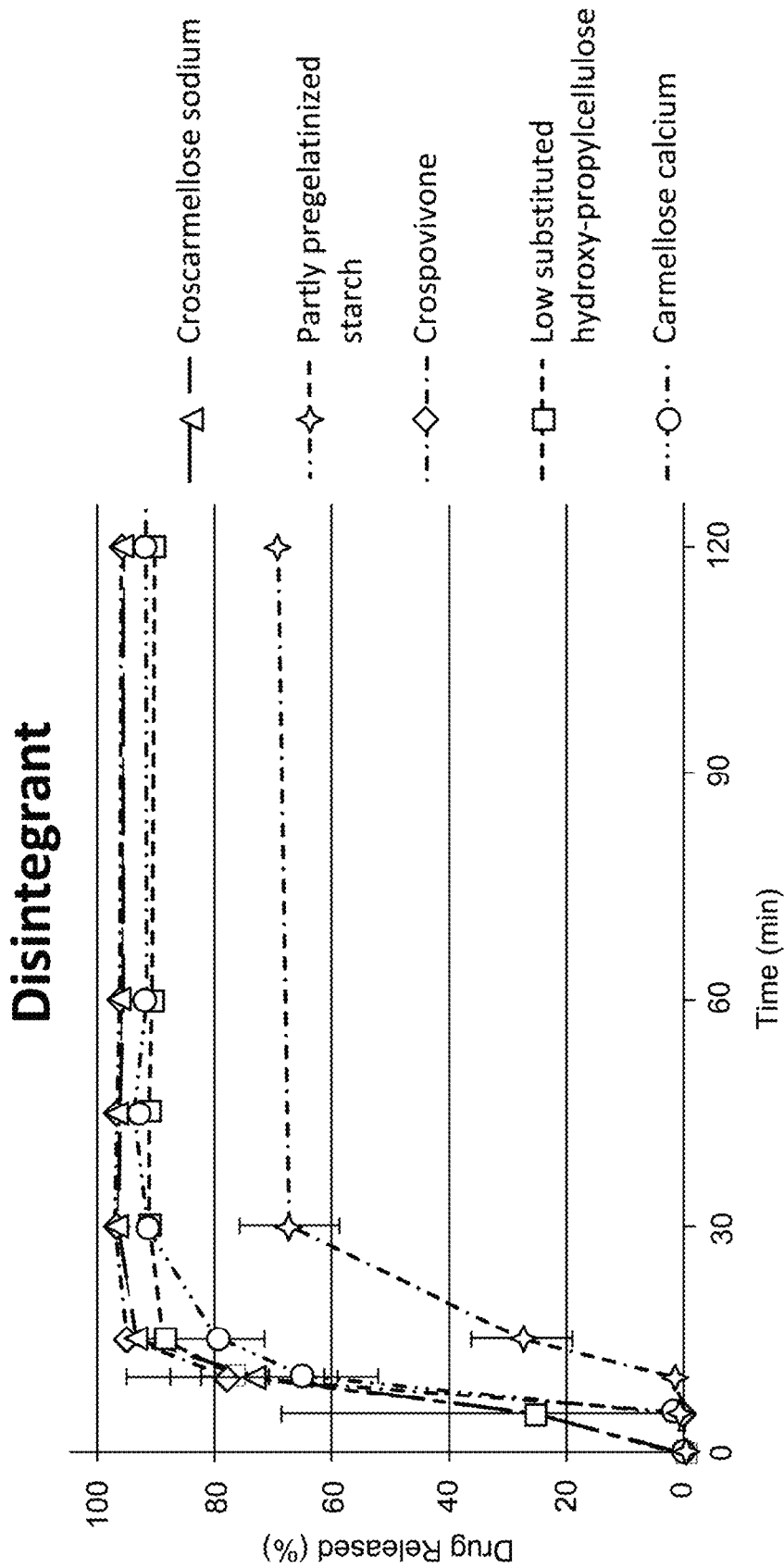
FIG. 9C is a graph of percentage of drug released versus time, and shows the amount of API released from various formulations of API and disintegrant in the excipient compatibility study described in Example 13.
Figure 9D:
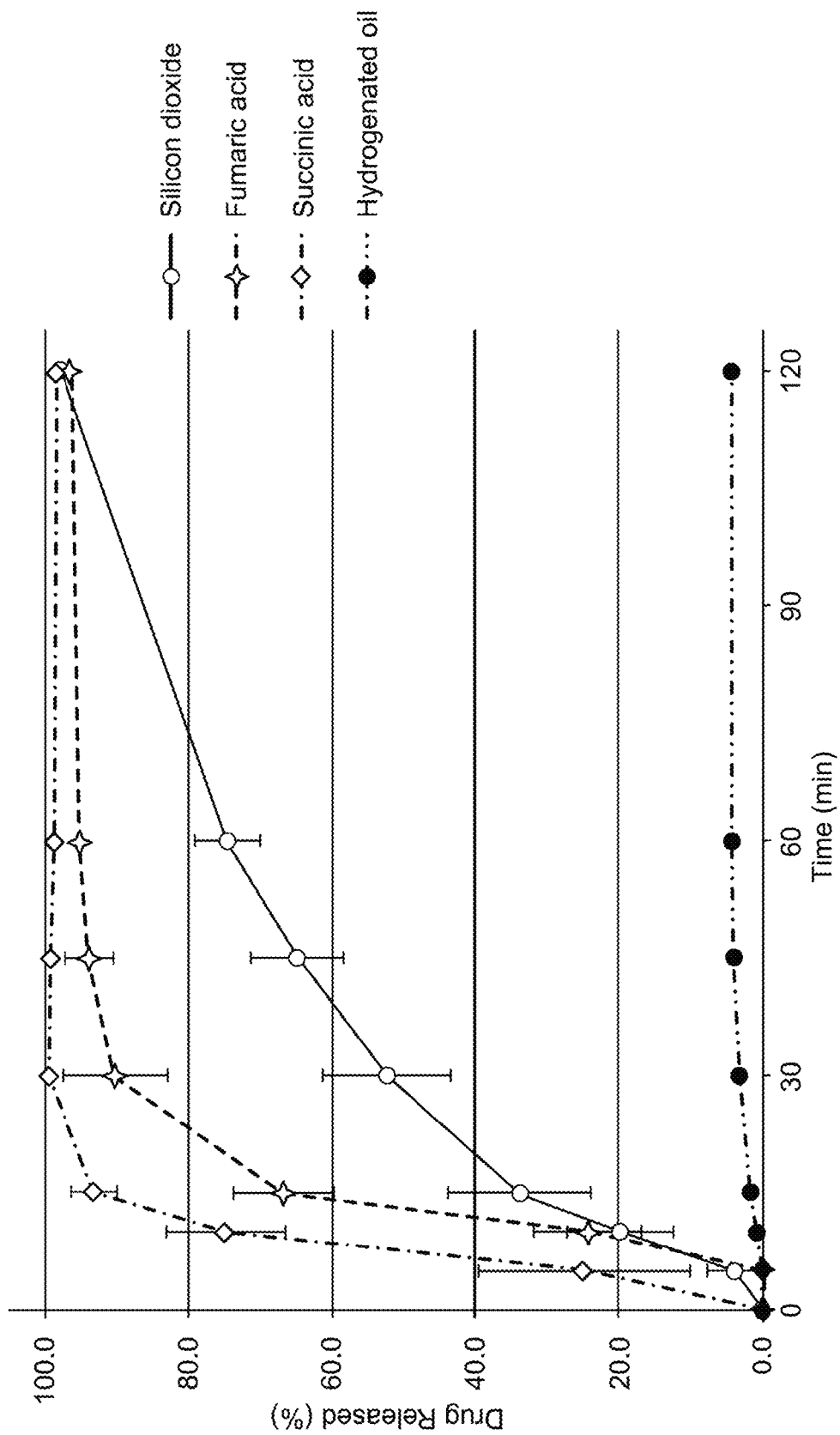
FIG. 9D is a graph of percentage of drug released versus time, and shows the amount of API released from various formulations of API and fluidizer/other excipient in the excipient compatibility study described in Example 13.

Form B has structure (II):

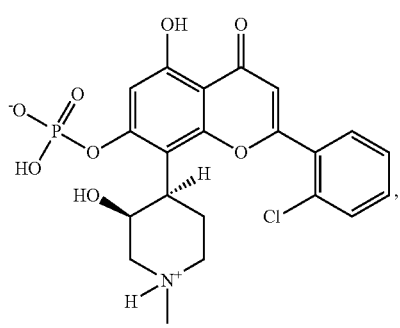

and is characterized, in some embodiments, by an x-ray powder diffraction (XRPD) pattern comprising at least three peaks (e.g., three peaks, at least four peaks, four peaks, at least five peaks, five peaks, six peaks) at 2-theta angles selected from the group consisting of 4.8±0.2, 10.8±0.2, 13.7±0.2°, 14.9±0.2°, 20.0±0.2° and 24.6±0.2°. In some embodiments, Form B is characterized by an XRPD pattern comprising peaks at the following 2-theta angles: 10.8±0.2, 14.9±0.2° and 20.0±0.2°. In some embodiments, Form B is characterized by an XRPD pattern comprising peaks at the following 2-theta angles: 4.8±0.2, 10.8±0.2°, 14.9±0.2° and 20.0±0.2°. In some embodiments, Form B is characterized by an XRPD pattern comprising peaks at the following 2-theta angles: 4.8±0.2, 10.8±0.2, 13.7±0.2°, 14.9±0.2° and 20.0±0.2°. In some embodiments, Form B has an XRPD pattern substantially in accordance with that depicted in FIG. 1. In some embodiments, Form B is characterized by a DSC thermogram comprising an endothermic peak at about 264° C. In some embodiments, Form B is characterized by a DSC thermogram substantially in accordance with that depicted in FIG. 8.

One embodiment provides a polymorph of a compound having the following structure (I):

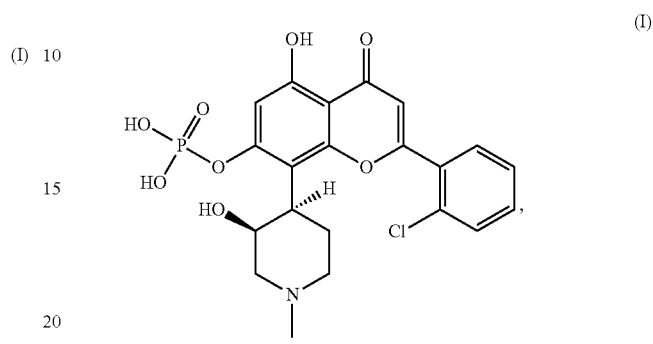

or a tautomer or zwitterionic form thereof, the polymorph having an X-ray powder diffraction pattern comprising the following:
D space (Å):
18.3±0.09
8.1±0.06
6.4±0.08
5.9±0.06
4.4±0.05
expressed in terms of "D" spacing.

In a related embodiment, the polymorph has an X-ray powder diffraction pattern comprising the following:
D space (Å):
18.38±0.003
8.15±0.008
6.47±0.002
5.95±0.007
4.44±0.006
expressed in terms of "D" spacing.

In yet another related embodiment, the polymorph has an X-ray powder diffraction pattern comprising the following:
D space (Å):
18.382
8.157
6.472
5.956
4.445
expressed in terms of "D" spacing.

One embodiment provides a polymorph of a compound of structure (I), or a tautomer or zwitterion thereof, wherein the polymorph is a crystalized form having a monoclinic space group P2$_1$ with lattice parameters of:
a=6.46(1) Å;
b=9.07(2) Å;
c=18.25(4) Å; and
β=95.457(2°);
and a volume of 1066.11(4) Å$^3$.

Another embodiment provides a polymorph of a compound of structure (I), or a tautomer or zwitterion thereof, wherein the polymorph is a crystalized form having a monoclinic space group P2$_1$ with lattice parameters of:
a=6.4695(1) Å;
b=9.0692(2) Å;
c=18.2530(4) Å; and
β=95.457(2°),
and a volume of 1066.11(4) Å$^3$.

Figure 1:
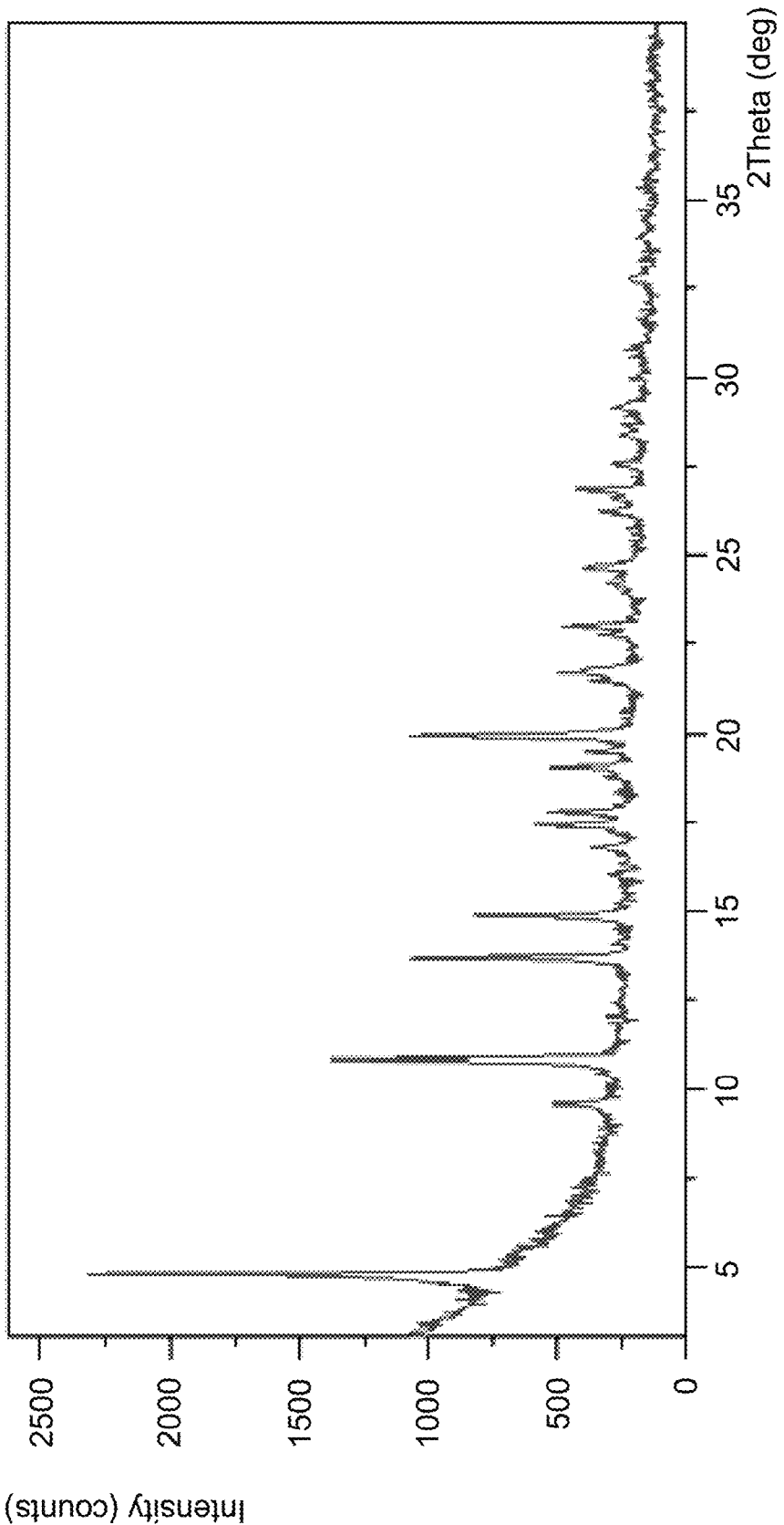
FIG. 1 illustrates an x-ray diffractogram obtained from XRPD analysis for polymorph Form B.

Yet another embodiment provides a polymorph of structure (I) or a tautomer or zwitterionic form thereof, wherein the polymorph has the X-ray diffraction pattern set forth in FIG. 1 (or substantially similar). In some embodiments, the polymorph has the X-ray diffraction pattern substantially similar to Table 6.

Another related embodiment provides a polymorph of a compound of structure (I) or a tautomer or zwitterionic form thereof, wherein the polymorph is Form B.

One embodiment provides a polymorph of a compound of structure (I) or a tautomer or zwitterionic form thereof wherein the polymorph is formed by a method comprising:
a) contacting an amorphous compound of structure (I) with a lattice forming reagent; and
b) treating the product of step a) with solvent having water content less than about 0.05% v/v and removing the solvent, thereby forming the polymorph.

In some more specific embodiments, the lattice forming reagent is maleic acid. In some embodiments, the solvent is ethanol or tetrahydrofuran. In some other embodiments, the contacting further comprises suspending the amorphous compound of structure (I) in aqueous tetrahydrofuran.

Another embodiment affords a polymorph of a compound of structure (I) or a tautomer or zwitterionic form thereof, wherein the polymorph has an initial purity of at least 99.5% and a subsequent purity of at least 99.5% after being stored from about 12 hours up to about 7 days above a temperature of about 22° C.

In certain related embodiments, the subsequent purity is at least 99.5% after being stored greater than about 7 days above a temperature of about 22° C. In some more specific embodiments, the subsequent purity is at least 99.5% after being stored greater than about 30 days above a temperature of about 20° C. In some embodiments, the initial purity and subsequent purity are as determined by HPLC.

Without wishing to be bound by theory, it is thought that the water content of the polymorph can have a significant effect on the purity and storage stability of the polymorph. That is, the polymorph can undergo a hydrolysis reaction that converts that phosphate moiety to a hydroxyl group. As such, an impurity may be present in the form of hydrolyzed structure (I) (i.e., alvocidib). However, it was unexpectedly discovered that keeping the water content of the polymorph and any subsequently formed compositions provided an active substance (i.e., the polymorphs of structure (I)) with much more robust stability.

Accordingly, some embodiments provide a polymorph of a compound of structure (I) or a tautomer or zwitterionic form thereof, wherein the polymorph has an initial purity of at least 99.5% and a subsequent purity of at least 99.5% after being stored from about 12 hours up to about 7 days above a temperature at about 25° C.±2° C. at a relative humidity of 60%. In some embodiments, the subsequent purity is at least 99.5% after being stored for greater than about 7 days at about 25° C.±2° C. at a relative humidity of 60%. In other embodiments, the subsequent purity is at least 99.5% after being stored for greater than about 30 days at about 25° C.±2° C. at a relative humidity of 60%. In some of the foregoing embodiments, the initial purity and subsequent purity are as determined by HPLC.

Still other embodiments provide a polymorph of a compound of structure (I) or a tautomer or zwitterionic form thereof, wherein the polymorph has an endotherm peak value at about 256.0° C.-268.0 (i.e., 262.0° C.±6.0) as determined by differential scanning calorimetry. In some embodiments, the endotherm peak value is at a temperature ranging from 256° C. to 268° C., from 257.0° C. to 266.0° C. or from 258.0° C. to 265.0° C. In some more specific embodiments, the endotherm peak value is at about 259.0° C.-265.0° C.

In some embodiments of the foregoing, the polymorph comprises a zwitterionic form having the following structure (II):

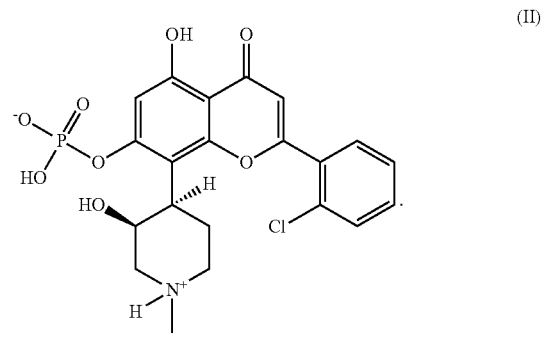

In some of the foregoing embodiments, the polymorph has water content less than 0.50% as determined by Karl Fischer titration. For example in some embodiments, the polymorph has water content less than 0.45%, less than 0.40%, less than 0.35%, less than 0.30%, less than 0.25%, less than 0.20%, less than 0.15%, or less than 0.10% as determined by Karl Fischer titration.

Preparation of Compounds Having Structure (I)

It will be appreciated by those skilled in the art that the processes and reactions for preparing the compounds described herein may be modified in accordance with standard techniques to include alternative reagents and/or reaction conditions. For example, a reaction including an acid as lattice forming reagent may alternatively employ another suitable reagent such as a base, a sugar derivative, a peptide or other reagent.

One embodiment provides a method for preparing a polymorph, the method comprising:
a) contacting an amorphous compound having the following structure (I):

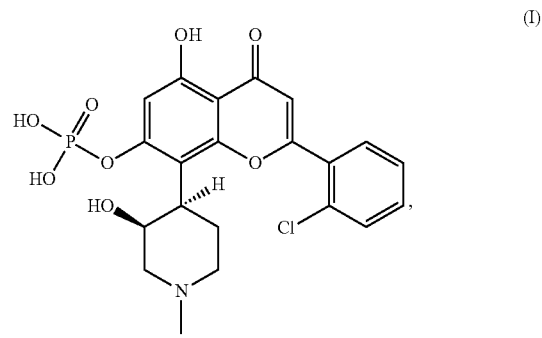

with a lattice forming reagent; and
b) treating the product of step a) with solvent having water content less than about 0.05% v/v; and removing the solvent, thereby forming the polymorph.

In some embodiments, the lattice forming reagent is an acid. For example, in some embodiments, the acid is an organic acid. In some embodiments the acid is an acid having a $pK_a$ greater than 1.0. In some embodiments the acid is a diprotic acid. In some specific embodiments, the acid is selected from the group consisting of maleic acid, fumaric acid, L-tartaric acid, hippuric acid, nicotinic acid, acetic acid, and combinations thereof. In some more specific embodiments, the lattice forming reagent is maleic acid.

In some specific embodiments, the contacting comprises adding the lattice forming reagent (e.g., maleic acid) in a 1:1±0.5 ratio (e.g., molar ratio) of the amorphous compound of structure (I) to maleic acid. In more specific embodiments the ratio (e.g., molar ratio) is 1:1±0.3, 1:1±0.2, or 1:1±0.1 compound of structure (I) to maleic acid. In other embodiments, the ratio (e.g., molar ratio) is from about 1:0.1 to about 1:10 (e.g., from about 1:0.1 to about 1:5) compound of structure (I) to maleic acid.

The lattice forming reagent is not limited to acids and can be any other compound that can be mixed with a compound of structure (I) and forms polymorph Form B. In particular, in some embodiments, the lattice forming reagent is a sugar or a peptide. In more specific embodiments, the lattice forming reagent is D-xylose. In other specific embodiments, the lattice forming reagent is aspartame.

The removing step is performed to remove residual solvent and lattice forming reagent and afford a solid product as a free base. Accordingly, in some embodiments the removing may involve reduced pressure (e.g., below 1 atm), a flow of air or inter gas (e.g., $N_2$), increased temperature (e.g., above 25° C.) or combinations thereof. In specific embodiments, the removing is at a pressure less than about 1 atm and a temperature greater than about 35° C. In some more specific embodiments, the pressure is less than about 0.9 atm, about 0.8 atm, about 0.7 atm, about 0.6 atm, or about 0.5 atm. In some embodiments, the temperature is above about 36° C., about 37° C., about 38° C., about 39° C., about 40° C., about 42° C., or about 45° C. In some embodiments, the temperature is above the boiling point of residual solvent, e.g., about 100° C. Each of the temperature and pressure values recited above include a range of ±5% of the recited value (i.e., about 45° C. includes 45° C.±2.25° C.).

In some embodiments, the removing comprises filtering the solid product away from residual solvent and/or lattice forming reagent.

Additionally, some embodiments of the methods recited above further comprise preparing a compound of structure (III):

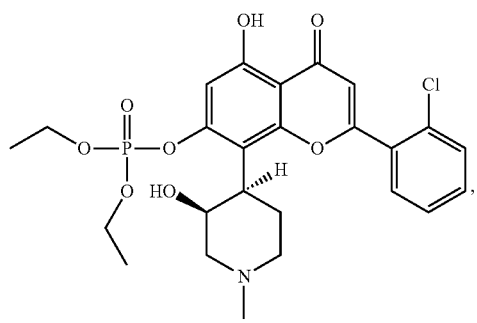

(III)

by reacting a compound having the following structure:

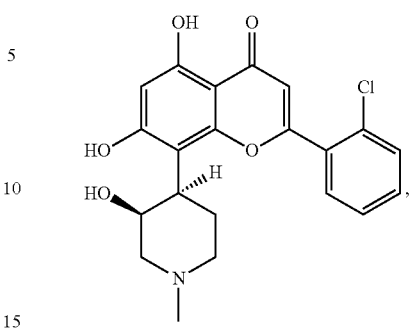

or a salt thereof, with a base and a compound having the following structure:

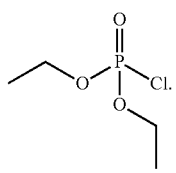

In some of the foregoing embodiments, the base is an amine base, (e.g., triethylamine, diisopropylethyl amine). In some of the foregoing embodiments, amine base is added in an organic solvent.

In some embodiments, the method further comprises preparing the amorphous compound of structure (I):

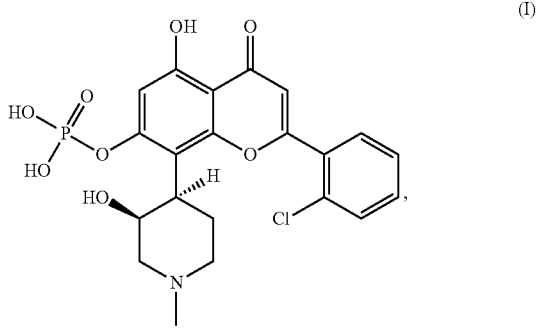 [SMILES: CN1CC[C@H](c2c(OP(=O)(O)O)cc(O)c3c(=O)cc(-c4ccccc4Cl)oc23)[C@H](O)C1 ; ","]

(I)

by reacting a compound of structure (III), or a salt thereof, with a phosphoester cleaving compound and treating with a basic solution.

In some embodiments, the phosphoester cleaving compound is an organosilicon (e.g., trimethyl silyl bromide, "TMSBr"). In some embodiments, the basic solution comprises ammonium (e.g., ammonium bicarbonate). In some embodiments, the basic solution comprises acetonitrile. In some embodiments, the basic solution comprises aqueous acetonitrile.

In some embodiments, the polymorph is a polymorph as described in the foregoing embodiments. Additionally, one embodiment provides a polymorph that is prepared according to any of the methods described herein.

Thus, in any of the embodiments described herein involving polymorph conversion/formation (e.g., preparation of crystalline Form B of a compound having structure (II)), the polymorph conversion/formation step(s) comprise crystallizing compound having structure (I) (e.g., amorphous compound having structure (I)), or a tautomer or zwitterionic form thereof, from an acidic solution (e.g., having a pH of greater than about 1; having a pH of greater than about 1 to less than about 5, for example, from about 1 to about 4, from about 2 to about 5). In some embodiments, the acidic solution comprises a lattice forming reagent (e.g., an acid, such as maleic acid; an acid having a pK$_a$ of greater than about 1; an acid having at least one pK$_a$ of less than about 5 and a pK$_a$ of greater than about 1, for example, at least one pK$_a$ of less than about 4 and a pK$_a$ of greater than about 1, at least one pK$_a$ of less than about 5 and a pK$_a$ of greater than about 2) and a solvent.

One embodiment is a method for preparing crystalline Form B of a compound having structure (II), the method comprising contacting amorphous compound having structure (I), or a tautomer or zwitterionic form thereof, with a lattice forming reagent (e.g., an acid, such as maleic acid; an acid having a pK$_a$ of greater than about 1; an acid having at least one pK$_a$ of less than about 5 and a pK$_a$ of greater than about 1, for example, an acid having at least one pK$_a$ of less than about 4 and a pK$_a$ of greater than about 1, an acid having at least one pK$_a$ of less than about 5 and a pK$_a$ of greater than about 2) in a solvent, thereby preparing the crystalline Form B of the compound having structure (II).

One embodiment is a method for preparing crystalline Form B of a compound having structure (II), the method comprising contacting a compound having structure (V):

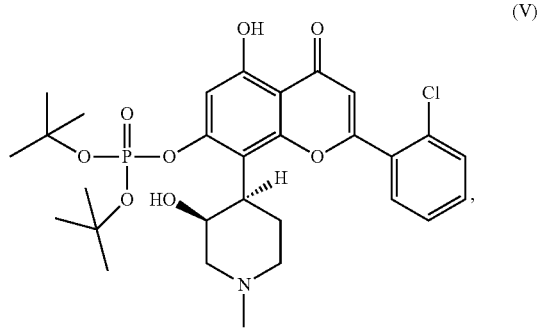 [SMILES: CN1CC[C@H](c2c(OP(=O)(OC(C)(C)C)OC(C)(C)C)cc(O)c3c(=O)cc(-c4ccccc4Cl)oc23)[C@H](O)C1 ; ","]

(V)

or a tautomer, salt or zwitterionic form thereof, with an acid in a solvent, thereby preparing the crystalline Form B of the compound having structure (II). In some embodiments, the molar ratio of acid to compound having structure (V), or a tautomer, salt or zwitterionic form thereof, is from about 0.1:1 to about 10:1 (e.g., from about 0.1:1 to about 5:1; from about 0.4:1 to about 1.1:1; about 0.5:1).

In one embodiment, the lattice forming reagent is an acid. In some embodiments, the acid for preparing crystalline Form B has at least one pK$_a$ value that is less than about 5 (e.g., less than about 4) and/or a pK$_a$ value of greater than about 1 (e.g., greater than about 2).

In some embodiments for preparing crystalline Form B, the acid is an organic acid. As used herein, "organic acid" is an organic compound with acidic properties. Typically, an organic acid contains at least one carboxyl group (—COOH). Organic acids include, but are not limited to, maleic acid, acetic acid, citric acid and propionic acid. In some embodiments, the organic acid is maleic acid.

As used herein, "solvent" refers to a liquid that serves as a medium for a chemical reaction or other procedure in which compounds are being manipulated (e.g., crystallization). Typically, the solvent in the methods disclosed herein is an organic solvent or water, or a combination thereof. Examples of organic solvents include polar, protic solvents (e.g., an alcohol such as methanol, ethanol, butanol), polar aprotic solvents (e.g., dimethylformamide, tetrahydrofuran, ethyl acetate, acetone, methyl ethyl ketone) or nonpolar solvents (e.g., diethyl ether). In some embodiments, the solvent comprises tetrahydrofuran. In some embodiments, the solvent is a mixture of methanol and acetone.

Also provided are methods for preparing a compound having structure (I), or a salt, tautomer or zwitterionic form thereof (e.g., a compound having structure (II)). The method comprises contacting a compound having the following structure (IV):

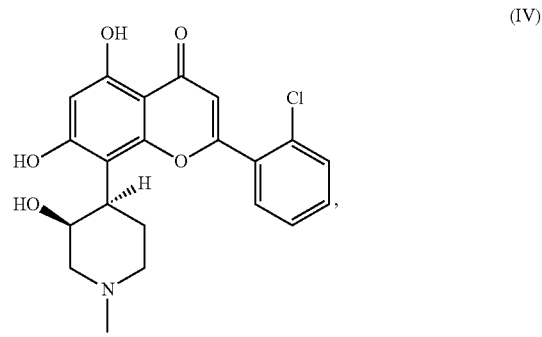 [SMILES: CN1CC[C@H](c2c(O)cc(O)c3c(=O)cc(-c4ccccc4Cl)oc23)[C@H](O)C1 ; ","]

(IV)

or a tautomer or salt thereof, with di-tert-butylhalophosphonate (e.g., di-tert-butylchlorophosphonate, di-tert-butylbromophosphonate) in the presence of an amine base, thereby forming a compound having structure (V), or a tautomer or salt thereof, and contacting the compound having structure (V), or a tautomer or salt thereof, with an acid (e.g., maleic acid), thereby preparing a compound having structure (I), or a salt, tautomer or zwitterionic form thereof. In some embodiments, the method further comprises contacting di-tert-butylphosphonate with carbon tetrahalide (e.g., carbon tetrachloride, carbon tetrabromide) to prepare the di-tert-butylhalophosphonate (e.g., di-tert-butylchlorophosphonate, di-tert-butylbromophosphonate, respectively). In some embodiments, the di-tert-butylhalophosphonate is prepared in situ with the compound having structure (IV), or a salt thereof, by contacting di-tert-butylphosphonate with carbon tetrahalide (e.g., carbon tetrachloride, carbon tetrabromide). In some embodiments, the acid is hydrochloric acid or acetic acid, or a combination thereof.

"Amine base," as used herein, refers to a compound that contains a nitrogen atom with a lone pair. "Amine base" includes primary, secondary and tertiary amine bases, as well as ammonia. Typically, the amine base is an organic amine base. Examples of organic amine bases include, but are not limited to, diisopropylethylamine, tert-butylamine and triethylamine.

It will be appreciated that when an acid having a pK$_a$ of less than about the pK$_a$ of the phosphate group (—PO$_2$OH) of a compound having structure (I) (e.g., hydrochloric acid) is used in the methods described herein, a salt (e.g., a hydrochloride salt) of the compound having structure (I) will result. Thus, in some embodiments, the compound formed by contacting a compound having structure (V), or a tautomer or salt thereof, with an acid is a salt of a compound having structure (I). In such instances, in some embodiments, the method further comprises contacting the salt of the compound having structure (I) with a base (e.g., ammonium bicarbonate), thereby forming the compound having structure (I), or a tautomer or zwitterionic form thereof.

One embodiment is a method for preparing crystalline Form B of a compound having structure (II). The method comprises contacting a compound having structure (IV), or a tautomer or salt thereof, with di-tert-butylhalophosphonate (e.g., di-tert-butylchlorophosphonate, di-tert-butylbromophosphonate) in the presence of an amine base, thereby forming a compound having structure (V), or a tautomer or salt thereof; and contacting the compound having structure (V), or a tautomer or salt thereof, in an organic solvent, with an acid having a $pK_a$ value of greater than about 1 (e.g., an acid having at least one $pK_a$ value that is less than about 5 and a $pK_a$ value of greater than about 1, for example, at least one $pK_a$ value that is less than about 4 and a $pK_a$ value of greater than about 1, at least one $pK_a$ value that is less than about 5 and a $pK_a$ value of greater than about 2), thereby preparing crystalline Form B of a compound having structure (II).

Another embodiment is a method for preparing crystalline Form B of a compound having structure (II), comprising contacting a compound having structure (IV), or a tautomer or salt thereof, with di-tert-butylhalophosphonate (e.g., di-tert-butylchlorophosphonate, di-tert-butylbromophosphonate) in the presence of an amine base, thereby forming a compound having structure (V), or a tautomer or salt thereof; and contacting the compound having structure (V), or a tautomer or salt thereof (e.g., in an organic solvent) with an acid having a $pK_a$ value of less than about 1, thereby forming a salt of a compound having structure (I); contacting the salt of a compound having structure (I) with a base, thereby forming amorphous compound having structure (I); and contacting the amorphous compound having structure (I) with an acid having a $pK_a$ value of greater than about 1 (e.g., an acid having at least one $pK_a$ value that is less than about 5 and a $pK_a$ value of greater than about 1, for example, at least one $pK_a$ value that is less than about 4 and a $pK_a$ value of greater than about 1, at least one $pK_a$ value that is less than about 5 and a $pK_a$ value of greater than about 2), thereby preparing crystalline Form B of a compound having structure (II).

It will also be appreciated by those skilled in the art that in the processes for preparing the compounds described herein, the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups are optionally added or removed in accordance with standard techniques, which are known to one skilled in the art and described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

The following General Reaction Scheme 1 illustrates an exemplary method of forming a polymorph of a compound of structure (I):

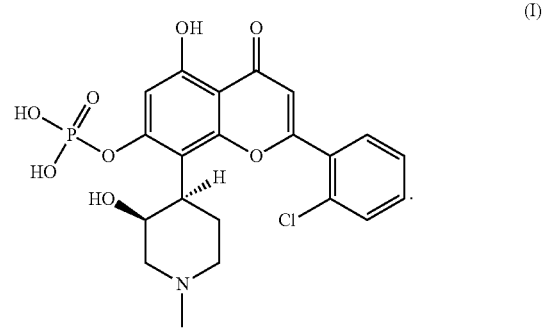

(I)

It is understood that one skilled in the art may be able to make these compounds by similar methods or by combining other methods known to one skilled in the art. It is also understood that one skilled in the art would be able to make, in a similar manner as described below, a compound of structure (I), or a tautomer, salt or zwitterionic form thereof, not specifically illustrated below by using the appropriate starting components and modifying the parameters of the synthesis as needed (e.g., reagents, solvents, reaction times and temperatures, etc.). In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, *Advanced Organic Chemistry: Reactions, Mechanisms, and Structure*, 5th edition (Wiley, December 2000)) or prepared as described in this invention.

Polymorphs and compounds were analyzed using techniques known in the art, for example, by x-ray powder diffraction (XRPD), dynamic vapor sorption (DVS), thermal gravimetric analysis (TGA), differential scanning calorimetry (DSC), mass spectrometry, high performance (or pressure) liquid chromatography (HPLC), $^{13}$C NMR, $^{31}$P NMR and/or $^1$H NMR. Synthetic procedures are described in more detail below.

General Reaction Scheme 1

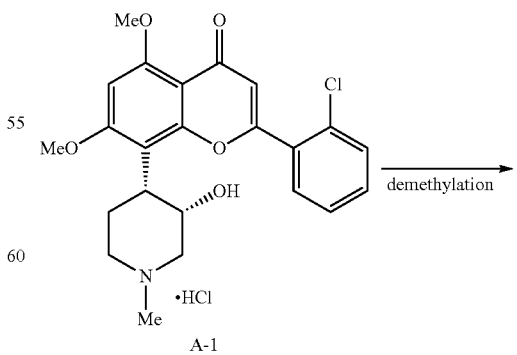

A-1

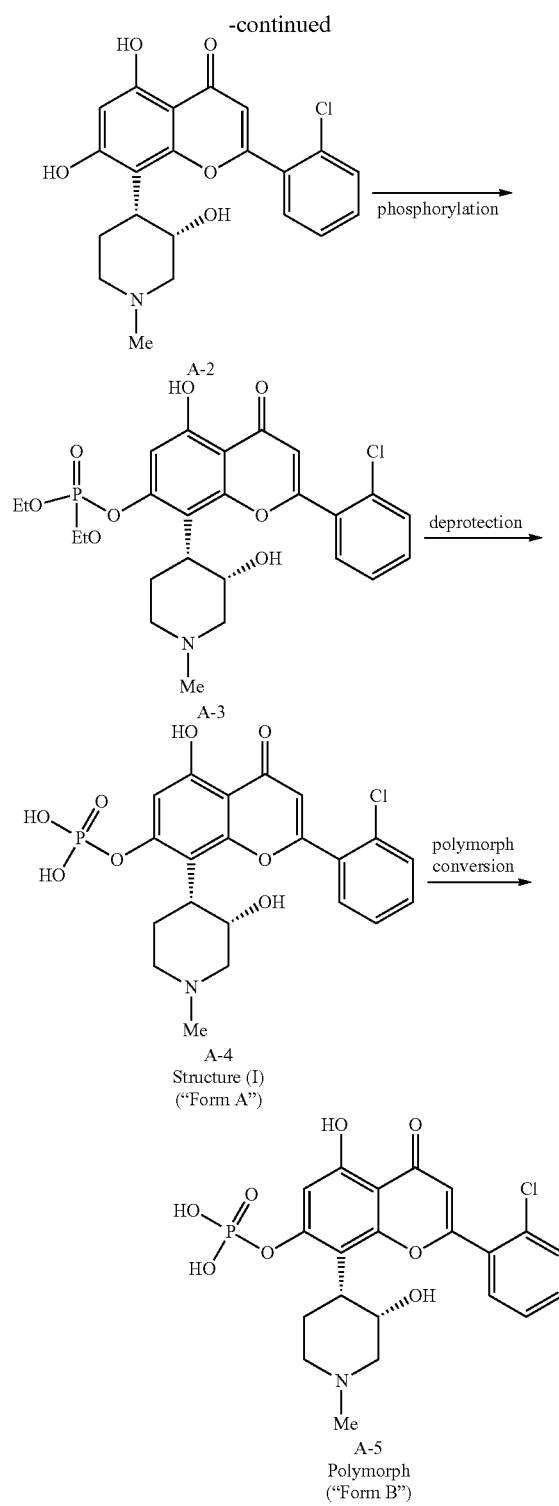

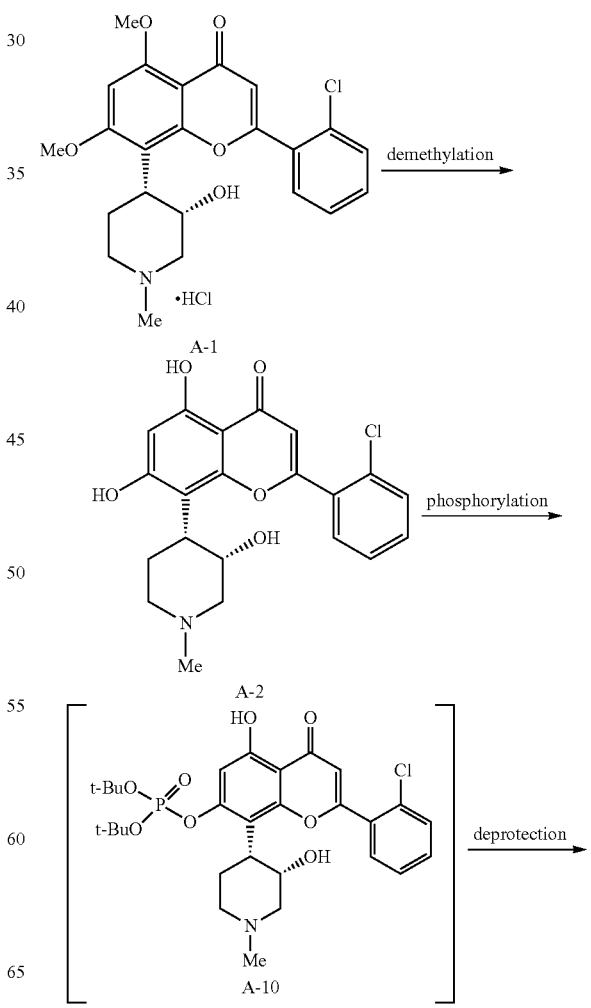

be purchased from commercial sources or prepared according to methods familiar to one of ordinary skill in the art. Reaction of A-1 with a strong Lewis acid (e.g., boron tribromide) affords A-2, which can then be phosphorylated with an activated protected phosphate reagent (e.g., diethyl chlorophosphate) under basic conditions (e.g., using diisopropyl ethyl amine as a base) in an appropriate solvent (e.g., NMP). The phosphorylated product (A-3) can then be deprotected under standard conditions (e.g., TMS-Br) and neutralized using suitable conditions (e.g., ammonium carbonate in aqueous acetonitrile). The resultant compound A-4 (i.e., an amorphous solid or "Form A") which is then converted to the polymorph A-5 using an appropriate lattice forming reagent (e.g., maleic acid) and a suitable solvent system (e.g., THF and water at 19:1 v/v). Finally, the lattice forming reagent is removed using a suitable, substantially anhydrous solvent (e.g., an alcohol such as ethanol) and dried to afford polymorph Form B.

It should be noted that the General Reaction Scheme 1 only depicts an exemplary method for preparation of the polymorph A-5 and other methods are available, using different reagents, and/or different intermediates, etc.

For example, General Reaction Scheme 2 describes another method for preparing Form A and Form B.

Embodiments of the polymorph of a compound of structure (I) as shown can be prepared according to General Reaction Scheme 1. Certain intermediates useful for preparation of the compound having structure (I), or a tautomer, salt or zwitterionic form thereof (e.g., A-1, A-2, A-3, A-4, A-10, A-11) can be prepared according to methods described in U.S. Pat. No. 9,758,539 and U.S. Pub. No. 2007/0015802, which are incorporated herein by reference in their entireties. As shown in the General Reaction Scheme 1, A-1 can

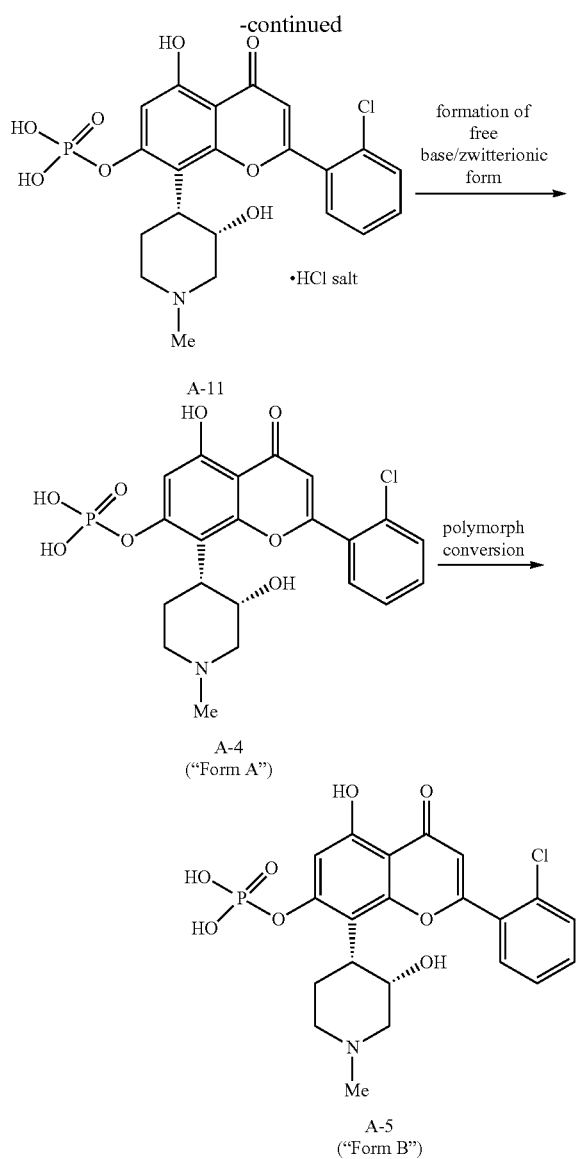

A-11

A-4 ("Form A")

A-5 ("Form B")

Reaction of A-1 with a strong Lewis acid (e.g., boron tribromide) affords A-2, which can then be phosphorylated with an activated protected phosphate reagent (e.g., di-tert-butyehalophosphonate, such as di-tert-butyechhorophosphonate or di-tert-butybromophosphonate) under basic conditions (e.g., using diisopropylethylamine as a base) in an appropriate solvent (e.g., dimethylfonnamide; DMF). In some embodiments employing di-tert-butylhalophosphonate, the di-tert-butylhalophosphonate can be prepared (e.g., in situ with A-2) by contacting di-tert-butylphosphonate with carbon tetrahalide (e.g., carbon tetrachloride, carbon tetrabromide). The phosphorylated product (A-10) can then be deprotected under acidic conditions (e.g., using hydrochloric and acetic acids). The resulting hydrochloride salt can then be converted to its free base and/or zwitterionic form, Form A (A-4), under neutralizing conditions (e.g., ammonium carbonate in aqueous acetonitrile). The resultant compound A-4 can then be converted to Form B (A-5) using an appropriate lattice forming reagent (e.g., an acid, such as maleic acid, acetic acid, citric acid, propionic acid) and a suitable solvent (e.g., THF and water at 19:1 v/v, methanol, methanol and aceton at 1:1 v/v). In some embodiments, the lattice forming reagent is removed from A-5 using a suitable, substantially anhydrous solvent (e.g., an alcohol such as ethanol), and resulting A-5 is dried to afford Form B.

General Reaction Scheme 3 provides yet another method for preparing Form B.

General Reaction Scheme 3

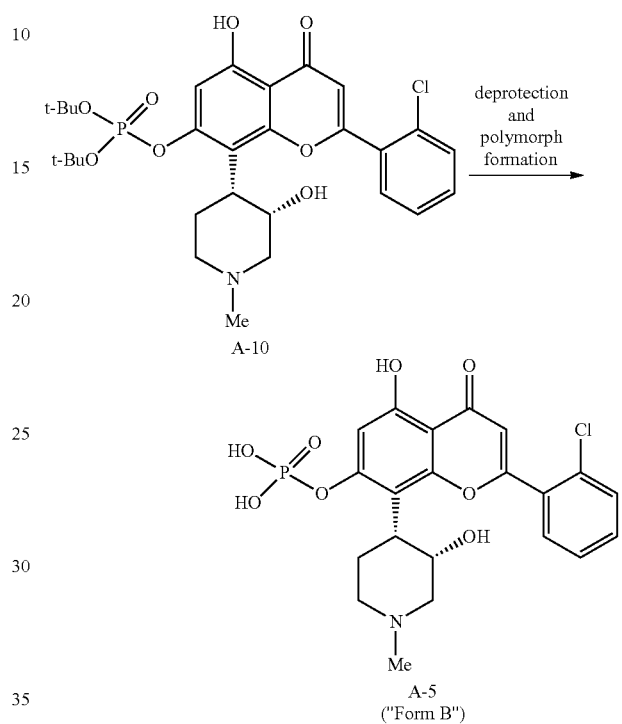

A-10

A-5 ("Form B")

As an alternative to performing the deprotection, free base/zwitterion formation and polymorph conversion steps in three, separate steps, some embodiments provide for deprotection and polymorph formation in a single step. Briefly, A-10 can be deprotected and converted to Form B (A-5) under acidic conditions (e.g., maleic acid in methanol and acetone at 1:1 v/v) to afford Form B.

Pharmaceutical Compositions

In some embodiments, the compound having structure (I) (e.g., a crystalline form and/or polymorph of a compound having structure (I)), or a tautomer, pharmaceutically acceptable salt or zwitterionic form thereof, is formulated into a pharmaceutical composition. In any of the pharmaceutical compositions described herein, the compound having structure (I), or a tautomer, pharmaceutically acceptable salt or zwitterionic form thereof can be the compound having structure (II), or any crystalline form or polymorph of a compound of structure (I), or a tautomer, pharmaceutically acceptable salt or zwitterionic form thereof described herein, e.g., Form B.

A pharmaceutical composition, as used herein, refers to a mixture of the compound having structure (I) (e.g. a crystalline form and/or polymorph of a compound having structure (I)), or a tautomer, pharmaceutically acceptable salt or zwitterionic form thereof, with other chemical components, such as carriers, stabilizers, diluents, dispersing agents, suspending agents, thickening agents, and/or excipients.

In particular, one embodiment provides a pharmaceutical composition comprising a crystalline form and/or polymorph of a compound of structure (I), or a tautomer or zwitterionic form thereof, and a pharmaceutically acceptable carrier or excipient.

In some embodiments, the pharmaceutical composition is formulated for oral administration. Pharmaceutical compositions described herein are formulated by combining the active (e.g., crystalline form and/or polymorph of a compound having structure (I), or a tautomer or zwitterionic form thereof) with, e.g., pharmaceutically acceptable carriers or excipients. In various embodiments, the crystalline form and/or polymorph of a compound of structure (I), or a tautomer or zwitterionic form thereof is formulated in an oral dosage form that includes, by way of example only, tablets, powders, pills, dragees, capsules, liquids, gels, syrups, elixirs, slurries, suspensions and the like. In some embodiments, the pharmaceutical composition comprises an oral capsule.

In some embodiments, the pharmaceutical composition comprises the compound having structure (I), or a tautomer, pharmaceutically acceptable salt or zwitterionic form thereof (e.g., in crystalline or polymorph form), in a concentration ranging from about 0.5 weight percent to about 11.25 weight percent. In other specific embodiments, the pharmaceutical composition comprises the compound having structure (I), or a tautomer, pharmaceutically acceptable salt or zwitterionic form thereof (e.g., in crystalline or polymorph form) in a concentration ranging from about 0.6 weight percent to about 11.05 weight percent.

In more specific embodiments, the pharmaceutical composition comprises about 0.6 weight percent of the compound having structure (I), or a tautomer, pharmaceutically acceptable salt or zwitterionic form thereof (e.g., in crystalline or polymorph form). In other specific embodiments, the pharmaceutical composition comprises about 2.5 weight percent of the compound having structure (I), or a tautomer, pharmaceutically acceptable salt or zwitterionic form thereof (e.g., in crystalline or polymorph form). In still other specific embodiments, the pharmaceutical composition comprises about 11.0 weight percent of the compound having structure (I), or a tautomer, pharmaceutically acceptable salt or zwitterionic form thereof (e.g., in crystalline or polymorph form).

In some more specific embodiments, the pharmaceutical composition comprises about 1 milligram (mg) of the compound having structure (I), or a tautomer, pharmaceutically acceptable salt or zwitterionic form thereof (e.g., in crystalline or polymorph form). In other specific embodiments, the pharmaceutical composition comprises about 4 mg of the compound having structure (I), or a tautomer, pharmaceutically acceptable salt or zwitterionic form thereof (e.g., in crystalline or polymorph form). In some embodiments, the pharmaceutical composition comprises about 16 mg of the compound having structure (I), or a tautomer, pharmaceutically acceptable salt or zwitterionic form thereof (e.g., in crystalline or polymorph form).

In embodiments, the excipient is anhydrous. In some embodiments, the excipient is anhydrous lactose or microcrystalline cellulose. In more specific embodiments, the excipient is anhydrous lactose. In some embodiments, the excipient is microcrystalline cellulose. In specific embodiments, the excipient is anhydrous microcrystalline cellulose.

In other embodiments, the excipient is anhydrous lactose or cornstarch (e.g., cornstarch).

In some of the foregoing embodiments, the pharmaceutical composition comprises the excipient in a concentration ranging from about 85 weight percent to about 98 weight percent. In more specific embodiments, the pharmaceutical composition comprises the excipient in a concentration ranging from about 87 weight percent to about 97.5 weight percent. In some embodiments, the pharmaceutical composition comprises about 87 weight percent of the excipient. In other embodiments, the pharmaceutical composition comprises about 95.5 weight percent of the excipient.

In related embodiments, the pharmaceutical composition further comprises a glidant. In some embodiments, the glidant is colloidal silicon dioxide. In some of these embodiments, the pharmaceutical composition comprises about 1 weight percent of the glidant (e.g., colloidal silicon dioxide).

In some related embodiments, the pharmaceutical composition further comprises a lubricant. In some embodiments, the lubricant is magnesium stearate. In some of these embodiments, the pharmaceutical composition comprises about 1 weight percent of the lubricant (e.g., magnesium stearate). Other examples of lubricants are described in Example 13 herein.

In some related embodiments, the pharmaceutical composition further comprises a disintegrant. In some embodiments, the disintegrant is partly pregelatinized starch, low-substituted hydroxyl propyl cellulose or carmellose calcium. Other examples of disintegrants are described in Example 13 herein.

One embodiment is a pharmaceutical composition comprising from about 0.5 weight percent to about 11.25 weight percent (e.g., from about 0.5 weight percent to about 1 weight percent, from about 10.5 weight percent to about 11.25 weight percent) of a compound having structure (I), or a tautomer, pharmaceutically acceptable salt or zwitterionic form thereof (e.g., a compound having structure (II)), and from about 85 weight percent to about 99.5 weight percent (e.g., from about 95 weight percent to about 99.5 weight percent, from about 85 weight percent to about 90 weight percent, respectively) of a pharmaceutically acceptable carrier or excipient.

One embodiment is a pharmaceutical composition comprising about 0.6 weight percent of a compound having structure (I), or a tautomer, pharmaceutically acceptable salt or zwitterionic form thereof (e.g., a compound having structure (II)), about 97.4 weight percent of anhydrous lactose, about 1 weight percent colloidal silicon dioxide, and about 1 weight percent magnesium stearate. In a specific aspect of this embodiment, the pharmaceutical composition comprises about 1 mg of the compound having structure (I), or a tautomer, pharmaceutically acceptable salt or zwitterionic form thereof (e.g., a compound having structure (II)).

One embodiment is a pharmaceutical composition comprising about 11 weight percent of a compound having structure (I), or a tautomer, pharmaceutically acceptable salt or zwitterionic form thereof (e.g., a compound having structure (II)), about 87 weight percent of anhydrous lactose, about 1 weight percent colloidal silicon dioxide, and about 1 weight percent magnesium stearate. In a specific aspect of this embodiment, the pharmaceutical composition comprises about 16 mg of the compound having structure (I), or a tautomer, pharmaceutically acceptable salt or zwitterionic form thereof (e.g., a compound having structure (II)).

One embodiment is a pharmaceutical composition comprising about 0.6 weight percent of a compound having structure (I), or a tautomer, pharmaceutically acceptable salt or zwitterionic form thereof (e.g., a compound having structure (II)), and from about 98 weight percent to about 99.5 weight percent of cornstarch. In a specific aspect of this embodiment, the pharmaceutical composition further comprises about 1 weight percent magnesium stearate.

One embodiment is a pharmaceutical composition comprising about 11 weight percent of a compound having structure (I), or a tautomer, pharmaceutically acceptable salt or zwitterionic form thereof (e.g., a compound having structure (II)), and about 88 weight percent of cornstarch. In a specific aspect of this embodiment, the pharmaceutical composition further comprises about 1 weight percent magnesium stearate.

In some of the foregoing embodiments, the pharmaceutical compositions are in the form of a capsule for oral administration.

In embodiments, a pharmaceutical composition described herein (e.g., comprising a crystalline form and/or polymorph of a compound of structure (I), or a tautomer or zwitterionic form thereof) is provided in the form of a rapid release formulation. As used herein, "rapid release formulation" refers to a formulation that does not delay or prolong release of an active contained therein. Typically, rapid release formulations release at least 70% of the active contained therein within 1 hour. In some embodiments, a rapid release formulation releases at least 75% of an active contained therein (e.g., a compound having structure (I), or a tautomer, pharmaceutically acceptable salt or zwitterionic form thereof) within about 45 minutes. "Rapid release formulation" is also referred to as "immediate release formulation."

In embodiments, a pharmaceutical composition described herein (e.g., comprising a crystalline form and/or polymorph of a compound of structure (I), or a tautomer or zwitterionic form thereof) is provided in the form of an extended release formulation. As used herein, "extended release formulation" refers to a formulation that releases an active contained therein in a controlled manner during an extended period of time, at a predetermined rate, duration, and location following administration.

In embodiments, a pharmaceutical composition described herein (e.g., comprising a crystalline form and/or polymorph of a compound of structure (I), or a tautomer or zwitterionic form thereof) is provided in the form of an intermediate release formulation. As used herein, "intermediate release formulation" refers to a formulation that delays or extends release of an active contained therein, or alters its site of release, but is not an extended release formulation, as that term is described herein.

The pharmaceutical composition may also be formulated for a route of administration other than oral. Other suitable routes of administration include intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a pharmaceutical composition described herein is administered in a local rather than systemic manner, for example, via injection of the pharmaceutical composition directly into an organ, often in a depot preparation or sustained release formulation. In specific embodiments, long-acting formulations are administered by implantation (for example, subcutaneously or intramuscularly) or by intramuscular injection. Furthermore, in other embodiments, the pharmaceutical composition is delivered in the form of a targeted drug delivery system, for example, a liposome coated with organ-specific antibody. In such embodiments, the liposomes are targeted to and taken up selectively by the organ. In yet other embodiments, the pharmaceutical composition is provided in the form of a rapid release formulation, in the form of an extended release formulation, or in the form of an intermediate release formulation. In yet other embodiments, the pharmaceutical composition is administered topically.

In other embodiments, the pharmaceutical composition is formulated for transmucosal administration. In specific embodiments, transmucosal formulations include penetrants that are appropriate to the barrier to be permeated. In still other embodiments, wherein the pharmaceutical composition is formulated for other parenteral injections; appropriate formulations include aqueous or non-aqueous solutions. In specific embodiments, such solutions include physiologically compatible buffers and/or excipients.

In other embodiments, pharmaceutical compositions described herein are formulated for buccal or sublingual administration. Formulations suitable for buccal or sublingual administration include, by way of example only, tablets, lozenges, or gels.

In still other embodiments, the pharmaceutical composition described herein is formulated for parental injection, including bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In additional embodiments, suspensions are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the active to allow for the preparation of highly concentrated solutions. Alternatively, in other embodiments, the active ingredient is in powder form for constitution with a suitable vehicle, e.g., sterile pyrogen-free water, before use.

In some embodiments, the pharmaceutical composition is administered in dosages. It is known in the art that due to intersubject variability in compound pharmacokinetics, individualization of dosing regimen is necessary for optimal therapy. Dosing for the compound having structure (I) (e.g., a crystalline form and/or polymorph of a compound having structure (I)), or a tautomer, pharmaceutically acceptable salt or zwitterionic form thereof, may be found by routine experimentation in light of the instant disclosure.

The compound having structure (I) (e.g., a crystalline form and/or polymorph of a compound having structure (I)), or a tautomer, pharmaceutically acceptable salt or zwitterionic form thereof, according to certain embodiments, is effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. In various embodiments, the dosage is 3, 6, 9, 12, 16, 21, 28, 32, 42, or 50 mg per day. In some embodiments, the dosage ranges from about 1 mg to about 30 mg per day, e.g., about 1 mg, about 2 mg, about 4 mg, about 8 mg, about 12 mg, about 16 mg or about 22 mg per day. The exact dosage will depend upon the route of administration, the form in which the compound having structure (I), or a tautomer, pharmaceutically acceptable salt or zwitterionic form thereof, is administered, the subject to be treated, the body weight of the subject to be treated, and the preference and experience of the attending physician.

In some embodiments, the compound having structure (I) (e.g., a crystalline form and/or polymorph of a compound having structure (I)), or a tautomer, pharmaceutically acceptable salt or zwitterionic form thereof, is administered in a single dose. Routes of administration are selected and used as appropriate. A single dose of the compound having structure (I), or a tautomer, pharmaceutically acceptable salt or zwitterionic form thereof, may also be used for treatment of an acute condition.

In some embodiments, the compound having structure (I) (e.g., a crystalline form and/or polymorph of a compound having structure (I)), or a tautomer, pharmaceutically acceptable salt or zwitterionic form thereof, is administered in multiple doses. In some embodiments, dosing is about once, twice, three times, four times, five times, six times, or more than six times per day (e.g., twice per day). In other embodiments, dosing is about once a month, once every two weeks, once a week, or once every other day.

In another embodiment, the compound having structure (I) (e.g., a crystalline form and/or polymorph of a compound having structure (I)), or a tautomer, pharmaceutically acceptable salt or zwitterionic form thereof, is administered about once per day to about 6 times per day. In another embodiment, the administration of the polymorph of a compound of structure (I) continues for less than about 7 days. In yet another embodiment, the administration continues for more than about 6, 10, 14, 28 days, two months, six months, or one year. In some cases, continuous dosing is achieved and maintained as long as necessary.

Administration of the compound having structure (I) (e.g., a crystalline form and/or polymorph of a compound having structure (I)), or a tautomer, pharmaceutically acceptable salt or zwitterionic form thereof, may continue as long as necessary. In some embodiments, the compound having structure (I) (e.g., a crystalline form and/or polymorph of a compound having structure (I)), or a tautomer, pharmaceutically acceptable salt or zwitterionic form thereof, is administered for more than 1, 2, 3, 4, 5, 6, 7, 14, or 28 days. In some embodiments, the compound having structure (I) (e.g., a crystalline form and/or polymorph of a compound having structure (I)), or a tautomer, pharmaceutically acceptable salt or zwitterionic form thereof, is administered for less than 28, 14, 7, 6, 5, 4, 3, 2, or 1 day. In some embodiments, the compound having structure (I) (e.g., a crystalline form and/or polymorph of a compound having structure (I)), or a tautomer, pharmaceutically acceptable salt or zwitterionic form thereof, is administered chronically on an ongoing basis, e.g., for the treatment of chronic effects. In some embodiments, the compound having structure (I) (e.g., a crystalline form and/or polymorph of a compound having structure (I)), or a tautomer, pharmaceutically acceptable salt or zwitterionic form thereof is administered once daily for the first 21 days out of a 28-day cycle. In some embodiments, the compound having structure (I) (e.g., a crystalline form and/or polymorph of a compound having structure (I)), or a tautomer, pharmaceutically acceptable salt or zwitterionic form thereof is administered twice daily for the first 21 days out of a 28-day cycle. A cycle may be repeated at least once, at least twice, at least three times, or at least four times.

In certain embodiments, the compound having structure (I) (e.g., a crystalline form and/or polymorph of a compound having structure (I)), or a tautomer, pharmaceutically acceptable salt or zwitterionic form thereof, is administered as a pharmaceutical composition in which the compound having structure (I), or a tautomer, pharmaceutically acceptable salt or zwitterionic form, is mixed with one or more other active ingredients, as in combination therapy. Accordingly, in embodiments, provided is a pharmaceutical combination comprising a compound having structure (I), or a tautomer, pharmaceutically acceptable salt or zwitterionic form thereof, and one or more additional therapeutic agents (e.g., chemotherapeutic agents). Encompassed herein are all combinations of actives set forth in the combination therapies section below and throughout this disclosure.

In some of the foregoing embodiments, the compound having structure (I) (e.g., a crystalline form and/or polymorph of a compound having structure (I)), or a tautomer, pharmaceutically acceptable salt or zwitterionic form thereof, has a water content less than 0.50%, as determined by Karl Fischer titration. For example, in some embodiments, the compound having structure (I) (e.g., a crystalline form and/or polymorph of a compound having structure (I)), or a tautomer, pharmaceutically acceptable salt or zwitterionic form thereof, has a water content less than 0.45%, less than 0.40%, less than 0.35%, less than 0.30%, less than 0.25%, less than 0.20%, less than 0.15%, or less than 0.10%, as determined by Karl Fischer titration.

Some particular embodiments provide a unit dose form comprising a pharmaceutical composition as described herein. In various embodiments, the unit dose form is formulated for oral administration. In some embodiments, the unit dose form is a capsule. In some embodiments, the unit dose form is a tablet.

In some embodiments, dosage forms, such as dragee cores and tablets, are provided with one or more suitable coatings. In specific embodiments, concentrated sugar solutions are used for coating the dosage form. The sugar solutions, optionally contain additional components, such as, by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In some embodiments, the unit dose form comprises the compound having structure (I) (e.g., a crystalline form and/or polymorph of a compound having structure (I)), or a tautomer, pharmaceutically acceptable salt or zwitterionic form thereof, in a concentration ranging from about 0.5 weight percent to about 11.25 weight percent. In other specific embodiments, the unit dose form comprises the polymorph in a concentration ranging from about 0.6 weight percent to about 11.05 weight percent.

In more specific embodiments, the unit dose form comprises about 0.6 weight percent of the compound having structure (I) (e.g., a crystalline form and/or polymorph of a compound having structure (I)), or a tautomer, pharmaceutically acceptable salt or zwitterionic form thereof. In other specific embodiments, the unit dose form comprises about 2.5 weight percent of the compound having structure (I) (e.g., a crystalline form and/or polymorph of a compound having structure (I)), or a tautomer, pharmaceutically acceptable salt or zwitterionic form thereof. In still other specific embodiments, the unit dose form comprises about 11.0 weight percent of the compound having structure (I) (e.g., a crystalline form and/or polymorph of a compound having structure (I)), or a tautomer, pharmaceutically acceptable salt or zwitterionic form thereof.

In some more specific embodiments, the unit dose form comprises about 1 milligram (mg) of the compound having structure (I) (e.g., a crystalline form and/or polymorph of a compound having structure (I)), or a tautomer, pharmaceutically acceptable salt or zwitterionic form thereof. In other specific embodiments, the unit dose form comprises about 4 mg of the compound having structure (I) (e.g., a crystalline form and/or polymorph of a compound having structure (I)), or a tautomer, pharmaceutically acceptable salt or zwitterionic form thereof. In some embodiments, the unit dose form comprises about 16 mg of the compound having structure (I) (e.g., a crystalline form and/or polymorph of a compound having structure (I)), or a tautomer, pharmaceutically acceptable salt or zwitterionic form thereof.

In some of the foregoing embodiments, the unit dose form comprises the excipient in a concentration ranging from about 85 weight percent to about 98 weight percent. In more specific embodiments, the unit dose form comprises the excipient in a concentration ranging from about 87 weight percent to about 97.5 weight percent. In some embodiments, the unit dose form comprises about 87 weight percent of the excipient. In other embodiments, the unit dose form comprises about 95.5 weight percent of the excipient.

In embodiments, the excipient is anhydrous. In some embodiments, the excipient is anhydrous lactose or microcrystalline cellulose. In more specific embodiments, the excipient is anhydrous lactose. In some embodiments, the excipient is microcrystalline cellulose. In specific embodiments, the excipient is anhydrous microcrystalline cellulose.

In some embodiments, the excipient is anhydrous lactose or cornstarch.

In related embodiments, the unit dose form further comprises a glidant. In some embodiments, the glidant is colloidal silicon dioxide. In some of these embodiments, the unit dose form comprises about 1 weight percent of the glidant (e.g., colloidal silicon dioxide).

In some related embodiments, the unit dose form further comprises a lubricant. In some embodiments, the lubricant is magnesium stearate. In some of these embodiments, the unit dose form comprises about 1 weight percent of the lubricant (e.g., magnesium stearate). Other examples of lubricants are described in Example 13 herein.

In some related embodiments, the pharmaceutical composition further comprises a disintegrant. In some embodiments, the disintegrant is partly pregelatinized starch, low-substituted hydroxyl propyl cellulose or carmellose calcium. Other examples of disintegrants are described in Example 13 herein.

In particular embodiments, the unit dose form is in the form of a capsule for oral administration, e.g., a hydroxypropylmethylcellulose capsule. In certain embodiments, the compound having structure (I) (e.g., a crystalline form and/or polymorph of a compound having structure (I)), or a tautomer, pharmaceutically acceptable salt or zwitterionic form thereof, are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more fillers. Fillers include, by way of example only, lactose, binders such as starches, and/or lubricants such as talc or magnesium stearate and, optionally, stabilizers. In other embodiments, soft capsules contain the compound having structure (I) (e.g., a crystalline form and/or polymorph of a compound having structure (I)), or a tautomer, pharmaceutically acceptable salt or zwitterionic form thereof, dissolved or suspended in a suitable liquid. Suitable liquids include, by way of example only, one or more fatty oil, liquid paraffin, or liquid polyethylene glycol. In addition, stabilizers are optionally added.

The pharmaceutical compositions described herein are formulated in any conventional manner using one or more physiologically acceptable carriers comprising excipients and auxiliaries which facilitate processing of the active compound(s) into preparations which can be used pharmaceutically. In certain embodiments, the formulation of the pharmaceutical composition facilitates administration to a subject.

Proper formulation is dependent upon the route of administration chosen. Any pharmaceutically acceptable techniques, carriers, and excipients are optionally used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), the relevant teachings of which are incorporated herein by reference in their entireties.

In embodiments, pharmaceutical compositions described herein are manufactured in a conventional manner, such as, by way of example only, by means of conventional mixing, dissolving, granulating, dragee-making, levigating, emulsifying, encapsulating, entrapping or compression processes.

In particular embodiments, the compound having structure (I) (e.g., a crystalline form and/or polymorph of a compound having structure (I)), or a tautomer, pharmaceutically acceptable salt or zwitterionic form thereof, is mixed with an excipient and, optionally, a lubricant and a glidant using direct blending techniques, and capsules are filled with the resulting mixture on a manual capsule filling machine. In some particular embodiments, the compound having structure (I) (e.g., a crystalline form and/or polymorph of a compound having structure (I)), or a tautomer, pharmaceutically acceptable salt or zwitterionic form thereof, the excipient and the optional glidant are put through a 500 μm screen, then mixed together, and blended for 16 minutes at 30 rpm. The optional lubricant is then sieved through a 250 μm screen and added to the mixture. The resulting mixture is then blended for 5 minutes at 30 rpm. Capsules are then filled using an overage of from 0% to about 5% (e.g., about 1%), using tamping and/or tapping, as needed.

In certain embodiments, pharmaceutical preparations for oral use are obtained by mixing one or more solid excipients with the compound having structure (I) (e.g., a crystalline form and/or polymorph of a compound having structure (I)), or a tautomer, pharmaceutically acceptable salt or zwitterionic form thereof, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others, such as polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

Additionally, the compound having structure (I) (e.g., a crystalline form and/or polymorph of a compound having structure (I)), or a tautomer, pharmaceutically acceptable salt or zwitterionic form thereof, can encompass unsolvated as well as solvated forms with pharmaceutically acceptable solvents such as, for example, ethanol, and the like. The solvated forms of the compound having structure (I), or a tautomer, pharmaceutically acceptable salt or zwitterionic form thereof, are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compound having structure (I) (e.g., a crystalline form and/or polymorph of a compound having structure (I)), or a tautomer, pharmaceutically acceptable salt or zwitterionic form thereof, include formulating with one or more inert, pharmaceutically acceptable excipients or carriers to form a solid, semi-solid or liquid. Solid compositions include powders, tablets, dispersible granules, capsules, cachets, and suppositories. Liquid compositions include solutions in which the compound having structure (I), or a tautomer, pharmaceutically acceptable salt or zwitterionic form thereof, is dissolved, emulsions comprising the compound having structure (I), or a tautomer, pharmaceutically acceptable salt or zwitterionic form thereof, or a solution containing liposomes, micelles, or nanoparticles comprising the compound having structure (I), or a tautomer, pharmaceutically acceptable salt or zwitterionic form thereof. Semi-solid compositions include gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, the pharmaceutical composition comprising the compound having structure (I) (e.g., a crystalline form and/or polymorph of a compound having structure (I)), or a tautomer, pharmaceutically acceptable salt or zwitterionic form thereof, takes the form of a liquid where the agents are present in solution, in suspension or both. Typically, when the composition is administered as a solution or suspension, a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers, such as cellulosic polymers, e.g., hydroxypropylmethylcellulose, and water-insoluble polymers, such as cross-linked carboxyl-containing polymers. Certain pharmaceutical compositions described herein comprise a mucoadhesive polymer, selected, for example, from carboxymethylcellulose, carbomer (acrylic acid polymer), poly(methylmethacrylate), polyacrylamide, polycarbophil, acrylic acid/butyl acrylate copolymer, sodium alginate or dextran.

Useful pharmaceutical compositions also, optionally, include solubilizing agents to aid in the solubility of the compound having structure (I), or a tautomer, pharmaceutically acceptable salt or zwitterionic form thereof. The term "solubilizing agent" generally includes agents that result in formation of a micellar solution or a true solution of the agent. Certain acceptable nonionic surfactants, for example, polysorbate 80, are useful as solubilizing agents, as are ophthalmically acceptable glycols, polyglycols, e.g., polyethylene glycol 400, and glycol ethers.

Furthermore, pharmaceutical compositions optionally include one or more pH adjusting agents or buffering agents, including acids, such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Pharmaceutical compositions also, optionally, include one or more salts in an amount required to bring osmolality of the composition into an acceptable range. Such salts include those having, for example, sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other pharmaceutical compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other pharmaceutical compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose, reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the active. Various sustained-release materials are useful herein. In some embodiments, sustained-release capsules release the active for a few weeks up to over 100 days. Depending on the chemical nature and the biological stability of the active, additional strategies for protein stabilization are employed.

In certain embodiments, the formulations described herein comprise one or more antioxidants, metal chelating agents, thiol-containing compounds and/or other general stabilizing agents. Examples of such stabilizing agents, include: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of the compound having structure (I), or a tautomer, pharmaceutically acceptable salt or zwitterionic form thereof, provided in a pharmaceutical composition or unit dose form is no more than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of the compound having structure (I), or a tautomer, pharmaceutically acceptable salt or zwitterionic form thereof, is in the range of from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, or approximately 1% to approximately 10% w/w, w/v or v/v.

In some embodiments, the concentration of the compound having structure (I), or a tautomer, pharmaceutically acceptable salt or zwitterionic form thereof, is in the range of from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, or approximately 0.1% to approximately 0.9% w/w, w/v or v/v.

In some embodiments, the amount of the compound having structure (I), or a tautomer, pharmaceutically acceptable salt or zwitterionic form thereof, provided in a pharmaceutical composition or unit dose form is no more than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

Methods of Treatment

Embodiments of the present disclosure include methods for treating a disease associated with overexpression of a cyclin-dependent kinase (CDK), such as CDK 9, 1, 2, 4 or 7 (e.g., CDK9), in a mammal in need thereof, comprising administering to the mammal a therapeutically effective amount of a compound having structure (I) (e.g., a crystalline form and/or polymorph thereof), or a tautomer, pharmaceutically acceptable salt or zwitterionic form thereof; pharmaceutical composition; and/or unit dose form described herein. In some embodiments, the disease associated with overexpression of a CDK is cancer.

Some embodiments include methods for treatment of cancer comprising administering an effective amount of a compound having structure (I) (e.g., a crystalline form and/or polymorph thereof), or a tautomer, pharmaceutically acceptable salt or zwitterionic form thereof, to a subject in need thereof. Certain embodiments provide a method for treatment of cancer, the method comprising administering an effective amount of a pharmaceutical composition comprising a compound having structure (I) (e.g., a crystalline form and/or polymorph thereof), or a tautomer, pharmaceutically acceptable salt or zwitterionic form thereof, to a subject in need thereof. The compound having structure (I), or a tautomer, pharmaceutically acceptable salt or zwitterionic form thereof, may be used singly or in combination with one or more therapeutic agents, for example, as components of one or more mixtures.

In some embodiments, the cancer treated is a hematologic cancer. Hematologic malignancies that can be treated with a compound having structure (I), or a tautomer or zwitterionic form thereof, include leukemias and lymphomas. In some embodiments, the hematologic cancer is selected from acute myelogenous leukemia (AML), follicular lymphoma, acute lymphoblastic leukemia (ALL), chronic lymphocytic leukemia (CLL), multiple myeloma (MM) and non-Hodgkin's lymphoma (e.g., AML, follicular lymphoma, ALL, CLL and non-Hodgkin's lymphoma). In more specific embodiments, the hematological cancer is AML. In other more specific embodiments, the hematologic cancer is CLL. In more specific embodiments, the hematologic cancer is MM. In still other specific embodiments, the hematologic cancer is myelodysplasic syndrome (MDS).

In other embodiments, the cancer comprises a solid tumor. Accordingly, in some embodiments, the cancer is a solid tumor cancer. In various embodiments, the solid tumor cancer is breast cancer, bladder cancer, liver cancer, pancreatic cancer, lung cancer, colorectal cancer, ovarian cancer, prostate cancer, or melanoma. In some embodiments, the cancer is bladder cancer. In some embodiments, the cancer is lung cancer. In other embodiments, the cancer is liver cancer. In some embodiments, the cancer is a sarcoma, bladder cancer or renal cancer. In some embodiments, the cancer is prostate cancer (e.g., castration-resistant prostate cancer, castration-sensitive prostate cancer). In other embodiments, the cancer is bladder cancer, pancreatic cancer, colorectal cancer, kidney cancer, non-small cell lung carcinoma, prostate cancer, sarcoma, skin cancer, thyroid cancer, testicular cancer or vulvar cancer. In some embodiments, the cancer is endometrial cancer, pancreatic cancer, testicular cancer, renal cancer, melanoma, colorectal cancer, thyroid cancer, bladder cancer, pancreatic cancer, vulvar cancer, sarcoma, prostate cancer, lung cancer or anal cancer.

In some embodiments, the cancer is a sarcoma. In some embodiments, the cancer is a renal cell carcinoma.

"Castration-resistant prostate cancer" refers to prostate cancer that progresses in a subject following administration of one or more androgen depletion therapies (ADTs). Progression of prostate cancer can be evidenced by, for example, a prostate-specific antigen doubling time (PSADT) of less than or equal to 10 months, the progression of pre-existing disease (e.g., radiographic progression, clinical progression, a skeletal-related event, prostate-specific antigen (PSA) progression), and/or the appearance of new metastases in a subject, and is typically driven by androgens, which are a class of hormones including testosterone and dihydrotestosterone (DHT). These androgens bind to the androgen receptor (AR), which is a transcription activator that promotes growth and survival of prostate cells, including prostate cancer cells. ADT refers to a therapy to suppress androgen levels (e.g., surgical castration or chemical castration) or androgen signaling (e.g., by reducing androgen binding to androgen receptor), which may be used to slow the progression of prostate cancer. Androgen deprivation therapy typically causes a temporary reduction in tumor burden concomitant with a decrease in serum PSA. Mechanisms of castration resistance include the emergence of AR variants that are active in the absence of androgen, including splice variants, point mutations to AR, and AR gene amplifications. Castration resistance can be biochemically characterized before the onset of symptoms by a rising titer of serum PSA (Miller, et al., 1992 J. Urol. 147, 956 961). Radiographic progression can be assessed with the use of sequential imaging, and is evidenced by, for example, bone scan identification of two or more new bone lesions with confirmation (according to the Prostate Cancer Clinical Trials Working Group 2 criteria). Response Evaluation Criteria in Solid Tumors (RECIST v 1.1) criteria can also be used to assess radiographic progression of soft tissue lesions. Guidelines for monitoring prostate cancer, including progression of prostate cancer, are described in NCCN Clinical Practice Guidelines in Oncology: Prostate Cancer, version 4.2019, Aug. 19, 2019, the relevant contents of which are incorporated herein by reference in their entirety. "Castration-resistant prostate cancer" is used interchangeably herein with "androgen-resistant prostate cancer", "androgen-independent prostate cancer" and "hormone-resistant prostate cancer".

"Castration-sensitive prostate cancer" refers to prostate cancer that does not progress (e.g., responds) following administration of one or more ADTs. Progression of prostate cancer can be assessed according to criteria described herein, for example, with respect to "castration-resistant prostate cancer," and guidelines for monitoring prostate cancer, including progression of prostate cancer, are described in NCCN Clinical Practice Guidelines in Oncology: Prostate Cancer, version 4.2019, Aug. 19, 2019, the relevant contents of which are incorporated herein by reference in their entirety. "Castration-sensitive prostate cancer" is used interchangeably herein with "androgen-sensitive prostate cancer", "androgen-dependent prostate cancer" and "hormone-sensitive prostate cancer".

Further examples of cancers treatable according to the methods described herein include, but are not limited to, Acute Lymphoblastic Leukemia (ALL); Acute Myeloid Leukemia (AML); Adrenocortical Carcinoma; Adrenocortical Carcinoma, Childhood; AIDS-Related Cancer (e.g., Kaposi Sarcoma, AIDS-Related Lymphoma, Primary CNS Lymphoma); Anal Cancer; Appendix Cancer; Astrocytomas, Childhood; Atypical Teratoid/Rhabdoid Tumor, Childhood, Central Nervous System; Basal Cell Carcinoma of the Skin; Bile Duct Cancer; Bladder Cancer; Bladder Cancer, Childhood; Bone Cancer (including Ewing Sarcoma, Osteosarcoma and Malignant Fibrous Histiocytoma); Brain Tumors/Cancer; Breast Cancer; Burkitt Lymphoma; Carcinoid Tumor (Gastrointestinal); Carcinoid Tumor, Childhood; Cardiac (Heart) Tumors, Childhood; Embryonal Tumors, Childhood; Germ Cell Tumor, Childhood; Primary CNS Lymphoma; Cervical Cancer; Childhood Cervical Cancer; Cholangiocarcinoma; Chordoma, Childhood; Chronic Lymphocytic Leukemia (CLL); Chronic Myelogenous Leukemia (CML); Chronic Myeloproliferative Neoplasms; Colorectal Cancer; Childhood Colorectal Cancer; Craniopharyngioma, Childhood; Cutaneous T-Cell Lymphoma (e.g., Mycosis Fungoides and Sézary Syndrome); Ductal Carcinoma In Situ (DCIS); Embryonal Tumors, Central Nervous System, Childhood; Endometrial Cancer (Uterine Cancer); Ependymoma, Childhood; Esophageal Cancer; Childhood Esophageal Cancer; Esthesioneuroblastoma; Ewing Sarcoma; Extracranial Germ Cell Tumor, Childhood; Extragonadal Germ Cell Tumor; Eye Cancer; Childhood Intraocular Melanoma; Intraocular Melanoma; Retinoblastoma; Fallopian Tube Cancer; Fibrous Histiocytoma of Bone, Malignant, and Osteosarcoma; Gallbladder Cancer; Gastric (Stomach) Cancer; Childhood Gastric (Stomach) Cancer; Gastrointestinal Carcinoid Tumor; Gastrointestinal Stromal Tumors (GIST); Childhood Gastrointestinal Stromal Tumors; Germ Cell Tumors; Childhood Central Nervous System Germ Cell Tumors (e.g., Childhood Extracranial Germ Cell Tumors, Extragonadal Germ Cell Tumors, Ovarian Germ Cell Tumors, Testicular Cancer); Gestational Trophoblastic Disease; Hairy Cell Leukemia; Head and Neck Cancer; Heart Tumors, Childhood; Hepatocellular (Liver) Cancer; Histiocytosis, Langerhans Cell; Hodgkin Lymphoma; Hypopharyngeal Cancer; Intraocular Melanoma; Childhood Intraocular Melanoma; Islet Cell Tumors, Pancreatic Neuroendocrine Tumors; Kaposi Sarcoma; Kidney (Renal Cell) Cancer; Langerhans Cell Histiocytosis; Laryngeal Cancer; Leukemia; Lip and Oral Cavity Cancer; Liver Cancer; Lung Cancer (Non-Small Cell and Small Cell); Childhood Lung Cancer; Lymphoma; Male Breast Cancer; Malignant Fibrous Histiocytoma of Bone and Osteosarcoma; Melanoma; Childhood Melanoma; Melanoma, Intraocular (Eye); Childhood Intraocular Melanoma; Merkel Cell Carcinoma; Mesothelioma, Malignant; Childhood Mesothelioma; Metastatic Cancer; Metastatic Squamous Neck Cancer with Occult Primary; Midline Tract Carcinoma With NUT Gene Changes; Mouth Cancer; Multiple Endocrine Neoplasia Syndromes; Multiple Myeloma/Plasma Cell Neoplasms; Mycosis Fungoides; Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms, Chronic; Nasal Cavity and Paranasal Sinus Cancer; Nasopharyngeal Cancer; Neuroblastoma; Non-Hodgkin Lymphoma; Non-Small Cell Lung Cancer; Oral Cancer, Lip and Oral Cavity Cancer and Oropharyngeal Cancer; Osteosarcoma and Malignant Fibrous Histiocytoma of Bone; Ovarian Cancer; Childhood Ovarian Cancer; Pancreatic Cancer; Childhood Pancreatic Cancer; Pancreatic Neuroendocrine Tumors; Papillomatosis (Childhood Laryngeal); Paraganglioma; Childhood Paraganglioma; Paranasal Sinus and Nasal Cavity Cancer; Parathyroid Cancer; Penile Cancer; Pharyngeal Cancer; Pheochromocytoma; Childhood Pheochromocytoma; Pituitary Tumor; Plasma Cell Neoplasm/Multiple Myeloma; Pleuropulmonary Blastoma; Pregnancy and Breast Cancer; Primary Central Nervous System (CNS)

Lymphoma; Primary Peritoneal Cancer; Prostate Cancer; Rectal Cancer; Recurrent Cancer; Renal Cell (Kidney) Cancer; Retinoblastoma; Rhabdomyosarcoma, Childhood; Salivary Gland Cancer; Sarcoma (e.g., Childhood Rhabdomyosarcoma, Childhood Vascular Tumors, Ewing Sarcoma, Kaposi Sarcoma, Osteosarcoma (Bone Cancer), Soft Tissue Sarcoma, Uterine Sarcoma); Sézary Syndrome; Skin Cancer; Childhood Skin Cancer; Small Cell Lung Cancer; Small Intestine Cancer; Soft Tissue Sarcoma; Squamous Cell Carcinoma of the Skin; Squamous Neck Cancer with Occult Primary, Metastatic; Stomach (Gastric) Cancer; Childhood Stomach (Gastric) Cancer; T-Cell Lymphoma, Cutaneous (e.g., Mycosis Fungoides and Sezary Syndrome); Testicular Cancer; Childhood Testicular Cancer; Throat Cancer (e.g., Nasopharyngeal Cancer, Oropharyngeal Cancer, Hypopharyngeal Cancer); Thymoma and Thymic Carcinoma; Thyroid Cancer; Transitional Cell Cancer of the Renal Pelvis and Ureter; Ureter and Renal Pelvis, Transitional Cell Cancer; Urethral Cancer; Uterine Cancer, Endometrial; Uterine Sarcoma; Vaginal Cancer; Childhood Vaginal Cancer; Vascular Tumors; Vulvar Cancer; and Wilms Tumor and Other Childhood Kidney Tumors.

Metastases of the aforementioned cancers can also be treated in accordance with the methods described herein. Thus, in some embodiments, the cancer is a metastatic cancer. In other embodiments, the cancer is a primary cancer.

In some embodiments, the cancer is MCL-1 dependent. As used herein, "MCL-1-dependent" refers to the subset of cancers (e.g., hematologic cancers) wherein myeloid cell leukemia 1 (MCL-1) is the primary driver of suppressing apoptosis. Typically, MCL-1 dependency promotes blast survival, and is associated with treatment resistance and relapse. MCL-1 dependence can be assessed, for example, by contacting a subject's cancer cell with a profiling peptide, as described in International Publication Nos. WO 2016/172214 and WO 2018/119000, the relevant contents of which are incorporated herein by reference in their entireties.

In some embodiments, the cancer is c-Myc-altered. As used herein, "c-Myc-altered" refers to the subset of cancers wherein c-Myc is altered compared to its native sequence, where its expression is amplified compared to an appropriate control (e.g., corresponding normal cells), and where protein levels suggest overexpression of c-Myc. For example, it has been found that c-Myc drives androgen independence in prostate cancer, and overexpression attenuates the anti-tumor activity of androgen receptor suppression. In addition, c-Myc is significantly upregulated in androgen receptor-sensitive prostate cancer. Examples of cancers that can be c-Myc-altered include, but are not limited to, lymphoma (e.g., Burkitt lymphoma, B-cell lymphoma, T-cell lymphoma), cervical cancer, colon cancer, ovarian cancer, breast cancer, lung cancer, prostate cancer, colorectal cancer, pancreatic cancer, gastric cancer and uterine cancer.

In some embodiments of the methods of treatment, the compound having structure (I), or a tautomer, pharmaceutically acceptable salt or zwitterionic form thereof, the pharmaceutical composition, or the unit dose form is administered orally.

Some embodiments provide methods for combination therapies in which an agent known to modulate other pathways, or other components of the same pathway, or even overlapping sets of target enzymes are used in combination with a compound having structure (I), or a tautomer, pharmaceutically acceptable salt or zwitterionic form thereof. In one aspect, such therapy includes the combination of the compound having structure (I), or a tautomer, pharmaceutically acceptable salt or zwitterionic form thereof, with a chemotherapeutic agent, therapeutic antibody, and/or radiation treatment, e.g., to provide a synergistic or additive therapeutic effect.

Many chemotherapeutics are presently known in the art and can be used in combination with a compound having structure (I), or a pharmaceutically acceptable salt or zwitterionic form thereof. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

For example, the further therapeutic agent may comprise an alkylating agent, such as chlorambucil, cyclophosphamide, cisplatin; a mitotic inhibitor such as docetaxel (Taxotere; 1,7β,10β-trihydroxy-9-oxo-5β,20-epoxytax-11-ene-2α,4,13α-triyl 4-acetate 2-benzoate 13-{(2R,3S)-3-[(tert-butoxycarbonyl)amino]-2-hydroxy-3-phenylpropanoate}) or paclitaxel; an antimetabolite such as 5-fluorouracil, cytarabine, methotrexate, or pemetrexed; an anti-tumor antibiotic such as daunorubicin or doxorubicin; a corticosteroid such as prednisone or methylprednisone; or a Bcl-2 inhibitor such as venetoclax.

In certain embodiments, the further therapeutic agent is docetaxel. Docetaxel (trade name TAXOTERE®) is a type of chemotherapeutic agent known as an antimicrotubule agent. Docetaxel is used for treating a variety of cancers, such as metastatic prostate cancer. Docetaxel treatment is often administered intravenously, and often includes pre-medication with a corticosteroid such as prednisone.

In certain aspects of all embodiments, the further therapeutic agent is venetoclax (GDC-0199, ABT199, RG7601, trade name VENCLEXTA® or VENCLYXTO®), which is a Bcl-2 inhibitor that can induce apoptosis in cancer cells. Venetoclax is typically administered orally.

The further therapeutic agent may be a pharmacological agent that is currently approved by the Food and Drug Administration (FDA) in the U.S. (or elsewhere by any other regulatory body) for use as pharmacological treatment of prostate cancer, or is currently being used experimentally as part of a clinical trial program that relates to prostate cancer. For example, the further therapeutic agents may comprise, without limitation, the chemical entity known as enzalutamide or MDV3100 (4-(3-(4-cyano-3-(trifluoromethyl)phenyl)-5,5-dimethyl-4-oxo-2-thioxoimidazolidin-1-yl)-2-fluoro-N-methylbenzamide) and related compounds; the chemical entity known as TOK 001 and related compounds; the chemical entity known as ARN-509; the chemical entity known as abiraterone (or CB-7630; (3S,8R,9S,10R,13S,14S)-10,13-dimethyl-17-(pyridin-3-yl) 2,3,4,7,8,9,10,11,12,13,14,15-dodecahydro-1H-cyclopenta[a]phenanthren-3-ol), and related molecules; the chemical entity known as bicalutamide (N-[4-cyano-3-(trifluoromethyl)phenyl]-3-[(4-fluorophenyl)sulfonyl]-2-hydroxy-2-methylpropanamide) and related compounds; the chemical entity known as nilutamide (5,5-dimethyl-3-[4-nitro-3-(trifluoromethyl)phenyl] imidazolidine-2,4-dione) and related compounds; the chemical entity known as flutamide (2-methyl-N-[4-nitro-3-(trifluoromethyl)phenyl]-propanamide) and related compounds; the chemical entity known as cyproterone acetate (6-chloro-13,23-dihydro-17-hydroxy-3'H-cyclopropa[1,2]pregna-4,6-diene-3,20-dione) and related compounds, which is currently used to treat prostate cancer, the chemical entity known as docetaxel and related compounds, which is currently used alone or in combination with prednisone to treat prostate cancer, the chemical entity known as bevacizumab (Avastin), a monoclonal antibody that may be used to treat prostate cancer, the chemical entity known as OSU-HDAC42 ((S)-(+)—N-hydroxy-4-(3-methyl-2-phenylbutyrylamino)-benzamide), and related compounds; the chemical entity known as VITAXIN, which may be used to treat prostate cancer, the chemical entity known as sunitumib (N-(2-diethylaminoethyl)-5-[(Z)-(5-fluoro-2-oxo-1H-indol-3-ylidene)methyl]-2,4-dimethyl-1H-pyrrole-3-carboxamide) and related compounds, which may be used for treatment of prostate cancer, the chemical entity known as ZD-4054 (N-(3-Methoxy-5-methylpyrazin-2-yl)-2-[4-(1,3,4-oxadiazol-2-yl)phenyl]pyridin-3-sulfonamid) and related compounds; the chemical entity known as VN/124-1 (3β-Hydroxy-17-(1H-benzimidazol-1-yl)androsta-5,16-diene), and related compounds; the chemical entity known as cabazitaxel (XRP-6258), and related compounds; the chemical entity known as MDX-010 (Ipilimumab); the chemical entity known as OGX 427; the chemical entity known as OGX 011; the chemical entity known as finasteride (Proscar, Propecia; N-(1,1-dimethylethyl)-3-oxo-(5α,17β)-4-azaandrost-1-ene-17-carboxamide), and related compounds; the chemical entity known as dutasteride (Avodart; 5α, 17β)-N-{2,5 bis(trifluoromethyl) phenyl}-3-oxo-4-azaandrost-1-ene-17-carboxamide) and related compounds; the chemical entity known as turosteride ((4aR,4bS,6aS,7S,9aS,9bS,11aR)-1,4a,6a-trimethyl-2-oxo-N-(propan-2-yl)-N-(propan-2 ylcarbamoyl)hexadecahydro-1H-indeno[5,4-f]quinoline-7-carboxamide), and related compounds; the chemical entity known as bexlosteride (LY-191,704; (4aS,10bR)-8-chloro-4-methyl-1,2,4a,5,6,10b-hexahydrobenzo[f]quinolin-3-one), and related compounds; the chemical entity known as izonsteride (LY-320,236; (4aR,10bR)-8-[(4-ethyl-1,3-benzothiazol-2-yl)sulfanyl]-4,10b-dimethyl-1,4,4a,5,6,10b-hexahydrobenzo[f]quinolin-3(2H)-one) and related compounds; the chemical entity known as FCE 28260 and related compounds; the chemical entity known as SKF105, 111, and related compounds; the chemical entity known as AZD3514; the chemical entity known as EZN-4176; the chemical entity known as ODM-201, sipuleucel-T, cabazitaxel; a combination of bevacizumab, docetaxel, thalidomide and prednisone; and/or abiraterone. In certain aspects of all embodiments, the further therapeutic agent is an androgen receptor antagonist that blocks androgen binding to androgen receptor. Examples of therapies that block androgen binding to androgen receptor include enzalutamide and apalutamide. In particular embodiments, the further therapeutic agent is enzalutamide. Enzalutamide (trade name XTANDI®) is an androgen receptor (AR) antagonist that is used for treating non-metastatic castration-resistant prostate cancer and metastatic castration-resistant prostate cancer. Enzalutamide treatment may be combined with castration (surgical or chemical).

In certain aspects of all embodiments, the further therapeutic agent is abiraterone. Abiraterone (trade name ZYTIGA®) is a CYP17A1 inhibitor, which significantly decreases testosterone production. Abiraterone treatment may be combined with other further therapies, such as a corticosteroid (e.g., prednisone) and/or castration (surgical or chemical).

In certain aspects of all embodiments, the further therapeutic agent is selected from at least one of: a bromodomain inhibitor, a histone methyltransferase inhibitor, a histone deacetylase inhibitor, or a histone demethylases inhibitor.

In certain aspects of all embodiments, the further therapeutic agent is a bromodomain inhibitor, for example, an inhibitor of a bromodomain protein such as Brd2, Brd3, Brd4 and/or BrdT. In particular embodiments, the further therapeutic agent comprises a BRD4 inhibitor. In some of these embodiments, the further therapeutic agent is JQ-1 (Nature 2010 Dec. 23; 468(7327):1067-73), BI2536 (ACS Chem. Biol. 2014 May 16; 9(5):1160-71; Boehringer Ingelheim), TG101209 (ACS Chem. Biol. 2014 May 16; 9(5): 1160-71), OTX015 (Mol. Cancer Ther. November 201312; C244; Oncoethix), IBET762 (J Med Chem. 2013 Oct. 10; 56(19):7498-500; GlaxoSmithKline), IBET151 (Bioorg. Med. Chem. Lett. 2012 Apr. 15; 22(8):2968-72; GlaxoSmithKline), PFI-1 (J. Med. Chem. 2012 Nov. 26; 55(22): 9831-7; Cancer Res. 2013 Jun. 1; 73(11):3336-46; Structural Genomics Consortium) or CPI-0610 (Constellation Pharmaceuticals). In other embodiments, the BRD inhibitor is IBET 762 (GSK525762), TEN-010 (Tensha Therapeutics), CPI-203 (*Leukemia.* 28 (10): 2049-59, 2014), RVX-208 (*Proceedings of the National Academy of Sciences of the United States of America.* 110 (49): 19754-9, 2013), LY294002 (*ACS Chemical Biology.* 9 (2): 495-502, 2014), AZD5153 (*Journal of Medicinal Chemistry.* 59 (17): 7801-17, 2016), MT-1 (*Nature Chemical Biology.* 12 (12): 1089-1096 2016) or MS645 (*Proceedings of the National Academy of Sciences of the United States of America.* 115 (31): 7949-7954, 2018).

In certain aspects of all embodiments, the further therapeutic agent is a histone methyltransferase inhibitor. In some of these embodiments, the further therapeutic agent comprises a DOT1-like histone methyltransferase (DOT1L) inhibitor. DOT1L is a histone methyltransferase enzyme that targets lysine 79 in the globular domain of histone H3 for mono-, di-, or trimethylation. In some of these embodiments, the further therapeutic agent is EPZ004777, EPZ-5676 (Blood. 2013 Aug. 8; 122(6):1017-25) or SGC0946 (Nat. Commun. 2012; 3:1288), for example, EPZ-5676.

In certain aspects of all embodiments, the further therapeutic agent is a histone deacetylase (HDAC) inhibitor. HDAC proteins may be grouped into classes based on homology to yeast HDAC proteins with Class I made up of HDAC1, HDAC2, HDAC3 and HDAC 8; Class IIa made up of HDAC4, HDAC5, HDAC7 and HDAC 9; Class IIb made up of HDAC6 and HDAC10; and Class IV made up of HDAC11. In some of these embodiments, the further therapeutic agent is trichostatin A, vorinostat (Proc. Natl. Acad. Sci. U.S.A. 1998 Mar. 17; 95(6):3003-7), givinostat, abexinostat (Mol. Cancer Ther. 2006 May; 5(5):1309-17), belinostat (Mol. Cancer Ther. 2003 August; 2(8):721-8), panobinostat (Clin. Cancer Res. 2006 Aug. 1; 12(15):4628-35), resminostat (Clin. Cancer Res. 2013 Oct. 1; 19(19): 5494-504), quisinostat (Clin. Cancer Res. 2013 Aug. 1; 19(15):4262-72), depsipeptide (Blood. 2001 Nov. 1; 98(9): 2865-8), entinostat (Proc. Natl. Acad. Sci. U.S.A. 1999 Apr. 13; 96(8):4592-7), mocetinostat (Bioorg. Med. Chem. Lett. 2008 Feb. 1; 18(3):1067-71) or valproic acid (EMBO J. 2001 Dec. 17; 20(24):6969-78). For example, in some embodiments, the further therapeutic agent is panobinostat. In other embodiments, the further therapeutic agent is panobinostat or SAHA.

In certain aspects of all embodiments, the further therapeutic agent is a histone demethylase inhibitor. In particular embodiments, the histone demethylase inhibitor is a lysine-specific demethylase 1A (Lsd1) inhibitor. In some of these embodiments, the further therapeutic agent is HCI-2509 (BMC Cancer. 2014 Oct. 9; 14:752), tranylcypromine or ORY-1001 (J. Clin. Oncol 31, 2013 (suppl; abstr e13543). In other embodiments, the further therapeutic agent is HCI-2509.

In certain aspects of all embodiments, the further therapeutic agent is a MLL-menin inhibitor. Menin is a co-factor of the oncogenic MLL fusion protein, and an MLL-menin inhibitor blocks the interaction of the two proteins. Examples of MLL-menin inhibitors include MI-453, M-525, and MI-503.

In certain aspects of all embodiments, the further therapeutic agent is a B-cell receptor signaling antagonist (e.g., a Bruton's tyrosine kinase (BTK) inhibitor, such as ibrutinib).

In certain aspects of all embodiments, the further therapeutic agents is an immunomodulator. Immunomodulators of particular interest for use in combination with compounds of the present disclosure include: afutuzumab (available from ROCHE®); pegfilgrastim (NEULASTA®); lenalidomide (CC-5013, REVLIMID®); thalidomide (THALOMID®); actimid (CC4047); and IRX-2 (mixture of human cytokines including interleukin 1, interleukin 2, and interferon 7, CAS 951209-71-5, available from IRX Therapeutics).

In certain aspects of all embodiments, the further therapeutic agent comprises a chimeric antigen receptor T-cell (CAR-T) therapy. CAR-T therapies of particular interest for use in combination with compounds of the present disclosure include: tisagenlecleucel (Novartis), axicabtagene ciloleucel (Kite), and tocilizumab and atlizumab (Roche).

In certain aspects of all embodiments, the further therapeutic agent is an immune checkpoint inhibitor (e.g., a PD-1 inhibitor, such as pembrolizumab or nivolumab; a PD-L1 inhibitor, such as atezolizumab, avelumab, or durvalumab; a CTLA-4 inhibitor; a LAG-3 inhibitor; or a Tim-3 inhibitor). Other immune checkpoint inhibitors of interest for use in combination with compounds of the present disclosure include: PD-1 inhibitors, such as pembrolizumab (KEYTRUDA®), nivolumab (OPDIVO®), cemiplimab (LIBTAYO®), spartalizumab (PDR001), pidilizumab (CureTech), MEDI0680 (Medimmune), cemiplimab (REGN2810), dostarlimab (TSR-042), PF-06801591 (Pfizer), tislelizumab (BGB-A317), camrelizumab (INCSHR1210, SHR-1210), and AMP-224 (Amplimmune); PD-L1 inhibitors, such as atezolizumab (TECENTRIQ®), avelumab (BAVENCIO®), durvalumab (IMFINZI®), FAZ053 (Novartis), and BMS-936559 (Bristol-Myers Squibb); and drugs that target CTLA-4, such as ipilimumab (YERVOY®).

In various embodiments, the immune checkpoint inhibitor is a PD-1 inhibitor. In specific embodiments, the PD-1 inhibitor is pembrolizumab, nivolumab, or a combination thereof. In particular embodiments, the PD-1 inhibitor is pembrolizumab (also known as lambrolizumab, MK-3475, MK03475, SCH-900475, or KEYTRUDA®). Pembrolizumab and other anti-PD-1 antibodies are disclosed in Hamid, O., et al. (2013) New England Journal of Medicine 369 (2): 134-44, U.S. Pat. No. 8,354,509, and WO 2009/114335, incorporated by reference in their entireties. In particular embodiments, the PD-1 inhibitor is nivolumab (also known as MDX-1106, MDX-1106-04, ONO-4538, BMS-936558, or OPDIVO®). Nivolumab (clone 5C4) and other anti-PD-1 antibodies are disclosed in U.S. Pat. No. 8,008,449 and WO 2006/121168, incorporated by reference in their entireties. In some other embodiments, the PD-1 inhibitor is AMP-224 (Amplimmune), CBT-501 (CBT Pharmaceuticals), CBT-502 (CBT Pharmaceuticals), JS001 (Junshi Biosciences), IBI308 (Innovent Biologics), INCSHR1210 (Incyte), also known as SHR-1210 (Hengrui Medicine), BGBA317 (Beigene), BGB-108 (Beigene), BAT-I306 (Bio-Thera Solutions), GLS-010 (Gloria Pharmaceuticals; WuXi Biologics), AK103, AK104, AK105 (Akesio Biopharma; Hangzhou Hansi Biologics; Hanzhong Biologics), LZM009 (Livzon), HLX-10 (Henlius Biotech), MEDI0680 (Medimmune), PDF001 (Novartis), PF-06801591 (Pfizer), pidilizumab (CureTech), REGN2810 (Regeneron), TSR-042 (Tesaro), also known as ANB011, or CS1003 (CStone Pharmaceuticals). MEDI0680 (Medimmune) is also known as AMP-514. MEDI0680 and other anti-PD-1 antibodies are disclosed in U.S. Pat. No. 9,205,148 and WO 2012/145493, incorporated by reference in their entireties. Pidilizumab is also known as CT-011. Pidilizumab and other anti-PD-1 antibodies are disclosed in Rosenblatt, J., et al. (2011) J Immunotherapy 34(5): 409-18, U.S. Pat. Nos. 7,695,715, 7,332,582, and 8,686,119, incorporated by reference in their entireties.

In one embodiment, the anti-PD-1 antibody molecule is cemiplimab. In one embodiment, the anti-PD-1 antibody molecule is sintilimab. In one embodiment, the anti-PD-1 antibody molecule is toripalimab. In one embodiment, the anti-PD-1 antibody molecule is camrelizumab.

Further known anti-PD-1 antibody molecules include those described, e.g., in WO 2015/112800, WO 2016/092419, WO 2015/085847, WO 2014/179664, WO 2014/194302, WO 2014/209804, WO 2015/200119, U.S. Pat. Nos. 8,735,553, 7,488,802, 8,927,697, 8,993,731, and 9,102,727, incorporated by reference in their entireties.

In one embodiment, the PD-1 inhibitor is an anti-PD-1 antibody molecule as described in US 2015/0210769. In one embodiment, the anti-PD-1 antibody molecule comprises the CDRs, variable regions, heavy chains and/or light chains of BAP049-Clone-E or BAP049-Clone-B disclosed in US 2015/0210769. The antibody molecules described herein can be made by vectors, host cells, and methods described in US 2015/0210769, incorporated by reference in its entirety.

In one embodiment, the PD-1 inhibitor is a peptide that inhibits the PD-1 signaling pathway, e.g., as described in U.S. Pat. No. 8,907,053, incorporated by reference in its entirety. In one embodiment, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In one embodiment, the PD-1 inhibitor is AMP-224 (B7-DCIg (Amplimmune), e.g., disclosed in WO 2010/027827 and WO 2011/066342, incorporated by reference in their entireties).

In some embodiments, the immune checkpoint inhibitor is a PD-L1 inhibitor. In some such embodiments, the PD-L1 inhibitor is atezolizumab, avelumab, durvalumab, or a combination thereof. In particular embodiments, the PD-L1 inhibitor is atezolizumab, also known as MPDL3280A, RG7446, R05541267, YW243.55.S70, or TECENTRIQ™ Atezolizumab and other anti-PD-L1 antibodies are disclosed in U.S. Pat. No. 8,217,149, incorporated by reference in its entirety. In particular embodiments, the PD-L1 inhibitor is avelumab, also known as MSB0010718C. Avelumab and other anti-PD-L1 antibodies are disclosed in WO 2013/079174, incorporated by reference in its entirety. In particular embodiments, the PD-L1 inhibitor is durvalumab, also known as MEDI4736. Durvalumab and other anti-PD-L1 antibodies are disclosed in U.S. Pat. No. 8,779,108, incorporated by reference in its entirety. In certain embodiments, the PD-L1 inhibitor is KN035 (Alphamab; 3DMed), BMS 936559 (Bristol-Myers Squibb), CS1001 (CStone Pharmaceuticals), FAZ053 (Novartis), SHR-1316 (Hengrui Medicine), TQB2450 (Chiatai Tianqing), STI-A1014 (Zhaoke Pharm; Lee's Pharm), BGB-A333 (Beigene), MSB2311 (Mabspace Biosciences), or HLX-20 (Henlius Biotech). In one embodiment, the anti-PD-L1 antibody molecule is BMS-936559 (Bristol-Myers Squibb), also known as MDX-1105 or 12A4. BMS-936559 and other anti-PD-L1 antibodies are disclosed in U.S. Pat. No. 7,943,743 and WO 2015/081158, incorporated by reference in their entireties. In some embodiments, the PD-L1 inhibitor is a monoclonal antibody (e.g., as made by Hisun Pharm and applying for clinical trials).

In one embodiment, the PD-L1 inhibitor is an anti-PD-L1 antibody molecule. In one embodiment, the PD-L1 inhibitor is an anti-PD-L1 antibody molecule as disclosed in US 2016/0108123, incorporated by reference in its entirety. In one embodiment, the anti-PD-L1 antibody molecule comprises the CDRs, variable regions, heavy chains and/or light chains of BAP058-Clone O or BAP058-Clone N disclosed in US 2016/0108123.

Further known anti-PD-L1 antibodies include those described, e.g., in WO 2015/181342, WO 2014/100079, WO 2016/000619, WO 2014/022758, WO 2014/055897, WO 2015/061668, WO 2013/079174, WO 2012/145493, WO 2015/112805, WO 2015/109124, WO 2015/195163, U.S. Pat. Nos. 8,168,179, 8,552,154, 8,460,927, and 9,175,082, incorporated by reference in their entireties.

In some embodiments, the immune checkpoint inhibitor is a CTLA-4 inhibitor. In certain embodiments, the CTLA-4 inhibitor is ipilimumab. In other embodiments, the CTLA4 inhibitor is tremelimumab.

In some embodiments, the immune checkpoint inhibitor is a LAG-3 inhibitor. In some embodiments, the LAG-3 inhibitor is chosen from LAG525 (Novartis), BMS-986016 (Bristol-Myers Squibb), or TSR-033 (Tesaro). In one embodiment, the LAG-3 inhibitor is an anti-LAG-3 antibody molecule. In one embodiment, the LAG-3 inhibitor is an anti-LAG-3 antibody molecule as disclosed in US 2015/0259420, incorporated by reference in its entirety. In one embodiment, the anti-LAG-3 antibody molecule comprises the CDRs, variable regions, heavy chains and/or light chains of BAP050-Clone I or BAP050-Clone J disclosed in US 2015/0259420.

In one embodiment, the anti-LAG-3 antibody molecule is BMS-986016 (Bristol-Myers Squibb), also known as BMS986016. BMS-986016 and other anti-LAG-3 antibodies are disclosed in WO 2015/116539 and U.S. Pat. No. 9,505,839, incorporated by reference in their entireties. In one embodiment, the anti-LAG-3 antibody molecule is TSR-033 (Tesaro). In one embodiment, the anti-LAG-3 antibody molecule is IMP731 or GSK2831781 (GSK and Prima BioMed). IMP731 and other anti-LAG-3 antibodies are disclosed in WO 2008/132601 and U.S. Pat. No. 9,244,059, incorporated by reference in their entireties. In one embodiment, the anti-LAG-3 antibody molecule is IMP761 (Prima BioMed).

Further known anti-LAG-3 antibodies include those described, e.g., in WO 2008/132601, WO 2010/019570, WO 2014/140180, WO 2015/116539, WO 2015/200119, WO 2016/028672, U.S. Pat. Nos. 9,244,059, 9,505,839, incorporated by reference in their entireties.

In one embodiment, the anti-LAG-3 inhibitor is a soluble LAG-3 protein, e.g., IMP321 (Prima BioMed), e.g., as disclosed in WO 2009/044273, incorporated by reference in its entirety.

In some embodiments, the immune checkpoint inhibitor is a TIM-3 inhibitor. In some embodiments, the TIM-3 inhibitor is MGB453 (Novartis) or TSR-022 (Tesaro).

In one embodiment, the TIM-3 inhibitor is an anti-TIM-3 antibody molecule. In one embodiment, the TIM-3 inhibitor is an anti-TIM-3 antibody molecule as disclosed in US 2015/0218274, incorporated by reference in its entirety. In one embodiment, the anti-TIM-3 antibody molecule comprises the CDRs, variable regions, heavy chains and/or light chains of ABTIM3-hum11 or ABTIM3-hum03 disclosed in US 2015/0218274.

In one embodiment, the anti-TIM-3 antibody molecule is TSR-022 (AnaptysBio/Tesaro). In one embodiment, the anti-TIM-3 antibody molecule comprises one or more of the CDR sequences (or collectively all of the CDR sequences), the heavy chain or light chain variable region sequence, or the heavy chain or light chain sequence of APE5137 or APE5121. APE5137, APE5121, and other anti-TIM-3 antibodies are disclosed in WO 2016/161270, incorporated by reference in its entirety. In one embodiment, the anti-TIM-3 antibody molecule is the antibody clone F38-2E2.

Further known anti-TIM-3 antibodies include those described, e.g., in WO 2016/111947, WO 2016/071448, WO 2016/144803, U.S. Pat. Nos. 8,552,156, 8,841,418, and 9,163,087, incorporated by reference in their entireties.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy in combination with compounds of the present disclosure. Suitable cytoprotective agents include amifostine (ETHYOL®), glutamine, dimesna (TAVOCEPT®), mesna (MESNEX®), dexrazoxane (ZINECARD® or TOTECT®), xaliproden (XAPRILA®), and leucovorin (also known as calcium leucovorin, citrovorum factor and folinic acid).

Some patients may experience allergic reactions to compounds of the present disclosure and/or other therapeutic agent(s) (e.g., anti-cancer agent(s)) during or after administration. Therefore, anti-allergic agents can be administered in combination with compounds of the present disclosure and/or other therapeutic agent(s) (e.g., anti-cancer agent(s)) to minimize the risk of an allergic reaction. Suitable anti-allergic agents include corticosteroids (Knutson, S., et al., *PLoS One, DOI:*10.1371/journal.pone.0111840 (2014)), such as dexamethasone (e.g., DECADRON®), beclomethasone (e.g., BECLOVENT®), hydrocortisone (also known as cortisone, hydrocortisone sodium succinate, hydrocortisone sodium phosphate, sold under the tradenames ALA-CORT®, hydrocortisone phosphate, SOLU-CORTEF®, HYDROCORT ACETATE® and LANACORT®), prednisolone (sold under the tradenames DELTA-CORTEL®, ORAPRED®, PEDIAPRED® and PRELONE®), prednisone (sold under the tradenames DELTASONE®, LIQUID RED®, METICORTEN® and ORASONE®), methylprednisolone (also known as 6-methylprednisolone, methylprednisolone acetate, methylprednisolone sodium succinate, sold under the tradenames DURALONE®, MEDRALONE®, MEDROL®, M-PREDNISOL® and SOLU-MEDROL®); antihistamines, such as diphenhydramine (e.g., BENADRYL®), hydroxyzine, and cyproheptadine; and bronchodilators, such as the beta-adrenergic receptor agonists, albuterol (e.g., PROVENTIL®), and terbutaline (BRETHINE®).

Some patients may experience nausea during and after administration of the compounds described herein and/or other therapeutic agent(s) (e.g., anti-cancer agent(s)). Therefore, anti-emetics can be used in combination with compounds of the present disclosure and/or other therapeutic agent(s) (e.g., anti-cancer agent(s)) to prevent nausea (upper stomach) and vomiting. Suitable anti-emetics include aprepitant (EMEND®), ondansetron (ZOFRAN®), granisetron HCl (KYTRIL®), lorazepam (ATIVAN®, dexamethasone (DECADRON®), prochlorperazine (COMPAZINE®), casopitant (REZONIC® and ZUNRISA®), and combinations thereof.

Medication to alleviate the pain experienced during treatment is often prescribed to make the patient more comfortable. Common over-the-counter analgesics, such TYLENOL®, can also be used in combination with compounds of the present disclosure and/or other therapeutic agent(s) (e.g., anti-cancer agent(s)). Opioid analgesic drugs such as hydrocodone/paracetamol or hydrocodone/acetaminophen (e.g., VICODIN®), morphine (e.g., ASTRAMORPH® or AVINZA®), oxycodone (e.g., OXYCONTIN® or PERCOCET®), oxymorphone hydrochloride (OPANA®), and fentanyl (e.g., DURAGESIC®) can be useful for moderate or severe pain, and can be used in combination with compounds of the present disclosure and/or other therapeutic agent(s) (e.g., anti-cancer agent(s)).

Embodiments

Embodiment 1. A polymorph of a compound having the following structure (I):

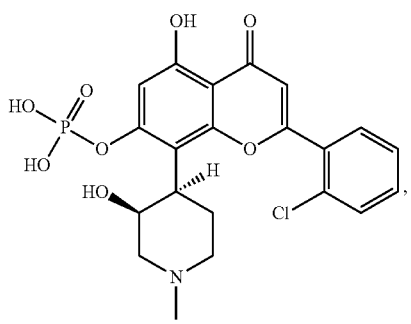

or a tautomer or zwitterionic form thereof, the polymorph having an X-ray powder diffraction pattern comprising the following:
D space (Å):
18.3±0.09
8.1±0.06
6.4±0.08
5.9±0.06
4.4±0.05
expressed in terms of "D" spacing.

Embodiment 2. The polymorph of Embodiment 1, wherein the X-ray powder diffraction pattern comprises the following:
D space (Å):
18.38±0.003
8.15±0.008
6.47±0.002
5.95±0.007
4.44±0.006
expressed in terms of "D" spacing.

Embodiment 3. The polymorph of Embodiment 1, wherein the X-ray powder diffraction pattern comprises the following:
D space (Å):
18.382
8.157
6.472
5.956
4.445
expressed in terms of "D" spacing.

Embodiment 4. A polymorph of a compound having the following structure

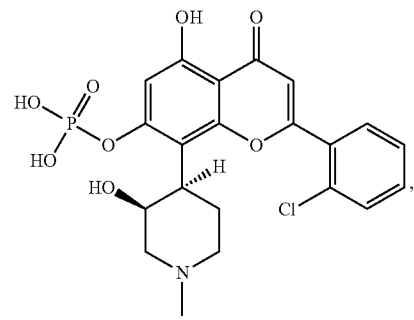

or a tautomer or zwitterion thereof, the polymorph being a crystalized form having a monoclinic space group $P2_1$ with lattice parameters of:
a=6.46(1) Å;
b=9.07(2) Å;
c=18.25(4) Å; and
β=95.457(2°);
and a volume of 1066.11(4) Å$^3$.

Embodiment 5. A polymorph of a compound having the following structure (I):

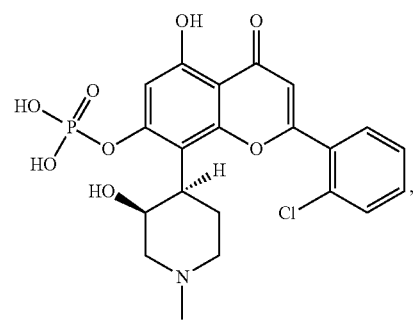

or a tautomer or zwitterionic form thereof, wherein the polymorph has the X-ray diffraction pattern set forth in FIG. 1.

Embodiment 6. A polymorph of a compound having the following structure (I):

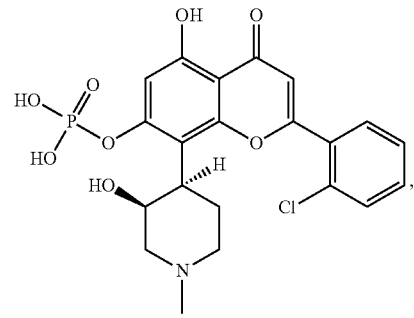

or a tautomer or zwitterionic form thereof, wherein the polymorph is Form B.

Embodiment 7. A polymorph of a compound having the following structure (I):

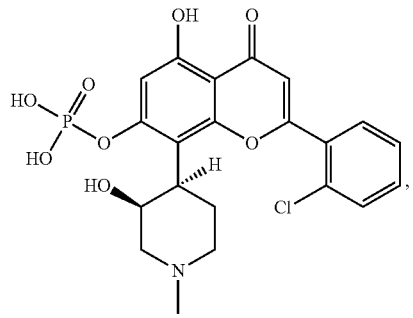

or a tautomer or zwitterionic form thereof wherein the polymorph is formed by a method comprising:
a) contacting an amorphous compound of structure (I) with a lattice forming reagent; and
b) treating the product of step a) with a solvent having water content less than about 0.05% v/v and removing the solvent, thereby forming the polymorph.

Embodiment 8. The polymorph of Embodiment 7, wherein the lattice forming reagent is maleic acid.

Embodiment 9. The polymorph of Embodiment 8, wherein the maleic acid is added at a ratio of 1:1±0.2 of amorphous compound to maleic acid.

Embodiment 10. The polymorph of any one of Embodiments 7-9, wherein the solvent is ethanol or tetrahydrofuran.

Embodiment 11. The polymorph of any one of Embodiments 7-10, wherein the contacting further comprises suspending the amorphous compound of structure (I) in aqueous tetrahydrofuran.

Embodiment 12. A polymorph of a compound having the following structure (I):

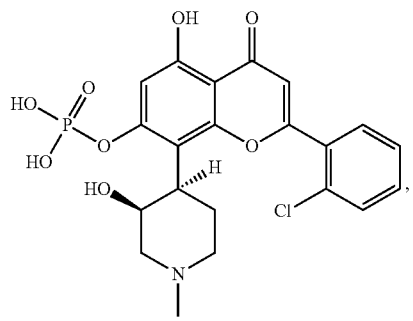

or a tautomer or zwitterionic form thereof, wherein the polymorph has an initial purity of at least 99.5% and a subsequent purity of at least 99.5% after being stored from about 12 hours up to about 7 days at about 25° C.±2° C. at a relative humidity of 60%.

Embodiment 13. The polymorph of Embodiment 12, wherein the subsequent purity is at least 99.5% after being stored for greater than about 7 days at about 25° C.±2° C. at a relative humidity of 60%.

Embodiment 14. The polymorph of Embodiment 12 or 13, wherein the subsequent purity is at least 99.5% after being stored for greater than about 30 days at about 25° C.±2° C. at a relative humidity of 60%.

Embodiment 15. The polymorph of any one of Embodiments 12-14, wherein the initial purity and subsequent purity are as determined by HPLC.

Embodiment 16. A polymorph of a compound having the following structure (I):

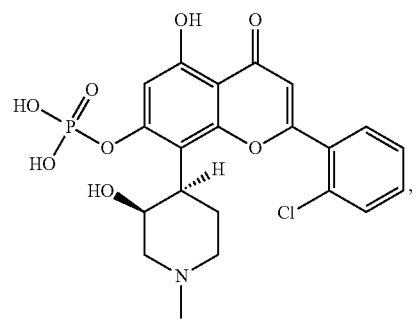

or a tautomer or zwitterionic form thereof, wherein the polymorph has an endotherm peak value at about 256° C.-268° C. as determined by differential scanning calorimetry.

Embodiment 17. The polymorph of Embodiment 16, wherein the endotherm peak value is at about 257.0° C.-266.0° C.

Embodiment 18. The polymorph of Embodiment 16 or 17, wherein the endotherm peak value is at about 258.0° C.-265.0.

Embodiment 19. The polymorph of any one of claims 1-18, wherein the polymorph comprises a zwitterionic form having the following structure (II):

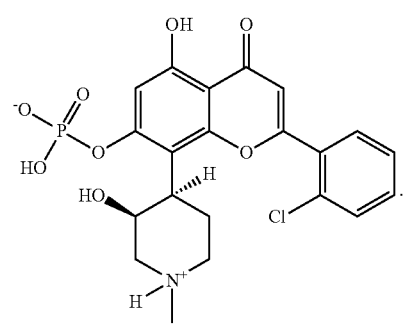

Embodiment 20. A pharmaceutical composition comprising the polymorph of any one of Embodiments 1-19 and a pharmaceutically acceptable carrier or excipient.

Embodiment 21. The pharmaceutical composition of Embodiment 20, wherein the pharmaceutical composition is formulated for oral administration.

Embodiment 22. The pharmaceutical composition of Embodiment 20 or 21, wherein the pharmaceutical composition comprises the polymorph in a concentration ranging from about 0.5 wt. % to about 11.25 wt. %.

Embodiment 23. The pharmaceutical composition of any one of Embodiments 20-22, wherein the pharmaceutical composition comprises the polymorph in a concentration ranging from about 0.6 wt. % to about 11.05 wt. %.

Embodiment 24. The pharmaceutical composition of any one of Embodiments 20-23, wherein the pharmaceutical composition comprises about 0.6 wt. % of the polymorph.

Embodiment 25. The pharmaceutical composition of any one of Embodiments 20-23, wherein the pharmaceutical composition comprises about 2.5 wt. % of the polymorph.

Embodiment 26. The pharmaceutical composition of any one of Embodiments 20-23, wherein the pharmaceutical composition comprises about 11.0 wt. % of the polymorph.

Embodiment 27. The pharmaceutical composition of any one of Embodiments 20-26, wherein the pharmaceutical composition comprises about 1 milligram (mg) of the polymorph.

Embodiment 28. The pharmaceutical composition of any one of Embodiments 20-26, wherein the pharmaceutical composition comprises about 4 mg of the polymorph.

Embodiment 29. The pharmaceutical composition of any one of Embodiments 20-26, wherein the pharmaceutical composition comprises about 16 mg of the polymorph.

Embodiment 30. The pharmaceutical composition of any one of Embodiments 20-29, wherein the excipient is anhydrous lactose or microcrystalline cellulose.

Embodiment 31. The pharmaceutical composition of any one of Embodiments 20-30, wherein the excipient is anhydrous lactose.

Embodiment 32. The pharmaceutical composition of any one of Embodiments 20-30, wherein the excipient is microcrystalline cellulose.

Embodiment 33. The pharmaceutical composition of any one of Embodiments 20-32, wherein the pharmaceutical composition comprises the excipient in a concentration ranging from about 85 wt. % to about 98 wt. %.

Embodiment 34. The pharmaceutical composition of any one of Embodiments 20-33, wherein the pharmaceutical composition comprises the excipient in a concentration ranging from about 87 wt. % to about 97.5 wt. %.

Embodiment 35. The pharmaceutical composition of any one of Embodiments 20-34, wherein the pharmaceutical composition comprises about 87 wt. % of the excipient.

Embodiment 36. The pharmaceutical composition of any one of Embodiments 20-34, wherein the pharmaceutical composition comprises about 95.5 wt. % of the excipient.

Embodiment 37. The pharmaceutical composition of any one of Embodiments 20-34, wherein the pharmaceutical composition comprises about 97.5 wt. % of the excipient.

Embodiment 38. The pharmaceutical composition of any one of Embodiments 20-37, further comprising colloidal silicon dioxide.

Embodiment 39. The pharmaceutical composition of Embodiment 38, wherein the pharmaceutical composition comprises about 1 wt. % of the colloidal silicon dioxide.

Embodiment 40. The pharmaceutical composition of any one of Embodiments 20-39 further comprising magnesium stearate.

Embodiment 41. The pharmaceutical composition of Embodiment 40, wherein the pharmaceutical composition comprises about 1 wt. % of the magnesium stearate.

Embodiment 42. The pharmaceutical composition of any one of Embodiments 20-41, in the form of a capsule for oral administration.

Embodiment 43. A pharmaceutical composition comprising a polymorph of any one of Embodiments 1-19 having water content less than 0.50% as determined by Karl Fischer titration.

Embodiment 44. A unit dose form comprising a pharmaceutical composition of any one of Embodiments 20-43.

Embodiment 45. A method for preparing a polymorph, the method comprising:

a) contacting an amorphous compound having the following structure (I):

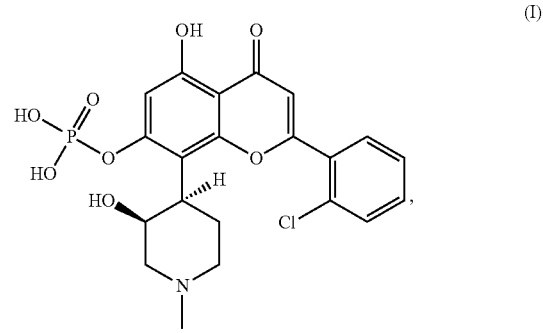 [SMILES: CN1CC[C@H](c2c(OP(=O)(O)O)cc(O)c3c(=O)cc(-c4ccccc4Cl)oc23)[C@H](O)C1 ; ","]

with a lattice forming reagent; and b) treating the product of step a) with solvent having water content less than about 0.05% v/v; and removing the solvent, thereby forming the polymorph.

Embodiment 46. The method of Embodiment 45, wherein the lattice forming reagent is an acid.

Embodiment 47. The method of Embodiment 46, wherein the acid is selected from the group consisting of maleic acid, fumaric acid, L-tartaric acid, hippuric acid, nicotinic acid, acetic acid, and combinations thereof.

Embodiment 48. The method of any one of Embodiments 45-47, wherein the lattice forming reagent is maleic acid.

Embodiment 49. The method of Embodiment 45, wherein the lattice forming reagent is aspartame.

Embodiment 50. The method of Embodiment 45, wherein the lattice forming reagent is D-xylose.

Embodiment 51. The method of any one of Embodiments 45-50, wherein the removing the solvent is at a pressure less than about 1 atm and a temperature greater than about 35° C.

Embodiment 52. The method of any one of Embodiments 45-51, wherein the method further comprises preparing a compound of structure (III):

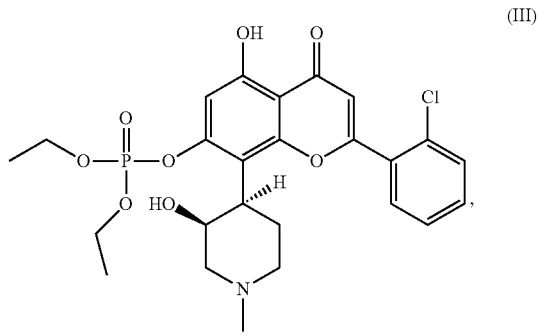 [SMILES: CCOP(=O)(OCC)Oc1cc(O)c2c(=O)cc(-c3ccccc3Cl)oc2c1[C@H]1CCN(C)C[C@H]1O ; ","]

by reacting a compound having the following structure:

[Chemical structure of a chromone compound with OH, HO substituents, chlorophenyl group, and piperidine ring]

or a salt thereof, with a base and a compound having the following structure:

[Chemical structure of diethyl chlorophosphate]

Embodiment 53. The method of Embodiment 52, wherein the base is an amine base.

Embodiment 54. The method of Embodiment 52 or 53, wherein the base is triethylamine or diisopropylethyl amine.

Embodiment 55. The method of any one of Embodiments 52-54, wherein the method further comprises preparing the amorphous compound of structure (I):

[Chemical structure (I) showing the phosphorylated chromone compound]

(I)

by reacting the compound of structure (III), or a salt thereof, with a phosphoester-cleaving compound and treating with a basic solution.

Embodiment 56. The method of Embodiment 55, wherein the phosphoester-cleaving compound is trimethyl silyl bromide (TMSBr), and the basic solution comprises ammonium bicarbonate.

Embodiment 57. The method of any one of Embodiments 45-56, wherein the polymorph is a polymorph according to any one of Embodiments 1-19.

Embodiment 58. A polymorph prepared according to the method of any one of Embodiments 45-57.

Embodiment 59. A method for treating a disease associated with overexpression of a cyclin-dependent kinase (CDK) in a mammal in need thereof, the method comprising administering a therapeutically effective amount of the polymorph of any one of Embodiments 1-19 or 58, the pharmaceutical composition of any one of Embodiments 20-43, or the unit dose form of Embodiment 43 to the mammal.

Embodiment 60. The method of Embodiment 59, wherein the disease is cancer.

Embodiment 61. The method of Embodiment 60, wherein the cancer is a hematologic cancer.

Embodiment 62. The method of Embodiment 60, wherein the hematologic cancer is selected from acute myelogenous leukemia (AML), follicular lymphoma, acute lymphoblastic leukemia (ALL), chronic lymphocytic leukemia (CLL), multiple myeloma (MM), and non-Hodgkin's lymphoma.

Embodiment 63. The method of Embodiment 62, wherein the hematological cancer is acute myelogenous leukemia (AML).

Embodiment 64. The method of Embodiment 62, wherein the hematologic cancer is chronic lymphocytic leukemia (CLL).

Embodiment 65. The method of Embodiment 62, wherein the hematologic cancer is myelodysplasic syndrome (MDS).

Embodiment 66. The method of Embodiment 62, wherein the hematologic cancer is multiple myeloma (MM).

Embodiment 67. The method of Embodiment 60, wherein the cancer comprises a solid tumor.

Embodiment 68. The method of Embodiment 60 or 67, wherein the cancer is bladder cancer.

Embodiment 69. The method of Embodiment 60 or 67, wherein the cancer is lung cancer.

Embodiment 70. The method of Embodiment 60 or 67, wherein the cancer is liver cancer.

Embodiment 71. The method of Embodiment 60 or 67, wherein the cancer is prostate cancer.

Embodiment 72. The method of any one of Embodiments 60-71, wherein the polymorph, the pharmaceutical composition, or the unit dose form is administered orally.

The examples and preparations provided below further illustrate and exemplify polymorph of a compound of structure (I), and methods of preparing the same. It is to be understood that the scope of the present invention is not limited in any way by the scope of the following examples and preparations. In the following examples, and throughout the specification and claims, molecules with a single stereocenter, unless otherwise noted, exist as a racemic mixture. Those molecules with two or more stereocenters, unless otherwise noted, exist as a racemic mixture of diastereomers. Single enantiomers/diastereomers may be obtained by methods known to those skilled in the art.

EXAMPLES

Data was acquired according to the parameters listed below:

X-Ray Powder Diffraction (XRPD):

Stoe Stadi P. Copper Kα1 radiation, 40 kV/40 mA; Mythen 1K detector transmission mode, curved monochromator, 0.02° 2θ step size, 12 s step time, 1.5-50.5° 2θ scanning range with 1° 2θ detector step in step-scan mode. Each sample (25-40 mg of powder) was placed between two cellulose acetate foils spaced with a metal washer (0.4 mm thick, 12-mm inner diameter; "sandwich element"). The sandwich element was transferred to a sample holder (SCell) that was sealed with acetate foils. Samples were acquired in ambient air atmosphere and rotated during measurements.

TG-FTIR:

Netzsch Thermo-Microbalance TG 209 with Bruker FT-IR Spectrometer IFS28 or Vector 22; Al crucible with microhole, N$_2$ atmosphere, 10 K/min heating rate, 25° C. to 300° C. (or 350° C. range).

HPLC:

The method used to detect and determine purity of compound of structure (I) and related substances (such as alvocidib) was a reverse-phase HPLC method with a gradient program and DAD detection technique. Reverse phase C$_{18}$ Waters X-bridge 150 mm×4.6 mm, 3.5-µm particle column; flow rate=1.0 mL/min; detection wavelength=265 nm; run time: 35.0 minutes; sample diluted in methanol; mobile phase A was 80:20 (v/v) pH 6.5 buffered aqueous acetonitrile; mobile phase B was 35:65 (v/v) pH 6.5 buffered aqueous acetonitrile; 1.0 mL/min; column temperature=35° C. The gradient program is depicted in the following table:

| Run Time (minutes) | Mobile Phase A (%) | Mobile Phase B (%) |
|---|---|---|
| 0 | 100 | 0 |
| 8 | 100 | 0 |
| 16 | 66 | 34 |
| 24 | 0 | 100 |
| 26 | 0 | 100 |
| 26.5 | 100 | 0 |
| 35 | 100 | 0 |

Total Impurities (%) was calculated by summing the percentages of each individual impurity, including alvocidib. Other Impurities (%) was calculated by summing the percentages of each individual impurity, excluding alvocidib. Purity of compound of structure (I) (%) was calculated by taking the difference between 100% and the Total Impurities (%). All individual impurities at and above 0.05% were taken for the calculation of total impurities.

$^1$H NMR:

Bruker DPX 300 using a frequency of 300.13 MHz, a 300 excitation pulse and a recycle delay of 1 s. 16-1024 scans were accumulated per spectrum; deuterated DMSO or D$_2$O was used as a solvent. Two-dimensional COSY spectra were acquired with 512 data points in the indirect dimension, an indirect time increment of 441.60 µs, 16 scans per slice and a recycle delay of 0.36 s.

Differential Scanning Calorimetry (DSC):

DSC was performed using a TA Q200/Q2000DSC from TA Instruments using a ramp method and a crimped, aluminum sample pan at 25° C. The heating rate was 10° C./minute, and the purge gas was nitrogen.

Example 1

Polymorph Synthesis

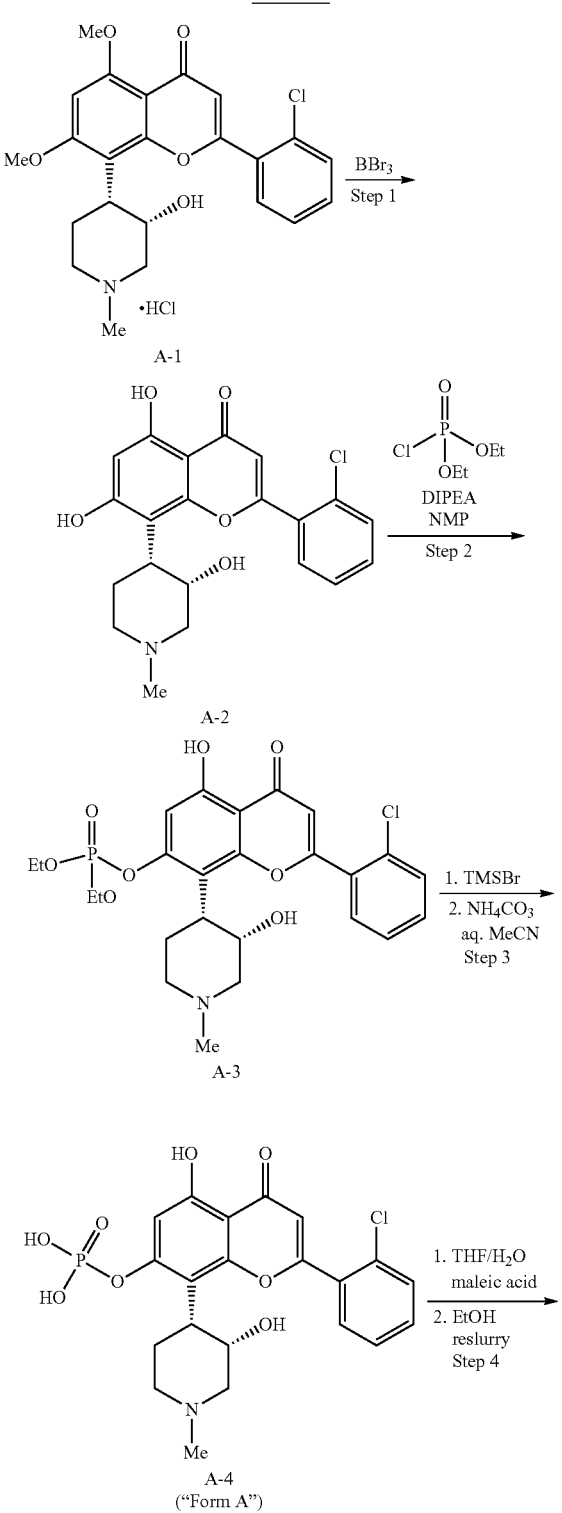

Scheme 1.

-continued

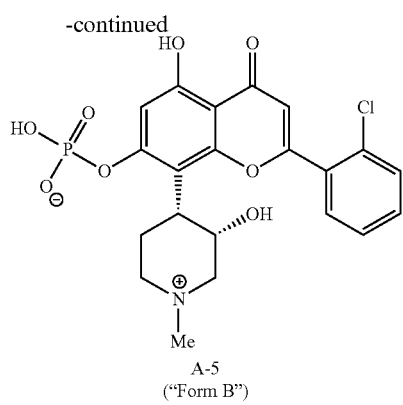

A-5
("Form B")

Step 1: A-1 was treated with boron tribromide in chlorobenzene. Removal of byproducts by distillation and crystallization from chlorobenzene-methanol-water resulted in A-2 as free base.

Step 2: A-2 (in free base form) was treated with diethyl chlorophosphate and diisopropylethylamine in N-methylpyrrolidone. Water was added to stop the reaction and precipitate the product. The resulting slurry was filtered, washed with water, and dried under vacuum to produce the compound A-3.

Step 3: A-3 was treated with trimethylsilyl bromide to deprotect A-3 and afford A-4 as a hydrobromide, which was treated with ammonium bicarbonate solution. The precipitated A-4 (i.e., compound of structure (I) having an amorphous crystal structure (i.e., "Form A") was filtered and dried.

Step 4: A-4 was suspended in a mixture of THF and water (19:1), and maleic acid was added. After stirring at room temperature, the solid was filtered and dried in a filter dryer to afford A-5. The resultant filtered solid compound A-5 was suspended in ethanol and re-slurried before an additional filtration. Filtered product (i.e., A-5 as polymorph form B) was washed with ethanol and dried to afford the desired product.

Synthesis of polymorph Form B according to Scheme 1 has been conducted using 5.72 kg A-1, 4.17 kg A-2 and 2.70 kg A-3. At this scale, the yield of Step 1 was 79.9%. After recrystallization, the yield of A-3 from Step 2 was 48%, and the purity of compound A-3 thus obtained was 86% by HPLC. The combined yield of Steps 3 and 4 was 37.5%. The overall yield of the process of Scheme 1 was 15%, and the process yielded 0.90 kg of A-5.

Example 2

Stability Study

Initial attempts to isolate the compound of structure (I) produced an amorphous form, designated "Form A." Form A showed poor stability, decomposing to compound A-2. The results of a DVS (dynamic vapor sorption) test of Form A showed that the compound was hygroscopic, taking in 12.5% of its weight of water at 80% relative humidity. After 10 days at room temperature, Form A showed 6.85% degradation to compound A-2.

Figure 2:
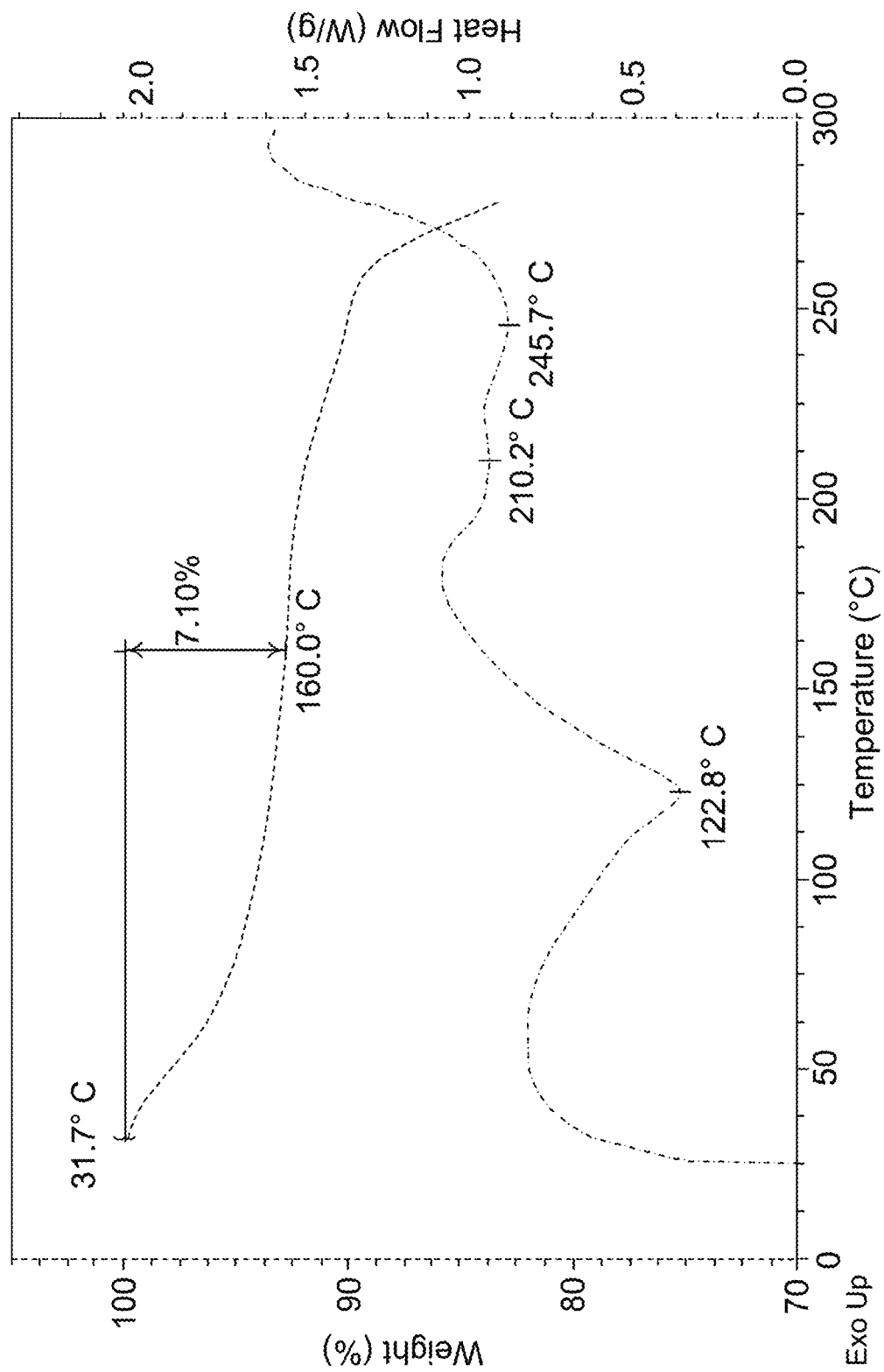
FIG. 2 shows a stability profile in the form of a TG-FTIR thermogram and a DSC spectrum for the amorphous form of structure (I) (i.e., Form A).

The decomposition exhibited a strong temperature dependence. Samples stored at −20° C. showed no degradant trends, but a stability test of Form A at 40° C. and 75% relative humidity for one week showed accelerated decomposition. The DSC and TGA plots of Form A exhibited the characteristics predicted by hydrolytic decomposition, as shown in FIG. 2.

Example 3

Salt Screening Study

A total of eight lattice/salt forming reagents (5 acids and 3 bases) and four solvent systems were selected for salt screening. Screening conditions are outline below in Table 1:

TABLE 1

Salt screening conditions

| Lattice forming reagents* | Solvent | | | |
|---|---|---|---|---|
| | A IPA | B Acetone | C ACN | D THF/H$_2$O (19:1) |
| Blank | Form A | Form A + Decomposition | Form A | Form A + B |
| H$_2$SO$_4$ | Amorphous | Amorphous | Sulfate Type A | Amorphous |
| H$_3$PO$_4$ | Phosphate Type A | Phosphate Type A | Phosphate Type A + Form A | Phosphate Type A |
| Maleic Acid | Form B | Form B | Form B | Form B |
| Fumaric Acid | Form B | Form B | Form B | Form A + B |
| L-tartaric acid | Form B | Form B | Form B | Form B |
| NaOH | Decomposition | Decomposition | Decomposition | Sodium Salt A** |
| K$_2$CO$_3$ | Decomposition | Decomposition | Decomposition | Decomposition |
| Ca(OH)$_2$ | Decomposition | Decomposition | Decomposition | Calcium Salt Type A** |

*the molar ratio of freebase and lattice forming reagent is 1:1.
**purity decrease (5~14 area %) was observed from HPLC results.

When the compound of structure (I) was crystallized together with maleic acid or L-tartaric acid in aqueous THF, the resulting crystal showed identical polymorph to Form B, indicating structure (I) does not form a salt with those acids. Although some amount of acid will remain in the isolated crystal with above recrystallization process for obtaining Form B, it was discovered that residual maleic acid could be removed via a re-slurry in ethanol. In contrast, the tartaric acid did not readily wash from the compound via the ethanol slurry.

Example 4

Salt Screening Study

Two larger scale pilot batches were synthesized according to the process described above in Example 1 to confirm and optimize the process. The results of these batches are shown in Tables 2, 3, and 4, below.

TABLE 2

Pilot Batches of Step 1

| Batch No. | Compound A-1 | Compound A-2 Yield (%) | HPLC purity |
|---|---|---|---|
| 1a | 165.0 g | 114 g (80.1%) | 97.61% |
| 2a | 94.0 g | 70 g (86.43%) | 98.86% |

TABLE 3

Pilot Batches of Step 2

| Batch No. | Compound A-2 | Compound A-3 Yield (%) | HPLC purity |
|---|---|---|---|
| 2a | 100 g | 82.4 g (67.1%) | 98.67% |
| 2a | 350 g | 320 g (62.8%) | 97.97% |

TABLE 4

Pilot batches of Step 3

| Batch No. | Compound A-3 | Compound A-4 Yield (%) | HPLC purity | Water Content (%) |
|---|---|---|---|---|
| 3b | 220 g | 54.5 g (26.9%) | 99.90% | 0.48% |
| 3b | 110 g | 24.8 g (25.3%) | 99.75% | 0.38% |

After removing the maleic acid from the polymorph of Form B (A-5) via a re-slurry in ethanol, the resultant polymorph was dried by a flow of nitrogen on a filter to reduce water to below 0.5%. Re-slurrying in ethanol does not increase the concentration of impurity (A-2) in the slurry. Without wishing to be bound by theory, it is thought that the formation of compound A-2 is sensitive to water included in the crystal/polymorph form after formation. That is, when water content kept low enough following polymorph formation, hydrolysis of the phosphate moiety is prevented but the lattice forming reagent (e.g., maleic acid) can be removed.

Example 5

Stability Study

A stability study of the polymorph of the compound of structure (I) (compound A-5) with low water content sample (0.38%) showed a pronounced improvement in the compound stability (Table 5), indicating improved stability of the polymorph having the lower water content.

TABLE 5

Room temperature stability Form B

| Storage conditions | | Ambient | −20° C. |
|---|---|---|---|
| HPLC area % Form B/Compound A-2 | initial | 99.75%/0.13% | |
| | 7 days | 99.89%/0.03% | — |
| | 30 days | 99.92%/0.03% | 99.93%/0.02% |

Based on this information, it can be concluded that the polymorph of the compound of structure (I) ("Form B") formed via a THF/water polymorph transformation with maleic acid, followed by ethanol re-slurry to remove the residual maleic acid and water from the polymorph provides an unexpectedly stable compound.

Example 5

Additional Polymorph Formation Studies—Powder X-Ray Diffraction

Figure 3:
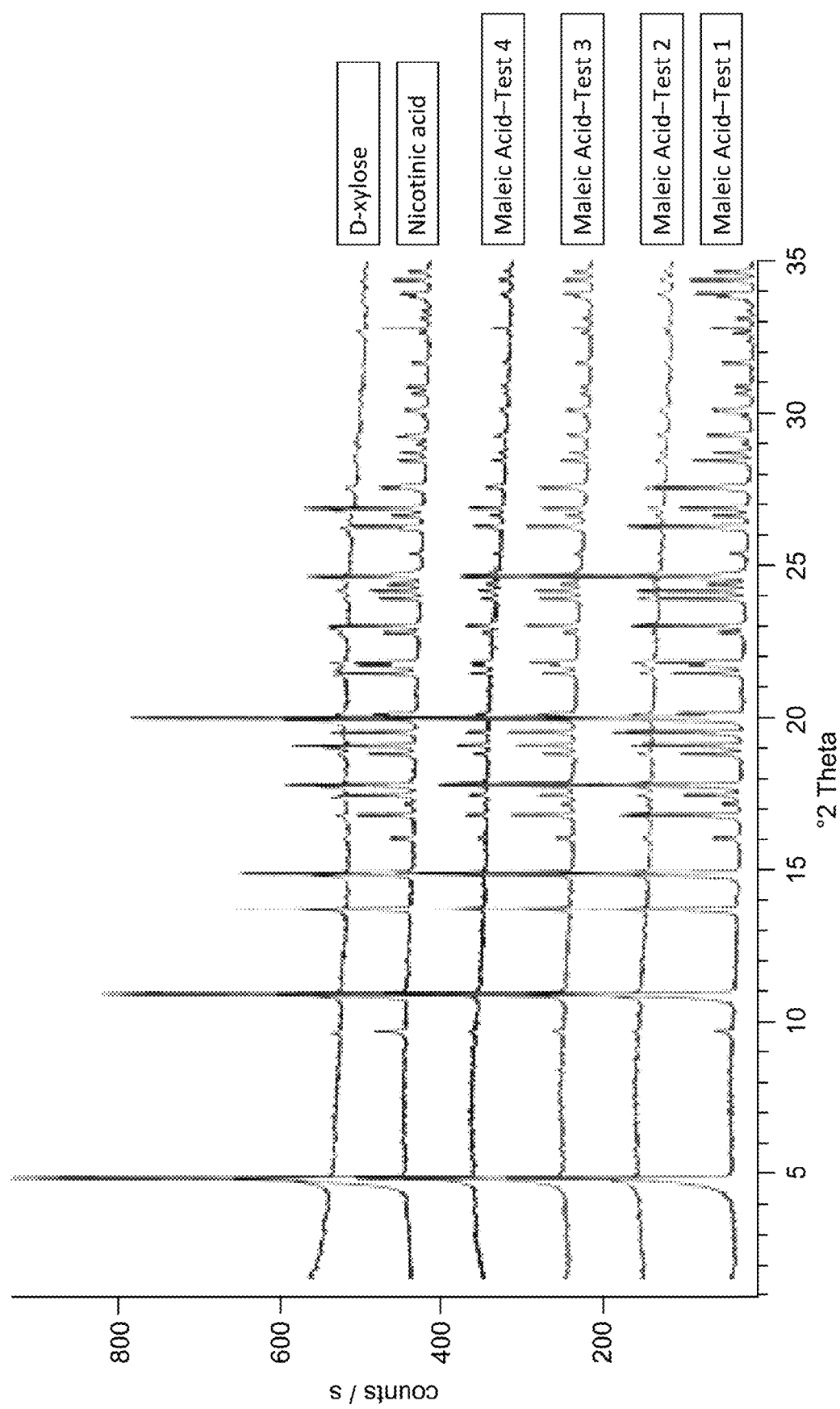
FIG. 3 illustrates a comparison of lattice forming reagents and the similarity of diffractogram patterns as determined by XRPD for polymorph Form B.

During preliminary salt co-crystal screening (Example 3, above), it became apparent that nearly identical polymorphs were being formed despite the use of different acids or co-crystal screening agents. This is illustrated in FIG. 3, which shows maleic and nicotinic acids along with D-xylose screening studies. This experiment provided evidence that these lattice forming reagents were not forming salts or co-crystals with the compound of structure (I), but were actually forming a polymorph (i.e., Form B) having the XRPD diffractogram shown in FIG. 1.

Example 6

Single Crystal X-Ray Diffraction

Figure 4:
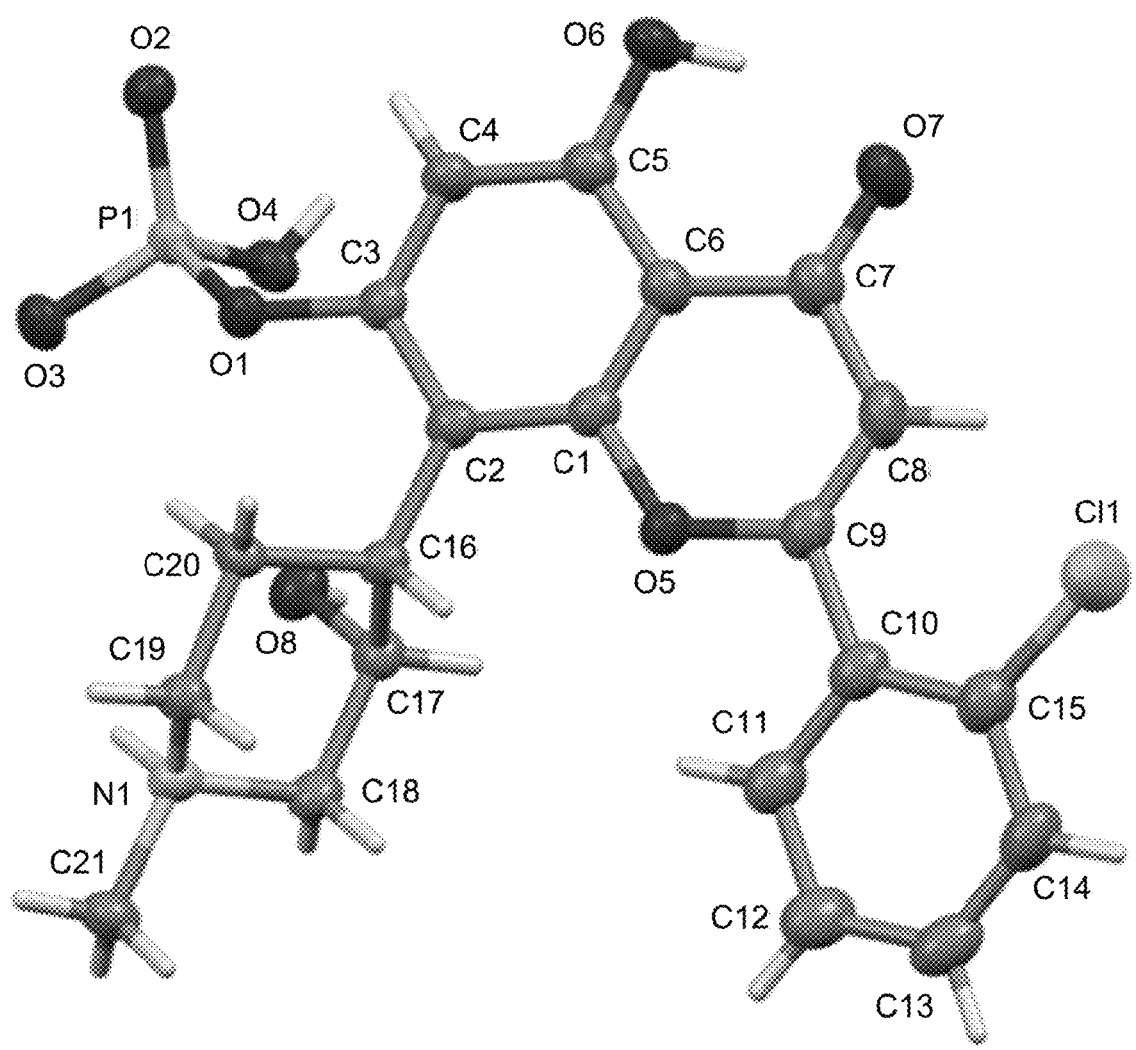
FIG. 4 depicts the Oak Ridge Thermal Ellipsoid Plot (ORTEP) diagrams of single crystal structure obtained for polymorph Form B.

The absolute stereochemistry, the position of the phosphoric acid moiety, as well as the zwitterionic nature of the polymorph of the compound of structure (I) (Form B) were determined by a single crystal X-ray diffraction. Single crystal X-ray diffraction of Form B is shown in FIG. 4. Form B crystallizes as an anhydrous molecule without solvent inclusion. Bond distances and angles are all within the expected values.

Example 7

Formation of Polymorph Form C

Figure 5:
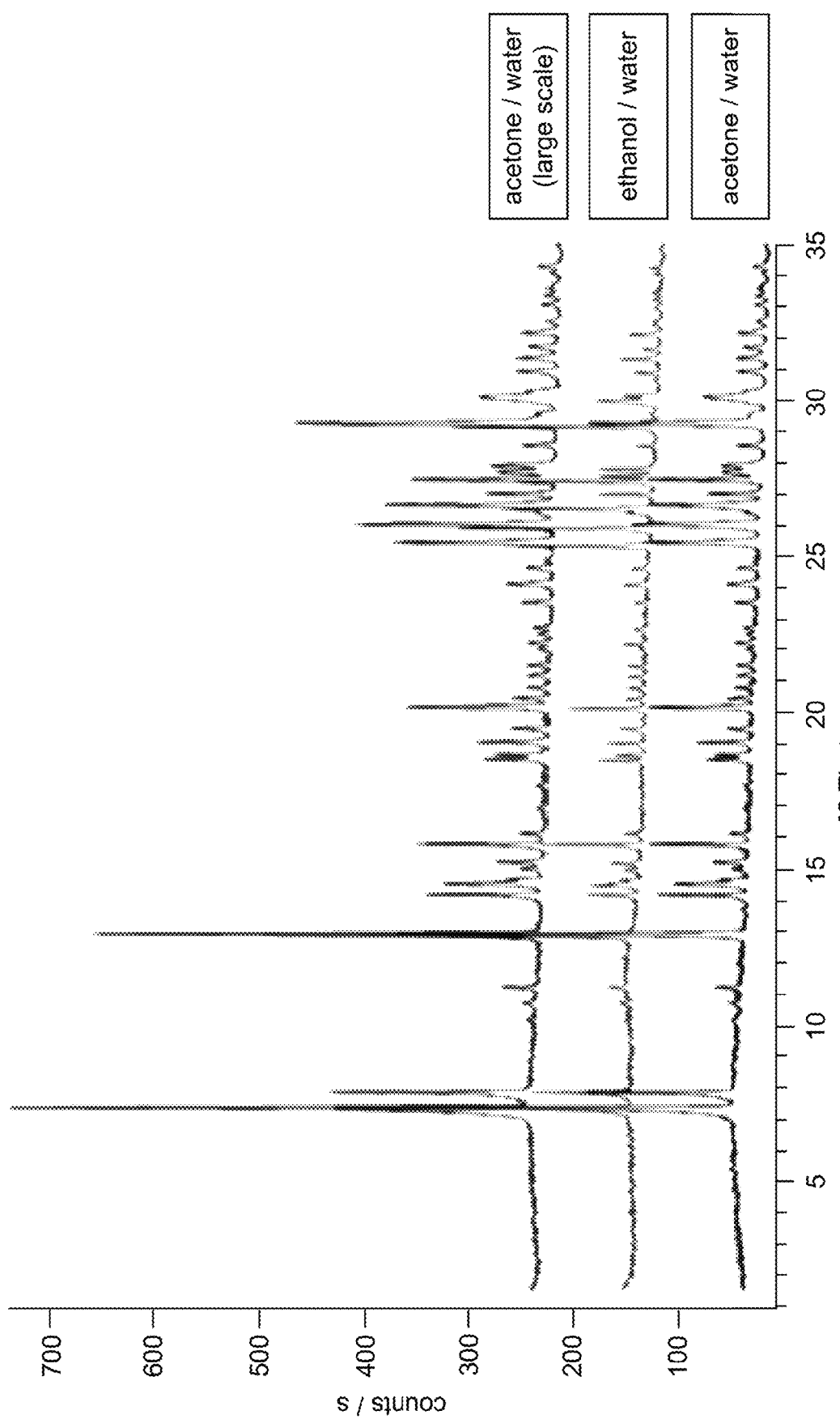
FIG. 5 shows diffractograms from XRPD analysis of three samples of polymorph Form C.
Figure 6A:
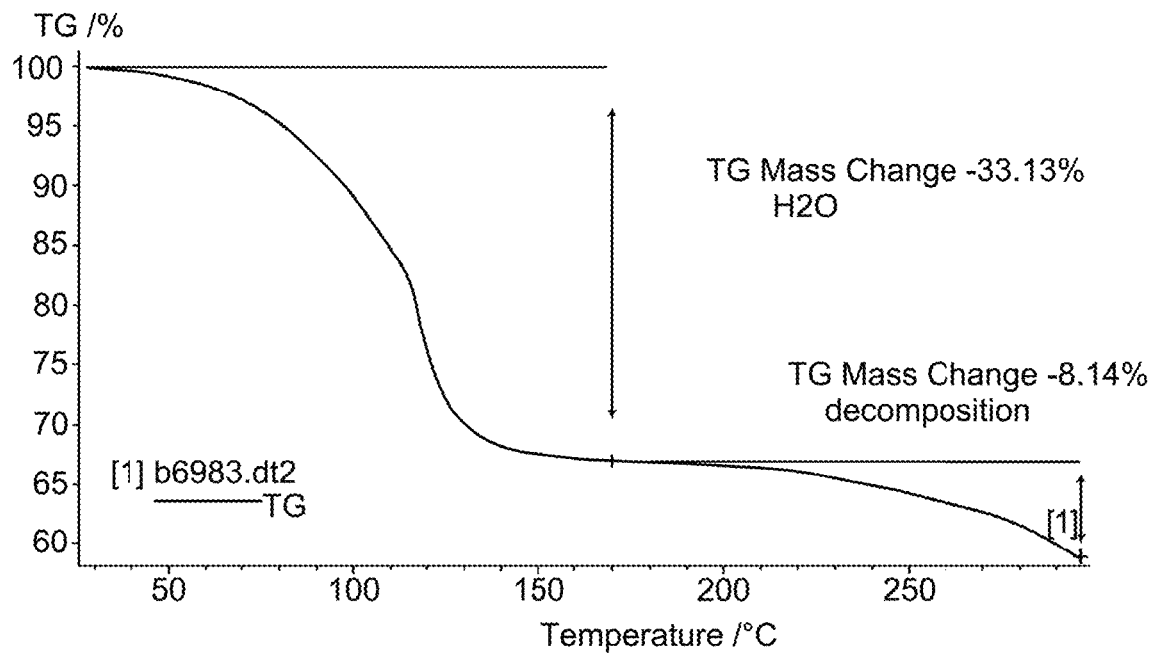
FIG. 6A-6B show TG-FTIR thermograms of polymorph Form C before (FIG. 6A) and after drying (FIG. 6B).

Two experimental conditions were explored for forming a new solid form of a compound of structure (I). A solvent mixture of acetone/water and ethanol/water were added to Form A. The experimental condition including acetone/water as the solvent was successfully reproduced on a larger scale. The diffractograms of the resultant solid form ("Form C") are shown in FIG. 5. Although the diffractograms indicate the resultant product is highly crystalline, a TG-FTIR thermogram (FIG. 6A) indicated Form C was associated with a significant amount of water. As evidenced by the thermogram, some solvent is released below the boiling point of water, but a large percentage appears to be tightly bound, which indicates that the sample is highly hydrated.

Figure 6B:
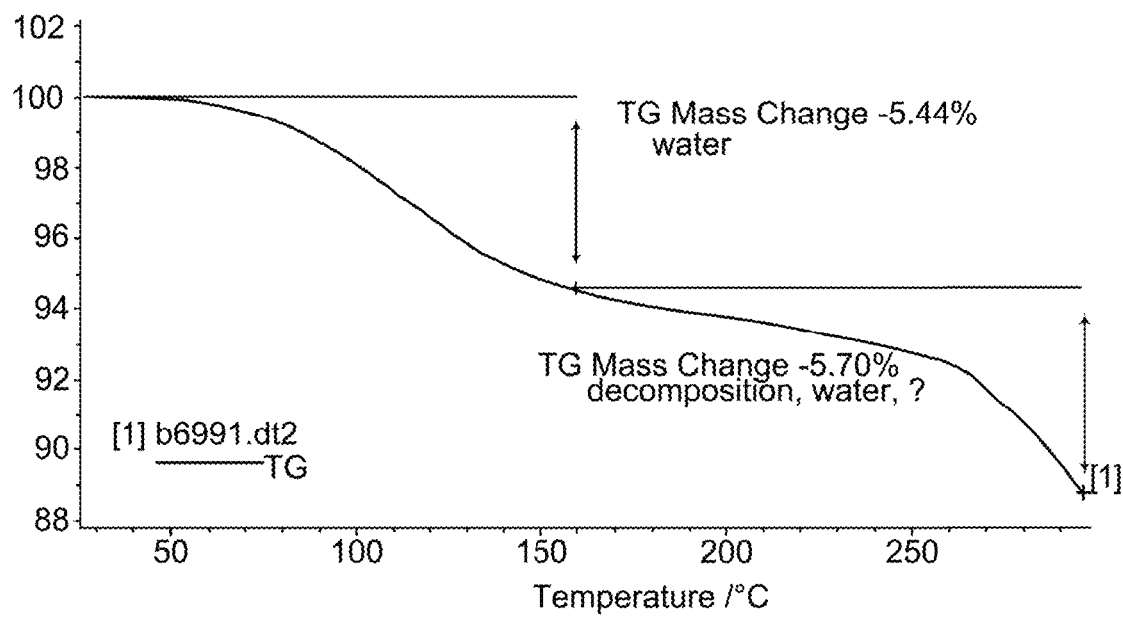

In order to determine whether Form C was stable with respect to dehydration, a sample of Form C was dried under vacuum at 40° C. for about 24 hours. After drying, the sample contained about 5.4 weight percent water, which was close to the 5.3 weight percent theoretically expected for a sesquihydrate (see FIG. 6B). However, this sample lost significant crystallinity upon drying, so it is not necessarily a stoichiometric hydrate. Form C was found not to be stable to drying conditions with the resultant product being poorly crystalline.

Figure 7:
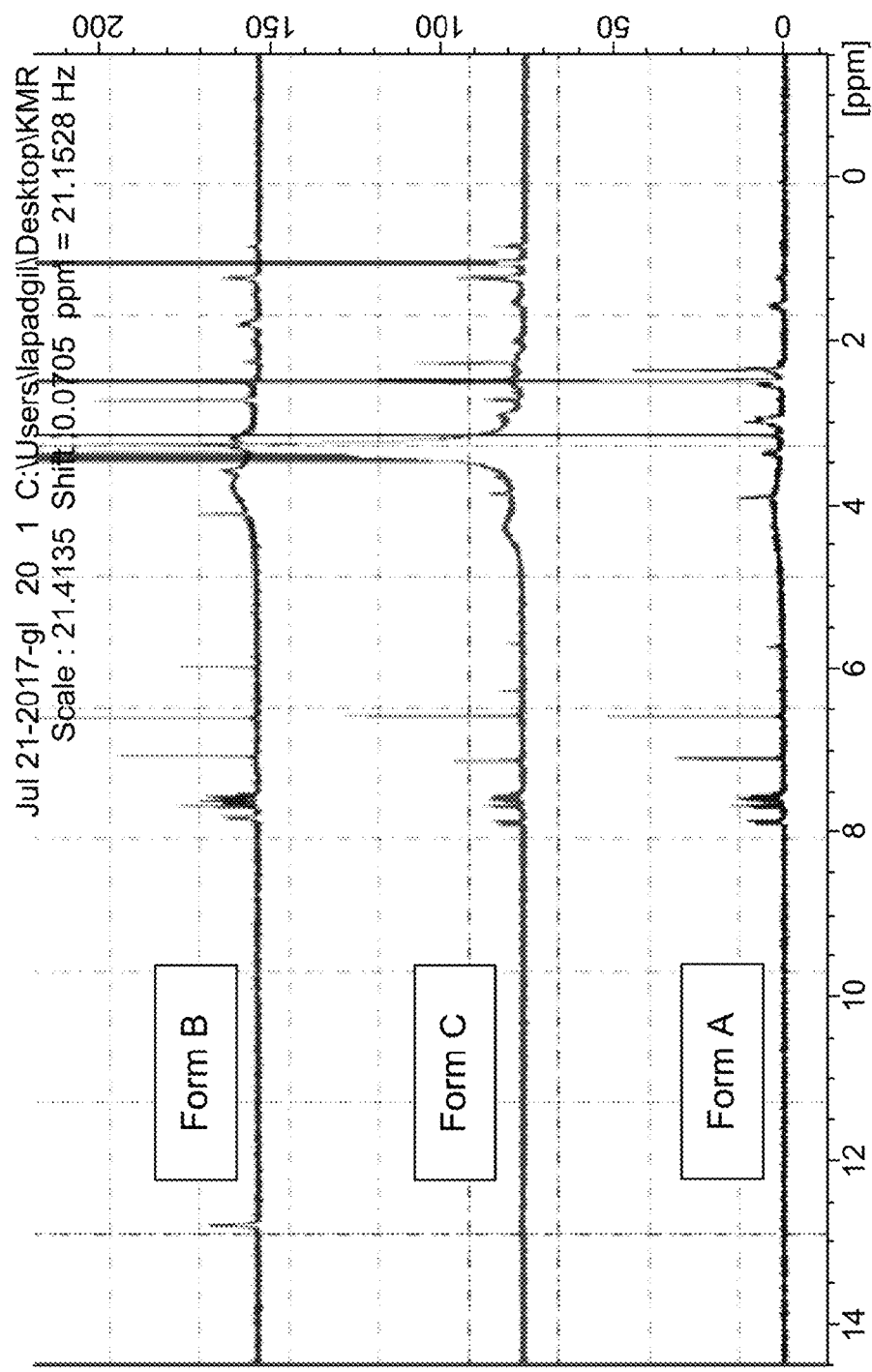
FIG. 7 shows a comparison of $^1$H NMR spectra acquired for forms A (amorphous), form B (polymorph) and form C.

The $^1$H NMR spectra of the three different forms (A, B and C) are distinguishable. All samples were recorded in DMSO-d6. The chemical shifts of the amorphous Form A and the Form C sample are substantially identical to each other but differ from those of Form B (FIG. 7). The position of the proton near 7 ppm is markedly different for the spectrum of Form B, as is the presence of the peak near 12.8 ppm for Form B (i.e., which is absent in Forms A and C.

Example 8

Powder X-Ray Diffraction Spectrum

Polymorph Form B was analyzed using XRPD using the parameters described above. The resultant diffractogram is shown in FIG. 1. Tabulated data generated for Form B is shown in Table 6, below:

TABLE 6

Tabulated data from XRPD diffractogram of Form B

| D value (Å) | 2θ | Intensity (relative) | Intensity (absolute) | FWHM |
|---|---|---|---|---|
| 18.382645 | 4.8032 | 55.17 | 3833 | 0.08 |
| 9.190754 | 9.6155 | 10.48 | 728 | 0.08 |
| 8.157735 | 10.8365 | 93.39 | 6489 | 0.06 |
| 6.471747 | 13.6717 | 49.51 | 3440 | 0.08 |
| 5.956605 | 14.8604 | 73.17 | 5084 | 0.04 |
| 5.524677 | 16.0296 | 11.07 | 769 | 0.06 |
| 5.281129 | 16.774 | 30.9 | 2147 | 0.06 |
| 5.172326 | 17.1295 | 9.19 | 639 | 0.06 |
| 5.080202 | 17.4425 | 17.69 | 1229 | 0.06 |
| 4.984581 | 17.7798 | 58 | 4030 | 0.04 |
| 4.722631 | 18.7747 | 18 | 1250 | 0.06 |
| 4.654062 | 19.0539 | 25.93 | 1802 | 0.04 |
| 4.552517 | 19.483 | 32.41 | 2252 | 0.06 |
| 4.445879 | 19.955 | 100 | 6948 | 0.06 |
| 4.144506 | 21.4226 | 19.68 | 1367 | 0.04 |
| 4.079254 | 21.7694 | 22.77 | 1582 | 0.06 |
| 3.90758 | 22.7383 | 9.77 | 679 | 0.04 |
| 3.867711 | 22.9759 | 28.61 | 1988 | 0.06 |
| 3.72577 | 23.8638 | 22.65 | 1573 | 0.06 |
| 3.6868 | 24.1198 | 25.68 | 1785 | 0.04 |
| 3.616616 | 24.5951 | 48.94 | 3401 | 0.06 |
| 3.512733 | 25.3344 | 7.74 | 538 | 0.06 |
| 3.394705 | 26.2307 | 28.77 | 1999 | 0.06 |
| 3.350985 | 26.5791 | 11.43 | 794 | 0.04 |
| 3.319773 | 26.8337 | 18.57 | 1290 | 0.06 |
| 3.241092 | 27.4977 | 23.54 | 1635 | 0.08 |
| 3.142734 | 28.376 | 15.33 | 1065 | 0.06 |
| 3.055085 | 29.208 | 12.7 | 882 | 0.08 |
| 2.973274 | 30.0303 | 10.91 | 758 | 0.14 |
| 2.920812 | 30.5827 | 6.32 | 439 | 0.06 |
| 2.830324 | 31.5856 | 9.24 | 642 | 0.08 |
| 2.748258 | 32.5546 | 6.82 | 474 | 0.04 |
| 2.731945 | 32.7544 | 11.76 | 817 | 0.06 |
| 2.703955 | 33.1032 | 6.09 | 423 | 0.06 |
| 2.64826 | 33.8201 | 10.18 | 707 | 0.04 |
| 2.640271 | 33.9255 | 14.93 | 1037 | 0.06 |
| 2.60744 | 34.3659 | 16.09 | 1118 | 0.06 |
| 2.587021 | 34.6457 | 11.27 | 783 | 0.06 |
| 2.540227 | 35.3046 | 5.6 | 389 | 0.06 |
| 2.424055 | 37.0566 | 5.24 | 364 | 0.06 |
| 2.216436 | 40.6738 | 7.03 | 488 | 0.06 |
| 2.125602 | 42.4942 | 10.93 | 760 | 0.06 |
| 2.078432 | 43.5072 | 4.98 | 346 | 0.14 |
| 2.042561 | 44.3113 | 12.61 | 876 | 0.1 |

TABLE 6-continued

Tabulated data from XRPD diffractogram of Form B

| D value (Å) | 2θ | Intensity (relative) | Intensity (absolute) | FWHM |
|---|---|---|---|---|
| 2.008764 | 45.0975 | 5.76 | 400 | 0.08 |
| 1.950189 | 46.5303 | 5.84 | 406 | 0.14 |

Example 9

Formulation Stability Study

Polymorph Form B (API) was formulated into two blends for four-week stability studies. Four excipients were tested in the following mixtures:

Binary mixtures (16 mg)
1. 11.43% API+87.57% DCP anhydrous+1% Magnesium stearate
2. 11.03% API+87.97% Lactose anhydrous+1% Magnesium stearate
3. 22.86% API+76.14% Avicel PH200 LM+1% Magnesium stearate
4. 17.78% API+80.22% Mannitol 200 SD+1% Magnesium stearate+1% Aerosil 200

Binary mixtures (1 mg)
1. 0.50% API+97.50% DCP anhydrous+1% Magnesium stearate+1% Aerosil 200
2. 0.53% API+97.47% Lactose anhydrous+1% Magnesium stearate+1% Aerosil 200
3. 1.18% API+97.82% Avicel PH200 LM+1% Magnesium stearate
4. 0.91% API+97.09% Mannitol 200 SD+1% Magnesium stearate+1% Aerosil 200

The appearance results for the study performed at 20° C. and 60% relative humidity (RH) and the study performed at 40° C. and 75% RH are shown in Table 7. The initial related substance results are shown in Table 8. The related substance results after two weeks at 25° C. and 60% RH are shown in Table 9, and after four weeks at 25° C. and 60% RH are shown in Table 10. The related substance results after two weeks at 40° C. and 75% RH are shown in Table 11, and after four weeks at 40° C. and 75% RH are shown in Table 12. The content uniformity for each batch of 16 mg capsules is shown in Table 13. The content uniformity for each batch of 1 mg capsules is shown in Table 14.

TABLE 7

| Specification Batch Details | Appearance | | | | |
|---|---|---|---|---|---|
| | Initial | 2 Weeks 25° C./60% RH | 4 Weeks 25° C./60% RH | 2 Weeks 40° C./75% RH | 4 Weeks 40° C./75% RH |
| Control | Pale yellow powder | Pale yellow powder | Pale yellow powder | Pale yellow powder with small agglomeration observed | Pale yellow powder with small agglomeration observed |
| Binary mixtures (16 mg) | | | | | |
| 1 | Pale yellow powder | Pale yellow powder | Pale yellow powder | Pale yellow powder | Pale yellow powder |
| 2 | Pale yellow powder | Pale yellow powder | Pale yellow powder | Pale yellow powder with small agglomeration observed | Pale yellow powder with small agglomeration observed |

TABLE 7-continued

| Specification Batch Details | Initial | 2 Weeks 25° C./60% RH | 4 Weeks 25° C./60% RH | 2 Weeks 40° C./75% RH | 4 Weeks 40° C./75% RH |
|---|---|---|---|---|---|
| 3 | Pale yellow powder | Pale yellow powder | Pale yellow powder | Pale yellow powder with small agglomeration observed | Pale yellow powder with small agglomeration observed |
| 4 | Pale yellow powder | Pale yellow powder | Pale yellow powder | Pale yellow powder with small agglomeration observed | Pale yellow powder with small agglomeration observed |
| Binary mixtures (1 mg) | | | | | |
| 1 | Off-white powder | Off-white powder | Off-white powder | Off-white powder | Off-white powder |
| 2 | Off-white powder | Off-white powder | Off-white powder | Off-white powder | Off-white powder |
| 3 | Off-white powder | Off-white powder | Off-white powder | Off-white powder | Off-white powder |
| 4 | Off-white nowder | Off-white powder | Off-white powder | Off-white powder | Off-white powder |

TABLE 8

| | Related Substance (% Area) (Reporting threshold = peaks ≥0.05%) Approximate Relative Retention Time (RRT) | | | | Total Related |
|---|---|---|---|---|---|
| Batch Number | RRT~0.59 | RRT~0.63 | RRT~0.90 | Alvocidib RRT~4.0 | substance (% Area) |
| Control | <0.05 | <0.05 | <0.05 | <0.05 | <0.05 |
| Binary mixtures (16 mg) | | | | | |
| 1 | <0.05 | <0.05 | <0.05 | 0.10 | 0.10 |
| 2 | <0.05 | <0.05 | <0.05 | 0.12 | 0.12 |
| 3 | <0.05 | <0.05 | <0.05 | 0.13 | 0.13 |
| 4 | <0.05 | <0.05 | <0.05 | 0.13 | 0.13 |
| Binary mixtures (1 mg) | | | | | |
| 1 | <0.05 | <0.05 | <0.05 | 0.18 | 0.18 |
| 2 | <0.05 | 0.07 | <0.05 | 0.13 | 0.20 |
| 3 | <0.05 | <0.05 | 0.06 | 0.19 | 0.25 |
| 4 | 0.05 | <0.05 | 0.05 | 0.18 | 0.27 |

TABLE 9

| | Related Substance (% Area) (Reporting threshold = peaks ≥0.05%) Approximate Relative Retention Time (RRT) | | | | | | Total Related substance (% Area) |
|---|---|---|---|---|---|---|---|
| Batch Number | RRT~0.43 | RRT~0.47 | RRT~0.59 | RRT~0.63 | RRT~0.90 | Alvocidib RRT~4.0 | |
| API | | | | | | | |
| Control | <0.05 | <0.05 | <0.05 | <0.05 | <0.05 | 0.05 | 0.05 |
| Binary mixtures (16 mg) | | | | | | | |
| 1 | <0.05 | <0.05 | <0.05 | <0.05 | <0.05 | 0.14 | 0.14 |
| 2 | <0.05 | <0.05 | <0.05 | <0.05 | <0.05 | 0.14 | 0.14 |
| 3 | <0.05 | <0.05 | <0.05 | <0.05 | <0.05 | 0.12 | 0.12 |
| 4 | <0.05 | <0.05 | <0.05 | <0.05 | <0.05 | 0.12 | 0.12 |
| Binary mixtures (1 mg) | | | | | | | |
| 1 | <0.05 | <0.05 | 0.07 | <0.05 | 0.10 | 2.33 | 2.50 |
| 2 | 0.15 | 0.32 | 0.08 | 0.06 | 0.08 | 1.23 | 1.92 |
| 3 | <0.05 | <0.05 | 0.11 | <0.05 | 0.13 | 0.78 | 1.02 |
| 4 | <0.05 | 0.07 | 0.08 | <0.05 | 0.08 | 1.35 | 1.58 |

TABLE 10

| Batch Number | Related Substance (% Area) (Reporting threshold = peaks ≥0.05%) Approximate Relative Retention Time (RRT) | | | | | | Total Related substance (% Area) |
|---|---|---|---|---|---|---|---|
| | RRT~0.43 | RRT~0.47 | RRT~0.59 | RRT~0.63 | RRT~0.90 | Alvocidib RRT~4.0 | |
| API | | | | | | | |
| Control | <0.05 | <0.05 | <0.05 | <0.05 | <0.05 | 0.07 | 0.07 |
| Binary mixtures (16 mg) | | | | | | | |
| 1 | <0.05 | <0.05 | <0.05 | <0.05 | <0.05 | 0.24 | 0.24 |
| 2 | <0.05 | 0.07 | <0.05 | <0.05 | <0.05 | 0.22 | 0.29 |
| 3 | <0.05 | <0.05 | <0.05 | <0.05 | <0.05 | 0.19 | 0.19 |
| 4 | <0.05 | <0.05 | <0.05 | <0.05 | <0.05 | 0.21 | 0.21 |
| Binary mixtures (1 mg) | | | | | | | |
| 1 | <0.05 | <0.05 | 0.08 | <0.05 | 0.12 | 4.18 | 4.38 |
| 2 | 0.14 | 0.37 | 0.11 | 0.07 | 0.10 | 2.12 | 2.90 |
| 3 | <0.05 | 0.07 | 0.12 | <0.05 | 0.16 | 1.20 | 1.55 |
| 4 | <0.05 | <0.05 | 0.09 | <0.05 | 0.10 | 2.32 | 2.51 |

TABLE 11

| Batch Number | Related Substance (% Area) (Reporting threshold = peaks ≥0.05%) Approximate Relative Retention Time (RRT) | | | | | | Total Related substance (% Area) |
|---|---|---|---|---|---|---|---|
| | RRT~0.43 | RRT~0.47 | RRT~0.59 | RRT~0.90 | RRT~2.06 | Alvocidib RRT~4.0 | |
| API | | | | | | | |
| Control | <0.05 | <0.05 | <0.05 | <0.05 | <0.05 | 0.12 | 0.12 |
| Binary mixtures (16 mg) | | | | | | | |
| 1 | <0.05 | <0.05 | <0.05 | <0.05 | <0.05 | 2.57 | 2.57 |
| 2 | <0.05 | <0.05 | <0.05 | <0.05 | <0.05 | 0.72 | 0.72 |
| 3 | <0.05 | <0.05 | <0.05 | <0.05 | <0.05 | 0.31 | 0.31 |
| 4 | <0.05 | <0.05 | <0.05 | <0.05 | <0.05 | 1.03 | 1.03 |
| Binary mixtures (1 mg) | | | | | | | |
| 1 | <0.05 | <0.05 | 0.15 | 0.06 | 0.12 | 20.42 | 20.75 |
| 2 | 0.18 | 0.26 | 0.24 | 0.50 | 0.13 | 14.04 | 15.35 |
| 3 | <0.05 | <0.05 | 0.17 | 0.21 | 0.06 | 4.96 | 5.40 |
| 4 | <0.05 | 0.06 | 0.31 | 0.50 | 0.30 | 24.72 | 25.88 |

TABLE 12

| Batch Number | Related Substance (% Area) (Reporting threshold = peaks ≥0.05%) Approximate Relative Retention Time (RRT) | | | | | | Total Related substance (% Area) |
|---|---|---|---|---|---|---|---|
| | RRT~0.43 | RRT~0.47 | RRT~0.59 | RRT~0.90 | RRT~2.06 | Alvocidib RRT~4.0 | |
| API | | | | | | | |
| Control | <0.05 | <0.05 | <0.05 | <0.05 | <0.05 | 0.21 | 0.21 |
| Binary mixtures (16 mg) | | | | | | | |
| 1 | <0.05 | <0.05 | <0.05 | <0.05 | <0.05 | 3.73 | 3.73 |
| 2 | <0.05 | <0.05 | <0.05 | <0.05 | <0.05 | 1.15 | 1.15 |
| 3 | <0.05 | <0.05 | <0.05 | <0.05 | <0.05 | 0.50 | 0.50 |
| 4 | <0.05 | <0.05 | <0.05 | <0.05 | <0.05 | 1.85 | 1.85 |
| Binary mixtures (1 mg) | | | | | | | |
| 1 | <0.05 | <0.05 | 0.12 | <0.05 | 0.22 | 24.43 | 24.77 |
| 2 | 0.19 | 0.25 | 0.27 | 0.33 | 0.27 | 18.84 | 20.15 |

TABLE 12-continued

| Batch Number | Related Substance (% Area) (Reporting threshold = peaks ≥0.05%) Approximate Relative Retention Time (RRT) | | | | | | Total Related substance (% Area) |
|---|---|---|---|---|---|---|---|
| | RRT~0.43 | RRT~0.47 | RRT~0.59 | RRT~0.90 | RRT~2.06 | Alvocidib RRT~4.0 | |
| 3 | <0.05 | <0.05 | 0.20 | 0.19 | 0.13 | 7.36 | 7.87 |
| 4 | <0.05 | <0.05 | 0.33 | 0.34 | 0.68 | 35.51 | 36.85 |

TABLE 13

| Binary mixture 1 (16 mg) | | Binary mixture 2 (16 mg) | | Binary mixture 3 (16 mg) | | Binary mixture 4 (16 mg) | |
|---|---|---|---|---|---|---|---|
| Replicate | % Label Claim | Replicate | % Label Claim | Replicate | % Label Claim | Replicate | % Label Claim |
| R1 | 97.3 | R1 | 98.4 | R1 | 87.4 | R1 | 91.4 |
| R2 | 91.8 | R2 | 99.3 | R2 | 87.1 | R2 | 89.2 |
| R3 | 94.9 | R3 | 99.8 | R3 | 88.5 | R3 | 92.0 |
| R4 | 96.3 | R4 | 99.1 | R4 | 84.8 | R4 | 94.5 |
| R5 | 94.3 | R5 | 94.5 | R5 | 85.9 | R5 | 93.4 |
| R6 | 93.1 | R6 | 95.3 | R6 | 94.2 | R6 | 89.7 |
| R7 | 90.6 | R7 | 93.9 | R7 | 87.5 | R7 | 87.0 |
| R8 | 94.2 | R8 | 98.3 | R8 | 88.5 | R8 | 89.2 |
| R9 | 95.1 | R9 | 92.1 | R9 | 87.0 | R9 | 83.2 |
| R10 | 92.1 | R10 | 89.1 | R10 | 83.9 | R10 | 83.5 |
| Min | 90.6 | Min | 89.1 | Min | 83.9 | Min | 83.2 |
| Max | 97.3 | Max | 99.8 | Max | 94.2 | Max | 94.5 |
| Mean | 94.0 | Mean | 96.0 | Mean | 87.5 | Mean | 89.3 |
| Std. Dev. | 2.1 | Std. Dev. | 3.6 | Std. Dev. | 2.8 | Std. Dev. | 3.8 |
| % RSD | 2.2 | % RSD | 3.7 | % RSD | 3.2 | % RSD | 4.3 |
| AV ≤ 15.0 | 9.5 Pass | AV ≤ 15.0 | 11.1 Pass | AV ≤ 15.0 | 17.7 Fail | AV ≤ 15.0 | 18.3 Fail |

TABLE 14

| Binary mixture 1 (1 mg) | | Binary mixture 2 (1 mg) | | Binary mixture 3 (1 mg) | | Binary mixture 4 (1 mg) | |
|---|---|---|---|---|---|---|---|
| Replicate | % Label Claim | Replicate | % Label Claim | Replicate | % Label Claim | Replicate | % Label Claim |
| R1 | 94.3 | R1 | 98.0 | R1 | 97.1 | R1 | 97.1 |
| R2 | 91.4 | R2 | 97.7 | R2 | 98.4 | R2 | 98.4 |
| R3 | 100.0 | R3 | 98.9 | R3 | 100.7 | R3 | 100.7 |
| R4 | 98.7 | R4 | 97.6 | R4 | 96.6 | R4 | 96.6 |
| R5 | 90.3 | R5 | 98.3 | R5 | 98.4 | R5 | 98.4 |
| R6 | 96.8 | R6 | 98.0 | R6 | 96.9 | R6 | 96.9 |
| R7 | 99.7 | R7 | 95.9 | R7 | 96.9 | R7 | 96.9 |
| R8 | 99.4 | R8 | 99.9 | R8 | 96.4 | R8 | 96.4 |
| R9 | 97.7 | R9 | 99.0 | R9 | 97.5 | R9 | 97.5 |
| R10 | 95.7 | R10 | 97.9 | R10 | 93.9 | R10 | 93.9 |
| Min | 90.3 | Min | 95.9 | Min | 93.9 | Min | 93.9 |
| Max | 100.0 | Max | 99.9 | Max | 100.7 | Max | 100.7 |
| Mean | 96.4 | Mean | 98.1 | Mean | 97.3 | Mean | 97.3 |
| Std. Dev. | 3.4 | Std. Dev. | 1.1 | Std. Dev. | 1.7 | Std. Dev. | 1.7 |
| % RSD | 3.6 | % RSD | 1.1 | % RSD | 1.8 | % RSD | 1.8 |
| AV ≤ 15.0 | 10.3 Pass | AV ≤ 15.0 | 2.9 Pass | AV ≤ 15.0 | 5.4 Pass | AV ≤ 15.0 | 5.4 Pass |

Example 10

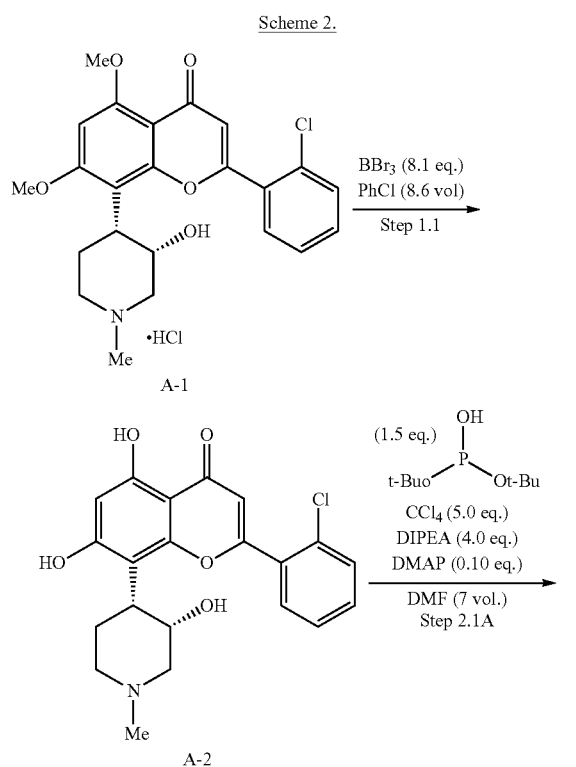

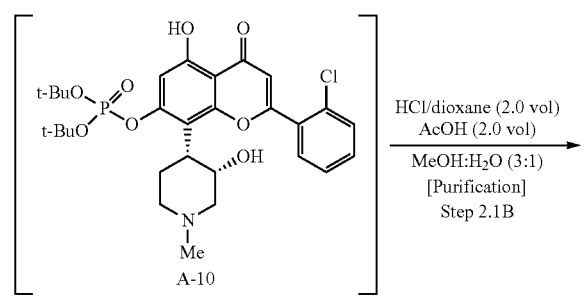

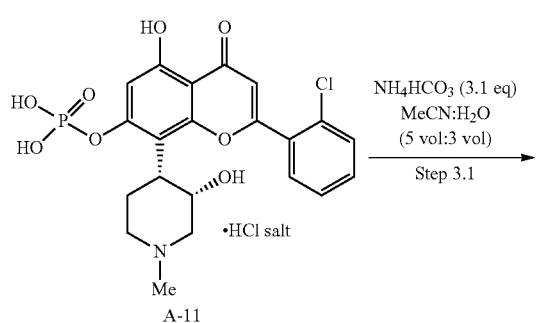

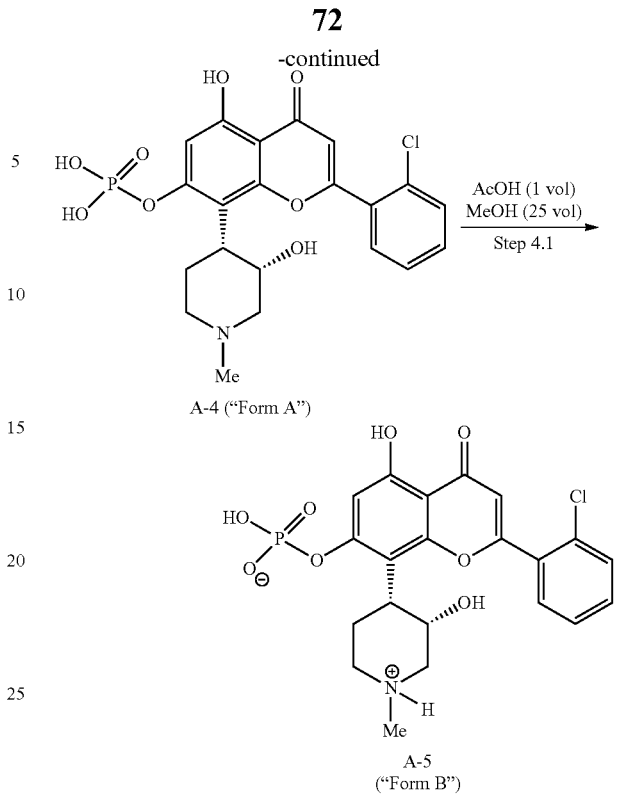

Step 1.1: To a clean and dry, three-necked, round-bottomed flask (RBF) (3 L) was added A-1 (90 g, 0.192 mol) and chlorobenzene (774 ml) at room temperature. To the reaction flask was slowly added BBr$_3$ (391.5 g) at room temperature. After completion of BBr$_3$ addition, the temperature of the reaction mixture was slowly raised to 80-83° C., and the reaction mixture was stirred at the same temperature for 10 hours. The reaction mixture temperature was further raised to 100-103° C., and the reaction mixture was maintained at 100-103° C. for 5 hours. The reaction progress was monitored by TLC and HPLC. After completion of the reaction, HBr and methyl bromide was removed at room temperature by nitrogen bubbling into the reaction mixture, while maintaining the vigorous stirring. The reaction mixture was slowly quenched with a mixture of methanol (180 ml)/water (90 ml) (270 ml), followed by methanol (180 ml). The solvent was removed under atmospheric distillation at 25-50° C. to reach the target reaction mass volume of 12 volumes (vol). Then, the reaction mixture pH was adjusted to 3.0±1 using sodium hydroxide solution (48.8 g dissolved in 135 ml of DM water) at 50-55° C. Again, the solvent was removed under atmospheric distillation at 50-100° C. to reach the target reaction volume of 12 vol. Then, the pH of the reaction mixture was adjusted to pH 8.1±0.2 using sodium hydroxide solution (8.5 g dissolved in 87 ml of DM water) at 50° C. followed by slow addition of water with constant stirring at 50° C. for 1 hour. The reaction mixture was slowly allowed to come to room temperature and maintained at room temperature for 3 hours. The resulting solid was filtered and washed with a mixture of methanol (315 ml)/water (135 ml) (3×450 ml) followed by water (5×450 ml). The solid was dried in a vacuum oven at 50-55° C. for 48 hours to obtain A-2 as a yellow solid (70 g, 90%). HPLC Purity: 99.72%.

Step 2.1A: To a clean and dry, three-necked RBF (3 L) was added A-2 (35.0 g, 0.087 mol) and DMF (245 ml), at room temperature, under nitrogen atmosphere. Then, DMAP (1.06 g, 0.0086 mol) followed by CCl$_4$ (66.5 g 0.434 mol) were added to the reaction mixture at room temperature. To the reaction mixture di-tertiary butyl phosphite (25.5 g, 0.131 mol) was added at room temperature. The reaction mixture was stirred at room temperature under nitrogen atmosphere for 24 hours. The reaction progress was monitored by HPLC. The reaction mixture was cooled to 0-5° C., and was quenched with slow addition of DM water (1950 ml) for 30 minutes at 0-5° C. Then, chloroform (1627.5 ml) was added to the reaction mixture, and the reaction mixture was stirred at 0-5° C. for 10 minutes. The organic layer was separated and dried over sodium sulfate. The solvent was removed under reduced pressure, while maintaining the bath temperature below 45° C. The resulting residue was co-distilled with toluene (4×175 ml). The residue was kept under high vacuum for 45 minutes to obtain A-10 as a pale yellow residue. (51.0 g, 98.5%). HPLC Purity: 91.48%.

Step 2.1B: To a clean and dry RBF (1 L) was added A-10 (51.0 g, 0.0858 mol) and acetic acid (102 ml) at room temperature. Then, 4N HCl solution in 1,4-dioxane (102 ml) was added dropwise at 25-30° C. The reaction mixture was stirred at 25-30° C. for 40 minutes. The reaction progress was monitored by TLC. After completion of the reaction, toluene (2×510 ml) was added to the reaction mixture under stirring, and the reaction mixture was maintained for 5 minutes. The stirring was stopped, and the solids in the reaction mixture were allowed to settle at 25-30° C. for 5 minutes. The solvent was decanted to obtain the semi-solid. The semi-solid was co-distilled with toluene (3×123 ml) to obtain pale yellow solid. The resulting pale yellow solid was taken into a clean RBF, and methanol was added (123 ml) followed by dropwise addition of water (41 ml) at 25-30° C. The reaction mixture was stirred at 25-30° C. for 2 hours to obtain pale yellow solid. The resulting solid was filtered and vacuum dried for 10 minutes to obtain A-11 as a pale yellow solid (36.5 g, 82%). HPLC Purity: 97.03%. This material was directly taken into Step 3.1 without further drying.

Step 3.1: To a clean and dry, three-necked, 500 ml RBF was added A-11 (34.0 g, 0.066 mol) and ACN (51 ml). To the reaction mixture was dropwise added ammonium bicarbonate solution (16.2 g dissolved in 170 ml of DM water) under stirring at 25-30° C. for 30 minutes. Again, ACN (51 ml) was slowly added at 25-30° C. for 30 minutes. The reaction mixture was cooled to 10-15° C. and stirred at 10-15° C. for 60 minutes. The resulting solid was filtered and washed with ACN (102 ml). The solid was dried in a vacuum oven at 25-30° C. for 16 hours to obtain A-4 as a pale yellow solid (28.5 g, 90.10%). HPLC Purity: 99.68%.

Step 4.1: To a clean and dry, 500-ml, three-necked RBF was added A-4 (7.5 g, 0.015 mol) and methanol (187.5 ml) at room temperature. To the reaction mixture was slowly added acetic acid (7.5 ml, 1.0 vol) at 50° C., under nitrogen atmosphere. The reaction mixture was stirred at 50° C. for 1 h, under nitrogen atmosphere. The reaction mixture was cooled to room temperature and stirred for 2 h. The solid was filtered and dried under vacuum to obtain 5.0 g A-5 (66.5%) as a pale yellow solid. HPLC Purity: 99.77%.

Several screens were conducted to identify the Step 4.1 conditions described above. In a first screen, A-4 was treated with acid (1.0 volume) and methanol (25 volumes) according to the conditions listed in Table 15 to obtain A-5 as a pale yellow solid.

TABLE 15

| Acid | Brief Procedure | A-4 (g) (HPLC Purity (%); A-2 (%)) | A-5 (g) | Yield (%) | HPLC Purity (%) | A-2 (%) |
| --- | --- | --- | --- | --- | --- | --- |
| Acetic acid | See description of Step 4.1 above. | 7.5 (99.68; 0.08) | 5.0 | 66.5 | 99.77 | 0.12 |
| Citric acid | To a clean and dry, 100-ml, three-necked RBF was added A-4 (1 g, 0.002 mol) and methanol (25 ml) at room temperature. To the reaction mixture was added citric acid (1.0 g, 2.5 eq) at 50° C., under nitrogen atmosphere. The reaction mixture was stirred at 50° C. for 1 h, under nitrogen atmosphere. The reaction mixture was cooled to room temperature and stirred for 2 h. The solid was filtered and dried under vacuum to obtain A-5 as a pale yellow solid. | 1.0 (99.72; 0.09) | 0.6 | 66.5 | 99.59 | 0.28 |
| Propionic acid | To a clean and dry, 100-ml, three-necked RBF was added A-4 (0.8 g, 0.001 mol) and methanol (20 ml) at room temperature. To the reaction mixture was dropwise added propionic acid (0.8 ml) at 50° C., under nitrogen atmosphere. The reaction mixture was stirred at 50° C. for 1 h, under nitrogen atmosphere. The reaction mixture was cooled to room temperature and stirred for 2 h. The resulting solid was filtered and dried under vacuum to obtain A-4 as a pale yellow solid. | 0.8 (99.72; 0.09) | 0.5 | 62.5 | 99.41 | 0.12 |

In another screen, A-4 was treated with acetic acid (1 volume) and a solvent (25 volumes) according to the conditions listed in Table 16 to obtain A-S as a pale yellow solid.

TABLE 16

| Solvent | Brief Procedure | A-4 (g) | A-5 (g) | Yield (%) | HPLC Purity (%) | A-2 (%) |
|---|---|---|---|---|---|---|
| n-butanol | To a clean and dry, 100-ml, three-necked RBF was added A-4 (2 g, 0.004 mol) and n-butanol (50 ml) at room temperature. Then, acetic acid (2.0 ml) was slowly added to the reaction mixture at 50° C., under nitrogen atmosphere. The resulting reaction mixture was stirred at 50° C. for 1 h, under nitrogen atmosphere. The reaction mixture was cooled to room temperature and stirred for 2 h. The resulting solid was filtered and dried under vacuum to obtain A-5 as a pale yellow solid. | 2.0 | 1.0 | 50 | 99.85 | 0.04 |
| Methyl ethyl ketone | | 2.0 | 1.2 | 60 | 99.48 | 0.25 |
| Ethanol | To a clean and dry, 100-ml, three-necked RBF was added A-4 (2 g, 0.004 mol) and ethanol (50 ml) at room temperature. Then, acetic acid (2.0 ml) was slowly added to the reaction mixture at 50° C., under nitrogen atmosphere. The resulting reaction mixture was stirred at 50° C. under nitrogen atmosphere for 1 h. The reaction mixture was cooled to room temperature and stirred for 2 h. The resulting solid was filtered and dried under vacuum to obtain A-5 as a pale yellow solid. | 2.0 | 1.4 | 70 | 99.88 | 0.03 |
| Ethanol (10 volumes) Acetone (10 volumes) | To a clean and dry, 100-ml, three-necked RBF was added A-4 (1 g, 0.002 mol), ethanol (10 ml) and acetone (10 ml) at room temperature. Then, acetic acid (1.0 ml) was slowly added to the reaction mixture at 50° C., under nitrogen atmosphere. The resulting reaction mixture was stirred at 50° C. under nitrogen atmosphere for 1 h. The reaction mixture was cooled to room temperature and stirred for 2 h. The resulting solid was filtered and dried under vacuum to obtain A-5 as a pale yellow solid. | 1.0 | 0.5 | 50 | 99.83 | 0.06 |

In another screen, A-4 was treated with acetic acid (1 volume) and a solvent according to the conditions listed in Table 17 to obtain A-5 as a pale yellow solid.

TABLE 17

| Solvent | Brief Procedure | A-4 (g) | A-5 (g) | Yield (%) | HPLC Purity (%) | A-2 (%) |
|---|---|---|---|---|---|---|
| Ethanol (15 volumes) Ethyl acetate (10 volumes) | To a clean and dry, 100-ml, three-necked RBF was added A-4 (1.5 g, 0.003 mol), ethanol (22.5 ml) and ethyl acetate (15 ml) at room temperature, under nitrogen atmosphere. Then, acetic acid (1.5 ml) was slowly added at 50° C. The resulting reaction mixture was stirred at 50° C. under nitrogen atmosphere for 1 h. The reaction mixture was cooled to room temperature and | 1.5 | 1.08 | 72 | 99.60 | 0.09 |

TABLE 17-continued

| Solvent | Brief Procedure | A-4 (g) | A-5 (g) | Yield (%) | HPLC Purity (%) | A-2 (%) |
|---|---|---|---|---|---|---|
| | stirred for 2 h. The resulting solid was filtered and dried under vacuum to obtain A-5 as a pale yellow solid. | | | | | |
| Ethanol (15 volumes) i-Pr$_2$O (10 volumes) | | 1.5 | 1.25 | 83 | 99.68 | 0.12 |
| Ethanol (15 volumes) Water (1 volume) | To a clean and dry, 100-ml, three-necked RBF was added A-4 (1.5 g, 0.003 mol), ethanol (22.5 ml) and DM water (1.5 ml) at room temperature. Then, acetic acid (1.5 ml) was slowly added to the reaction mixture at 50° C. The resulting reaction mixture was stirred at 50° C. for 1 h. The reaction mixture was cooled to room temperature and stirred for 2 h. The resulting solid was filtered and dried under vacuum to obtain A-5 as a pale yellow solid. | 1.5 | 1.1 | 73 | 99.60 | 0.09 |

In another screen, A-4 was treated with acetic acid and ethanol (25 volumes) according to the conditions listed in Table 18 to obtain A-S as a pale yellow solid.

As an alternative to conducting Step 4.1 using the conditions cited above in Example 10, a procedure similar to that described in Step 4 of Example 1 can be used to effect

TABLE 18

| Acetic Acid | Brief Procedure | A-4 (g) | A-5 (g) | Yield (%) | HPLC Purity (%) | A-2 (%) |
|---|---|---|---|---|---|---|
| 0.8 volumes | To a clean and dry, 100-ml, three-necked RBF was added A-4 (1.5 g, 0.003 mol) and ethanol (37.5 ml) at room temperature, under nitrogen atmosphere. Then, acetic acid (1.2 ml) was slowly added at 50° C. The resulting reaction mixture was stirred under nitrogen atmosphere at 50° C. for 1 h. The reaction mixture was cooled to room temperature and stirred for 2 h. The resulting solid was filtered and dried under vacuum to obtain A-5 as a pale yellow solid. | 1.5 | 1.15 | 76 | 99.70 | 0.12 |
| 0.6 volumes | To a clean and dry, 100-ml, three-necked RBF was added A-4 (1.5 g, 0.003 mol) and ethanol (37.5 ml) at room temperature, under nitrogen atmosphere. Then, acetic acid (0.9 ml) was slowly added at 50° C. The resulting reaction mixture was stirred at 50° C., under nitrogen atmosphere for 1 h. The reaction mixture was cooled to room temperature and stirred for 2 h. The resulting solid was filtered and dried under vacuum to obtain A-5 as a pale yellow solid. | 1.5 | 1.17 | 78 | 99.73 | 0.09 |
| 0.4 volumes | To a clean and dry, 100-ml, three-necked RBF was added A-4 (1.5 g, 0.003 mol) and ethanol (37.5 ml) at room temperature, under nitrogen atmosphere. Then, acetic acid (0.6 ml) was slowly added at 50° C. The resulting reaction mixture was stirred at 50° C., under nitrogen atmosphere for 1 h. The reaction mixture was cooled to room temperature and stirred for 2 h. The resulting solid was filtered and dried under vacuum to obtain A-5 as a pale yellow solid. | 1.5 | 1.0 | 66 | 99.71 | 0.10 | polymorph conversion. Thus, in another experiment, to a clean and dry, 100-ml, three-necked RBF was added A-4 (2.0 g, 0.004 mol), THF (29 ml) and DM water (1.7 ml) at room temperature. Then, maleic acid (0.44 g) was added to the reaction mixture at room temperature. The reaction mixture was stirred at room temperature for 12 h. The resulting solid was filtered and vacuum dried. The wet solid was dissolved in ethanol (12 ml) at room temperature and was stirred for 24 h. The resulting solid was filtered, washed with ethanol (2.5 ml), vacuum dried to obtain A-5 (1.5 g, 60%) as a pale yellow solid. HPLC Purity: 99.91%.

Example 11

Formulation Stability Study

Polymorph Form B obtained using various Step 2.1B reaction conditions was submitted to a four-week stability study. The results of the stability study appear in Table 19. The Reference Standard is a sample obtained using the synthetic procedure described in Example 1.

TABLE 19

| Study No. | Step 2.1B Reaction Conditions | Stability at 40° C. ± 2° C., 75 ± 5% RH, sealed vial, HPLC Purity of A-5 (%)/A-2 (%) | | | | |
|---|---|---|---|---|---|---|
| | | Initial | 3 days ± 1 day | 7 days ± 1 day | 14 days ± 1 day | 28 days ± 1 day |
| 1 | 4N HCl in 1,4-dioxane | 99.89/0.03 | 98.83/0.94 | 98.37/1.37 | 97.58/2.14 | 96.73/2.95 |
| 2 | 10% HCl in EtOAc | 99.69/0.16 | 99.52/0.32 | 99.31/0.51 | 98.96/0.81 | 98.40/1.34 |
| 3 | Conc. HCl in IPA | 99.65/0.19 | 99.09/0.72 | 98.52/1.24 | 97.76/1.96 | 96.67/2.95 |
| 4 | Acetic acid in methanol | 99.77/0.09 | 99.64/0.23 | 99.42/0.40 | 99.24/0.58 | |
| Reference Standard | N/A | 99.90/0.03 | 99.91/0.06 | 99.81/0.13 | 99.70/0.24 | 99.41/0.53 |

Polymorph Form B obtained using the Step 2.1B reaction conditions described in Scheme 2 was submitted to a four-week stability study to test the effects of different packing conditions on the stability of A-5. Under Packing Condition 1, polymorph Form B was packed into an amber-colored bottle, which was closed with a rubber stopper and sealed with a flip-off aluminum cap. Under Packing Condition 2, polymorph Form B was packed in a low-density polyethylene bag (LDPE) twisted and tied. The LDPE bag was then inserted into a black, LDPE bag along with one silica gel bag, and the black, LDPE bag was heat sealed under nitrogen atmosphere. The black, LDPE bag was then inserted into a triple-laminated aluminum bag along with one silica gel bag, and the aluminum bag was heat sealed under nitrogen atmosphere. The triple-laminated aluminum bag containing polymorph Form B was kept in a high-density polyethylene container. The results of the stability study appear in Table 20.

TABLE 20

| Packing Condition | Stability at 40° C. ± 2° C., 75 ± 5% RH, sealed vial, HPLC Purity of A-5 (%)/A-2 (%) | | | | |
|---|---|---|---|---|---|
| | Initial | 3 days ± 1 day | 7 days ± 1 day | 14 days ± 1 day | 28 days ± 1 day |
| 1 | 99.77/0.09 | 99.64/0.23 | 99.42/0.40 | 99.24/0.58 | 98.59/1.23 |
| 2 | 99.77/0.09 | 99.68/0.18 | 99.50/0.30 | 99.23/0.59 | 99.10/0.74 |

Example 12

Formulation Stability Study

Polymorph Form B obtained using various Step 4.1 reaction conditions described in Example 10 was submitted to a four-week stability study. The results of the stability study appear in Table 21.

TABLE 21

Stability at 40° C. ± 2° C., 75 ± 5% RH, sealed vial, HPLC Purity of A-5 (%)/A-2 (%)

| Conditions | Initial | 7 days ± 1 day | 14 days ± 1 day | 21 days ± 1 day | 28 days ± 1 day |
|---|---|---|---|---|---|
| Citric acid | 99.2/0.6 | 96.6/3.06 | 93.12/6.08 | 91.3/8.0 | 89.7/9.6 |
| Propionic acid | 99.6/0.21 | 99.0/0.87 | 98.4/1.38 | 97.8/1.94 | 97.5/2.2 |
| n-butanol | 99.8/0.1 | 99.1/0.47 | 98.9/0.82 | 98.6/1.2 | 98.1/1.6 |
| Ethanol | 99.7/0.14 | 99.1/0.81 | 98.3/1.3 | 98.1/1.7 | 97.4/2.2 |
| Ethanol + acetone | 99.7/0.14 | 98.6/1.2 | 97.9/1.8 | 97.3/2.3 | 96.9/2.8 |
| A-11 (not submitted to Step 3.1 or 4.1) | 97.0/1.02 | 91.3/6.6 | 84.12/13.7 | 78.5/19.0 | 75.0/22.2 |
| Ethanol (15 volumes) Ethyl acetate (10 volumes) | 99.5/0.17 | 98.7/0.92 | 97.9/1.6 | 97.6/2.0 | 96.9/2.6 |
| Ethanol (15 volumes) Water (1 volume) | 99.8/0.04 | 99.6/0.25 | 99.3/0.41 | 99.2/0.58 | 99.1/0.73 |
| Ethanol:AcOH (0.8 volumes) | 99.7/0.14 | 99.3/0.46 | 99.0/0.68 | 98.6/0.98 | 98.6/1.1 |
| Ethanol:AcOH (0.6 volumes) | 99.7/0.11 | 99.1/0.6 | 98.5/0.99 | 98.3/1.3 | 98.1/1.7 |
| Ethanol:AcOH (0.4 volumes) | 99.7/0.14 | 99.3/0.51 | 98.5/1.1 | 98.3/1.4 | 98.0/1.7 |
| Maleic acid | 99.9/0.04 | 99.8/0.07 | 99.6/0.11 | 99.7/0.17 | 99.7/0.18 |
| Ethanol (15 volumes) Diisopropyl ether (10 volumes) | 98.9/0.71 | 97.6/1.86 | 98.3/1.5 | | |
| A-4 (not submitted to Step 4.1) | 99.2/0.44 | 98.6/0.88 | 97.5/2.2 | | |

Example 13

Excipient Compatibility Study

The compatibility of binary mixtures of 95% excipient and 5% compound of structure (I) (equivalent to a 20:1 excipient:compound of structure (I) ratio) was studied. The following excipients formed part of the excipient compatibility study:

| Category | | Product name |
|---|---|---|
| Filler | D-Mannitol | PEARITOL 50C |
| | Anhydrous lactose | SuperTab22AN |
| | Microcrystalline cellulose | AvicelPH112 |
| | Cornstarch | Cornstarch (JP) |
| | Anhydrous dibasic calcium phosphate | Anhydrous dibasic calcium phosphate |
| Disintegrant | Croscarmellose sodium | Ac-Di-Sol SD-711 |
| | Partly pregelatinized starch | Starch1500G |
| | Crospovidone | KollidonCL |
| | Low substituted hydroxylpropylcellulose | L-HPC(LH-21) |
| | Carmellose calcium | ECG505 |

-continued

| Category | | Product name |
|---|---|---|
| Lubricant | Magnesium stearate | LIGAMED MF-2-V |
| | Sodium stearyl fumarate | PRUV |
| | Talc | Talc MS-P |
| Fluidizer | Silicon dioxide | Aerosil 200 |
| Others | Fumaric acid | Fumaric acid NF |
| | Succinic acid | Succinic acid cryst EMPROVE ESSENTIAL NF JPE ACS |

Samples were tested for related substances (Total Impurities, by HPLC) at 50° C. and 85% RH, and at 60° C. at two- and four-week time points. Anhydrous lactose, cornstarch, partly pregelatinized starch, low-substituted hydroxyl propyl cellulose, carmellose calcium and magnesium stearate demonstrated compatibility with the compound of structure (I). The results of the excipient compatibility study are described in Tables 22A-22P.

TABLE 22A

| | PEARITOL 50C | | | | | | |
|---|---|---|---|---|---|---|---|
| | | 60° C. | | 50° C. 85% | | Photostability | |
| Filler RRT | Initial % Area | 2 W % Area | 4 W % Area | 2 W % Area | 4 W % Area | 60 Lux % Area | 120 Lux % Area |
| 0.4-0.45 | N.D. | N.D. | N.D. | N.D. | N.D. | N.D. | N.D. |
| 0.48-0.51 | N.D. | N.D. | N.D. | N.D. | N.D. | N.D. | N.D. |
| 0.57-0.59 | N.D. | 0.05 | 0.05 | 0.07 | 0.15 | <0.05 | <0.05 |
| 0.87-0.89 | N.D. | N.D. | N.D. | <0.05 | 0.07 | <0.05 | <0.05 |
| 1.00 | 99.64 | 94.79 | 93.91 | 87.82 | 66.13 | 99.41 | 99.02 |
| 1.35-1.37 | N.D. | N.D. | N.D. | N.D. | N.D. | N.D. | N.D. |
| 2.19-2.25 | N.D. | 0.13 | 0.18 | 0.14 | 0.64 | N.D. | N.D. |
| 3.36-3.45 | N.D. | N.D. | N.D. | N.D. | N.D. | N.D. | N.D. |
| 3.67-3.72(3.77-3.79)Alvocidib | 0.36 | 5.03 | 5.85 | 11.94 | 33.01 | 0.55 | 0.92 |
| Total impurity | 0.36 | 5.21 | 6.08 | 12.15 | 33.87 | 0.55 | 0.92 |
| Δimpurity | | 4.85 | 5.72 | 11.79 | 33.51 | 0.19 | 0.56 |

TABLE 22B

| | SUperTab22AN | | | | | | |
|---|---|---|---|---|---|---|---|
| | | 60° C. | | 50° C. 85% | | Photostability | |
| Filler RRT | Initial % Area | 2 W % Area | 4 W % Area | 2 W % Area | 4 W % Area | 60 Lux % Area | 120 Lux % Area |
| 0.4-0.45 | N.D. | 0.09 | N.D. | <0.05 | N.D. | N.D. | N.D. |
| 0.48-0.51 | N.D. | N.D. | N.D. | N.D. | N.D. | N.D. | N.D. |
| 0.57-0.59 | N.D. | 0.09 | 0.09 | 0.10 | 0.15 | <0.05 | <0.05 |
| 0.87-0.89 | N.D. | 0.07 | 0.05 | 0.05 | 0.05 | <0.05 | <0.05 |
| 1.00 | 99.64 | 96.90 | 96.85 | 89.04 | 80.08 | 99.70 | 99.49 |
| 1.35-1.37 | N.D. | N.D. | N.D. | N.D. | N.D. | N.D. | N.D. |
| 2.19-2.25 | N.D. | 0.09 | 0.14 | 0.23 | 0.65 | N.D. | N.D. |
| 3.36-3.45 | N.D. | N.D. | N.D. | N.D. | <0.05 | N.D. | N.D. |
| 3.67-3.72(3.77-3.79)Alvocidib | 0.36 | 2.76 | 2.88 | 10.55 | 19.04 | 0.25 | 0.45 |
| Total impurity | 0.36 | 3.10 | 3.16 | 10.93 | 19.89 | 0.25 | 0.45 |
| Δimpurity | | 2.74 | 2.80 | 10.57 | 19.53 | −0.11 | 0.09 |

TABLE 22C

| | AvicelPH112 | | | | | | |
|---|---|---|---|---|---|---|---|
| | | 60° C. | | 50° C. 85% | | Photostability | |
| Filler RRT | Initial % Area | 2 W % Area | 4 W % Area | 2 W % Area | 4 W % Area | 60 Lux % Area | 120 Lux % Area |
| 0.4-0.45 | N.D. | 0.06 | N.D. | N.D. | <0.05 | N.D. | N.D. |
| 0.48-0.51 | N.D. | <0.05 | N.D. | N.D. | N.D. | N.D. | N.D. |
| 0.57-0.59 | N.D. | 0.17 | 0.16 | 0.13 | 0.16 | <0.05 | <0.05 |
| 0.87-0.89 | N.D. | 0.13 | 0.09 | 0.05 | <0.05 | 0.05 | 0.08 |
| 1.00 | 99.74 | 96.17 | 96.17 | 84.69 | 77.55 | 99.58 | 99.34 |
| 1.35-1.37 | N.D. | N.D. | <0.05 | N.D. | N.D. | N.D. | N.D. |
| 2.19-2.25 | N.D. | 0.23 | 0.29 | 0.29 | 0.49 | N.D. | N.D. |
| 3.36-3.45 | N.D. | N.D. | <0.05 | <0.05 | 0.05 | N.D. | N.D. |
| 3.67-3.72(3.77-3.79)Alvocidib | 0.26 | 3.21 | 3.22 | 14.82 | 21.69 | 0.33 | 0.53 |
| Total impurity | 0.26 | 3.80 | 3.76 | 15.29 | 22.39 | 0.38 | 0.61 |
| Δimpurity | | 3.54 | 3.50 | 15.03 | 22.13 | 0.12 | 0.35 |

TABLE 22D

| | | Cornstarch(JP) | | | | | |
|---|---|---|---|---|---|---|---|
| | | 60° C. | | 50° C. 85% | | Photostability | |
| Filler RRT | Initial % Area | 2 W % Area | 4 W % Area | 2 W % Area | 4 W % Area | 60 Lux % Area | 120 Lux % Area |
| 0.4-0.45 | N.D. | <0.05 | N.D. | N.D. | N.D. | <0.05 | N.D. |
| 0.48-0.51 | N.D. | N.D. | N.D. | N.D. | N.D. | N.D. | N.D. |
| 0.57-0.59 | N.D. | 0.12 | 0.12 | 0.07 | 0.09 | <0.05 | <0.05 |
| 0.87-0.89 | N.D. | 0.09 | 0.07 | <0.05 | <0.05 | <0.05 | 0.05 |
| 1.00 | 99.64 | 96.60 | 96.43 | 93.74 | 90.03 | 99.62 | 99.46 |
| 1.35-1.37 | N.D. | N.D. | <0.05 | N.D. | N.D. | N.D. | N.D. |
| 2.19-2.25 | N.D. | 0.21 | 0.28 | 0.16 | 0.32 | N.D. | N.D. |
| 3.36-3.45 | N.D. | <0.05 | <0.05 | N.D. | 0.06 | N.D. | N.D. |
| 3.67-3.72(3.77-3.79)Alvocidib | 0.36 | 2.93 | 3.05 | 5.99 | 9.47 | 0.30 | 0.46 |
| Total impurity | 0.36 | 3.35 | 3.52 | 6.22 | 9.94 | 0.30 | 0.51 |
| Δimpurity | | 2.99 | 3.16 | 5.86 | 9.58 | −0.06 | 0.15 |

TABLE 22E

| | | Anhydrous dibasic calcium phosphate | | | | | |
|---|---|---|---|---|---|---|---|
| | | 60° C. | | 50° C. 85% | | Photostability | |
| Filler RRT | Initial % Area | 2 W % Area | 4 W % Area | 2 W % Area | 4 W % Area | 60 Lux % Area | 120 Lux % Area |
| 0.4-0.45 | N.D. | N.D. | N.D. | N.D. | N.D. | N.D. | N.D. |
| 0.48-0.51 | N.D. | N.D. | N.D. | N.D. | N.D. | N.D. | N.D. |
| 0.57-0.59 | N.D. | <0.05 | <0.05 | <0.05 | 0.06 | N.D. | N.D. |
| 0.87-0.89 | N.D. | N.D. | N.D. | <0.05 | N.D. | N.D. | N.D. |
| 1.00 | 99.85 | 97.45 | 97.32 | 83.48 | 79.63 | 99.54 | 99.25 |
| 1.35-1.37 | N.D. | N.D. | N.D. | N.D. | N.D. | N.D. | N.D. |
| 2.19-2.25 | N.D. | 0.08 | 0.12 | 0.18 | 0.35 | N.D. | N.D. |
| 3.36-3.45 | N.D. | N.D. | N.D. | N.D. | <0.05 | N.D. | N.D. |
| 3.67-3.72(3.77-3.79)Alvocidib | 0.15 | 2.43 | 2.52 | 16.27 | 19.93 | 0.46 | 0.75 |
| Total impurity | 0.15 | 2.51 | 2.64 | 16.45 | 20.34 | 0.46 | 0.75 |
| Δimpurity | | 2.36 | 2.49 | 16.30 | 20.19 | 0.31 | 0.60 |

TABLE 22F

| | | Ac-Di-Sol | | | | | |
|---|---|---|---|---|---|---|---|
| | | 60° C. | | 50° C. 85% | | Photostability | |
| Disintegrant RRT | Initial % Area | 2 W % Area | 4 W % Area | 2 W % Area | 4 W % Area | 60 Lux % Area | 120 Lux % Area |
| 0.26-0.27 | N.D. | N.D. | N.D. | N.D. | N.D. | N.D. | N.D. |
| 0.38-0.41 | N.D. | N.D. | N.D. | N.D. | N.D. | N.D. | N.D. |
| 0.4-0.45 | N.D. | N.D. | <0.05 | N.D. | N.D. | N.D. | N.D. |
| 0.48-0.51 | N.D. | <0.05 | N.D. | N.D. | N.D. | N.D. | N.D. |
| 0.57-0.59 | N.D. | 0.10 | 0.09 | 0.06 | 0.08 | <0.05 | <0.05 |
| 0.59 | N.D. | N.D. | N.D. | N.D. | N.D. | N.D. | N.D. |
| 0.72 | N.D. | N.D. | N.D. | N.D. | N.D. | N.D. | N.D. |
| 0.87-0.89 | N.D. | 0.07 | 0.05 | N.D. | N.D. | 0.05 | 0.07 |
| 1.00 | 99.90 | 98.29 | 98.16 | 87.67 | 78.62 | 99.79 | 99.70 |

TABLE 22F-continued

| | Ac-Di-Sol | | | | | | |
| --- | --- | --- | --- | --- | --- | --- | --- |
| | | 60° C. | | 50° C. 85% | | Photostability | |
| Disintegrant RRT | Initial % Area | 2 W % Area | 4 W % Area | 2 W % Area | 4 W % Area | 60 Lux % Area | 120 Lux % Area |
| 1.35-1.37 | N.D. | N.D. | N.D. | N.D. | N.D. | N.D. | N.D. |
| 2.19-2.25 | N.D. | 0.12 | 0.17 | 0.11 | 0.28 | N.D. | N.D. |
| 2.37-2.39 | N.D. | N.D. | N.D. | N.D. | N.D. | N.D. | N.D. |
| 3.36-3.45 | N.D. | N.D. | N.D. | N.D. | <0.05 | N.D. | N.D. |
| 3.67-3.72(3.77-3.79)Alvocidib | 0.10 | 1.39 | 1.51 | 12.17 | 20.98 | 0.13 | 0.20 |
| 4.75-4.91 | N.D. | N.D. | N.D. | N.D. | N.D. | N.D. | N.D. |
| Total impurity | 0.10 | 1.68 | 1.82 | 12.34 | 21.34 | 0.18 | 0.27 |
| Δimpurity | | 1.58 | 1.72 | 12.24 | 21.24 | 0.08 | 0.17 |

TABLE 22G

| | Starch1500G | | | | | | |
| --- | --- | --- | --- | --- | --- | --- | --- |
| | | 60° C. | | 50° C. 85% | | Photostability | |
| Disintegrant RRT | Initial % Area | 2 W % Area | 4 W % Area | 2 W % Area | 4 W % Area | 60 Lux % Area | 120 Lux % Area |
| 0.26-0.27 | N.D. | 0.09 | 0.08 | 0.09 | 0.09 | 0.07 | 0.06 |
| 0.38-0.41 | N.D. | N.D. | N.D. | <0.05 | N.D. | N.D. | N.D. |
| 0.4-0.45 | N.D. | <0.05 | N.D. | <0.05 | N.D. | N.D. | N.D. |
| 0.48-0.51 | N.D. | N.D. | N.D. | N.D. | N.D. | N.D. | N.D. |
| 0.57-0.59 | N.D. | <0.05 | 0.05 | 0.05 | 0.09 | N.D. | N.D. |
| 0.59 | N.D. | N.D. | N.D. | N.D. | N.D. | N.D. | N.D. |
| 0.72 | N.D. | N.D. | N.D. | N.D. | N.D. | N.D. | N.D. |
| 0.87-0.89 | N.D. | <0.05 | <0.05 | <0.05 | <0.05 | N.D. | <0.05 |
| 1.00 | 99.64 | 98.59 | 98.54 | 94.86 | 90.67 | 99.73 | 99.63 |
| 1.35-1.37 | N.D. | N.D. | N.D. | N.D. | <0.05 | N.D. | N.D. |
| 2.19-2.25 | N.D. | 0.06 | 0.11 | 0.19 | 0.47 | N.D. | N.D. |
| 2.37-2.39 | N.D. | N.D. | N.D. | N.D. | N.D. | N.D. | N.D. |
| 3.36-3.45 | N.D. | N.D. | N.D. | <0.05 | 0.11 | N.D. | N.D. |
| 3.67-3.72(3.77-3.79)Alvocidib | 0.36 | 1.15 | 1.21 | 4.71 | 8.50 | 0.20 | 0.29 |
| 4.75-4.91 | N.D. | N.D. | N.D. | N.D. | N.D. | N.D. | N.D. |
| Total impurity | 0.36 | 1.30 | 1.45 | 5.04 | 9.26 | 0.27 | 0.35 |
| Δimpurity | | 0.94 | 1.09 | 4.68 | 8.90 | −0.09 | −0.01 |

TABLE 22H

| | KollidonCL | | | | | | |
| --- | --- | --- | --- | --- | --- | --- | --- |
| | | 60° C. | | 50° C. 85% | | Photostability | |
| Disintegrant RRT | Initial % Area | 2 W % Area | 4 W % Area | 2 W % Area | 4 W % Area | 60 Lux % Area | 120 Lux % Area |
| 0.26-0.27 | N.D. | N.D. | N.D. | N.D. | N.D. | N.D. | N.D. |
| 0.38-0.41 | N.D. | N.D. | N.D. | N.D. | N.D. | N.D. | N.D. |
| 0.4-0.45 | N.D. | <0.05 | N.D. | N.D. | <0.05 | N.D. | N.D. |
| 0.48-0.51 | N.D. | N.D. | N.D. | N.D. | N.D. | N.D. | N.D. |
| 0.57-0.59 | N.D. | 0.19 | 0.33 | 0.10 | 0.21 | N.D. | <0.05 |
| 0.59 | N.D. | N.D. | N.D. | 0.28 | 0.14 | N.D. | N.D. |
| 0.72 | N.D. | N.D. | N.D. | <0.05 | N.D. | N.D. | N.D. |
| 0.87-0.89 | N.D. | 0.07 | 0.18 | 0.07 | 0.08 | <0.05 | 0.07 |
| 1.00 | 99.62 | 96.41 | 98.26 | 78.75 | 59.59 | 99.66 | 99.48 |
| 1.35-1.37 | N.D. | N.D. | N.D. | N.D. | N.D. | N.D. | N.D. |
| 2.19-2.25 | N.D. | 0.20 | 0.09 | 0.27 | 0.70 | N.D. | N.D. |

TABLE 22H-continued

| | KollidonCL | | | | | | |
|---|---|---|---|---|---|---|---|
| | | 60° C. | | 50° C. 85% | | Photostability | |
| Disintegrant RRT | Initial % Area | 2 W % Area | 4 W % Area | 2 W % Area | 4 W % Area | 60 Lux % Area | 120 Lux % Area |
| 2.37-2.39 | N.D. | N.D. | N.D. | 0.11 | 0.23 | N.D. | N.D. |
| 3.36-3.45 | N.D. | <0.05 | N.D. | N.D. | 0.06 | N.D. | N.D. |
| 3.67-3.72(3.77-3.79)Alvocidib | 0.38 | 2.71 | 1.14 | 18.88 | 38.97 | 0.30 | 0.41 |
| 4.75-4.91 | N.D. | 0.38 | N.D. | 1.50 | N.D. | N.D. | N.D. |
| Total impurity | 0.38 | 3.55 | 1.74 | 21.21 | 40.39 | 0.30 | 0.48 |
| Δimpurity | | 3.17 | 1.36 | 20.83 | 40.01 | −0.08 | 0.10 |

TABLE 22I

| | L-HPC(LH-21) | | | | | | |
|---|---|---|---|---|---|---|---|
| | | 60° C. | | 50° C. 85% | | Photostability | |
| Disintegrant RRT | Initial % Area | 2 W % Area | 4 W % Area | 2 W % Area | 4 W % Area | 60 Lux % Area | 120 Lux % Area |
| 0.26-0.27 | N.D. | N.D. | N.D. | N.D. | N.D. | N.D. | N.D. |
| 0.38-0.41 | N.D. | <0.05 | N.D. | N.D. | N.D. | N.D. | N.D. |
| 0.4-0.45 | N.D. | <0.05 | N.D. | N.D. | <0.05 | N.D. | N.D. |
| 0.48-0.51 | N.D. | N.D. | N.D. | N.D. | N.D. | N.D. | N.D. |
| 0.57-0.59 | N.D. | 0.09 | 0.09 | 0.06 | 0.08 | N.D. | <0.05 |
| 0.59 | N.D. | N.D. | N.D. | N.D. | N.D. | N.D. | N.D. |
| 0.72 | N.D. | N.D. | N.D. | N.D. | N.D. | N.D. | N.D. |
| 0.87-0.89 | N.D. | 0.06 | 0.05 | <0.05 | <0.05 | 0.05 | 0.07 |
| 1.00 | 99.63 | 97.29 | 97.20 | 94.21 | 91.11 | 99.67 | 99.47 |
| 1.35-1.37 | N.D. | N.D. | N.D. | N.D. | N.D. | N.D. | N.D. |
| 2.19-2.25 | N.D. | 0.19 | 0.24 | 0.17 | 0.31 | N.D. | N.D. |
| 2.37-2.39 | N.D. | N.D. | N.D. | N.D. | N.D. | N.D. | N.D. |
| 3.36-3.45 | N.D. | N.D. | <0.05 | <0.05 | 0.07 | N.D. | N.D. |
| 3.67-3.72(3.77-3.79)Alvocidib | 0.37 | 2.31 | 2.40 | 5.50 | 8.37 | 0.28 | 0.43 |
| 4.75-4.91 | N.D. | N.D. | N.D. | N.D. | N.D. | N.D. | N.D. |
| Total impurity | 0.37 | 2.65 | 2.78 | 5.73 | 8.83 | 0.33 | 0.50 |
| Δimpurity | | 2.28 | 2.41 | 5.36 | 8.46 | −0.04 | 0.13 |

TABLE 22J

| | ECG505 | | | | | | |
|---|---|---|---|---|---|---|---|
| | | 60° C. | | 50° C. 85% | | Photostability | |
| Disintegrant RRT | Initial % Area | 2 W % Area | 4 W % Area | 2 W % Area | 4 W % Area | 60 Lux % Area | 120 Lux % Area |
| 0.26-0.27 | N.D. | N.D. | N.D. | N.D. | N.D. | N.D. | N.D. |
| 0.38-0.41 | N.D. | N.D. | N.D. | N.D. | N.D. | N.D. | N.D. |
| 0.4-0.45 | N.D. | N.D. | N.D. | N.D. | N.D. | N.D. | N.D. |
| 0.48-0.51 | N.D. | N.D. | N.D. | N.D. | N.D. | N.D. | N.D. |
| 0.57-0.59 | N.D. | 0.07 | 0.07 | 0.05 | 0.07 | N.D. | <0.05 |
| 0.59 | N.D. | N.D. | N.D. | N.D. | N.D. | N.D. | N.D. |
| 0.72 | N.D. | N.D. | N.D. | N.D. | N.D. | N.D. | N.D. |
| 0.87-0.89 | N.D. | 0.07 | 0.05 | <0.05 | <0.05 | <0.05 | <0.05 |
| 1.00 | 99.72 | 98.81 | 98.75 | 96.51 | 94.81 | 99.81 | 99.72 |
| 1.35-1.37 | N.D. | N.D. | N.D. | N.D. | N.D. | N.D. | N.D. |
| 2.19-2.25 | N.D. | 0.05 | 0.09 | 0.08 | 0.18 | N.D. | N.D. |

TABLE 22J-continued

| | ECG505 | | | | | | |
|---|---|---|---|---|---|---|---|
| | Initial | 60° C. | | 50° C. 85% | | Photostability | |
| Disintegrant RRT | % Area | 2 W % Area | 4 W % Area | 2 W % Area | 4 W % Area | 60 Lux % Area | 120 Lux % Area |
| 2.37-2.39 | N.D. | N.D. | N.D. | N.D. | N.D. | N.D. | N.D. |
| 3.36-3.45 | N.D. | N.D. | N.D. | N.D. | <0.05 | N.D. | N.D. |
| 3.67-3.72(3.77-3.79)Alvocidib | 0.28 | 1.00 | 1.04 | 3.33 | 4.89 | 0.17 | 0.22 |
| 4.75-4.91 | N.D. | N.D. | N.D. | N.D. | N.D. | N.D. | N.D. |
| Total impurity | 0.28 | 1.19 | 1.25 | 3.46 | 5.14 | 0.17 | 0.22 |
| Δimpurity | | 0.91 | 0.97 | 3.18 | 4.86 | −0.11 | −0.06 |

TABLE 22K

| | LIGAMED MF-2-V | | | | | | |
|---|---|---|---|---|---|---|---|
| | Initial | 60° C. | | 50° C. 85% | | Photostability | |
| Lubricant RRT | % Area | 2 W % Area | 4 W % Area | 2 W %Area | 4 W % Area | 60 Lux % Area | 120 Lux % Area |
| 0.4-0.45 | N.D. | <0.05 | N.D. | N.D. | <0.05 | <0.05 | N.D. |
| 0.48-0.51 | N.D. | N.D. | <0.05 | <0.05 | 0.05 | <0.05 | N.D. |
| 0.57-0.59 | N.D. | 0.08 | 0.13 | 0.10 | 0.25 | 0.08 | <0.05 |
| 0.59 | N.D. | N.D. | N.D. | 0.09 | N.D. | N.D. | N.D. |
| 0.68 | N.D. | N.D. | N.D. | N.D. | N.D. | N.D. | N.D. |
| 0.76-0.77 | N.D. | N.D. | <0.05 | N.D. | N.D. | N.D. | N.D. |
| 0.87-0.89 | N.D. | 0.17 | 0.10 | 0.17 | 0.16 | N.D. | <0.05 |
| 1.00 | 99.88 | 97.61 | 97.55 | 88.71 | 68.97 | 99.74 | 99.77 |
| 1.17-1.18 | N.D. | N.D. | N.D. | N.D. | N.D. | N.D. | N.D. |
| 1.35-1.37 | N.D. | N.D. | <0.05 | 0.17 | 0.36 | <0.05 | N.D. |
| 2.19-2.25 | N.D. | 0.09 | 0.13 | 1.00 | 3.24 | N.D. | N.D. |
| 3.36-3.45 | N.D. | N.D. | N.D. | 0.14 | 0.66 | N.D. | N.D. |
| 3.67-3.72(3.77-3.79)Alvocidib | 0.12 | 2.03 | 2.03 | 9.59 | 26.29 | 0.10 | 0.17 |
| 4.75-4.91 | N.D. | N.D. | N.D. | <0.05 | N.D. | N.D. | N.D. |
| Total impurity | 0.12 | 2.37 | 2.39 | 11.26 | 31.01 | 0.18 | 0.17 |
| Δimpurity | | 2.25 | 2.27 | 11.14 | 30.89 | 0.06 | 0.05 |

TABLE 22L

| | PRUV | | | | | | |
|---|---|---|---|---|---|---|---|
| | Initial | 60° C. | | 50° C. 85% | | Photostability | |
| Lubricant RRT | % Area | 2 W % Area | 4 W % Area | 2 W % Area | 4 W % Area | 60 Lux % Area | 120 Lux % Area |
| 0.4-0.45 | N.D. | N.D. | N.D. | N.D. | N.D. | N.D. | N.D. |
| 0.48-0.51 | N.D. | N.D. | N.D. | N.D. | <0.05 | N.D. | N.D. |
| 0.57-0.59 | N.D. | <0.05 | 0.10 | <0.05 | 0.70 | 0.17 | <0.05 |
| 0.59 | N.D. | N.D. | N.D. | N.D. | N.D. | N.D. | N.D. |
| 0.68 | N.D. | N.D. | N.D. | N.D. | N.D. | N.D. | N.D. |
| 0.76-0.77 | N.D. | N.D. | N.D. | N.D. | N.D. | N.D. | N.D. |
| 0.87-0.89 | N.D. | N.D. | N.D. | <0.05 | 0.20 | <0.05 | N.D. |
| 1.00 | 99.89 | 99.54 | 97.78 | 98.00 | 7.62 | 99.63 | 99.81 |
| 1.17-1.18 | N.D. | N.D. | <0.05 | N.D. | N.D. | <0.05 | N.D. |
| 1.35-1.37 | N.D. | N.D. | <0.05 | N.D. | 0.10 | <0.05 | N.D. |
| 2.19-2.25 | N.D. | N.D. | 0.11 | 0.10 | 5.01 | N.D. | N.D. |

TABLE 22L-continued

| | PRUV | | | | | | |
|---|---|---|---|---|---|---|---|
| | | 60° C. | | 50° C. 85% | | Photostability | |
| Lubricant RRT | Initial % Area | 2 W % Area | 4 W % Area | 2 W % Area | 4 W % Area | 60 Lux % Area | 120 Lux % Area |
| 3.36-3.45 | N.D. | N.D. | N.D. | <0.05 | 0.57 | N.D. | N.D. |
| 3.67-3.72(3.77-3.79)Alvocidib | 0.11 | 0.43 | 1.97 | 1.80 | 85.74 | 0.11 | 0.16 |
| 4.75-4.91 | N.D. | N.D. | N.D. | N.D. | N.D. | N.D. | N.D. |
| Total impurity | 0.11 | 0.43 | 2.18 | 1.90 | 92.32 | 0.28 | 0.16 |
| Δimpurity | | 0.32 | 2.07 | 1.79 | 92.21 | 0.17 | 0.05 |

TABLE 22M

| | Talc MS-P | | | | | | |
|---|---|---|---|---|---|---|---|
| | | 60° C. | | 50° C. 85% | | Photostability | |
| Lubricant RRT | Initial % Area | 2 W % Area | 4 W % Area | 2 W % Area | 4 W % Area | 60 Lux % Area | 120 Lux % Area |
| 0.4-0.45 | N.D. | <0.05 | N.D. | N.D. | N.D. | N.D. | N.D. |
| 0.48-0.51 | N.D. | N.D. | N.D. | N.D. | N.D. | N.D. | N.D. |
| 0.57-0.59 | N.D. | N.D. | 0.05 | 0.19 | 0.05 | N.D. | N.D. |
| 0.59 | N.D. | N.D. | N.D. | 0.08 | N.D. | N.D. | N.D. |
| 0.68 | N.D. | N.D. | N.D. | <0.05 | N.D. | N.D. | N.D. |
| 0.76-0.77 | N.D. | N.D. | N.D. | N.D. | N.D. | N.D. | N.D. |
| 0.87-0.89 | N.D. | <0.05 | <0.05 | 0.24 | <0.05 | N.D. | N.D. |
| 1.00 | 99.74 | 99.71 | 99.04 | 79.22 | 96.62 | 99.90 | 99.84 |
| 1.17-1.18 | N.D. | N.D. | N.D. | N.D. | N.D. | N.D. | N.D. |
| 1.35-1.37 | N.D. | N.D. | N.D. | 0.06 | <0.05 | N.D. | N.D. |
| 2.19-2.25 | N.D. | N.D. | 0.10 | 0.70 | 0.21 | N.D. | N.D. |
| 3.36-3.45 | N.D. | N.D. | N.D. | 0.05 | 0.05 | N.D. | N.D. |
| 3.67-3.72(3.77-3.79)Alvocidib | 0.26 | 0.24 | 0.77 | 19.44 | 3.02 | 0.10 | 0.26 |
| 4.75-4.91 | N.D. | N.D. | N.D. | N.D. | N.D. | N.D. | N.D. |
| Total impurity | 0.26 | 0.24 | 0.92 | 20.76 | 3.33 | 0.10 | 0.26 |
| Δimpurity | | −0.02 | 0.66 | 20.50 | 3.07 | −0.16 | 0.00 |

TABLE 22N

| | Aerosil 200 | | | | | | |
|---|---|---|---|---|---|---|---|
| | | 60° C. | | 50° C. 85% | | Photostability | |
| Fluidizer RRT | Initial % Area | 2 W % Area | 4 W % Area | 2 W % Area | 4 W % Area | 60 Lux % Area | 120 Lux % Area |
| 0.4-0.45 | N.D. | <0.05 | N.D. | N.D. | N.D. | N.D. | N.D. |
| 0.57-0.59 | N.D. | N.D. | N.D. | 0.12 | 0.14 | N.D. | N.D. |
| 0.87-0.89 | N.D. | N.D. | 0.05 | <0.05 | 0.05 | <0.05 | N.D. |
| 1.00 | 99.69 | 99.46 | 99.45 | 84.21 | 77.22 | 99.80 | 99.77 |
| 2.19-2.25 | N.D. | N.D. | <0.05 | 0.17 | 0.32 | N.D. | N.D. |
| 3.67-3.72(3.77-3.79)Alvocidib | 0.31 | 0.52 | 0.47 | 15.46 | 22.27 | 0.17 | 0.23 |
| Total impurity | 0.31 | 0.52 | 0.52 | 15.75 | 22.78 | 0.17 | 0.23 |
| Δimpurity | | 0.21 | 0.21 | 15.44 | 22.47 | −0.14 | −0.08 |

TABLE 22O

| Others RRT | Initial % Area | Fumaric acid | | | | | |
|---|---|---|---|---|---|---|---|
| | | 60° C. | | 50° C. 85% | | Photostability | |
| | | 2 W % Area | 4 W % Area | 2 W % Area | 4 W % Area | 60 Lux % Area | 120 Lux % Area |
| 0.38-0.41 | N.D. | N.D. | N.D. | N.D. | N.D. | N.D. | N.D. |
| 0.4-0.45 | N.D. | N.D. | N.D. | N.D. | 61.79 | N.D. | N.D. |
| 0.48-0.51 | N.D. | 0.06 | 0.07 | <0.05 | <0.05 | N.D. | <0.05 |
| 0.57-0.59 | N.D. | 0.07 | 0.08 | 0.05 | 0.07 | N.D. | <0.05 |
| 0.72 | N.D. | N.D. | N.D. | N.D. | N.D. | N.D. | N.D. |
| 0.76-0.77 | N.D. | N.D. | N.D. | N.D. | N.D. | N.D. | N.D. |
| 0.87-0.89 | N.D. | 0.05 | 0.05 | <0.05 | <0.05 | N.D. | <0.05 |
| 1.00 | 99.50 | 98.57 | 98.61 | 96.65 | 34.52 | 99.71 | 99.35 |
| 1.28 | N.D. | N.D. | N.D. | N.D. | N.D. | N.D. | N.D. |
| 1.35-1.37 | N.D. | N.D. | N.D. | N.D. | <0.05 | N.D. | N.D. |
| 2.08 | N.D. | N.D. | N.D. | N.D. | N.D. | N.D. | N.D. |
| 2.19-2.25 | N.D. | <0.05 | 0.06 | 0.11 | 0.20 | N.D. | N.D. |
| 2.37-2.39 | N.D. | N.D. | N.D. | N.D. | N.D. | N.D. | N.D. |
| 2.49 | N.D. | N.D. | N.D. | N.D. | N.D. | N.D. | N.D. |
| 3.16 | N.D. | N.D. | N.D. | N.D. | N.D. | N.D. | N.D. |
| 3.36-3.45 | N.D. | N.D. | N.D. | N.D. | <0.05 | N.D. | N.D. |
| 3.59 | N.D. | N.D. | N.D. | N.D. | N.D. | N.D. | N.D. |
| 3.62-3.71 | N.D. | N.D. | N.D. | N.D. | N.D. | N.D. | N.D. |
| 3.67-3.72(3.77-3.79)Alvocidib | 0.50 | 1.22 | 1.14 | 3.13 | 3.31 | 0.29 | 0.57 |
| 3.89 | N.D. | N.D. | N.D. | N.D. | N.D. | N.D. | N.D. |
| 4.27 | N.D. | N.D. | N.D. | N.D. | N.D. | N.D. | N.D. |
| 4.51 | N.D. | N.D. | N.D. | N.D. | N.D. | N.D. | N.D. |
| 4.61 | N.D. | N.D. | N.D. | N.D. | N.D. | N.D. | N.D. |
| 4.70 | N.D. | N.D. | N.D. | N.D. | N.D. | N.D. | N.D. |
| 4.75-4.91 | N.D. | N.D. | N.D. | N.D. | N.D. | N.D. | N.D. |
| 5.03 | N.D. | N.D. | N.D. | N.D. | N.D. | N.D. | N.D. |
| 5.14 | N.D. | N.D. | N.D. | N.D. | N.D. | N.D. | N.D. |
| 5.32 | N.D. | N.D. | N.D. | N.D. | N.D. | N.D. | N.D. |
| 5.58 | N.D. | N.D. | N.D. | N.D. | N.D. | N.D. | N.D. |
| 6.05 | N.D. | N.D. | N.D. | N.D. | N.D. | N.D. | N.D. |
| 6.13 | N.D. | N.D. | N.D. | N.D. | N.D. | N.D. | N.D. |
| 6.34 | N.D. | N.D. | N.D. | N.D. | N.D. | N.D. | N.D. |
| 6.46 | N.D. | N.D. | N.D. | N.D. | N.D. | N.D. | N.D. |
| 6.54 | N.D. | N.D. | N.D. | N.D. | N.D. | N.D. | N.D. |
| 7.05 | N.D. | N.D. | N.D. | N.D. | N.D. | N.D. | N.D. |
| 7.09 | N.D. | N.D. | N.D. | N.D. | N.D. | N.D. | N.D. |
| Total impurity | 0.50 | 1.40 | 1.40 | 3.29 | 65.37 | 0.29 | 0.57 |
| Δimpurity | | 0.90 | 0.90 | 2.79 | 64.87 | −0.21 | 0.07 |

TABLE 22P

| Others RRT | Initial % Area | Succinic acid | | | | | |
|---|---|---|---|---|---|---|---|
| | | 60° C. | | 50° C. 85% | | Photostability | |
| | | 2 W % Area | 4 W % Area | 2 W % Area | 4 W % Area | 60 Lux % Area | 120 Lux % Area |
| 0.38-0.41 | N.D. | N.D. | N.D. | N.D. | N.D. | N.D. | N.D. |
| 0.4-0.45 | N.D. | 0.22 | N.D. | <0.05 | N.D. | N.D. | N.D. |
| 0.48-0.51 | N.D. | <0.05 | N.D. | 0.15 | 0.09 | N.D. | N.D. |
| 0.57-0.59 | N.D. | 0.28 | 0.21 | 2.31 | 2.34 | <0.05 | <0.05 |
| 0.72 | N.D. | N.D. | N.D. | N.D. | N.D. | N.D. | N.D. |
| 0.76-0.77 | N.D. | N.D. | N.D. | N.D. | N.D. | N.D. | N.D. |
| 0.87-0.89 | N.D. | 0.09 | N.D. | 0.78 | 0.26 | <0.05 | <0.05 |
| 1.00 | 99.50 | 93.38 | 93.23 | 26.27 | 0.41 | 99.53 | 99.16 |
| 1.28 | N.D. | N.D. | N.D. | N.D. | N.D. | N.D. | N.D. |
| 1.35-1.37 | N.D. | N.D. | N.D. | 0.06 | N.D. | N.D. | N.D. |
| 2.08 | N.D. | N.D. | N.D. | N.D. | N.D. | N.D. | N.D. |
| 2.19-2.25 | N.D. | 0.24 | 0.36 | 2.87 | 4.49 | N.D. | N.D. |
| 2.37-2.39 | N.D. | N.D. | N.D. | N.D. | N.D. | N.D. | N.D. |
| 2.49 | N.D. | N.D. | N.D. | N.D. | N.D. | N.D. | N.D. |
| 3.16 | N.D. | N.D. | N.D. | N.D. | N.D. | N.D. | N.D. |
| 3.36-3.45 | N.D. | N.D. | <0.05 | 0.08 | 0.20 | N.D. | N.D. |
| 3.59 | N.D. | N.D. | <0.05 | N.D. | N.D. | N.D. | N.D. |
| 3.62-3.71 | N.D. | 0.19 | 0.19 | 1.05 | 0.36 | N.D. | N.D. |
| 3.67-3.72(3.77- | 0.50 | 5.55 | 5.96 | 66.40 | 91.85 | 0.42 | 0.75 |

TABLE 22P-continued

| | Succinic acid | | | | | | |
|---|---|---|---|---|---|---|---|
| | | 60° C. | | 50° C. 85% | | Photostability | |
| Others RRT | Initial % Area | 2 W % Area | 4 W % Area | 2 W % Area | 4 W % Area | 60 Lux % Area | 120 Lux % Area |
| 3.79)Alvocidib | | | | | | | |
| 3.89 | N.D. | N.D. | N.D. | N.D. | N.D. | N.D. | N.D. |
| 4.27 | N.D. | N.D. | N.D. | N.D. | N.D. | N.D. | N.D. |
| 4.51 | N.D. | N.D. | N.D. | N.D. | N.D. | N.D. | N.D. |
| 4.61 | N.D. | N.D. | N.D. | N.D. | N.D. | N.D. | N.D. |
| 4.70 | N.D. | N.D. | N.D. | N.D. | N.D. | N.D. | N.D. |
| 4.75-4.91 | N.D. | N.D. | N.D. | N.D. | N.D. | N.D. | N.D. |
| 5.03 | N.D. | N.D. | N.D. | N.D. | N.D. | N.D. | N.D. |
| 5.14 | N.D. | N.D. | N.D. | N.D. | N.D. | N.D. | N.D. |
| 5.32 | N.D. | N.D. | N.D. | N.D. | N.D. | N.D. | N.D. |
| 5.58 | N.D. | N.D. | N.D. | N.D. | N.D. | N.D. | N.D. |
| 6.05 | N.D. | N.D. | N.D. | N.D. | N.D. | N.D. | N.D. |
| 6.13 | N.D. | N.D. | N.D. | N.D. | N.D. | N.D. | N.D. |
| 6.34 | N.D. | N.D. | N.D. | N.D. | N.D. | N.D. | N.D. |
| 6.46 | N.D. | N.D. | N.D. | N.D. | N.D. | N.D. | N.D. |
| 6.54 | N.D. | N.D. | N.D. | N.D. | N.D. | N.D. | N.D. |
| 7.05 | N.D. | N.D. | N.D. | N.D. | N.D. | N.D. | N.D. |
| 7.09 | N.D. | N.D. | N.D. | N.D. | N.D. | N.D. | N.D. |
| Total impurity | 0.50 | 6.57 | 6.72 | 73.70 | 99.59 | 0.42 | 0.75 |
| Δimpurity | | 6.07 | 6.22 | 73.20 | 99.09 | −0.08 | 0.25 |

Samples were also tested for dissolution. Six capsules were tested for dissolution according to the parameters outlined in Table 23. Each capsule was weighed prior to dissolution testing. The stated amount of dissolution medium was transferred into each vessel in accordance with the capsule strength under analysis. The dissolution medium was allowed to equilibrate in the dissolution bath to 37° C.±0.5° C. The temperature of the dissolution medium checked at the start and end of the dissolution test for each vessel. At each sample point, the solution was transferred directly into an HPLC vial.

TABLE 23

| Dissolution Conditions | |
|---|---|
| Apparatus | USP Apparatus II (Paddles) |
| Paddle Speed | 50 ± 2 rpm |
| Temperature | 37° C. ± 0.5° C. |
| Filters | 45 μm Polyethylene (Distek) inline filters or GF-D filters |
| Dissolution Medium | USP pH 6.8 Phosphate buffer |
| Vessel Volume | 900 ml |
| Sample Times | 5, 10, 15, 30, 45 and 60 minutes |
| Infinity Time | 15 minutes (75 minutes sampling point) |
| Sampling Method -1 | Automated |
| Infinity spin speed | Automatic (200 rpm) |
| Sample Volume | 1.5 ml (Autosampler) |
| Pre-sample Rinse | 10.0 ml |
| Recirculate Media | No |
| Sampling Method - 2 | Manual |
| Infinity spin speed | 200 rpm |
| Sampling Volume | 10 ml |
| Transfer Volume | 1.5 ml into HPLC vial for injection |

The following calculations were used to calculate the sample concentration, amount released and percent released, respectively. P811 corresponds to the compound of structure (I).

$$k = \frac{A_{sam} \times W_{std} \times P}{A_{std} \times D_{std}}$$

Where:
k=P811 concentration (mg/ml)
Astd=mean area of the P811 peak in the standard chromatograms
Wstd weight of the reference standard (mg)
P=purity of the reference standard (expressed as a decimal)
Asamn=area of the P811 peak in the sample chromatogram
Dstd dilution of standard (ml)

$$A_n = k[M-(n-1)(T)] + \Sigma_{i=1}^{n-1} C_i T$$

Where:
An=cumulative amount of dissolved P811 from the first to the $n^{th}$ transfer (mg)
k=P811 concentration measured for the current transfer (mg/mi)
M initial medium volume (ml) ie. 900 ml
n=an index of dissolution transfers where n=1 for the $1^{st}$ transfer (5 minutes), n=2 for the $2^{nd}$ transfer (10 minutes), n=3 for the $3^{rd}$ transfer (16 minutes), n=4 for the $4^{th}$ transfer (30 minutes), n=5 for the $5^{th}$ transfer (45 minutes), n=6 for the $6^{th}$ transfer (60 minutes), n=7 for the $7^{th}$ transfer (75 minutes),
T=volume of sample removed (mi) i.e. 100 ml
$C_i$=concentration for the $i^{th}$ dissolution transfer (mg/ml)
For example:
At sampling point 1: $A_1 = kM$
At sampling point 2: $A_2 = k[M-T] + C_1 T$
At sampling point 3: $A_3 = k[M-2(T)] + C_1 T + C_2 T$ $$\% \text{ Released} = \frac{A_n}{LC} \times 100$$

Where:
An=cumulative amount of dissolved P811 from the first to the $n^{th}$ transfer (mg)
LC=label claim (16 mg, 4 mg and 1 mg)
The results of the dissolution testing are shown in FIGS. 9A-9D.

Example 14

Formulations of Compound of Structure (I) and Stabilities Thereof

The following mixtures of the compound of structure (I) were formulated into 1-mg strength capsules, wherein the percentages are calculated on a weight/weight basis:

| Formulation No. | 401-01 | 401-02 | 401-03 | 401-04 | 401-05 |
|---|---|---|---|---|---|
| Compound of Structure (I) | 0.60% | 0.60% | 0.60% | 0.60% | 0.60% |
| Lactose anhydrous | 97.40% | 98.40% | 99.40% | | |
| Cornstarch | | | | 98.40% | 99.40% |
| Light anhydrous silicic acid | 1% | | | | |
| Magnesium stearate | 1% | 1% | | 1% | |

The following mixture of the compound of structure (I) was formulated into a 4-mg strength capsule, wherein the percentages are calculated on a weight/weight basis:

| Formulation No. | 402 |
|---|---|
| Compound of Structure (I) | 2.47% |
| Lactose anhydrous | 95.53% |
| Light anhydrous silicic acid | 1% |
| Magnesium stearate | 1% |

The following mixtures of the compound of structure (I) were formulated into 16-mg strength capsules, wherein the percentages are calculated on a weight/weight basis:

| Formulation No. | 401-06 | 401-08 | 401-09 |
|---|---|---|---|
| Compound of Structure (I) | 11.03% | 11.03% | 11.03% |
| Lactose anhydrous | 86.97% | 88.97% | |
| Cornstarch | | | 87.97% |
| Light anhydrous silicic acid | 1% | | |
| Magnesium stearate | 1% | | 1% |

For manufacturing, a powder blend of compound of structure (I) and the indicated excipients were encapsulated into #4 hydroxypropylmethylcellulose (HPMC) capsules. The resulting capsules were immediate-release capsules.

Prior to encapsulation into the capsules, the drug product was made by direct blending via triturating the compound of structure (I) into the indicated excipients, followed by filling the capsules on a manual capsule filling machine in 100-capsule plates.

The capsules were packaged in aluminum blister packaging, with one capsule per blister and seven capsules per blister sheet. Three blisters on each sheet were left empty.

Figure 10A:
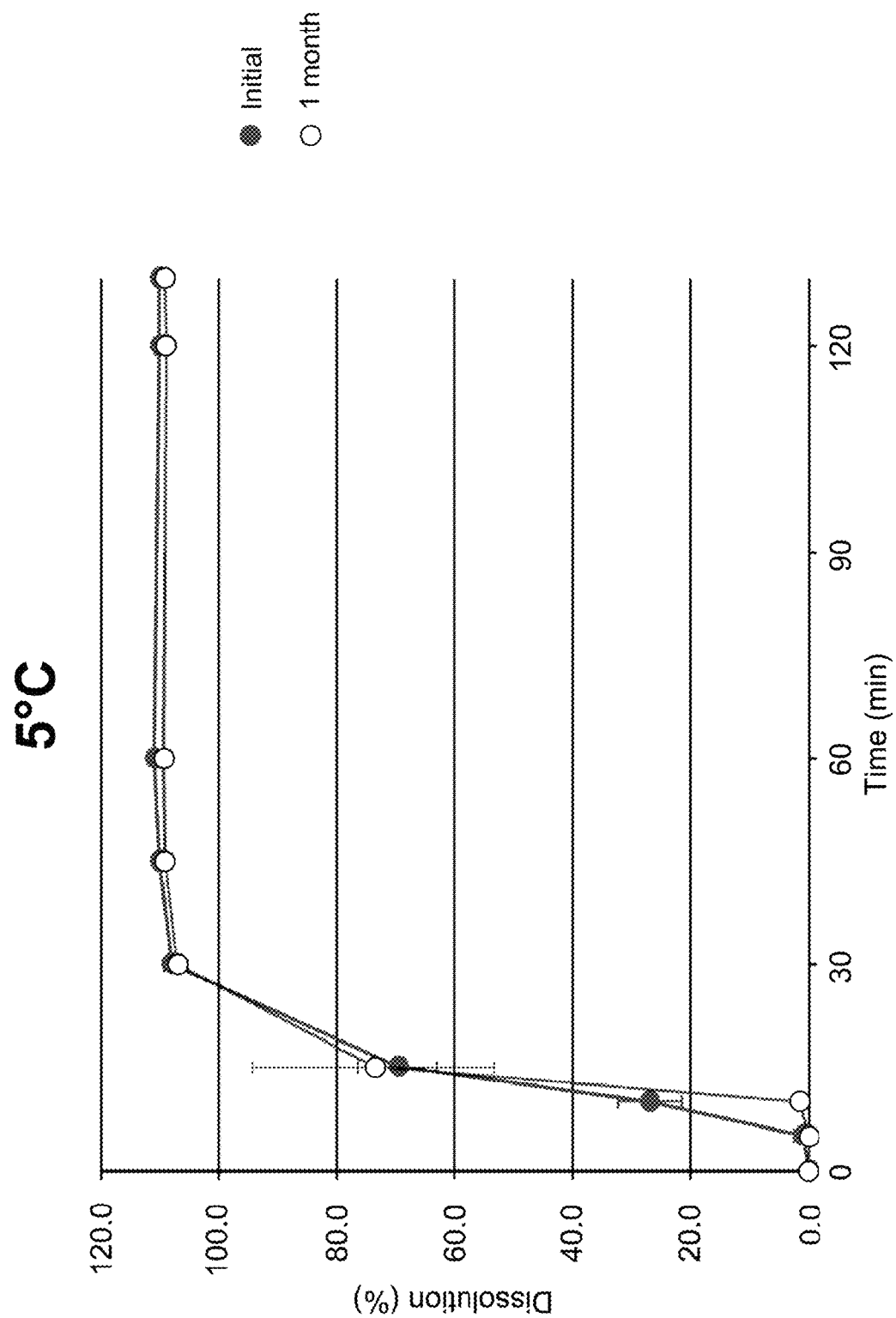
FIG. 10A is a graph of dissolution (%) versus time, and shows the amount of compound of structure (I) released from Formulation No. 401-01 of Example 14 stored at 5° C.
Figure 10B:
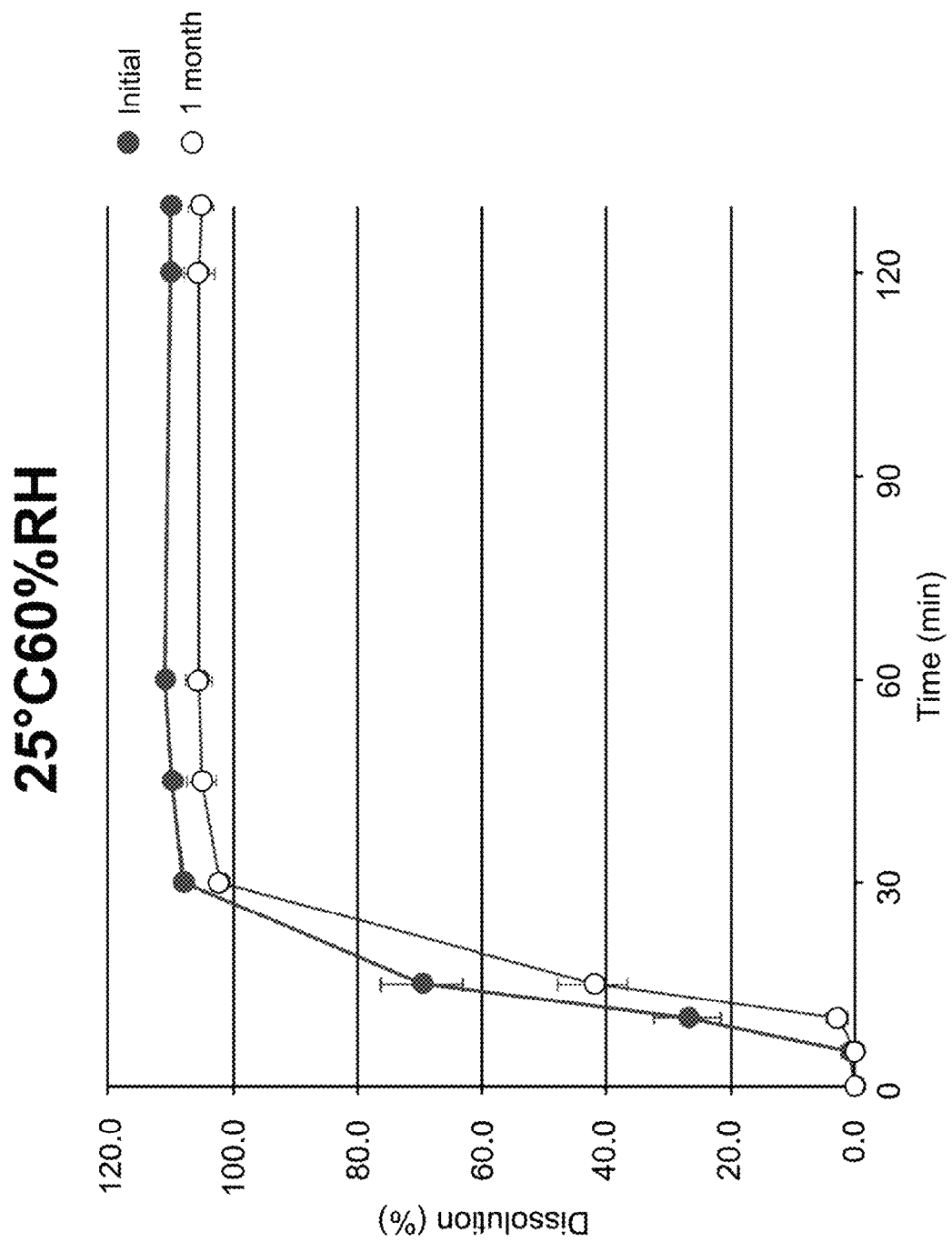
FIG. 10B is a graph of dissolution (%) versus time, and shows the amount of compound of structure (I) released from Formulation No. 401-01 of Example 14 stored at 25° C. and 60% relative humidity (RH).
Figure 10C:
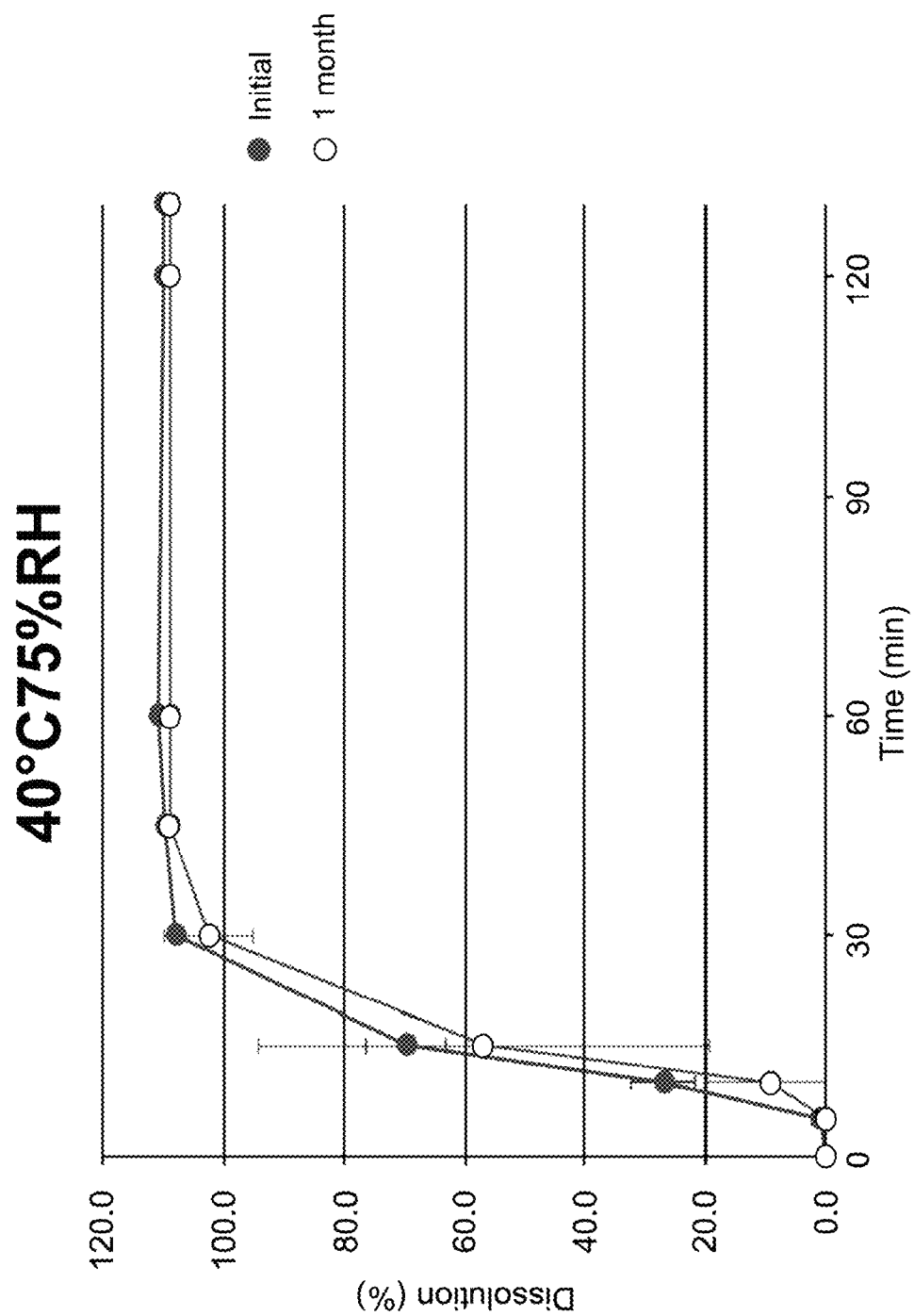
FIG. 10C is a graph of dissolution (%) versus time, and shows the amount of compound of structure (I) released from Formulation No. 401-01 of Example 14 stored at 40° C. and 75% RH.
Figure 10D:
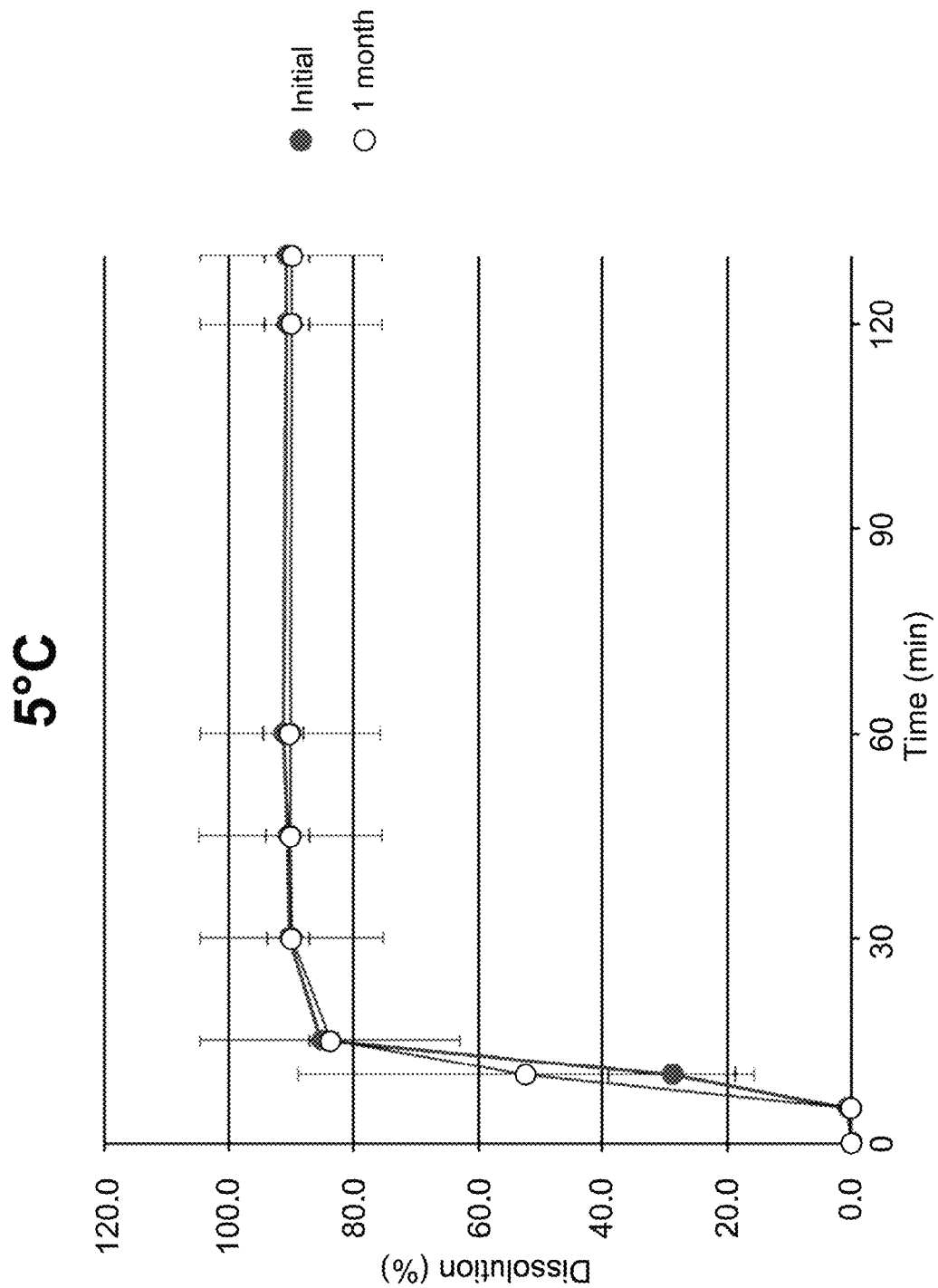
FIG. 10D is a graph of dissolution (%) versus time, and shows the amount of compound of structure (I) released from Formulation No. 401-02 of Example 14 stored at 5° C.
Figure 10E:
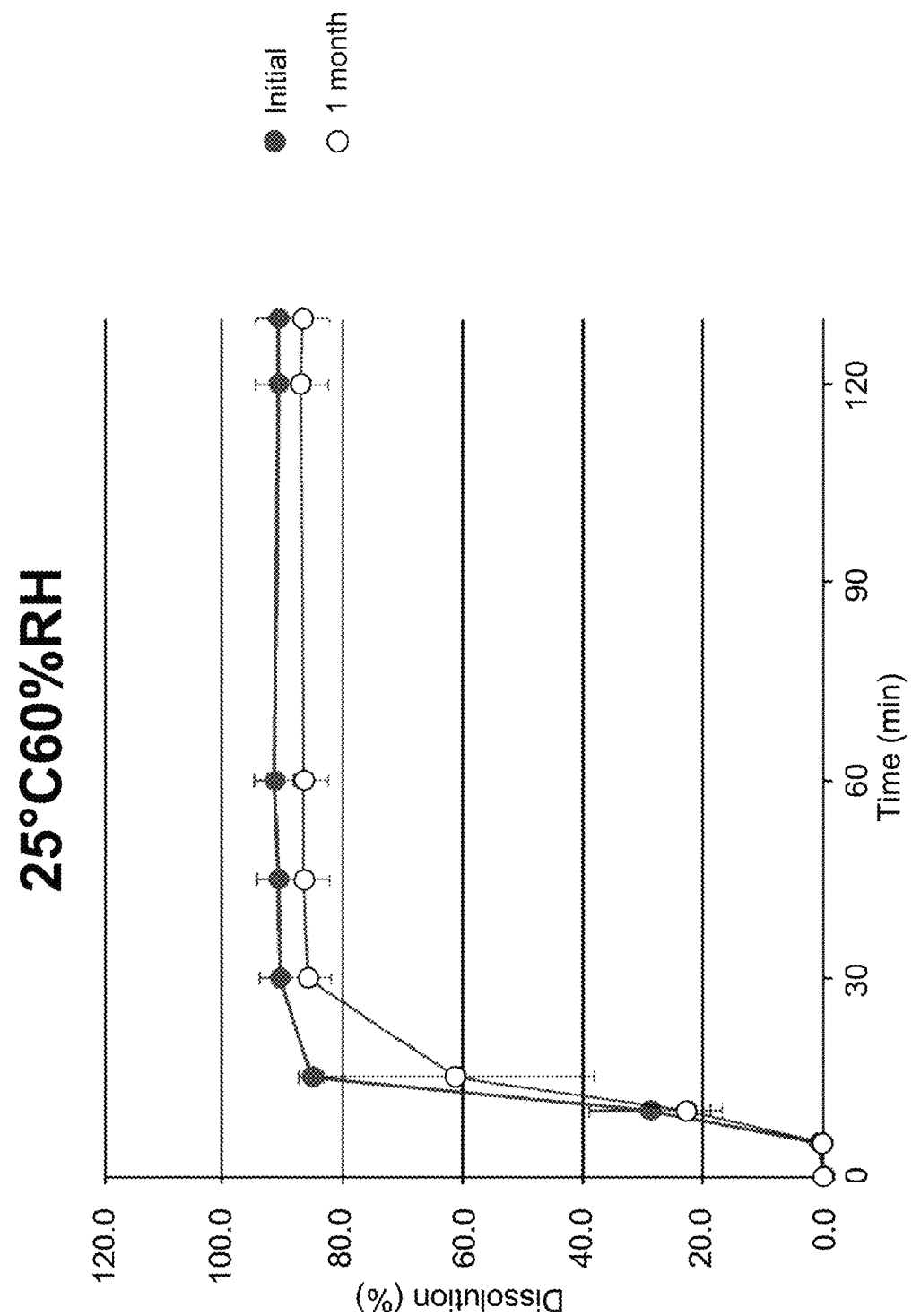
FIG. 10E is a graph of dissolution (%) versus time, and shows the amount of compound of structure (I) released from Formulation No. 401-02 of Example 14 stored at 25° C. and 60% RH.
Figure 10F:
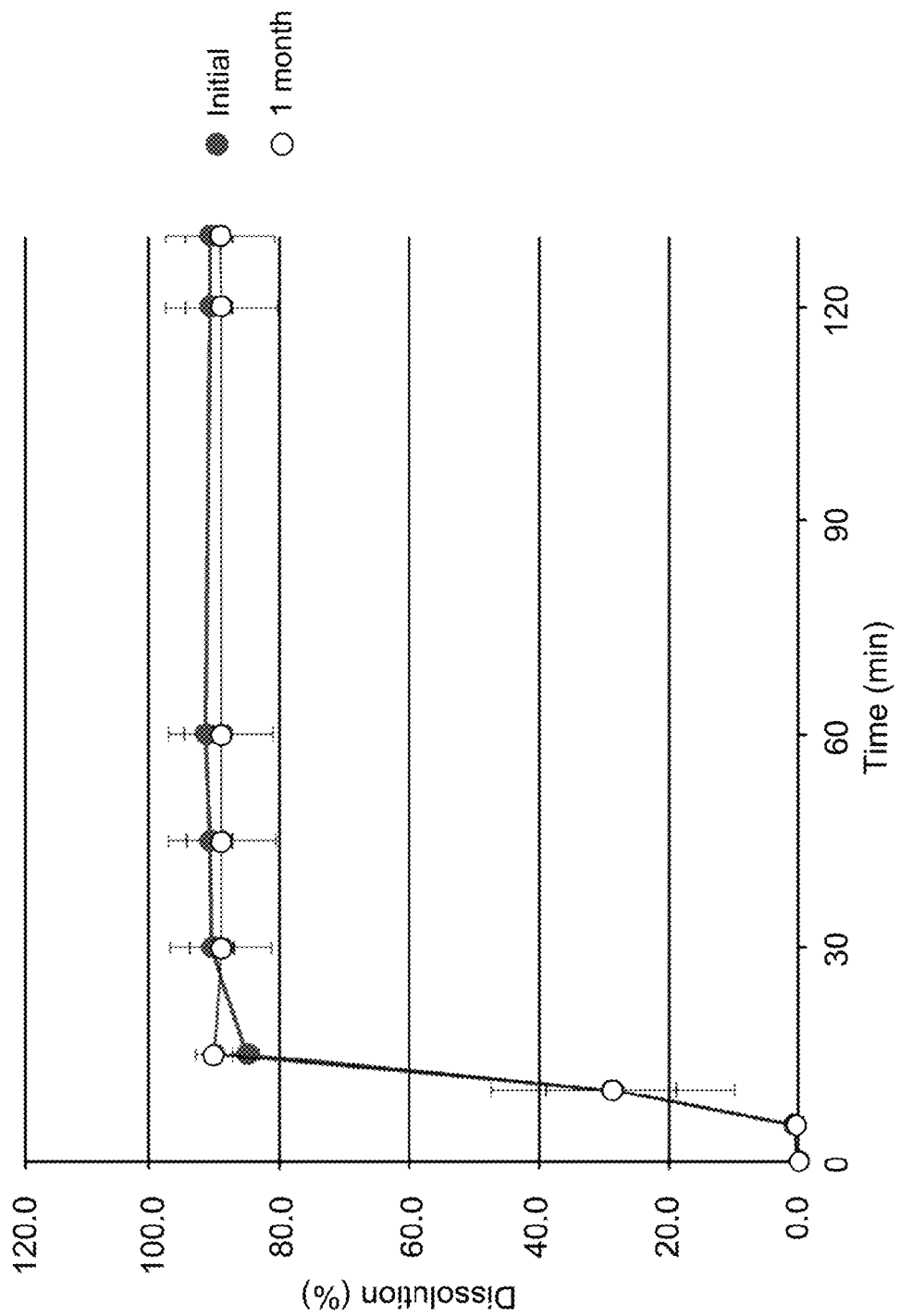
FIG. 10F is a graph of dissolution (%) versus time, and shows the amount of compound of structure (I) released from Formulation No. 401-02 of Example 14 stored at 40° C. and 75% RH.
Figure 10G:
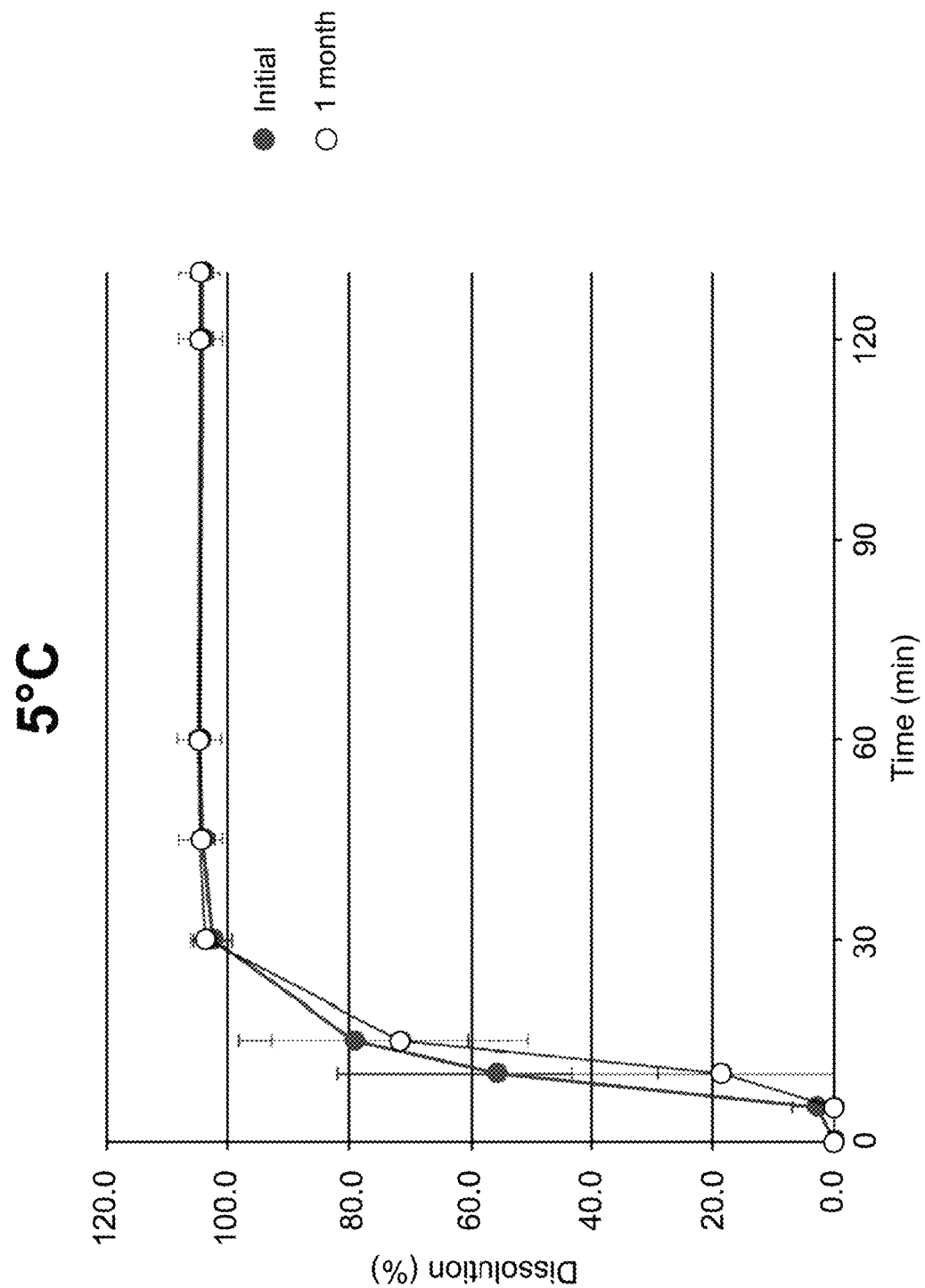
FIG. 10G is a graph of dissolution (%) versus time, and shows the amount of compound of structure (I) released from Formulation No. 401-03 of Example 14 stored at 5° C.
Figure 10H:
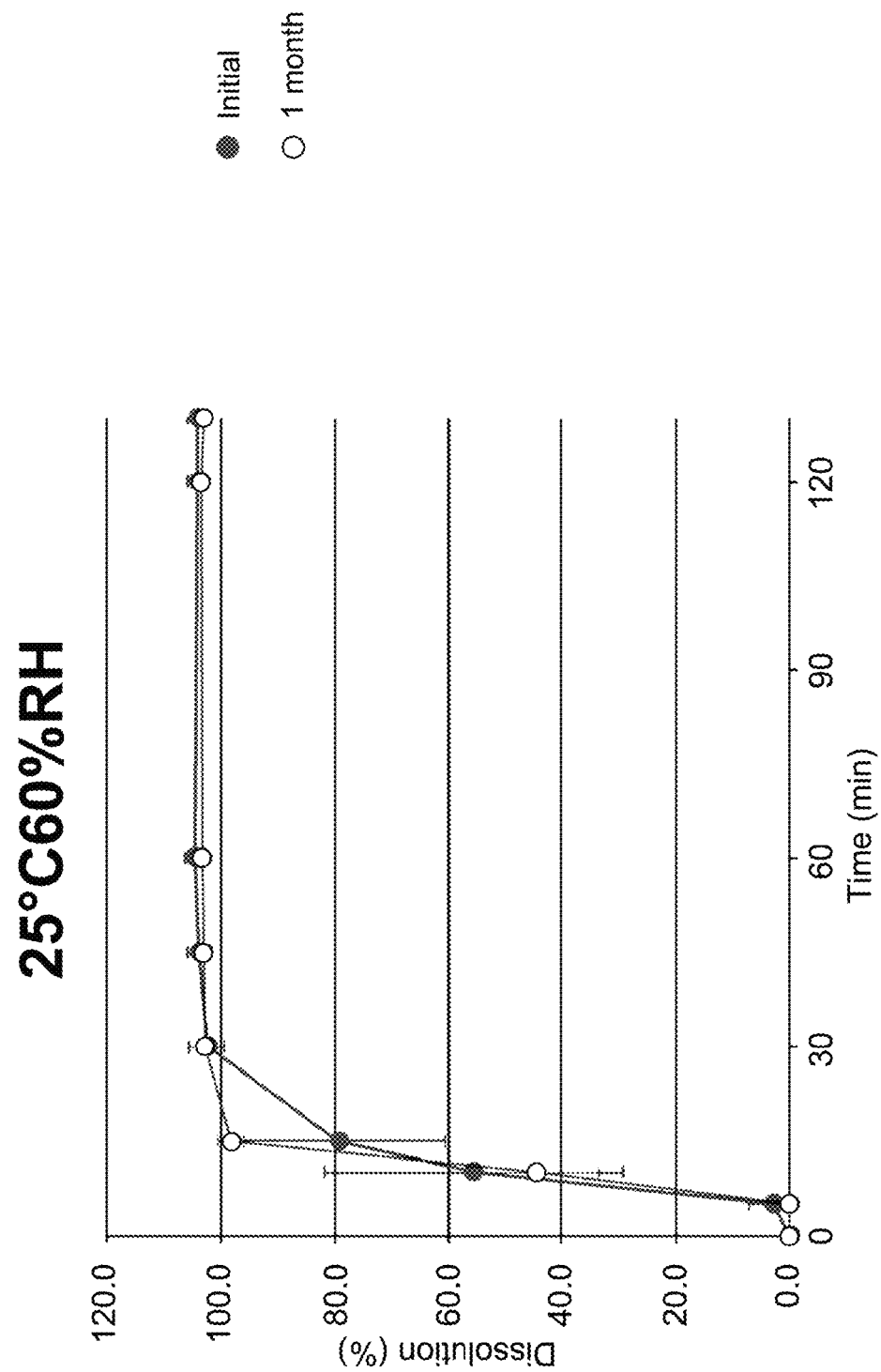
FIG. 10H is a graph of dissolution (%) versus time, and shows the amount of compound of structure (I) released from Formulation No. 401-03 of Example 14 stored at 25° C. and 60% RH.
Figure 10I:
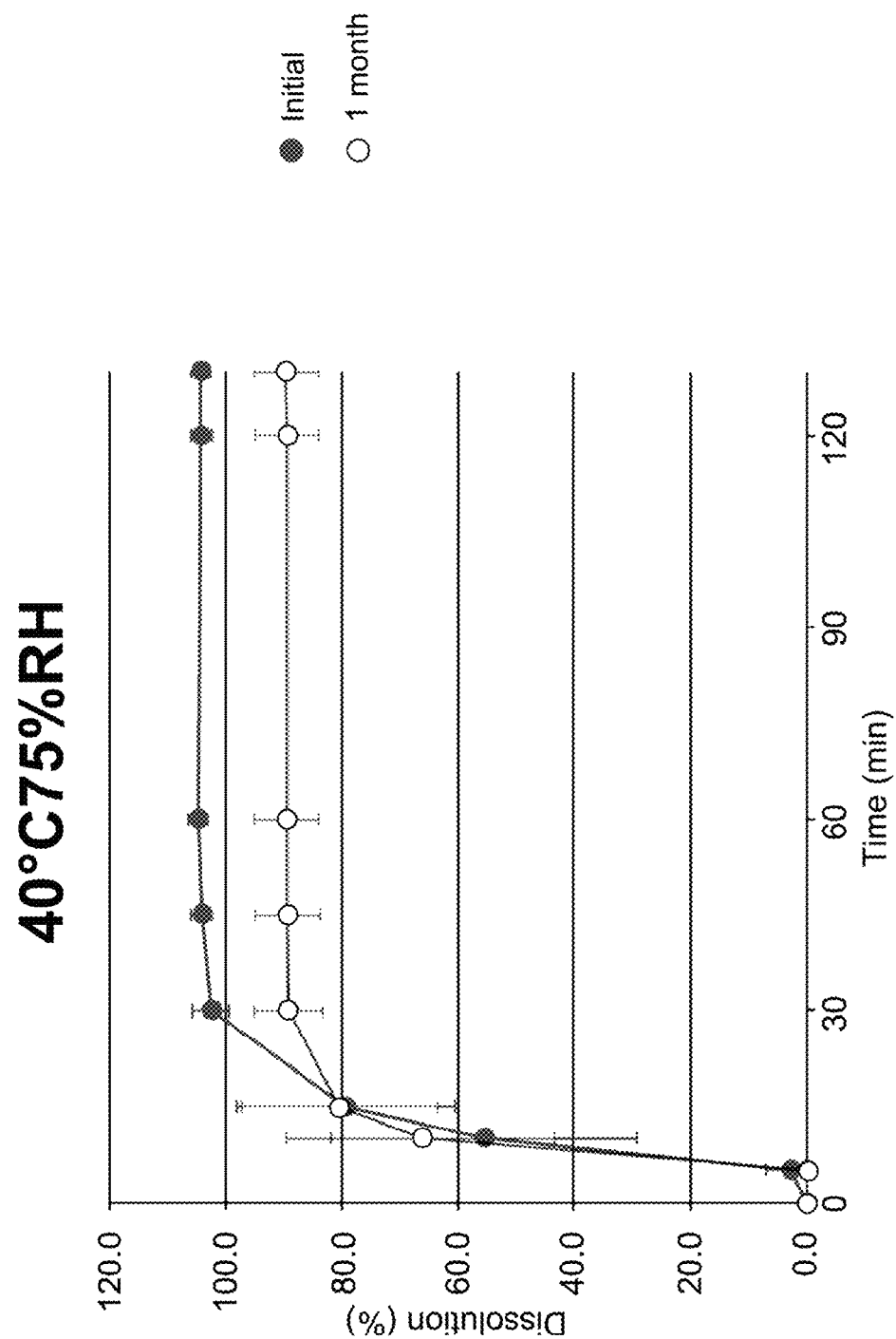
FIG. 10I is a graph of dissolution (%) versus time, and shows the amount of compound of structure (I) released from Formulation No. 401-03 of Example 14 stored at 40° C. and 75% RH.
Figure 10J:
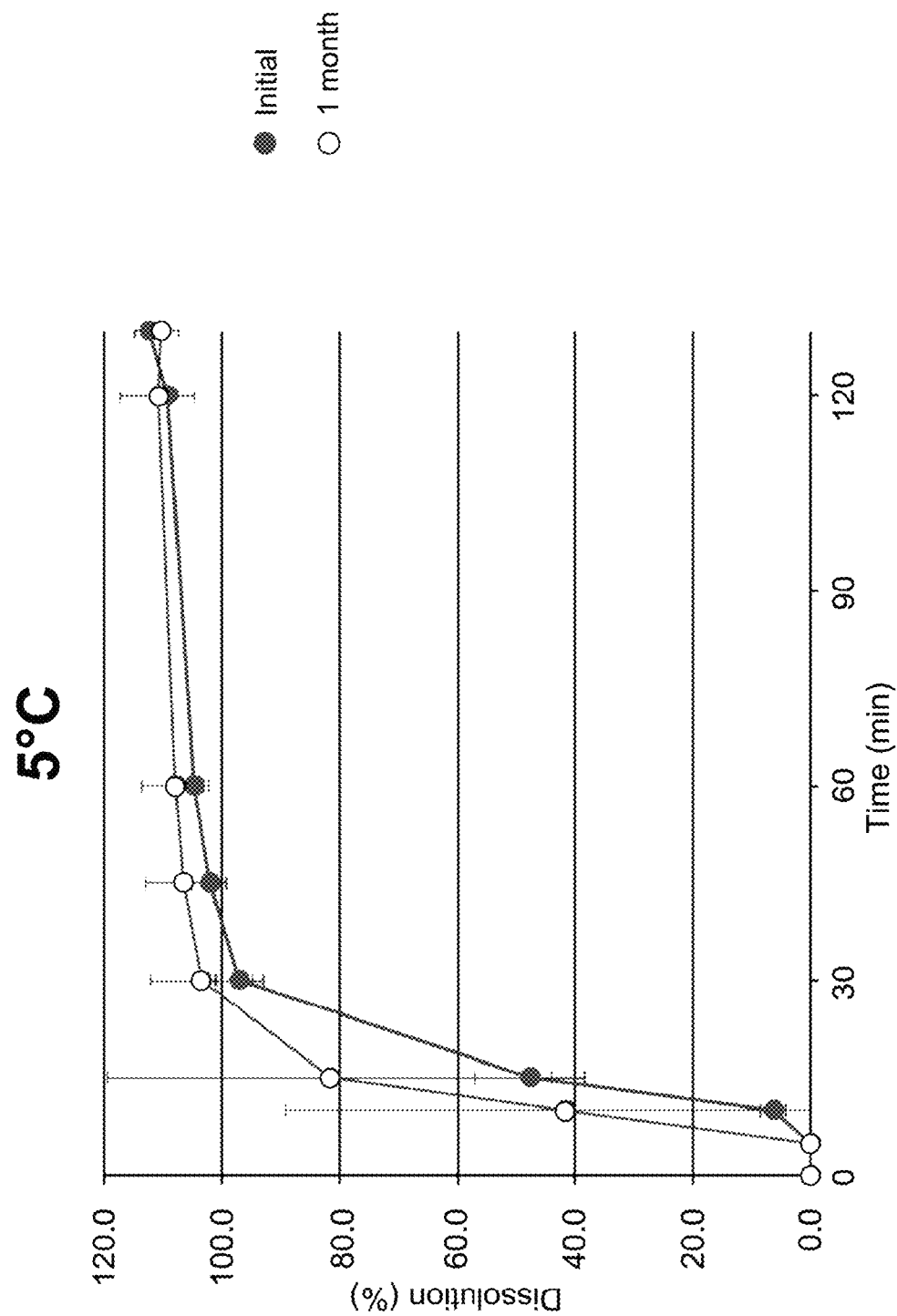
FIG. 10J is a graph of dissolution (%) versus time, and shows the amount of compound of structure (I) released from Formulation No. 401-04 of Example 14 stored at 5° C.
Figure 10K:
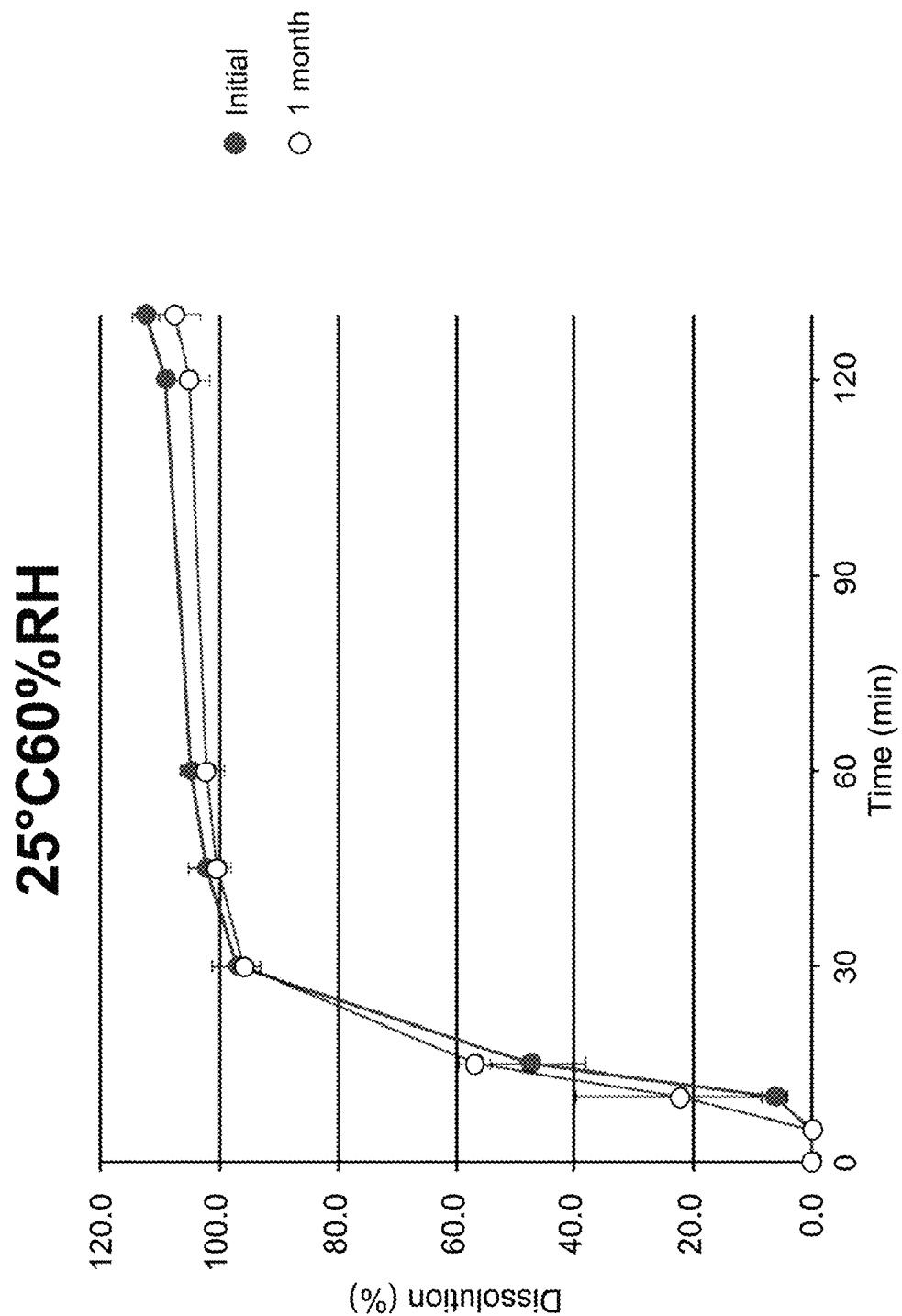
FIG. 10K is a graph of dissolution (%) versus time, and shows the amount of compound of structure (I) released from Formulation No. 401-04 of Example 14 stored at 25° C. and 60% RH.
Figure 10L:
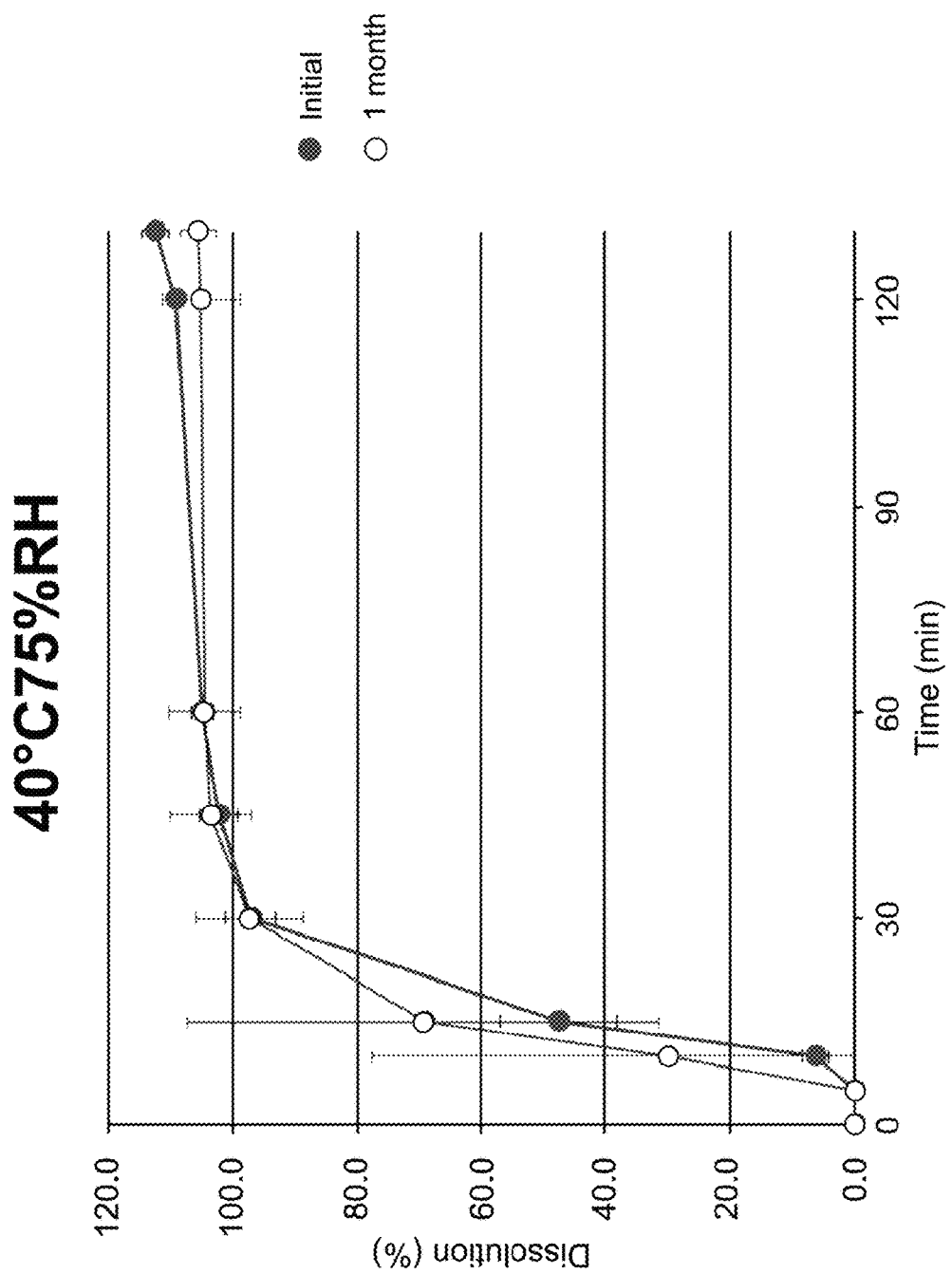
FIG. 10L is a graph of dissolution (%) versus time, and shows the amount of compound of structure (I) released from Formulation No. 401-04 of Example 14 stored at 40° C. and 75% RH.
Figure 10M:
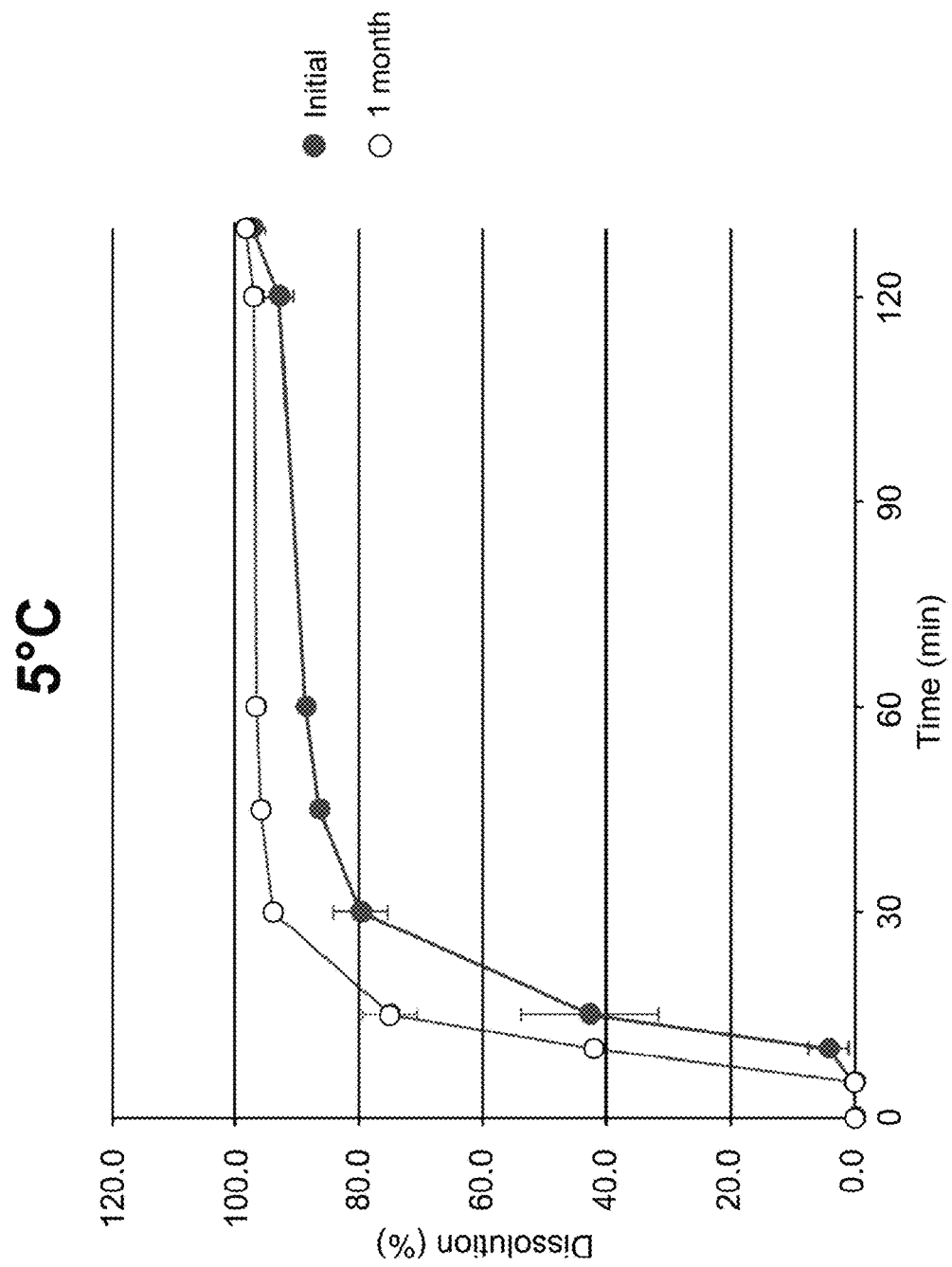
FIG. 10M is a graph of dissolution (%) versus time, and shows the amount of compound of structure (I) released from Formulation No. 401-05 of Example 14 stored at 5° C.
Figure 10N:
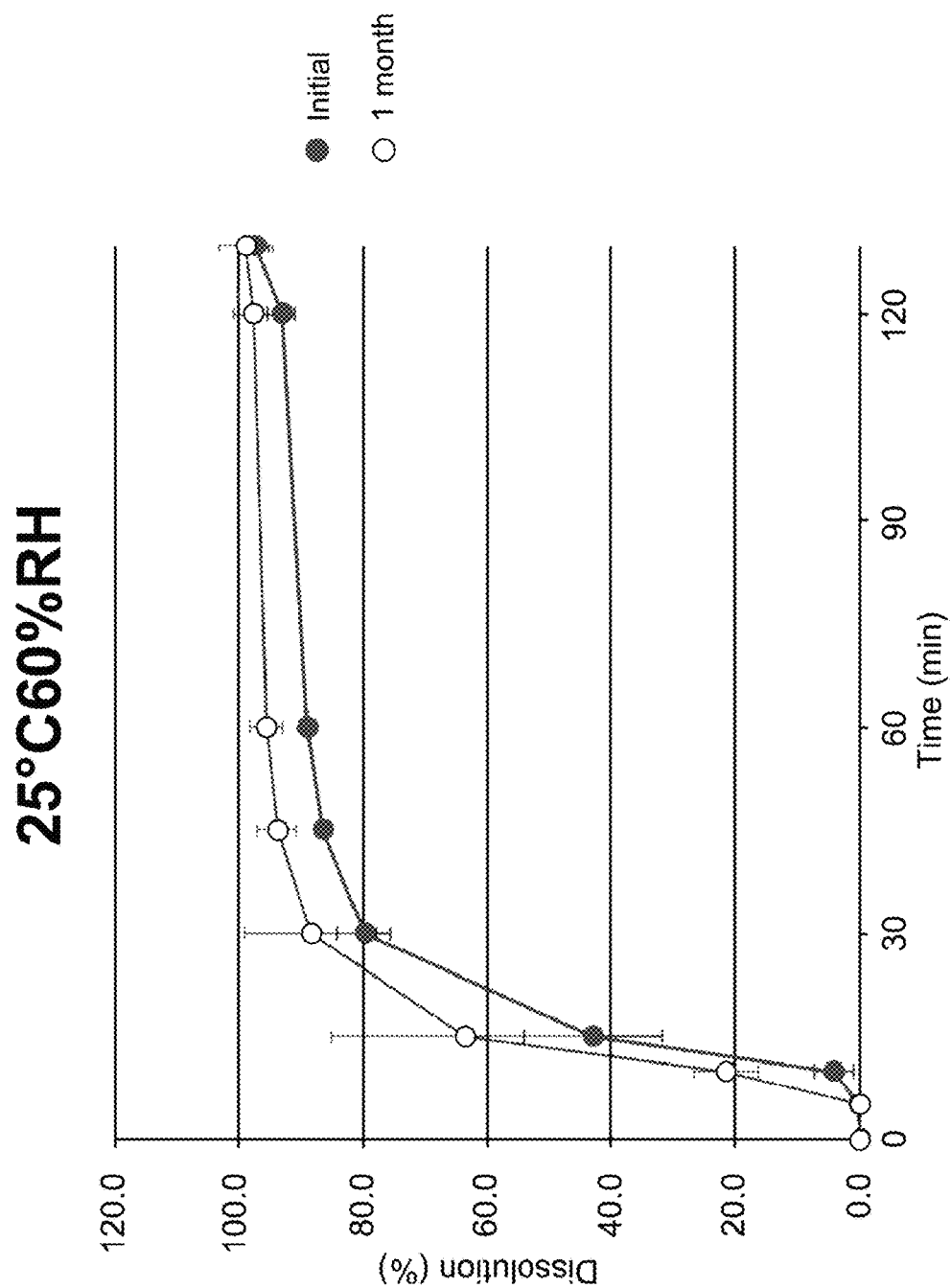
FIG. 10N is a graph of dissolution (%) versus time, and shows the amount of compound of structure (I) released from Formulation No. 401-05 of Example 14 stored at 25° C. and 60% RH.
Figure 10O:
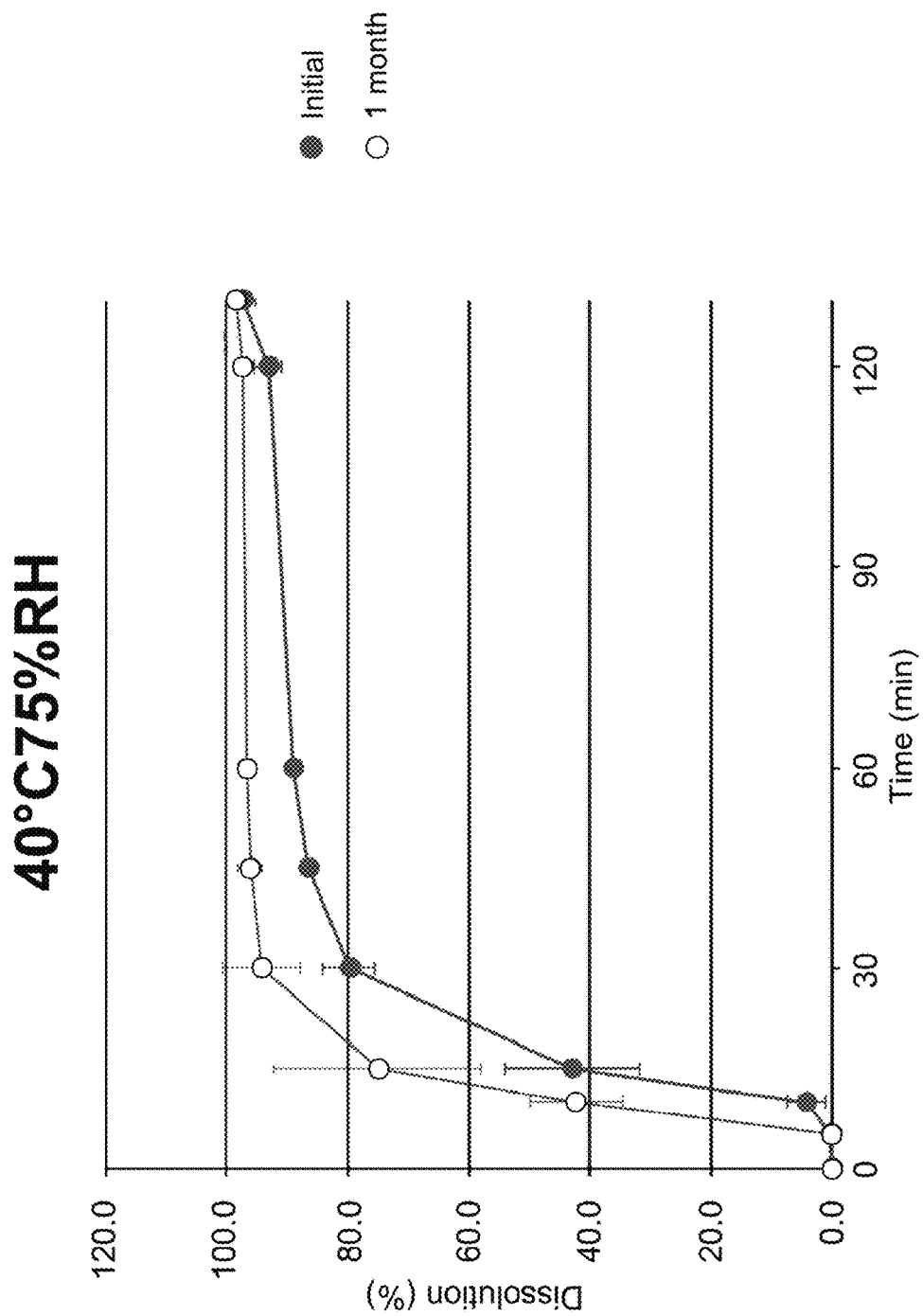
FIG. 10O is a graph of dissolution (%) versus time, and shows the amount of compound of structure (I) released from Formulation No. 401-05 of Example 14 stored at 40° C. and 75% RH.
Figure 10P:
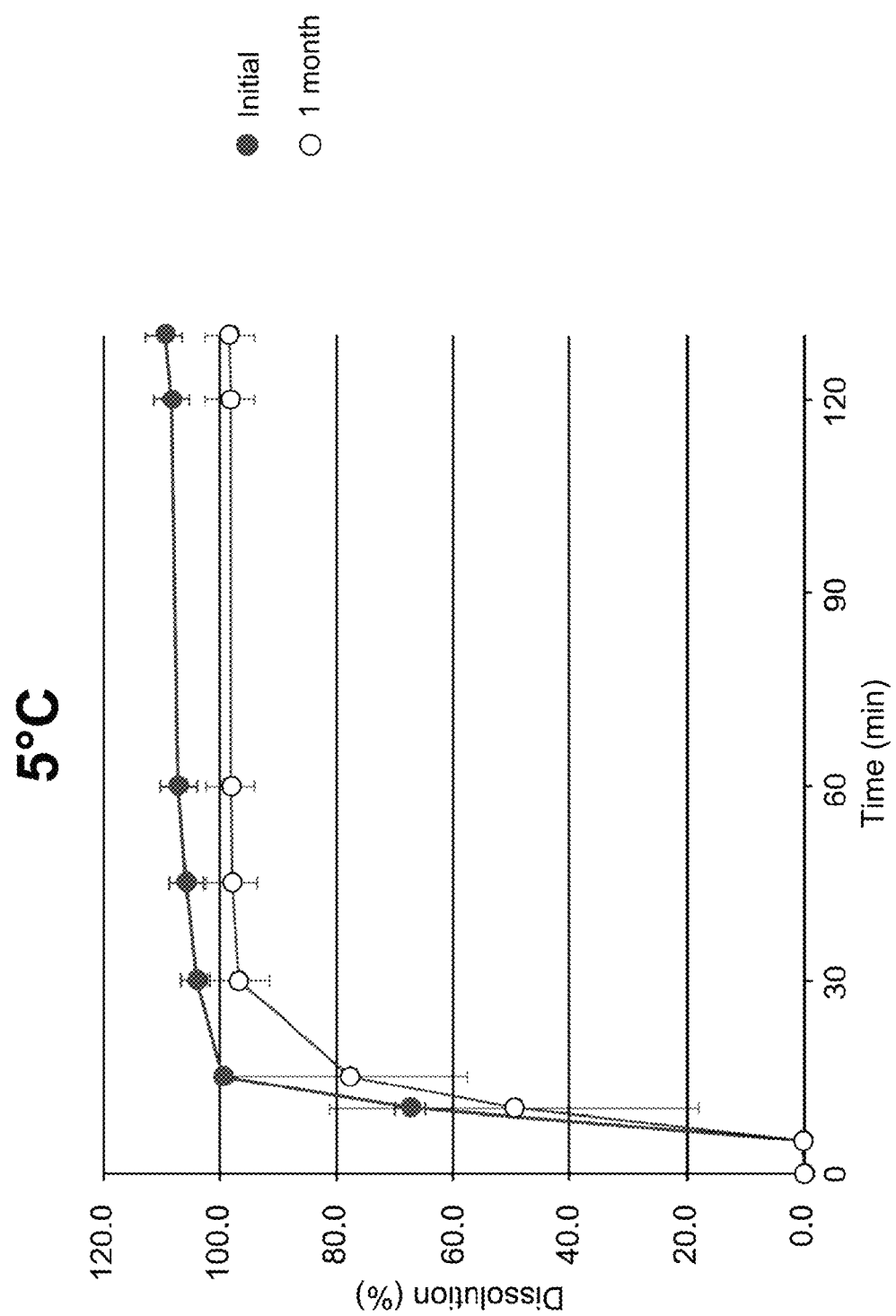
FIG. 10P is a graph of dissolution (%) versus time, and shows the amount of compound of structure (I) released from Formulation No. 401-06 of Example 14 stored at 5° C.
Figure 10Q:
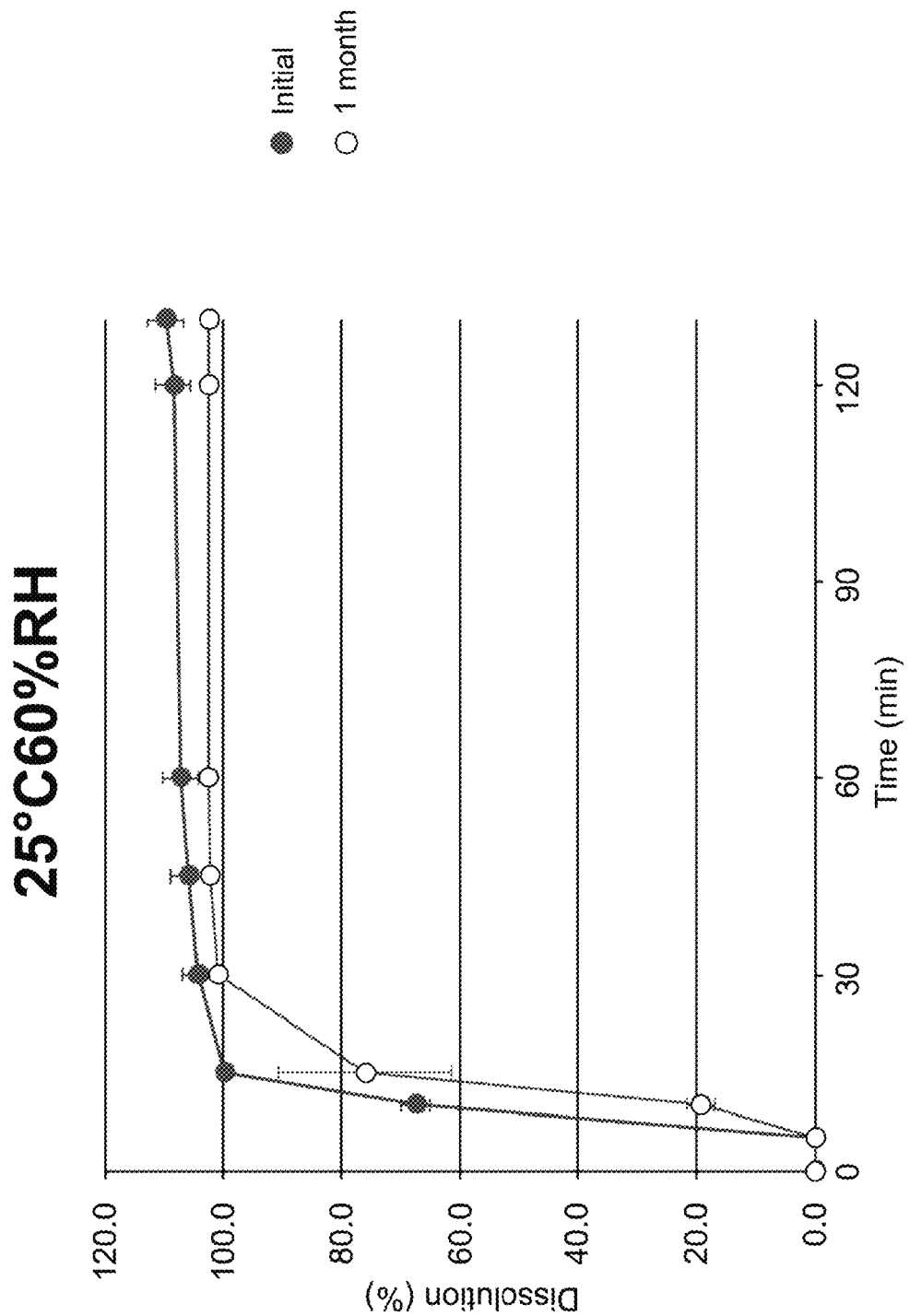
FIG. 10Q is a graph of dissolution (%) versus time, and shows the amount of compound of structure (I) released from Formulation No. 401-06 of Example 14 stored at 25° C. and 60% RH.
Figure 10R:
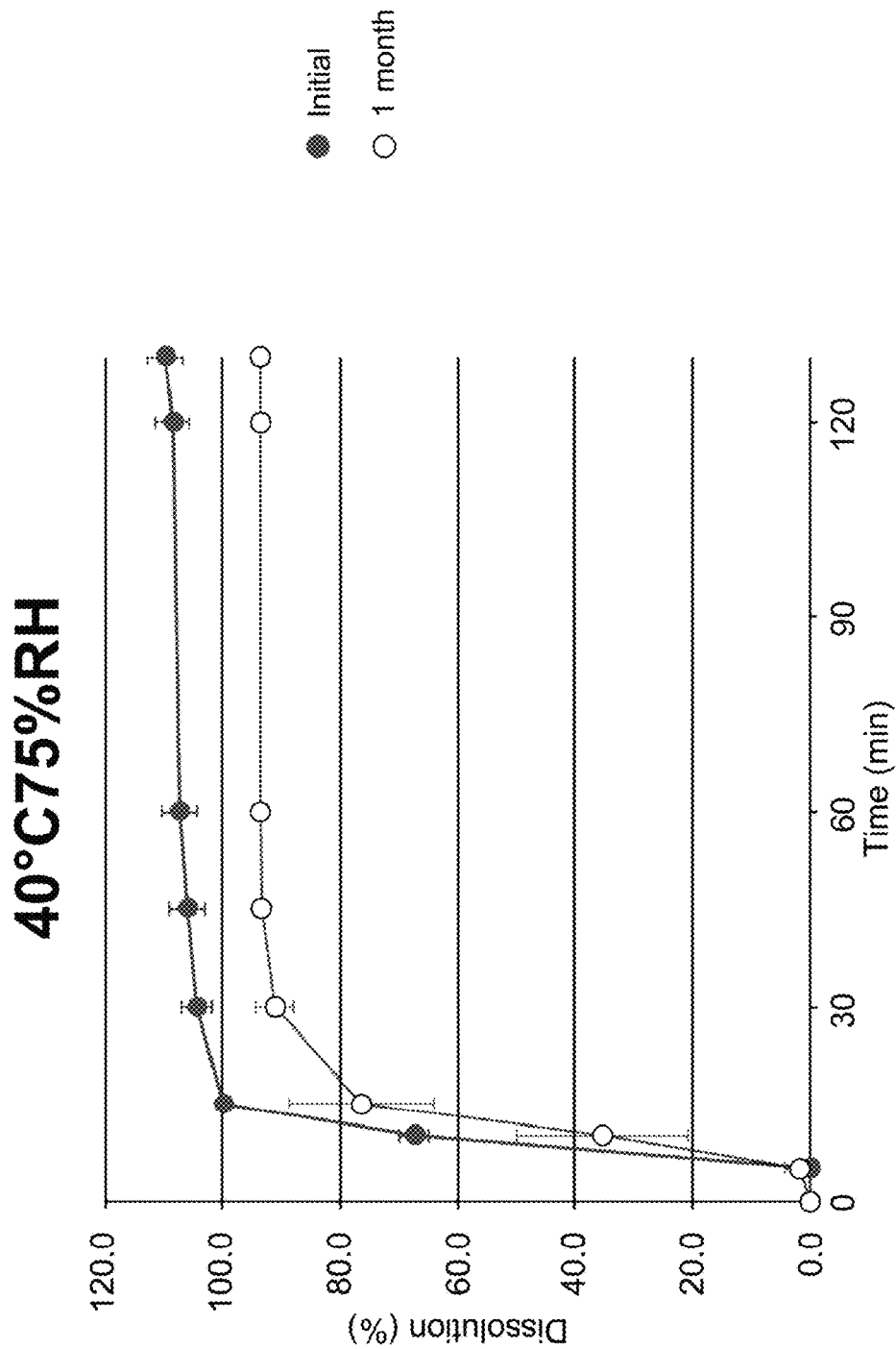
FIG. 10R is a graph of dissolution (%) versus time, and shows the amount of compound of structure (I) released from Formulation No. 401-06 of Example 14 stored at 40° C. and 75% RH.
Figure 10S:
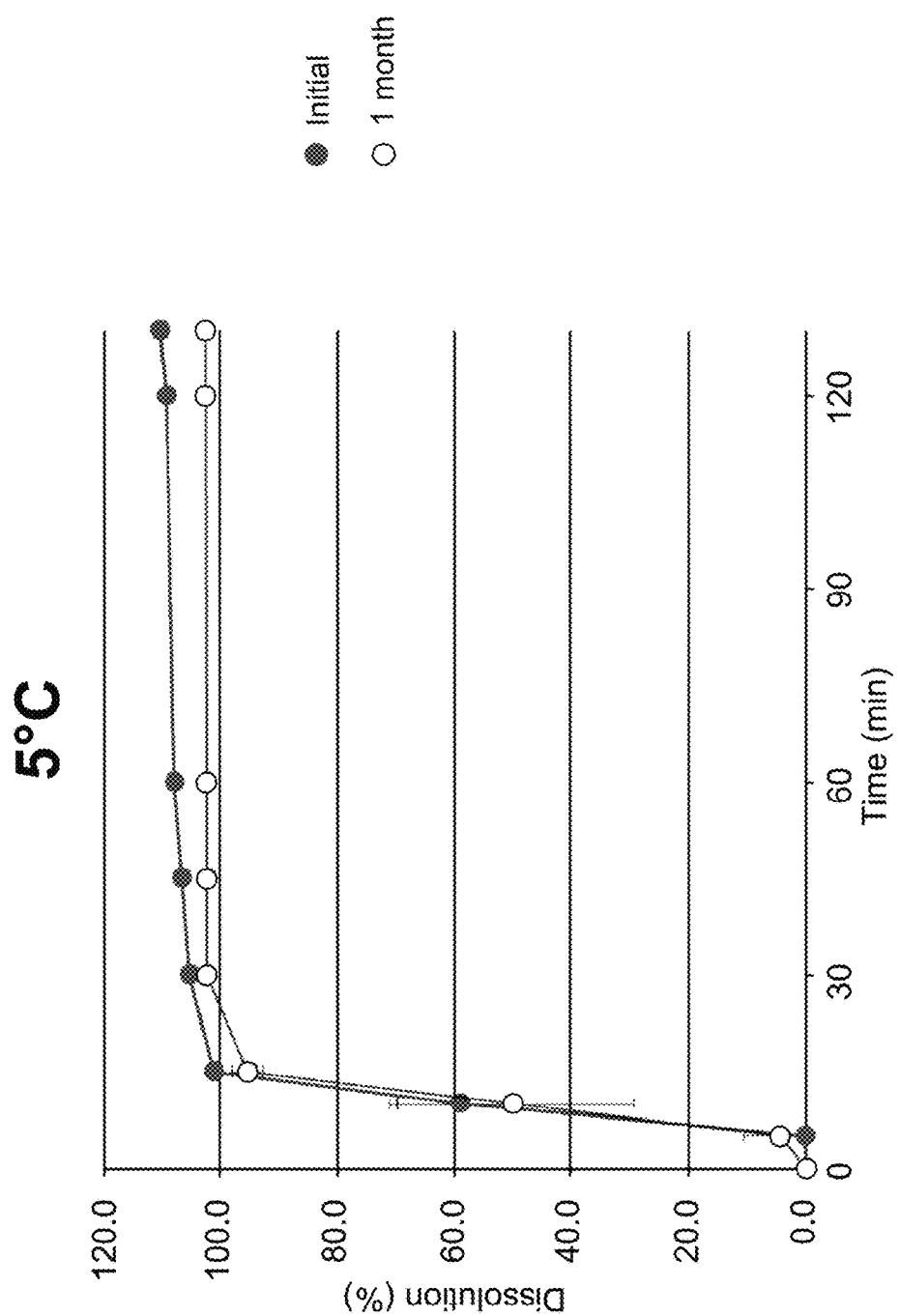
FIG. 10S is a graph of dissolution (%) versus time, and shows the amount of compound of structure (I) released from Formulation No. 401-08 of Example 14 stored at 5° C.
Figure 10T:
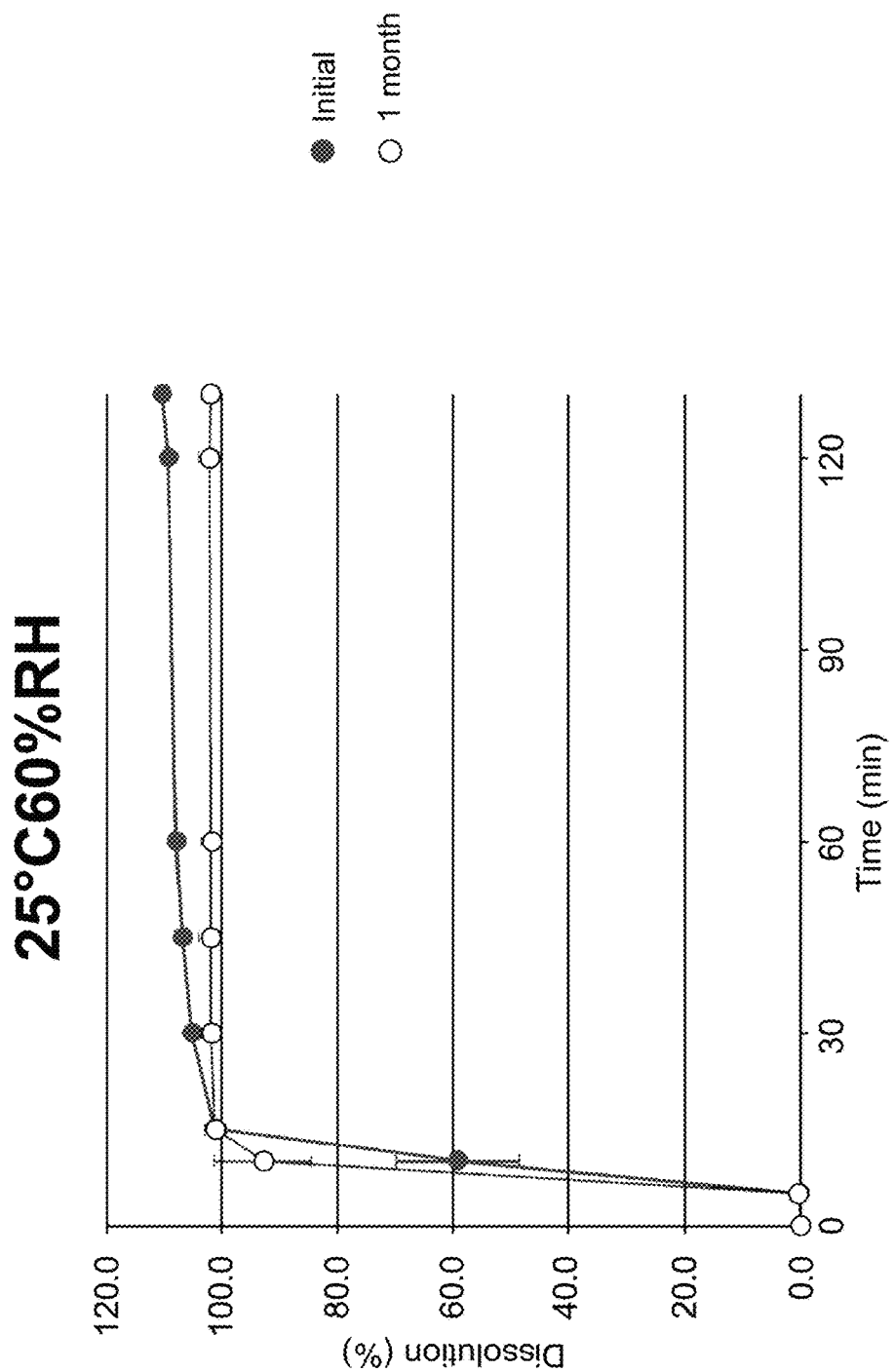
FIG. 10T is a graph of dissolution (%) versus time, and shows the amount of compound of structure (I) released from Formulation No. 401-08 of Example 14 stored at 25° C. and 60% RH.
Figure 10U:
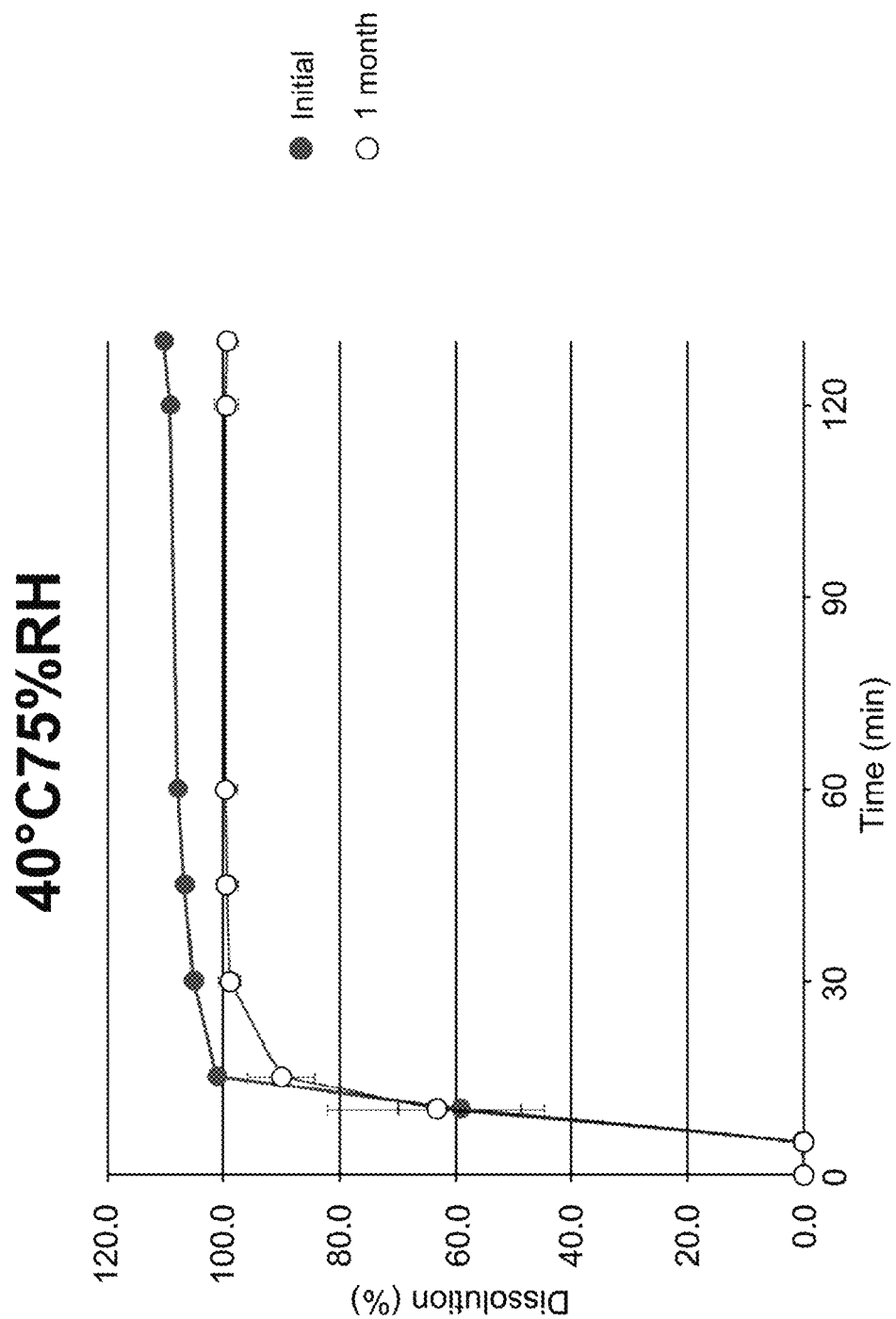
FIG. 10U is a graph of dissolution (%) versus time, and shows the amount of compound of structure (I) released from Formulation No. 401-08 of Example 14 stored at 40° C. and 75% RH.
Figure 10V:
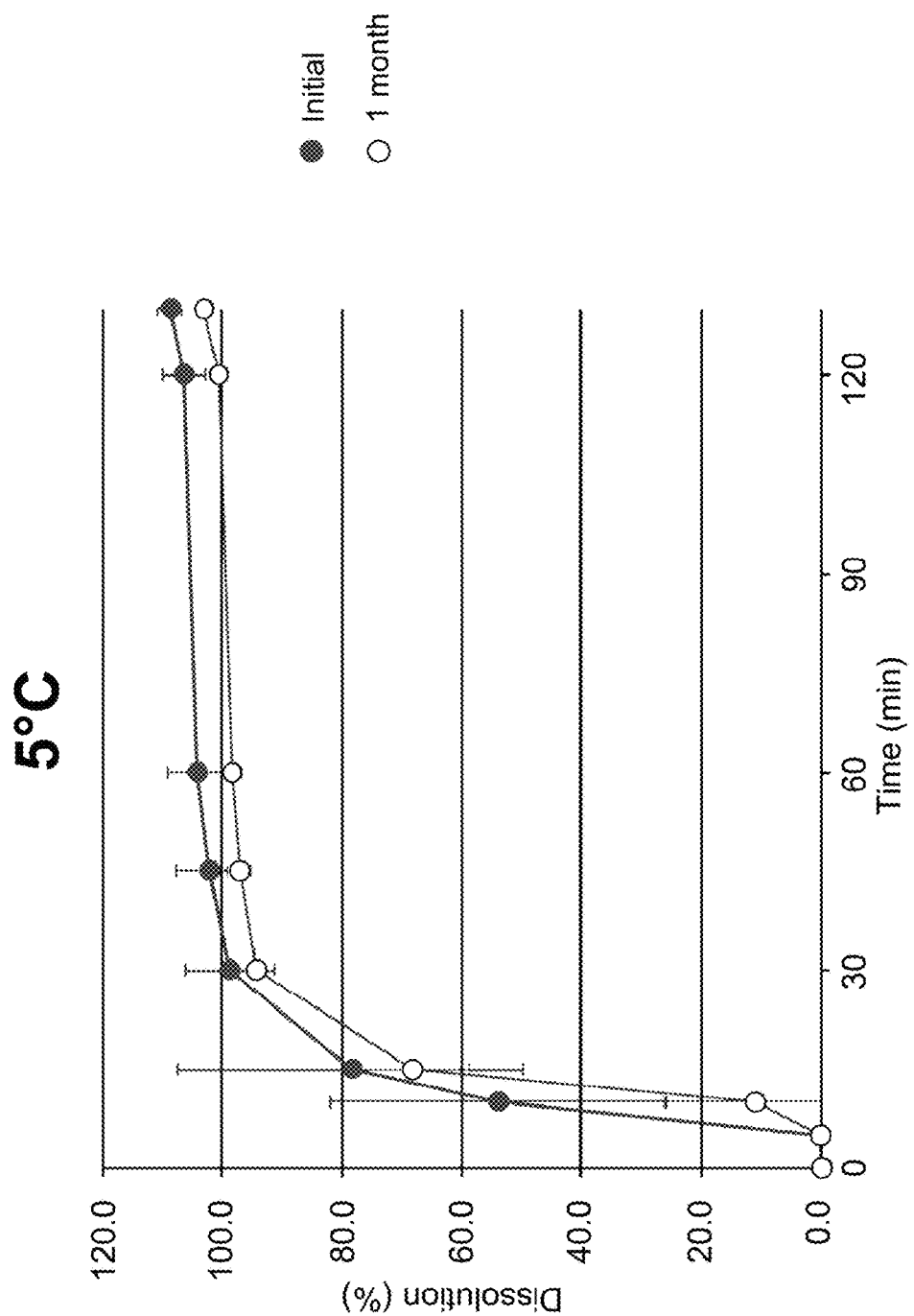
FIG. 10V is a graph of dissolution (%) versus time, and shows the amount of compound of structure (I) released from Formulation No. 401-09 of Example 14 stored at 5° C.
Figure 10W:
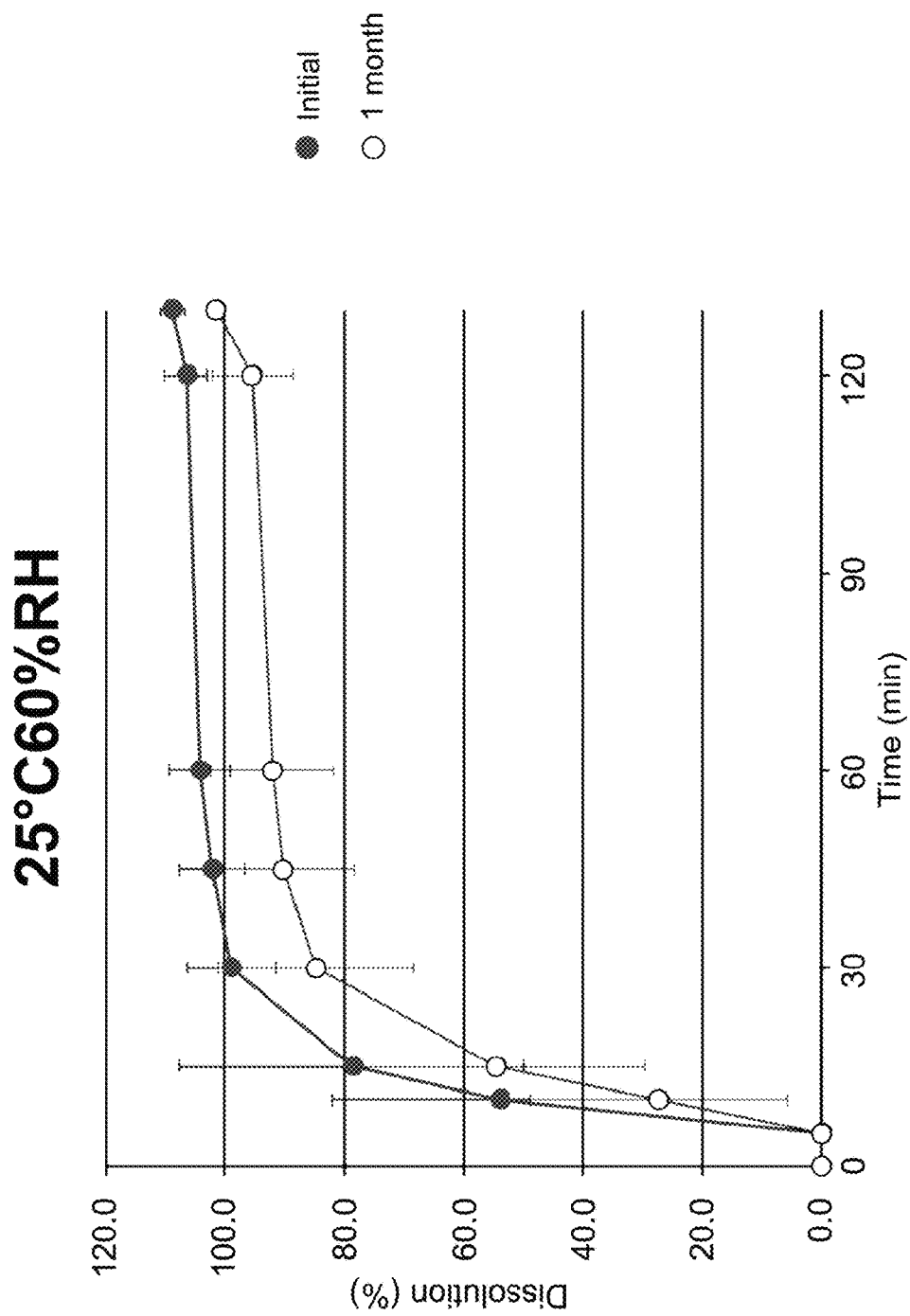
FIG. 10W is a graph of dissolution (%) versus time, and shows the amount of compound of structure (I) released from Formulation No. 401-09 of Example 14 stored at 25° C. and 60% RH.
Figure 10X:
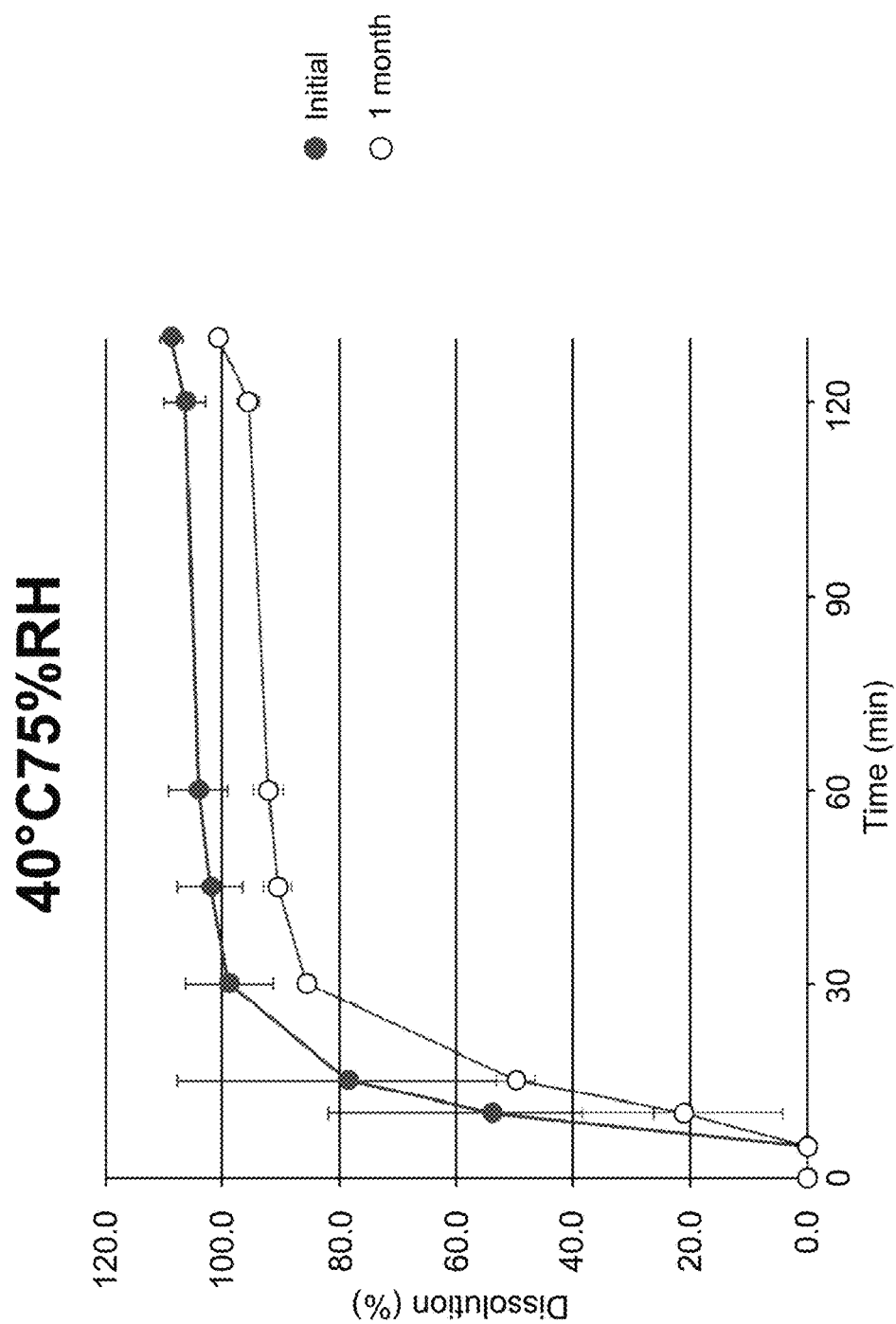
FIG. 10X is a graph of dissolution (%) versus time, and shows the amount of compound of structure (I) released from Formulation No. 401-09 of Example 14 stored at 40° C. and 75% RH.

One-month stability testing of the compositions of the compound of structure (I) was performed at 40° C. and 75% RH, 25° C. and 60% RH or 5° C. The compositions were tested for HPLC purity, impurities and dissolution. Tables 24-1 to 24-8 report the results of the impurity testing, and show that cornstarch-based formulations improved capsule stability compared to Formulation Nos. 401-01 and 401-06. Tables 25-1 to 25-8 report the results of the HPLC purity assay. FIGS. 10A to 10X show the results of the dissolution testing conducted according to the dissolution procedure described in Example 13. All of the formulations submitted to dissolution testing met the criteria of Q (compound of structure (I))=75% within 45 minutes.

TABLE 24-1

| | | | | | | | | |
|---|---|---|---|---|---|---|---|---|
| | | 401-01 | | | | | | |
| | | | Blend before | 40° C. | | 25° C. | | 5° C. | |
| RRT | | encapsulation | Initial | 2 W | 1M | 2 W | 1M | 2 W | 1M |
| 0.51-0.52 | | N.D. | 0.09 | 0.07 | N.D. | 0.07 | N.D. | 0.05 | 0.05 |
| 0.63-0.64 | | N.D. | <0.05 | <0.05 | N.D. | <0.05 | <0.05 | N.D. | N.D. |
| 0.83 | | N.D. | <0.05 | N.D. | N.D. | N.D. | N.D. | N.D. | N.D. |
| 0.88 | | N.D. | N.D. | 0.11 | 0.07 | N.D. | N.D. | N.D. | N.D. |
| 1.00 (cmpd of structure (I)) | | 100 | 99.91 | 97.13 | 97.38 | 99.73 | 99.61 | 99.88 | 99.87 |
| 2.2 | | N.D. | N.D. | 0.05 | <0.05 | N.D. | N.D. | N.D. | N.D. |
| 3.71-3.72 (Alvocidib) | | N.D. | <0.05 | 2.64 | 2.55 | 0.2 | 0.32 | 0.07 | 0.07 |
| Imp(%) | | 0 | 0.09 | 2.87 | 2.62 | 0.27 | 0.32 | 0.12 | 0.12 |

TABLE 24-2

| RRT | Blend before encapsulation | Initial | 40° C. 2 W | 1M | 25° C. 2 W | 1M | 5° C. 2 W | 1M |
|---|---|---|---|---|---|---|---|---|
| 0.51-0.52 | N.D. | 0.1 | 0.07 | N.D. | 0.07 | 0.09 | 0.08 | 0.07 |
| 0.63 | N.D. | <0.05 | <0.05 | <0.05 | <0.05 | 0.05 | 0.05 | N.D. |
| 0.88 | N.D. | N.D. | 0.06 | 0.11 | N.D. | N.D. | N.D. | N.D. |
| 1.00 (cmpd of structure (I)) | 100 | 99.85 | 98.63 | 95 | 99.77 | 99.57 | 99.8 | 99.86 |
| 2.19 | N.D. | N.D. | N.D. | 0.13 | N.D. | N.D. | N.D. | N.D. |
| 3.71 (Alvocidib) | N.D. | <0.05 | 1.24 | 4.76 | 0.16 | 0.29 | 0.07 | 0.06 |
| Imp(%) | 0 | 0.1 | 1.37 | 5 | 0.23 | 0.43 | 0.2 | 0.13 |

TABLE 24-3

| RRT | Blend before encapsulation | Initial | 40° C. 2 W | 1M | 25° C. 2 W | 1M | 5° C. 2 W | 1M |
|---|---|---|---|---|---|---|---|---|
| 0.51-0.52 | N.D. | 0.07 | 0.06 | 0.07 | 0.07 | 0.08 | 0.07 | 0.06 |
| 0.63-0.64 | N.D. | <0.05 | N.D. | <0.05 | <0.05 | <0.05 | <0.05 | <0.05 |
| 0.88 | N.D. | N.D. | 0.09 | 0.07 | N.D. | N.D. | N.D. | N.D. |
| 1.00 (cmpd of structure (I)) | 100 | 99.93 | 92.33 | 92.03 | 99.66 | 99.45 | 99.8 | 99.83 |
| 1.11 | N.D. | N.D. | N.D. | 0.19 | N.D. | N.D. | N.D. | N.D. |
| 2.2 | N.D. | N.D. | N.D. | 0.22 | N.D. | N.D. | N.D. | N.D. |
| 3.71 (Alvocidib) | N.D. | <0.05 | 0.15 | 7.42 | 0.27 | 0.47 | 0.13 | 0.11 |
| Imp(%) | 0 | 0.07 | 0.3 | 7.97 | 0.34 | 0.55 | 0.2 | 0.17 |

TABLE 24-3

| RRT | Blend before encapsulation | Initial | 40° C. 2 W | 1 M | 25° C. 2 W | 1 M | 5° C. 2 W | 1 M |
|---|---|---|---|---|---|---|---|---|
| 0.51-0.52 | N.D. | 0.07 | 0.06 | 0.07 | 0.07 | 0.08 | 0.07 | 0.06 |
| 0.63-0.64 | N.D. | <0.05 | N.D. | <0.05 | <0.05 | <0.05 | <0.05 | <0.05 |
| 0.88 | N.D. | N.D. | 0.09 | 0.07 | N.D. | N.D. | N.D. | N.D. |
| 1.00 (cmpd of structure (I)) | 100 | 99.93 | 92.33 | 92.03 | 99.66 | 99.45 | 99.8 | 99.83 |
| 1.11 | N.D. | N.D. | N.D. | 0.19 | N.D. | N.D. | N.D. | N.D. |
| 2.2 | N.D. | N.D. | N.D. | 0.22 | N.D. | N.D. | N.D. | N.D. |
| 3.71 (Alvocidib) | N.D. | <0.05 | 0.15 | 7.42 | 0.27 | 0.47 | 0.13 | 0.11 |
| Imp(%) | 0 | 0.07 | 0.3 | 7.97 | 0.34 | 0.55 | 0.2 | 0.17 |

TABLE 24-5

| RRT | Blend before encapsulation | Initial | 40° C. 2 W | 1 M | 25° C. 2 W | 1 M | 5° C. 2 W | 1 M |
|---|---|---|---|---|---|---|---|---|
| 0.66 | N.D. | N.D. | N.D. | N.D. | N.D. | N.D. | N.D. | N.D. |
| 0.72-0.73 | N.D. | <0.05 | <0.05 | <0.05 | <0.05 | <0.05 | <0.05 | <0.05 |

TABLE 24-5-continued

| | | | 401-05 | | | | | |
| --- | --- | --- | --- | --- | --- | --- | --- | --- |
| | Blend before | | 40° C. | | 25° C. | | 5° C. | |
| RRT | encapsulation | Initial | 2 W | 1 M | 2 W | 1 M | 2 W | 1 M |
| 1.00 (cmpd of structure (I)) | 100 | 100 | 99.66 | 99.41 | 99.83 | 99.8 | 99.87 | 99.89 |
| 3.47-3.48 | N.D. | <0.05 | N.D. | N.D. | <0.05 | <0.05 | N.D. | N.D. |
| 3.59 | N.D. | N.D. | N.D. | N.D. | N.D. | N.D. | <0.05 | N.D. |
| 3.69-3.73 (Alvocidib) | N.D. | <0.05 | 0.34 | 0.59 | 0.17 | 0.2 | N.D. | 0.11 |
| 3.81 | N.D. | N.D. | N.D. | N.D. | N.D. | N.D. | 0.13 | N.D. |
| Imp(%) | 0 | 0 | 0.34 | 0.59 | 0.17 | 0.2 | 0 | 0.11 |

TABLE 24-6

| | | | 401-06 | | | | | |
| --- | --- | --- | --- | --- | --- | --- | --- | --- |
| | Blend before | | 40° C. | | 25° C. | | 5° C. | |
| RRT | encapsulation | Initial | 2 W | 1 M | 2 W | 1 M | 2 W | 1 M |
| 0.89 | N.D. | N.D. | N.D. | <0.05 | N.D. | N.D. | N.D. | N.D. |
| 1.00 (cmpd of structure (I)) | 100 | 99.93 | 99.2 | 98.01 | 99.81 | 99.77 | 99.87 | 99.88 |
| 2.2 | N.D. | N.D. | N.D. | 0.05 | N.D. | N.D. | N.D. | N.D. |
| 3.71 (Alvocidib) | N.D. | 0.07 | 0.8 | 1.94 | 0.19 | 0.23 | 0.13 | 0.12 |
| Imp(%) | 0 | 0.07 | 0.8 | 1.99 | 0.19 | 0.23 | 0.13 | 0.12 |

TABLE 24-7

| | | | 401-08 | | | | | |
| --- | --- | --- | --- | --- | --- | --- | --- | --- |
| | Blend before | | 40° C. | | 25° C. | | 5° C. | |
| RRT | encapsulation | Initial | 2 W | 1 M | 2 W | 1 M | 2 W | 1 M |
| 1.00 (cmpd of structure (I)) | 100 | 99.94 | 99.51 | 99.53 | 99.82 | 99.79 | 99.87 | 99.88 |
| 3.71 (Alvocidib) | N.D. | 0.06 | 0.49 | 0.47 | 0.18 | 0.21 | 0.13 | 0.12 |
| Imp(%) | 0 | 0.06 | 0.49 | 0.47 | 0.18 | 0.21 | 0.13 | 0.12 |

TABLE 24-8

| | | | 401-09 | | | | | |
| --- | --- | --- | --- | --- | --- | --- | --- | --- |
| | Blend before | | 40° C. | | 25° C. | | 5° C. | |
| RRT | encapsulation | Initial | 2 W | 1 M | 2 W | 1 M | 2 W | 1 M |
| 1.00 (cmpd of structure (I)) | 100 | 99.92 | 99.61 | 98.98 | 99.83 | 99.82 | 99.87 | 99.88 |
| 2.2 | N.D. | N.D. | N.D. | <0.05 | N.D. | N.D. | N.D. | N.D. |
| 3.71 (Alvocidib) | N.D. | 0.08 | 0.39 | 1.02 | 0.17 | 0.18 | 0.13 | 0.12 |
| Imp(%) | 0 | 0.08 | 0.39 | 1.02 | 0.17 | 0.18 | 0.13 | 0.12 |

TABLE 25-1

| | | 401-01 | | | | | | |
|---|---|---|---|---|---|---|---|---|
| | Blend before | | 40° C. | | 25° C. | | 5° C. | |
| | encapsulation | Initial | 2 W | 1 M | 2 W | 1 M | 2 W | 1 M |
| Assay (%) | 87.19 | 80.59 | 74.38 | 71.04 | 77.47 | 82.29 | 86.63 | 82.94 |

TABLE 25-2

| | | 401-02 | | | | | | |
|---|---|---|---|---|---|---|---|---|
| | Blend before | | 40° C. | | 25° C. | | 5° C. | |
| | encapsulation | Initial | 2 W | 1 M | 2 W | 1 M | 2 W | 1 M |
| Assay (%) | 60.43 | 74.35 | 71.53 | 56.95 | 71.39 | 69.59 | 67.14 | 63.79 |

TABLE 25-3

| | | 401-03 | | | | | | |
|---|---|---|---|---|---|---|---|---|
| | Blend before | | 40° C. | | 25° C. | | 5° C. | |
| | encapsulation | Initial | 2 W | 1 M | 2 W | 1 M | 2 W | 1 M |
| Assay (%) | 78.96 | 85.92 | 72.91 | 76.47 | 80.38 | 79.82 | 84.56 | 84.13 |

TABLE 25-4

| | | 401-04 | | | | | | |
|---|---|---|---|---|---|---|---|---|
| | Blend before | | 40° C. | | 25° C. | | 5° C. | |
| | Encapsulation | Initial | 2 W | 1 M | 2 W | 1 M | 2 W | 1 M |
| Assay (%) | 111.03 | 97.37 | 102.4 | 101.93 | 105.47 | 97.26 | 99.83 | 97.39 |

TABLE 25-5

| | | 401-05 | | | | | | |
|---|---|---|---|---|---|---|---|---|
| | Blend before | | 40° C. | | 25° C. | | 5° C. | |
| | encapsulation | Initial | 2 W | 1 M | 2 W | 1 M | 2 W | 1 M |
| Assay (%) | 110.38 | 116.65 | 113.04 | 104.43 | 108.77 | 109.76 | 102.53 | 98.67 |

TABLE 25-6

| | | 401-06 | | | | | | |
|---|---|---|---|---|---|---|---|---|
| | Blend before | | 40° C. | | 25° C. | | 5° C. | |
| | encapsulation | Initial | 2 W | 1 M | 2 W | 1 M | 2 W | 1 M |
| Assay (%) | 87.71 | 85.53 | 80.88 | 81.06 | 85.17 | 84.29 | 85.27 | 82.61 |

TABLE 25-7

| | Blend before encapsulation | Initial | 40° C. 2 W | 40° C. 1 M | 25° C. 2 W | 25° C. 1 M | 5° C. 2 W | 5° C. 1 M |
|---|---|---|---|---|---|---|---|---|
| | 401-08 | | | | | | | |
| Assay (%) | 81.89 | 85.63 | 82.14 | 88.59 | 80.26 | 81.44 | 83.55 | 80.64 |

TABLE 25-8

| | Blend before encapsulation | Initial | 40° C. 2 W | 40° C. 1 M | 25° C. 2 W | 25° C. 1 M | 5° C. 2 W | 5° C. 1 M |
|---|---|---|---|---|---|---|---|---|
| | 401-09 | | | | | | | |
| Assay (%) | 105.3 | 105.59 | 102.08 | 88.85 | 102.9 | 102.38 | 102.59 | 102.89 |

Example 15

Phase I, Pharmacokinetic (Pk) and Pharmacodynamic (Pd), Dose-Escalation Study of Oral Compound of Structure (I) Administered to Patients with Advanced Solid Tumors Patients with advanced metastatic or progressive solid tumors who were refractory to, or intolerant of, established therapy known to provide clinical benefit for their condition were enrolled. Cohorts of 3-6 patients each received escalating doses of compound of structure (I) using a modified Fibonacci dose escalation approach. Once the optimal dose has been established, additional patients may be enrolled to confirm safety and to explore efficacy.

This is an ongoing Phase 1, open-label, dose-escalation, safety, PK and PD study. The proposed starting dose and schedule for oral compound of structure (I) was a 1-mg flat dose once daily (QD) for 14 days followed by a 7-day drug-free recovery period (each cycle=21 days). In the absence of dose-limiting toxicities (DLTs) in the first cohort of at least 3 patients, the dose was increased using a modified Fibonacci dose escalation scheme, and BID dosing commenced according to the dose escalation schedule described in Table 28. The first patient in cohort 6 has been treated at 8 mg compound of structure (I) BID. The baseline demographics of the first 14 patients enrolled in the study are described in Table 26.

TABLE 26

| Baseline Demographics (N = 14 ITT) | |
|---|---|
| Median Age | 65 (45-78) |
| Median Number of Prior Therapies | 4 (1-10) |
| ECOG Score | ECOG 0: 1 (7%) |
| | ECOG 1: 13 (93%) |
| Primary Tumor Type | Bladder: 2 |
| | Pancreas: 2 |
| | Colorectal: 2 |
| | Kidney: 1 |
| | NSCLC: 1 |
| | Prostate: 1 |
| | Sarcoma: 1 |
| | Skin: 1 |
| | Thyroid: 1 |

TABLE 26-continued

| Baseline Demographics (N = 14 ITT) | |
|---|---|
| | Testicular: 1 |
| | Vulvar: 1 |
| Gender | Male: 8 (57.1%) |
| | Female: 6 (42.9%) |

FIG. 12 is a graph depicting completed cycles on the study through Cohort 5.

To date, there is no unexplained toxicity, and no evidence of dose-limiting diarrhea or neutropenia. The treatment-emergent adverse events of grade ≥3 observed thus far are reported in Table 27.

TABLE 27

| Treatment-emergent adverse events grade ≥3. | | | |
|---|---|---|---|
| MedDRA Preferred Term | Grade 3 | Grade 4 | Grade 5 |
| Anemia | 1 (7%) | — | — |
| Chest Pain | 1 (7%) | — | — |
| Pain | 1 (7%) | — | — |
| Swelling | 1 (7%) | — | — |
| Malignant Pleural Effusion | 1 (7%) | — | — |
| Haematuria | 1 (7%) | — | — |
| Hypoxia | 1 (7%) | — | — |
| Hypotension | 1 (7%) | — | — |

Sequential cohorts of 3 patients will continue to be treated with escalating doses according to Table 28 until the MTD is established.

TABLE 28

| Dose Level | Proposed Daily Dose | Total Daily Dose | Increment from Previous Dose[a] | No. of Patients Per Cohort |
|---|---|---|---|---|
| −1[b] | 1 mg QOD | N/A | −50% | 3-6 |
| 1[c] | 1 mg QD | 1 mg | Starting Dose | 3-6 |
| 2 | 1 mg BID | 2 mg | 100% | 3-6 |
| 3 | 2 mg BID | 4 mg | 100% | 3-6 |
| 4 | 4 mg BID | 8 mg | 100% | 3-6 |

TABLE 28-continued

| Dose Level | Proposed Daily Dose | Total Daily Dose | Increment from Previous Dose[a] | No. of Patients Per Cohort |
|---|---|---|---|---|
| 5 | 6 mg BID | 12 mg | 50% | 3-6 |
| 6 | 8 mg BID | 16 mg | 33% | 3-6 |
| 7 [d] | 11 mg BID | 22 mg | 33% | 3-6 |

[a] It is possible for additional and/or intermediate dose levels to be added during the course of the study.
[b] Dose level-1 represents a treatment dose for patients requiring a dose reduction from the starting dose level. It will also serve as a lower dose level if the Starting Dose level is initially associated with unexpected or unacceptable toxicity. Please note that the dosing in this instance is a single morning dose every other day (QOD) (no evening doses required).
[c] Please note that the dosing in Cohort 1 is a single daily (QD) morning dose (no evening dose required).
[d] If clinically indicated, dose levels higher than 11 mg BID may be investigated.

If a DLT is observed in 1 of 3 patients at a given dose level, up to 3 additional patients will be enrolled and treated at that dose level. When up to 3 additional patients are added to a given dose level, if only 1 out of those 6 patients experiences a DLT, the dose will be increased to the next dose level. If ≥2 out of 3-6 patients at a dose level experience DLTs, the dose will be decreased to the previous (lower) dose level and 3 additional patients will be enrolled at that dose level.

If 0 or 1 patient in any of the 6 patients experience a DLT, but the next higher dose level has already been studied, then the current dose will be declared the MTD and the study will advance to the expansion cohort.

The MTD is defined as the dose at which ≤1 of 6 patients experience a DLT during Cycle 1 with the next higher dose having at least 2 of 3 to 6 patients experiencing a DLT during Cycle 1.

Once the MTD has been established, 20 additional patients will be enrolled at the MTD. Data collected from patients enrolled at the MTD will be used to confirm safety, explore potential biomarkers, and evaluate potential signals of compound of structure (I) activity.

All patients may continue to receive compound of structure (I) in 21-day cycles (14 days of active treatment) at the same dose given during Cycle 1 until they experience unacceptable toxicity or unequivocal disease progression. No intra-patient escalation of the compound of structure (I) dose is permitted during the escalation phase until MTD is established.

Patients met all of the following inclusion criteria:
1. Have a histologically confirmed diagnosis of advanced metastatic or progressive solid tumor excluding tumor types with rapid cell turnover, i.e., small cell cancer (lung and extra pulmonary), inflammatory breast cancer (IBC), medulloblastoma, neuroblastoma and melanoma with extensive liver metastasis (≥50% of the liver involved; patients with melanoma and metastasis to <50% of the liver were eligible)
2. Be refractory to, or intolerant of, established therapy known to provide clinical benefit for their condition
3. Have one or more tumors measurable or evaluable as outlined by the Response Evaluation Criteria in Solid Tumors (RECIST) v1.1
4. Have an Eastern Cooperative Oncology Group (ECOG) performance status of ≤1
5. Have a life expectancy ≥3 months
6. Be ≥18 years of age
7. Have a negative pregnancy test (if female of childbearing potential)
8. Have acceptable liver function:
    a) Bilirubin ≤1.5× upper limit of normal (ULN) (unless associated with Gilbert syndrome)
    b) Aspartate aminotransferase (AST/SGOT), alanine aminotransferase (ALT/SGPT) and alkaline phosphatase ≤2.5×ULN*
    *if liver metastases were present, then 3×ULN was allowed
9. Have acceptable renal function: calculated creatinine clearance ≥30 mL/min
10. Have acceptable hematologic status:
    c) Granulocyte ≥1500 cells/mm$^3$
    d) Platelet count ≥100,000 (plt/mm$^3$)
    e) Hemoglobin ≥8 g/dL
11. Have acceptable coagulation status:
    f) Prothrombin time (PT) within 1.5× normal limits
    g) Activated partial thromboplastin time (aPTT) within 1.5× normal limits
12. Be nonfertile or agree to use an adequate method of contraception. Sexually active patients and their partners used an effective method of contraception (hormonal or barrier method of birth control; or abstinence) prior to study entry and for the duration of study participation and for at least 3 months (males) and 6 months (females) after the last study drug dose.
13. Have read and signed the Institutional Review Board (IRB)-approved informed consent form (ICF) prior to any study-related procedure.

Patients meeting any one of the following exclusions criteria were prohibited from participating in the study:
1. History of congestive heart failure (CHF); cardiac disease, myocardial infarction within the past 6 months prior to Cycle 1/Day 1; left ventricular ejection fraction (LVEF)<45% by echocardiogram (ECHO), unstable arrhythmia, or evidence of ischemia on electrocardiogram (ECG) within 14 days prior to Cycle 1/Day 1
2. Have a corrected QT interval (using Fridericia's correction formula) (QTcF) of >450 msec in men and >470 msec in women
3. Have a seizure disorder requiring anticonvulsant therapy
4. Presence of symptomatic central nervous system metastatic disease or disease that requires local therapy such as radiotherapy, surgery, or increasing dose of steroids within the prior 2 weeks
5. Have severe chronic obstructive pulmonary disease with hypoxemia (defined as resting $O_2$ saturation of ≤90% breathing room air)
6. Have undergone major surgery within 2 weeks prior to Cycle 1/Day 1
7. Have active, uncontrolled bacterial, viral, or fungal infections, requiring systemic therapy
8. Are pregnant or nursing
9. Received treatment with radiation therapy, surgery, chemotherapy, or investigational therapy within 28 days or 5 half-lives, whichever occurs first, prior to study entry (6 weeks for nitrosoureas or mitomycin C)
10. Are unwilling or unable to comply with procedures required in this protocol
11. Have known infection with human immunodeficiency virus, hepatitis B, or hepatitis C. Patients with history of chronic hepatitis that is currently not active are eligible
12. Have a serious nonmalignant disease (eg, hydronephrosis, liver failure, or other conditions) that could compromise protocol objectives in the opinion of the Investigator and/or the Sponsor
13. Are currently receiving any other investigational agent
14. Have exhibited allergic reactions to a similar structural compound, biological agent, or formulation 15. Have malabsorption conditions (e.g., Crohn's disease) or have undergone significant surgery to the gastrointestinal tract that could impair absorption or that could result in short bowel syndrome with diarrhea due to malabsorption.

DLT was defined as any one of the following events observed in cycle 1, regardless of investigator attribution, unless there was a clear alternative explanation:
1. Grade 3 or greater febrile neutropenia
2. Grade 4 neutropenia for ≥7 consecutive days
3. Grade 4 thrombocytopenia or Grade 3 thrombocytopenia with clinically significant bleeding or that requires a platelet transfusion
4. Grade 3 or 4 nonhematologic AEs will be considered dose limiting, regardless of duration aside from the specific parameters described herein
5. Grade 4 nausea, vomiting, or diarrhea, regardless of duration
6. Dosing delays >1 week due to treatment-emergent adverse events (TEAEs) or related severe laboratory test values
7. Any AST and ALT elevation >3×ULN (if baseline value was normal) or ≥3× the baseline value (if baseline value was abnormal) accompanied by serum bilirubin levels >2×ULN
8. Any Grade ≥3 electrolyte disturbances (eg, hyperkalemia, hypophosphatemia, hyperuricemia) that do not resolve within <72 hours
9. Any Grade ≥3 elevations in creatinine
10. Any Grade 5 toxicity Plasma PK parameters of compound of structure (I) and alvocidib were evaluated in Cohorts 1-5 at specific timepoints during the study. Blood was collected from patients in Cohorts 1-5 according to the pharmacokinetic sampling schedule described in Table 29.

TABLE 29

| Pharmacokinetic Sampling Schedule | | | | | | | |
|---|---|---|---|---|---|---|---|
| Cycle No. | | CYCLE 1 | | | | CYCLE 2 | |
| Time Points (hrs) | AM Day 1 | PM [a] Day 1 | AM Day 2 | AM Day 14 | PM [a] Day 14 | AM Day 15 | AM Day 1 | End of Study |
| 0 (pre-dose) | X | | X [b] | X [b] | | X [b] | X | X |
| 0.5 | X | X | | X | X | | | |
| 1 | X | X | | X | X | | | |
| 2 | X | X | | X | X | | | |
| 4 | X | | | X | | | | |
| 8 [c] | X | | | X | | | | |

[a] No evening (PM) samples were collected from patients enrolled in the first dose cohort receiving compound structure (I) as a once daily (QD) morning dose.
[b] Approximately 24 hours after taking the previous days' morning dose and prior to taking current days' dose (i.e., sampling on Cycle 1/Day 2 would be performed 24 hrs after taking the morning dose on Day 1 and before taking the morning dose on Day 2)
[c] The 8-hour samples were collected prior to taking that day's evening dose (for patients receiving compound of structure (I) BID), or 8 hours after taking that day's dose (for patients receiving compound of structure (I) QD).

PK parameters were estimated using standard noncompartmental methods. Actual sample collection times were used rather than scheduled collection times. Plasma concentrations below the limit of quantification were treated as 0. Imbedded missing plasma concentrations (e.g., missing values between two observed values) were estimated using linear extrapolation. This is consistent with using the trapezoidal rule to calculate AUC. Other missing plasma concentrations were excluded from calculations to estimate PK parameters.

FIGS. 11A and 11B are graphs of plasma alvocidib concentration (ng/mL) versus time, and show the concentration of alvocidib in the plasma of patients in Cohort 1 on days 1 and 14, respectively, following daily oral QD dosing with a 1-mg strength capsule containing Formulation No. 401-01. Subject 104 showed some accumulation of alvocidib after 24 hours on day 14. Subject 102 was discontinued prior to day 14 dosing.

FIGS. 11C and 11D are graphs of plasma alvocidib concentration (ng/mL) versus time, and show the concentration of alvocidib in the plasma of patients in cohort 2 on days 1 and 14, respectively, following daily oral BID dosing with a 1-mg strength capsule containing Formulation No. 401-01. Only alvocidib was detectable at 1 mg BID, and no compound of structure (I) was detected at any timepoint for any sample. No drug was detectable (less than 1.0 ng/mL of alvocidib) by 8 hours and again at 24 hours in any subject on day 1. However, there was detectable accumulation of alvocidib on day 14 for subjects 201 and 202 (average=2.39 ng/mL), suggesting that BID dosing helped to maintain drug levels by day 14.

FIGS. 11E and 11F are graphs of plasma alvocidib concentration (ng/mL) versus time, and show the concentration of alvocidib in the plasma of patients in Cohort 5 on days 1 and 14, respectively, following daily oral BID dosing with 6 mg of Formulation No. 401-01. Table 30 reports $T_{max}$, $C_{max}$ and $AUC_{(0-24)}$ of alvocidib for patients in Cohort 5 on days 1 and 14 of cycle 1.

TABLE 30

| | Cycle 1 | | | | | |
|---|---|---|---|---|---|---|
| Cohort 5 6 mg BID | Day 1 | | | Day 14 | | |
| Subject (#) | $T_{max}$ (Hours) | $C_{max}$ (ng/mL) | $AUC_{(0-24)}$ (ng*h/mL) | $T_{max}$ (Hours) | $C_{max}$ (ng/mL) | $AUC_{(0-24)}$ (ng*h/mL) |
| 501 | 0.5 | 28 | 230 | 0.5 | 40.2 | 192 |
| 502 | 2 | 19 | 208 | 2 | 30.4 | 516 |
| 503 | 0.5 | 29.3 | 376 | 0.5 | 51.7 | 407 |
| Mean | 1.0 | 25.4 | 271.3 | 1.0 | 40.8 | 371.7 |
| SD | 0.9 | 5.6 | 91.3 | 0.9 | 10.7 | 164.9 |

FIG. 11G is a graph of alvocidib (ng/mL) versus cohort, and shows the mean $C_{max}$ of alvocidib on day 1 and day 14 following daily oral QD dosing with a 1-mg strength capsule containing Formulation No. 401-01. FIG. 11H is a graph of alvocidib (ng*hr/mL) versus cohort, and shows the area under the curve (AUC) of alvocidib on day 1 ($AUC_{0-8}$) and day 14 ($AUC_{0-8}$ and $AUC_{0-24}$) following daily oral BID dosing with a 1-mg strength capsule containing Formulation No. 401-01. There was no detectable compound of structure (I) at any timepoint. Cohort 2 showed marked increase in average $C_{max}$ and AUC from day 1 to day 14, illustrating the impact of BID versus QD dosing. The $C_{max}$ for Cohort 5 increased by 46% compared to Cohort 4 on day 1, and by 69% for day 14. The corresponding increase in AUC was 52% on day 1 and 30% on day 14.

FIG. 11I is a graph of mean concentration of alvocidib (nM) versus time, and shows the mean concentration of alvocidib in plasma of Cohort 5 patients over a 24-hour period. By administering alvocidib as compound of structure (I), alvocidib can be given at a lower dose over a longer time, with less toxicity and similar exposure.

Example 16

Alternative Synthesis of Structure (I)

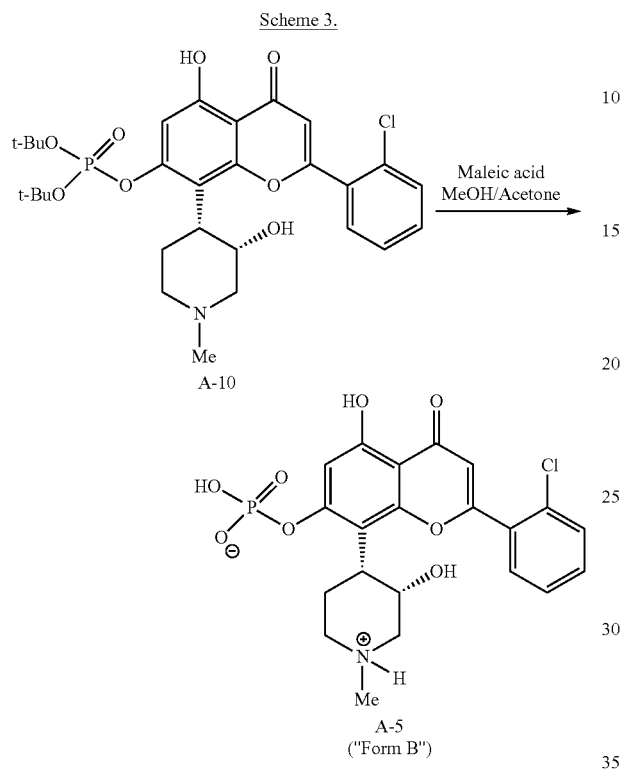

A-10 was obtained according to Steps 1.1 and 2.1A, depicted in Scheme 2 and described in Example 10. A-10 (100 mg) was substantially dissolved in methanol (1 ml) at 50° C. A solution of maleic acid (12.2 mg, 0.5 equiv) in methanol (1.5 ml) was added dropwise to the mixture of A-10 in methanol, followed by acetone (2.5 ml). The resulting reaction mixture was stirred for one hour at room temperature, and then filtered to obtain A-5 (77.4 mg) having a crystallinity of 94%. Residual maleic acid was confirmed by $^1$H NMR (0.01 proton).

Example 17

A Phase II Study of Oral Compound of Structure (I) Administered Once Daily for 21 Days to Patients with Metastatic Castrate-Resistant Prostate Cancer This is a Phase 2, open-label, non-randomized, Simon 2-stage design study to establish the efficacy and safety of compound of structure (I) (e.g., Form B of compound of structure (I)) taken once daily for 21 days of a 28-day cycle in patients with metastatic castration-resistant prostate cancer who have progressed on frontline treatment with androgen signaling inhibitors. A biopsy sub-study in 20 patients will enable the evaluation of tissue biomarkers in a subset of patients.

Sixty (60) patients will be enrolled. Data will be used to assess efficacy, confirm safety, and explore correlative potential biomarkers.

All patients may continue to receive compound of structure (I) in 28-day cycles (21 days of active treatment) at the same dose given during Cycle 1 until they experience unacceptable toxicity or unequivocal disease progression.

Patients must meet all of the following inclusion criteria to be eligible:
1. Male patients who also have histologically or cytologically confirmed adenocarcinoma of the prostate; AND:
   a) Be castrate-resistant on treatment with androgen deprivation therapy (ADT) (or status post bilateral orchiectomy) and with testosterone levels of less than (<) 50 nanogram per deciliter (50 ng/dL, equivalent to 1.7 nmol/L); AND:
   b) Have radiographic progression according to according to Prostate Cancer Clinical Trials Working Group 3 (PCWG3) criteria, while being treated with abiraterone acetate or enzalutamide in combination with ADT
2. Be refractory to, or intolerant of, established therapy known to provide clinical benefit for their condition
3. Have one or more tumors measurable as outlined by the Response Evaluation Criteria in Solid Tumors (RECIST) v1.1
4. Willingness to undergo two (2) on-study biopsies (biopsy sub-study cohort only)
5. Have an Eastern Cooperative Oncology Group (ECOG) performance status of ≤1
6. Have a life expectancy ≥3 months
7. Be ≥18 years of age
8. Have acceptable liver function:
   a) Bilirubin ≤1.5× upper limit of normal (ULN) (unless associated with Gilbert syndrome)
   b) Aspartate aminotransferase (AST/SGOT), alanine aminotransferase (ALT/SGPT) and alkaline phosphatase ≤2.5×ULN*

*If liver metastases are present, then 3×ULN is allowed.
9. Have acceptable renal function: calculated creatinine clearance ≥30 mL/min
10. Have acceptable hematologic status:
    a) Granulocyte ≥1500 cells/mm$^3$
    b) Platelet count ≥100,000 (plt/mm$^3$)
    c) Hemoglobin ≥8 g/dL
11. Have acceptable coagulation status:
    a) Prothrombin time (PT) within 1.5× normal limits
    b) Activated partial thromboplastin time (aPTT) within 1.5× normal limits
12. Be nonfertile or agree to use an adequate method of contraception. Sexually active patients and their partners must use an effective method of contraception (hormonal or barrier method of birth control; or abstinence) prior to study entry and for the duration of study participation and for at least 3 months (males) and 6 months (females) after the last study drug dose. Should a woman become pregnant or suspect she is pregnant while her partner is participating in this study, she should inform her treating physician immediately.
13. Have read and signed the Institutional Review Board (IRB)-approved informed consent form (ICF) prior to any study-related procedure. (In the event that the patient is rescreened for study participation or a protocol amendment alters the care of an ongoing patient, a new ICF must be signed.)

Patients meeting any one of these exclusion criteria will be prohibited from participating in this study:
1. History of congestive heart failure (CHF); cardiac disease, myocardial infarction within the past 6 months prior to Cycle 1/Day 1

2. Have a corrected QT interval (using Fridericia's correction formula) (QTcF) of >450 msec in men and >470 msec in women
3. Have a seizure disorder requiring anticonvulsant therapy
4. Presence of symptomatic central nervous system metastatic disease or disease that requires local therapy such as radiotherapy, surgery, or increasing dose of steroids within the prior 2 weeks
5. Have severe chronic obstructive pulmonary disease with hypoxemia (defined as resting $O_2$ saturation of ≤90% breathing room air)
6. Have undergone major surgery within 2 weeks prior to Cycle 1/Day 1
7. Have active, uncontrolled bacterial, viral, or fungal infections, requiring systemic therapy
8. Are pregnant or nursing
9. Received treatment with radiation therapy, surgery, chemotherapy, or investigational therapy within 28 days or 5 half-lives, whichever occurs first, prior to study entry (6 weeks for nitrosoureas or mitomycin C)
10. Are unwilling or unable to comply with procedures required in this protocol
11. Have known infection with human immunodeficiency virus, hepatitis B, or hepatitis C. Patients with history of chronic hepatitis that is currently not active are eligible
12. Have a serious nonmalignant disease (e.g., hydronephrosis, liver failure, or other conditions) that could compromise protocol objectives in the opinion of the Investigator and/or the Sponsor
13. Are currently receiving any other investigational agent
14. Have exhibited allergic reactions to a similar structural compound, biological agent, or formulation
15. Have malabsorption conditions (e.g., Crohn's disease, etc.) or have undergone significant surgery to the gastrointestinal tract that could impair absorption or that could result in short bowel syndrome with diarrhea due to malabsorption.

Enrolled patients will receive compound of structure (I) (e.g., given as a 1-mg capsule containing Formulation No. 401-01, wherein the compound of structure (I) is Form B of the compound of structure (I)), administered once daily (QD) for the first 21 days of a 28-day cycle. Patients who successfully complete a 4-week treatment cycle without evidence of significant treatment-related toxicity or progressive disease will continue to receive treatment with the same dose and dosing schedule.

Efficacy assessments will be performed based on PCWG3-modified RECIST v1.1 guidelines, to include the assessment of objective response rate (ORR), DoR, type of response (e.g., complete remission, partial remission, stable disease), and time to progression. The ORR is defined as the percent of patients with CR or PR according to PCWG3-modified RECIST v1.1 criteria, relative to the Response Evaluable population. ORR will be summarized by number and percentage of patients meeting the definition of ORR along with the corresponding exact 95% confidence intervals.

Tolerance and toxicity of oral compound of structure (I) will be assessed through evaluation of physical examinations, vital signs, laboratory parameters, AEs including DLTs, and all causes of mortality.

Incidence rates of treatment-emergent adverse events (TEAEs) will be summarized within each dose level at the Medical Dictionary for Regulatory Activities (MedDRA) preferred term and primary system organ class levels. Similar summaries will be made for subsets of AEs such as (1) those judged by the Investigator to be related to study treatment, and (2) serious adverse events (SAEs).

Other routine safety assessments (e.g., clinical laboratory parameters and vital signs) will be summarized by compound of structure (I) dose level using mean, standard deviation, median, minimum, and maximum changes from baseline values.

PD parameters and assessment of potential tumor and peripheral blood biomarkers including, but not limited to, CDK9-related genes (including c-Myc) in biopsy and CTC samples; Phospho-AR; PhosphoRNAPol2 on biopsy and PBMC samples; serum PSA.

Blood will be collected from all patients for evaluation of compound of structure (I) pharmacodynamics and potential biomarkers. Biopsy samples will be taken at baseline (prior to dosing on Cycle 1/Day 1) and at the end of cycle two (2) in a subset of patients participating in the biopsy sub-study.

The most recent archived tumor tissue (primary and metastatic site(s), if available) will be requested from all patients to assess potential biomarkers.

All of the U.S. patents, U.S. patent application publications, U.S. patent applications, foreign patents, foreign patent applications and non-patent publications referred to in this specification or the attached Application Data Sheet are incorporated herein by reference, in their entirety to the extent not inconsistent with the present description.

From the foregoing it will be appreciated that, although specific embodiments of the disclosure have been described herein for purposes of illustration, various modifications may be made without deviating from the spirit and scope of the disclosure.

The invention claimed is:

1. A method for treating a cancer in a mammal in need thereof, comprising administering to the mammal crystalline Form B of a compound having the following structure (I):

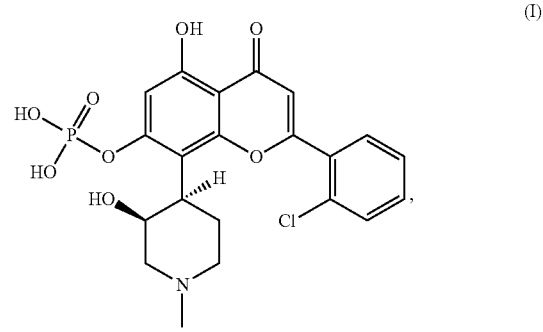 [SMILES: CN1CC[C@H](c2c(OP(=O)(O)O)cc(O)c3c(=O)cc(-c4ccccc4Cl)oc23)[C@H](O)C1 ; ","]

or a zwitterionic form thereof, in an amount of from about 1 mg to about 50 mg per day, wherein crystalline Form B is characterized by an x-ray powder diffraction pattern comprising at least three peaks at 2-theta angles selected from the group consisting of 4.8±0.2°, 10.8±0.2°, 13.7±0.2°, 14.9±0.2°, 20.0±0.2° and 24.6±0.2°.

2. The method of claim 1, wherein crystalline Form B is characterized by an x-ray powder diffraction pattern comprising peaks at the following 2-theta angles: 10.8±0.2°, 14.9±0.2° and 20.0±0.2°.

3. The method of claim 1, wherein crystalline Form B has an x-ray powder diffraction pattern substantially in accordance with that depicted in FIG. 1.

4. The method of claim 1, wherein crystalline Form B is a compound having structure (II):

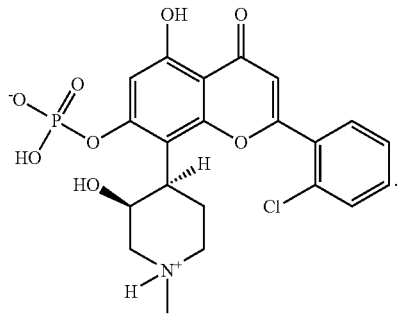

(II)

5. The method of claim 1, wherein about 32 mg per day of crystalline Form B of a compound having structure (I), or a zwitterionic form thereof, is administered to the mammal.

6. The method of claim 1, wherein crystalline Form B of a compound having structure (I), or a zwitterionic form thereof, is administered to the mammal once per day.

7. The method of claim 1, wherein crystalline Form B of a compound having structure (I), or a zwitterionic form thereof, is administered to the mammal twice per day.

8. The method of claim 1, wherein crystalline Form B of a compound having structure (I), or a zwitterionic form thereof, is administered to the mammal daily.

9. The method of claim 1, wherein the cancer comprises a solid tumor.

10. The method of claim 1, wherein the cancer is prostate cancer.

11. The method of claim 1, wherein the cancer is a sarcoma.

12. The method of claim 11, wherein the sarcoma is Kaposi sarcoma, Ewing sarcoma, osteosarcoma, rhabdomyosarcoma, soft tissue sarcoma or uterine sarcoma.

13. The method of claim 1, wherein the cancer is a sarcoma, bladder cancer or renal cancer.

14. The method of claim 1, wherein the cancer is a renal cell carcinoma.

15. The method of claim 1, wherein the cancer is a hematologic cancer.

16. The method of claim 15, wherein the hematologic cancer is selected from acute myelogenous leukemia (AML), follicular lymphoma, acute lymphoblastic leukemia (ALL), chronic lymphocytic leukemia (CLL), multiple myeloma (MM) or non-Hodgkin's lymphoma.

17. The method of claim 1, wherein crystalline Form B of a compound having structure (I), or a zwitterionic form thereof, is administered to the mammal continuously.

18. The method of claim 1, wherein crystalline Form B of a compound having structure (I), or a zwitterionic form thereof, is administered to the mammal once or twice daily for the first 21 days out of a 28-day cycle.

19. The method of claim 1, wherein the cancer is MCL-1 dependent.

20. A method for treating a renal cancer in a mammal in need thereof, comprising administering to the mammal crystalline Form B of a compound having the following structure (I):

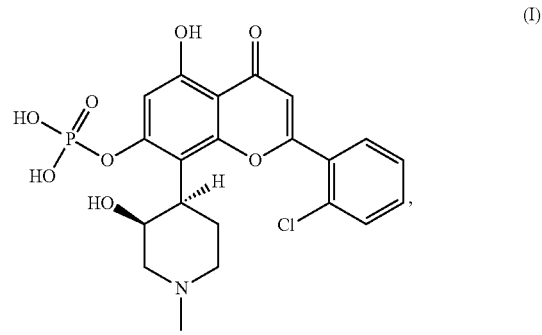 [SMILES: CN1CC[C@H](c2c(OP(=O)(O)O)cc(O)c3c(=O)cc(-c4ccccc4Cl)oc23)[C@H](O)C1 ; ","]

(I)

or a zwitterionic form thereof, in an amount of from about 1 mg to about 50 mg per day, wherein crystalline Form B is characterized by an x-ray powder diffraction pattern comprising at least three peaks at 2-theta angles selected from the group consisting of 4.8±0.2°, 10.8±0.2°, 13.7±0.2°, 14.9±0.2°, 20.0±0.2° and 24.6±0.2°.

* * * * *